United States Patent
Ahrens et al.

(10) Patent No.: US 9,156,784 B2
(45) Date of Patent: Oct. 13, 2015

(54) HERBICIDAL SULFINIMIDOYL- AND SULFONIMIDOYL BENZOYL DERIVATIVES

(71) Applicant: BAYER INTELLECTUAL PROPERTY GMBH, Monheim (DE)

(72) Inventors: Hartmut Ahrens, Egelsbach (DE); Simon Doerner-Rieping, Neu-Anspach (DE); Stefan Lehr, Lyons (FR); Hansjoerg Dietrich, Liederbach am Taunus (DE); Elmar Gatzweiler, Bad Nauheim (DE); Christopher Hugh Rosinger, Hofheim am Taunus (DE); Dirk Schmutzler, Hattersheim (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/379,513

(22) PCT Filed: Feb. 18, 2013

(86) PCT No.: PCT/EP2013/053151
§ 371 (c)(1),
(2) Date: Aug. 19, 2014

(87) PCT Pub. No.: WO2013/124230
PCT Pub. Date: Aug. 29, 2013

(65) Prior Publication Data
US 2015/0031536 A1    Jan. 29, 2015

(30) Foreign Application Priority Data

Feb. 21, 2012 (EP) .................................. 12156310

(51) Int. Cl.
| | | |
|---|---|---|
| *C07D 231/20* | (2006.01) | |
| *C07D 231/12* | (2006.01) | |
| *C07D 261/08* | (2006.01) | |
| *C07C 381/10* | (2006.01) | |
| *A01N 41/02* | (2006.01) | |
| *A01N 43/56* | (2006.01) | |
| *A01N 43/80* | (2006.01) | |
| *A01N 41/10* | (2006.01) | |

(52) U.S. Cl.
CPC .............. *C07C 381/10* (2013.01); *A01N 41/02* (2013.01); *A01N 41/10* (2013.01); *A01N 43/56* (2013.01); *A01N 43/80* (2013.01); *C07D 231/12* (2013.01); *C07D 231/20* (2013.01); *C07D 261/08* (2013.01); *C07C 2101/02* (2013.01); *C07C 2101/16* (2013.01); *C07C 2102/44* (2013.01)

(58) Field of Classification Search
USPC ................. 558/390; 548/369.4, 248; 564/102
See application file for complete search history.

(56) References Cited

U.S. PATENT DOCUMENTS

| | | | |
|---|---|---|---|
| 7,196,229 | B2 | 3/2007 | Von Deyn et al. |
| 8,114,816 | B2 | 2/2012 | Ahrens et al. |
| 8,193,121 | B2 | 6/2012 | Ahrens et al. |
| 2011/0144345 | A1 | 6/2011 | Tamai et al. |
| 2015/0018209 | A1* | 1/2015 | Ahrens et al. ................. 504/105 |

FOREIGN PATENT DOCUMENTS

| | | |
|---|---|---|
| WO | 2003014071 A1 | 2/2003 |
| WO | 2004052849 A1 | 6/2004 |
| WO | 2008125214 A1 | 10/2008 |
| WO | 2009149806 A2 | 12/2009 |
| WO | 2011012247 A1 | 2/2011 |

OTHER PUBLICATIONS

International Search Report received in corresponding PCT/EP2013/053151, mailed May 23, 2013.

\* cited by examiner

*Primary Examiner* — Nyeemah A Grazier
(74) *Attorney, Agent, or Firm* — Miles & Stockbridge P.C.

(57) ABSTRACT

The invention relates to sulfmimidoyl- and sulfonimidoyl-benzoyl derivatives of the general formula (I). In said formula (I), R, R', X, W and Z represent radicals such as hydrogen, organic radicals such as alkyl, and other radicals such as halogens. Q represents a cyclohexandionyl-, pyrazolyl-oder isoxazolyl radical.

13 Claims, No Drawings

HERBICIDAL SULFINIMIDOYL- AND SULFONIMIDOYL BENZOYL DERIVATIVES

CROSS REFERENCE TO RELATED APPLICATIONS

This application is a §371 National Stage Application of PCT/EP2013/053151, filed Feb. 18, 2013, which claims priority to EP 12156310.0, filed Feb. 21, 2012.

BACKGROUND

1. Field of the Invention

The invention relates to the technical field of the herbicides, in particular to that of the herbicides for the selective control of broad-leafed leaves and weed grasses in crops of useful plants.

2. Description of Related Art

WO 03/014071 A1 and WO 2011/012247 A1 disclose herbicidally active benzoylcyclohexanediones carrying an alkylsulfenyl, alkylsulfinyl or alkylsulfonyl group in the 3-position of the phenyl ring. Herbicidally active benzoylpyrazoles carrying an alkylsulfenyl, alkylsulfinyl or alkylsulfonyl group in the 3-position of the phenyl ring are known from WO 2008/125214 A1 and WO 2009/149806 A2. US 2011/0144345 A1 and WO 2004/052849 A1 each disclose benzoyl derivatives carrying a sulfoximino group in the 3-position of the phenyl ring. However, the herbicidal activity and/or the crop plant compatibility of the compounds mentioned in these publications is not always sufficient.

SUMMARY

It is an object of the present invention to provide herbicidally active compounds having improved properties compared to the compounds known from the prior art.

It has now been found that benzoyl derivatives carrying a sulfin- or sulfonimidoyl group in the 3-position of the phenyl ring are particularly suitable as herbicides.

Accordingly, the present invention provides sulfinimidoyl- and Sulfonimidoylbenzoyl derivatives of the formula (I) or salts thereof

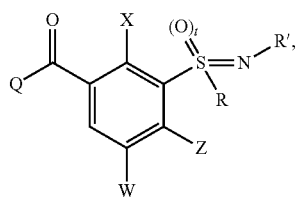
(I)

in which the symbols and indices have the following meanings:

Q is a radical Q1, Q2, Q3, Q4 or Q5,

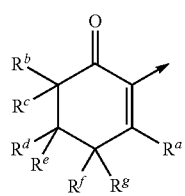
Q1

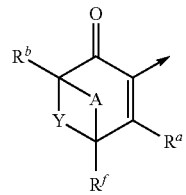
Q2

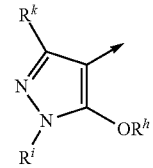
Q3

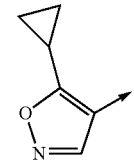
Q4

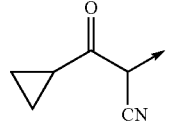
Q5

$R^a$ is hydroxyl, $R^6S$, $R^7(R^8)N$, $R^b$, $R^c$, $R^f$ and $R^e$ independently of one another are each hydrogen or $(C_1\text{-}C_4)$-alkyl, $R^d$, $R^e$ independently of one another are each hydrogen or $(C_1\text{-}C_4)$-alkyl or together with the carbon atom to which they are attached form a carbonyl group, $R^h$ is hydrogen, $(C_1\text{-}C_6)$-alkylsulfonyl, $(C_1\text{-}C_4)$-alkoxy-$(C_1\text{-}C_6)$-alkylsulfonyl, phenylsulfonyl, phiophenyl-2-sulfonyl, benzoyl, benzoyl-$(C_1\text{-}C_6)$-alkyl, benzyl, where the five last-mentioned radicals may optionally be mono- or polysubstituted by halogen, $(C_1\text{-}C_4)$-alkyl or $(C_1\text{-}C_4)$-alkoxy, $R^i$ is $(C_1\text{-}C_4)$-alkyl, $R^k$ is hydrogen, $(C_1\text{-}C_4)$-alkyl, $(C_3\text{-}C_7)$-cycloalkyl, A and Y independently of one another are each oxygen, $S(O)_n$, $N(R^3)$, carbonyl or $(C_1\text{-}C_4)$-alkylene which is substituted by n radicals $R^9$ and interrupted by n elements from the group consisting of oxygen, $S(O)_n$, $N(R^3)$ and carbonyl, X is nitro, halogen, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, halo-$(C_3\text{-}C_6)$-cycloalkyl, $(C_3\text{-}C_6)$-cycloalkenyl, halo-$(C_3\text{-}C_6)$-cycloalkenyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $(C_3\text{-}C_6)$-cycloalkenyl-$(C_1\text{-}C_6)$-alkyl, halo-$(C_3\text{-}C_6)$-cycloalkenyl-$(C_1\text{-}C_6)$-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C\text{—}(C_1\text{-}C_6)$-alkyl, $R^1O(O)C\text{—}(C_1\text{-}C_6)$-alkyl, $(R^1)_2N(O)C\text{—}(C_1\text{-}C_6)$-alkyl, $(R^1O)(R^1)N(O)C\text{—}(C_1\text{-}C_6)$-alkyl, $(R^1)_2N(R^1)N(O)C\text{—}(C_1\text{-}C_6)$-alkyl, $R^1(O)C(R^1)N(O)C\text{—}(C_1\text{-}C_6)$-alkyl, $R^2O(O)C$ (R$^1$)N(O)C—(C$_1$-C$_6$)-alkyl, (R$^1$)$_2$N(O)C(R$^1$)N(O)C—(C$_1$-C$_6$)-alkyl, R$^2$(O)$_2$S(R$^1$)N(O)C—(C$_1$-C$_6$)-alkyl, R$^1$O(O)$_2$S(R$^1$)N(O)C—(C$_1$-C$_6$)-alkyl, (R$^1$)$_2$N(O)$_2$S(R$^1$)N(O)C—(C$_1$-C$_6$)-alkyl, NC—(C$_1$-C$_6$)-alkyl, R$^1$O—(C$_1$-C$_6$)-alkyl, R$^1$(O)CO—(C$_1$-C$_6$)-alkyl, R$^2$(O)$_2$SO—(C$_1$-C$_6$)-alkyl, R$^2$O(O)CO—(C$_1$-C$_6$)-alkyl, (R$^1$)$_2$N(O)CO—(C$_1$-C$_6$)-alkyl, (R$^1$)$_2$N—(C$_1$-C$_6$)-alkyl, R$^1$(O)C(R$^1$)N—(C$_1$-C$_6$)-alkyl, R$^2$(O)$_2$S(R$^1$)N—(C$_1$-C$_6$)-alkyl, R$^2$O(O)C(R$^1$)N—(C$_1$-C$_6$)-alkyl, (R$^1$)$_2$N(O)C(R$^1$)N—(C$_1$-C$_6$)-alkyl, R$^1$O(O)$_2$S(R$^1$)N—(C$_1$-C$_6$)-alkyl, (R$^1$)$_2$N(O)$_2$S(R$^1$)N—(C$_1$-C$_6$)-alkyl, R$^2$(O)$_n$S—(C$_1$-C$_6$)-alkyl, R$^1$O(O)$_2$S—(C$_1$-C$_6$)-alkyl, (R$^1$)$_2$N(O)$_2$S—(C$_1$-C$_6$)-alkyl, R$^1$(O)C(R$^1$)N(O)$_2$S—(C$_1$-C$_6$)-alkyl, R$^2$O(O)C(R$^1$)N(O)$_2$S—(C$_1$-C$_6$)-alkyl, (R$^1$)$_2$N(O)C(R$^1$)N(O)$_2$S—(C$_1$-C$_6$)-alkyl, (R$^5$O)$_2$(O)P—(C$_1$-C$_6$)-alkyl, phenyl, heteroaryl, heterocyclyl, phenyl-(C$_1$-C$_6$)-alkyl, heteroaryl-(C$_1$-C$_6$)-alkyl, heterocyclyl-(C$_1$-C$_6$)-alkyl, where the six last-mentioned radicals are each substituted by s radicals from the group consisting of nitro, halogen, cyano, thiocyanato, (C$_1$-C$_6$)-alkyl, halo-(C$_1$-C$_6$)-alkyl, (C$_3$-C$_6$)-cycloalkyl, R$^1$O(O)C, (R$^1$)$_2$N(O)C, R$^1$O, (R$^1$)$_2$N, R$^2$(O)$_n$S, R$^1$O(O)$_2$S, (R$^1$)$_2$N(O)$_2$S and R$^1$O—(C$_1$-C$_6$)-alkyl, and where heterocyclyl carries n oxo groups, Z is hydrogen, nitro, halogen, cyano, thiocyanato, (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_3$-C$_6$)-alkynyl, (C$_3$-C$_6$)-cycloalkyl, halo-(C$_3$-C$_6$)-cycloalkyl, (C$_3$-C$_6$)-cycloalkenyl, halo-(C$_3$-C$_6$)-cycloalkenyl, (C$_3$-C$_6$)-cycloalkyl-(C$_1$-C$_6$)-alkyl, halo-(C$_3$-C$_6$)-cycloalkyl-(C$_1$-C$_6$)-alkyl, (C$_3$-C$_6$)-cycloalkenyl-(C$_1$-C$_6$)-alkyl, halo-(C$_3$-C$_6$)-cycloalkenyl-(C$_1$-C$_6$)-alkyl, R$^1$(O)C, R$^1$(R$^1$ON=)C, R$^1$O(O)C, (R$^1$)$_2$N(O)C, R$^1$(R$^1$O)N(O)C, (R$^1$)$_2$N(R$^1$)N(O)C, R$^1$(O)C(R$^1$)N(O)C, R$^2$O(O)C(R$^1$)N(O)C, (R$^1$)$_2$N(O)C(R$^1$)N(O)C, R$^2$(O)$_2$S(R$^1$)N(O)C, R$^1$O(O)$_2$S(R$^1$)N(O)C, (R$^1$)$_2$N(O)$_2$S(R$^1$)N(O)C, R$^1$O, R$^1$(O)CO, R$^2$(O)$_2$SO, R$^2$O(O)CO, (R$^1$)$_2$N(O)CO, (R$^1$)$_2$N, R$^1$(O)C(R$^1$)N, R$^2$(O)$_2$S(R$^1$)N, R$^2$O(O)C(R$^1$)N, (R$^1$)$_2$N(O)C(R$^1$)N, R$^1$O(O)$_2$S(R$^1$)N, (R$^1$)$_2$N(O)$_2$S(R$^1$)N, R$^2$(O)$_n$S, R$^1$O(O)$_2$S, (R$^1$)$_2$N(O)$_2$S, R$^1$(O)C(R$^1$)N(O)$_2$S, R$^2$O(O)C(R$^1$)N(O)$_2$S, (R$^1$)$_2$N(O)C(R$^1$)N(O)$_2$S, (R$^5$O)$_2$(O)P, R$^1$(O)C—(C$_1$-C$_6$)-alkyl, R$^1$O(O)C—(C$_1$-C$_6$)-alkyl, (R$^1$)$_2$N(O)C—(C$_1$-C$_6$)-alkyl, (R$^1$O)(R$^1$)N(O)C—(C$_1$-C$_6$)-alkyl, (R$^1$)$_2$N(R$^1$)N(O)C—(C$_1$-C$_6$)-alkyl, R$^1$(O)C(R$^1$)N(O)C—(C$_1$-C$_6$)-alkyl, R$^2$O(O)C(R$^1$)N(O)C—(C$_1$-C$_6$)-alkyl, (R$^1$)$_2$N(O)C(R$^1$)N(O)C—(C$_1$-C$_6$)-alkyl, R$^2$(O)$_2$S(R$^1$)N(O)C—(C$_1$-C$_6$)-alkyl, R$^1$O(O)$_2$S(R$^1$)N(O)C—(C$_1$-C$_6$)-alkyl, (R$^1$)$_2$N(O)$_2$S(R$^1$)N(O)C—(C$_1$-C$_6$)-alkyl, NC—(C$_1$-C$_6$)-alkyl, R$^1$O—(C$_1$-C$_6$)-alkyl, R$^1$(O)CO—(C$_1$-C$_6$)-alkyl, R$^2$(O)$_2$SO—(C$_1$-C$_6$)-alkyl, R$^2$O(O)CO—(C$_1$-C$_6$)-alkyl, (R$^1$)$_2$N(O)CO—(C$_1$-C$_6$)-alkyl, (R$^1$)$_2$N—(C$_1$-C$_6$)-alkyl, R$^1$(O)C(R$^1$)N—(C$_1$-C$_6$)-alkyl, R$^2$(O)$_2$S(R$^1$)N—(C$_1$-C$_6$)-alkyl, R$^2$O(O)C(R$^1$)N—(C$_1$-C$_6$)-alkyl, (R$^1$)$_2$N(O)C(R$^1$)N—(C$_1$-C$_6$)-alkyl, R$^1$O(O)$_2$S(R$^1$)N—(C$_1$-C$_6$)-alkyl, (R$^1$)$_2$N(O)$_2$S(R$^1$)N—(C$_1$-C$_6$)-alkyl, R$^2$(O)$_n$S—(C$_1$-C$_6$)-alkyl, R$^1$O(O)$_2$S—(C$_1$-C$_6$)-alkyl, (R$^1$)$_2$N(O)$_2$S—(C$_1$-C$_6$)-alkyl, R$^1$(O)C(R$^1$)N(O)$_2$S—(C$_1$-C$_6$)-alkyl, R$^2$O(O)C(R$^1$)N(O)$_2$S—(C$_1$-C$_6$)-alkyl, (R$^1$)$_2$N(O)C(R$^1$)N(O)$_2$S—(C$_1$-C$_6$)-alkyl, (R$^5$O)$_2$(O)P—(C$_1$-C$_6$)-alkyl, phenyl, heteroaryl, heterocyclyl, phenyl-(C$_1$-C$_6$)-alkyl, heteroaryl-(C$_1$-C$_6$)-alkyl, heterocyclyl-(C$_1$-C$_6$)-alkyl, where the six last-mentioned radicals are each substituted by s radicals from the group consisting of nitro, halogen, cyano, thiocyanato, (C$_1$-C$_6$)-alkyl, halo-(C$_1$-C$_6$)-alkyl, (C$_3$-C$_6$)-cycloalkyl, R$^1$O(O)C, (R$^1$)$_2$N(O)C, R$^1$O, (R$^1$)$_2$N, R$^2$(O)$_n$S, R$^1$O(O)$_2$S, (R$^1$)$_2$N(O)$_2$S and R$^1$O—(C$_1$-C$_6$)-alkyl, and where heterocyclyl carries n oxo groups, W is hydrogen, halogen, nitro, cyano, thiocyanato, (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, (C$_3$-C$_7$)-cycloalkyl, halo-(C$_3$-C$_7$)-cycloalkyl, (C$_1$-C$_6$)-alkoxy, halo-(C$_1$-C$_6$)-alkoxy, (C$_1$-C$_6$)-alkyl-(O)$_n$S—, (C$_1$-C$_6$)-haloalkyl-(O)$_n$S—, (C$_1$-C$_6$)-alkoxy-(C$_1$-C$_4$)-alkyl, (C$_1$-C$_6$)-alkoxy-(C$_1$-C$_4$)-haloalkyl, R$^1$(O)C, R$^1$(R$^1$ON=)C, R$^1$O(O)C, (R$^1$)$_2$N, R$^1$(O)C(R$^1$)N or R$^2$(O)$_2$S(R$^1$)N, R is (C$_1$-C$_6$)-alkyl, (C$_2$-C$_6$)-alkenyl or (C$_2$-C$_6$)-alkynyl, each of which is substituted by s radicals from the group consisting of nitro, halogen, cyano, thiocyanato, (C$_3$-C$_6$)-cycloalkyl, R$^1$(O)C, R$^1$(R$^1$ON=)C, R$^1$O(O)C, (R$^1$)$_2$N(O)C, R$^1$(R$^1$O)N(O)C, R$^2$(O)$_2$S(R$^1$)N(O)C, R$^1$O(O)$_2$S(R$^1$)N(O)C, (R$^1$)$_2$N(O)$_2$S(R$^1$)N(O)C, R$^1$S(O)C, R$^1$O, R$^1$(O)CO, R$^2$(O)$_2$SO, R$^2$O(O)CO, (R$^1$)$_2$N(O)CO, (R$^1$)$_2$N, R$^1$O(R$^1$)N, R$^1$(O)C(R$^1$)N, R$^2$(O)$_2$S(R$^1$)N, R$^2$O(O)C(R$^1$)N, (R$^1$)$_2$N(O)C(R$^1$)N, R$^1$O(O)$_2$S(R$^1$)N, (R$^1$)$_2$N(O)$_2$S(R$^1$)N, R$^2$(O)$_n$S, R$^1$C(O)S, R$^1$O(O)$_2$S, (R$^1$)$_2$N(O)$_2$S, R$^1$(O)C(R$^1$)N(O)$_2$S, R$^2$O(O)C(R$^1$)N(O)$_2$S, (R$^1$)$_2$N(O)C(R$^1$)N(O)$_2$S and (R$^5$O)$_2$(O)P, or is (C$_3$-C$_6$)-cycloalkyl, (C$_3$-C$_6$)-cycloalkenyl, phenyl, phenyl-(C$_1$-C$_6$)-alkyl, heteroaryl, heteroaryl-(C$_1$-C$_6$)-alkyl, heterocyclyl, heterocyclyl-(C$_1$-C$_6$)-alkyl, phenyl-O—(C$_1$-C$_6$)-alkyl, heteroaryl-O—(C$_1$-C$_6$)-alkyl, heterocyclyl-O—(C$_1$-C$_6$)-alkyl, phenyl-N(R$^1$)—(C$_1$-C$_6$)-alkyl, heteroaryl-N(R$^1$)—(C$_1$-C$_6$)-alkyl, heterocyclyl-N(R$^1$)—(C$_1$-C$_6$)-alkyl, phenyl-S(O)$_n$—(C$_1$-C$_6$)-alkyl, heteroaryl-S(O)$_n$—(C$_1$-C$_6$)-alkyl or heterocyclyl-S(O)$_n$—(C$_1$-C$_6$)-alkyl, each of which is substituted in the cyclic moiety by s radicals from the group consisting of nitro, halogen, cyano, thiocyanato, (C$_1$-C$_6$)-alkyl, halo-(C$_1$-C$_6$)-alkyl, (C$_3$-C$_6$)-cycloalkyl, R$^1$(O)C, R$^1$(R$^1$ON=)C, R$^1$O(O)C, (R$^1$)$_2$N(O)C, R$^1$(R$^1$O)N(O)C, R$^2$(O)$_2$S(R$^1$)N(O)C, R$^1$O(O)$_2$S(R$^1$)N(O)C, (R$^1$)$_2$N(O)$_2$S(R$^1$)N(O)C, R$^1$S(O)C, R$^1$O, R$^1$(O)CO, R$^2$(O)$_2$SO, R$^2$O(O)CO, (R$^1$)$_2$N(O)CO, (R$^1$)$_2$N, R$^1$O(R$^1$)N, R$^1$(O)C(R$^1$)N, R$^2$(O)$_2$S(R$^1$)N, R$^2$O(O)C(R$^1$)N, (R$^1$)$_2$N(O)C(R$^1$)N, R$^1$O(O)$_2$S(R$^1$)N, (R$^1$)$_2$N(O)$_2$S(R$^1$)N, R$^2$(O)$_n$S, R$^1$C(O)S, R$^1$O(O)$_2$S, (R$^1$)$_2$N(O)$_2$S, R$^1$(O)C(R$^1$)N(O)$_2$S, R$^2$O(O)C(R$^1$)N(O)$_2$S, (R$^1$)$_2$N(O)C(R$^1$)N(O)$_2$S, (R$^5$O)$_2$(O)P and R$^1$O—(C$_1$-C$_6$)-alkyl, and where heterocyclyl carries n oxo groups, R' is hydrogen, nitro, halogen, cyano, (C$_1$-C$_6$)-alkyl, halo-(C$_1$-C$_6$)-alkyl, (C$_3$-C$_6$)-alkenyl, halo-(C$_3$-C$_6$)-alkenyl, (C$_2$-C$_6$)-alkynyl, halo-(C$_3$-C$_6$)-alkynyl, (C$_3$-C$_6$)-cycloalkyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, R$^1$(O)C, R$^2$O(O)C, (R$^1$)$_2$N(O)C, R$^2$S(O)C, (R$^1$)$_2$N(S)C, R$^1$(R$^1$O)N(O)C, R$^2$(O)$_2$S(R$^1$)N(O)C, (R$^1$)$_2$N(O)$_2$S(R$^1$)N(O)C, R$^1$O, (R$^1$)$_2$N, R$^2$(O)$_n$S, (R$^2$)$_3$Si—(C$_1$-C$_6$)-alkyl-(O)$_n$S, R$^1$O(O)$_2$S, (R$^1$)$_2$N(O)$_2$S, R$^1$(O)C(R$^1$)N(O)$_2$S, R$^2$O(O)C(R$^1$)N(O)$_2$S, (R$^1$)$_2$N(O)C(R$^1$)N(O)$_2$S, R$^2$(O)$_2$S(R$^1$)N(O)$_2$S, (R$^5$O)$_2$(O)P, (R$^2$)$_3$Si, R$^1$(O)C—(C$_1$-C$_6$)-alkyl, R$^1$O(O)C—(C$_1$-C$_6$)-alkyl, (R$^1$)$_2$N(O)C—(C$_1$-C$_6$)-alkyl, (R$^1$O)(R$^1$)N(O)C—(C$_1$-C$_6$)-alkyl, R$^2$(O)$_2$S(R$^1$)N(O)C—(C$_1$-C$_6$)-alkyl, R$^1$O(O)$_2$S(R$^1$)N(O)C—(C$_1$-C$_6$)-alkyl, (R$^1$)$_2$N(O)$_2$S(R$^1$)N(O)C—(C$_1$-C$_6$)-alkyl, R$^1$O—(C$_1$-C$_6$)-alkyl, R$^1$(O)CO—(C$_1$-C$_6$)-alkyl, R$^2$(O)$_2$SO—(C$_1$-C$_6$)-alkyl, R$^2$O(O)CO—(C$_1$-C$_6$)-alkyl, (R$^1$)$_2$N(O)CO—(C$_1$-C$_6$)-alkyl, (R$^1$)$_2$N—(C$_1$-C$_6$)-alkyl, R$^1$(O)C(R$^1$)N—(C$_1$-C$_6$)-alkyl, R$^2$(O)$_2$S(R$^1$)N—(C$_1$-C$_6$)-alkyl, R$^2$O(O)C(R$^1$)N—(C$_1$-C$_6$)-alkyl, (R$^1$)$_2$N(O)C(R$^1$)N—(C$_1$-C$_6$)-alkyl, R$^1$O(O)$_2$S(R$^1$)N—(C$_1$-C$_6$)-alkyl, (R$^1$)$_2$N(O)$_2$S(R$^1$)N—(C$_1$-C$_6$)-alkyl, R$^2$(O)$_n$S—(C$_1$-C$_6$)-alkyl, R$^1$O(O)$_2$S—(C$_1$-C$_6$)-alkyl, (R$^1$)$_2$N(O)$_2$S—(C$_1$-C$_6$)-alkyl, R$^1$(O)C(R$^1$)N(O)$_2$S—(C$_1$-C$_6$)-alkyl, R$^2$O(O)C(R$^1$)N(O)$_2$S—(C$_1$-C$_6$)-alkyl, (R$^1$)$_2$N(O)C(R$^1$)N(O)$_2$S—(C$_1$-C$_6$)-alkyl, (R$^5$O)$_2$(O)P—(C$_1$-C$_6$)-alkyl, (R$^2$)$_3$Si—(C$_1$-C$_6$)-alkyl, phenyl, heteroaryl, heterocyclyl, phenyl-(C$_1$-C$_6$)-alkyl, heteroaryl-(C$_1$-C$_6$)-alkyl, heterocyclyl-(C$_1$-C$_6$)-alkyl, where the six above-mentioned phenyl, heteroaryl and heterocyclyl radicals are substituted in the cyclic moiety by s radicals from the group consisting of nitro, halogen, cyano, thiocyanato, (C$_1$-C$_6$)-alkyl, halo-(C$_1$-C$_6$)-alkyl, (C$_3$-C$_6$)-cycloalkyl, R$^1$O(O)C, (R$^1$)$_2$N(O)C, R$^1$O, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl carries n oxo groups, $R^1$ is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, $(C_3$-$C_6)$-cycloalkenyl, halo-$(C_3$-$C_6)$-cycloalkyl, $(C_3$-$C_6)$-cycloalkyl-$(C_1$-$C_6)$-alkyl, $(C_1$-$C_6)$-alkyl-O—$(C_1$-$C_6)$-alkyl, cycloalkyl-$(C_1$-$C_6)$-alkyl-O—$(C_1$-$C_6)$-alkyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl, heterocyclyl-O—$(C_1$-$C_6)$-alkyl, phenyl-$N(R^3)$—$(C_1$-$C_6)$-alkyl, heteroaryl-$N(R^3)$—$(C_1$-$C_6)$-alkyl, heterocyclyl-$N(R^3)$—$(C_1$-$C_6)$-alkyl, phenyl-$S(O)_n$—$(C_1$-$C_6)$-alkyl, heteroaryl-$S(O)_n$—$(C_1$-$C_6)$-alkyl, heterocyclyl-$S(O)_n$—$(C_1$-$C_6)$-alkyl, where the fifteen last-mentioned radicals are each substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1$-$C_6)$-alkyl, and where heterocyclyl carries n oxo groups, $R^2$ is $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, $(C_3$-$C_6)$-cycloalkenyl, halo-$(C_3$-$C_6)$-cycloalkyl, $(C_3$-$C_6)$-cycloalkyl-$(C_1$-$C_6)$-alkyl, $(C_1$-$C_6)$-alkyl-O—$(C_1$-$C_6)$-alkyl, cycloalkyl-$(C_1$-$C_6)$-alkyl-O—$(C_1$-$C_6)$-alkyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl, heterocyclyl-O—$(C_1$-$C_6)$-alkyl, phenyl-$N(R^3)$—$(C_1$-$C_6)$-alkyl, heteroaryl-$N(R^3)$—$(C_1$-$C_6)$-alkyl, heterocyclyl-$N(R^3)$—$(C_1$-$C_6)$-alkyl, phenyl-$S(O)_n$—$(C_1$-$C_6)$-alkyl, heteroaryl-$S(O)_n$—$(C_1$-$C_6)$-alkyl, heterocyclyl-$S(O)_n$—$(C_1$-$C_6)$-alkyl, where the fifteen last-mentioned radicals are each substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1$-$C_6)$-alkyl, and where heterocyclyl carries n oxo groups, $R^3$ is hydrogen, $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkyl-$(C_1$-$C_6)$-alkyl or phenyl, $R^4$ is $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkyl-$(C_1$-$C_6)$-alkyl or phenyl, $R^5$ is hydrogen or $(C_1$-$C_4)$-alkyl, $R^6$ is $(C_1$-$C_4)$-alkyl or is phenyl which is substituted by m radicals from the group consisting of halogen, nitro, cyano, $(C_1$-$C_4)$-alkyl, $(C_1$-$C_4)$-haloalkyl, $(C_1$-$C_4)$-alkoxy and $(C_1$-$C_4)$-haloalkoxy, $R^7$ is hydrogen, $(C_1$-$C_4)$-alkyl or $(C_1$-$C_4)$-alkoxy, $R^8$ is hydrogen or $(C_1$-$C_4)$-alkyl, or $R^7$ and $R^8$ together with the nitrogen atom to which they are attached form a 5- or 6-membered saturated, partially saturated or unsaturated ring which additionally contained n heteroatoms from the group consisting of nitrogen, oxygen and sulfur and which is substituted by m radicals from the group consisting of halogen, cyano, $(C_1$-$C_4)$-alkyl, $(C_1$-$C_4)$-haloalkyl, $(C_1$-$C_4)$-alkoxy and $(C_1$-$C_4)$-haloalkoxy, $R^9$ is halogen, $(C_1$-$C_4)$-alkyl, $(C_1$-$C_4)$-haloalkyl, $(C_1$-$C_4)$-alkoxy, $(C_1$-$C_4)$-haloalkoxy or $(C_1$-$C_4)$-alkoxy-$(C_1$-$C_4)$-alkyl, m is 0, 1, 2, 3, 4 or 5, n is 0, 1 or 2, s is 0, 1, 2 or 3, t is 0 or 1.

DETAILED DESCRIPTION OF A PREFERRED EMBODIMENT

In formula (I) and all formulae given below, alkyl radicals which have more than two carbon atoms may be straight-chain or branched. Alkyl radicals are, for example, methyl, ethyl, n- or isopropyl, n-, iso-, t- or 2-butyl, pentyls, hexyls, such as n-hexyl, isohexyl and 1,3-dimethylbutyl. Analogously, alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl. Alkynyl is, for example, propargyl, but-2-yn-1-yl, but-3-yn-1-yl, 1-methyl-but-3-yn-1-yl. In each case, the multiple bond may be located in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be located in any position.

Halogen is fluorine, chlorine, bromine or iodine.

Heterocyclyl is a saturated, partially saturated or completely unsaturated cyclic radical which comprises 3 to 6 ring atoms, 1 to 4 of which are from the group consisting of oxygen, nitrogen and sulfur, and which may additionally be condensed with a benzo ring. Heterocyclyl is, for example, piperidinyl, pyrrolidinyl, tetrahydrofuranyl, dihydrofuranyl and oxetanyl, Heteroaryl is an aromatic cyclic radical which comprises 3 to 6 ring atoms, 1 to 4 of which are from the group consisting of oxygen, nitrogen and sulfur, and which may additionally be condensed with a benzo ring. Heteroaryl is, for example, benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is substituted by a plurality of radicals, this means that this group is substituted by one or more identical or different of the radicals mentioned. This applies analogously to the construction of ring systems from different atoms and elements. Here, compounds of which the skilled worker knows that they are chemically unstable under standard temperature and pressure conditions are excluded from the claims.

Depending on the nature and the attachment of the substituents, the compounds of the formula (I) may be present as stereoisomers. If, for example, one or more asymmetrically substituted carbon atoms are present, it is possible for enantiomers and diastereomers to occur. Stereoisomers also occur when n in the grouping $S(O)_n$ n is 1 (sulfoxides). Moreover, the sulfur atom in the sulfoximino group or the sulfilimino group is a center of chirality. Stereoisomers can be obtained by customary separation methods, for example by chromatographic separation procedures, from the mixtures obtained in the preparation. It is also possible to selectively prepare stereoisomers by employing stereoselective reactions using optically active starting materials and/or auxiliaries. The invention also relates to all stereoisomers embraced by the formula (I) but not shown in their specific stereoform, and mixtures thereof.

The compounds of the formula (I) are capable of forming salts. Salt formation may occur by action of a base on those compounds of the formula (I) which carry an acidic hydrogen atom, for example in the case where $R^a$ is a hydroxyl group or $R^h$ is hydrogen. Suitable bases are, for example, organic amines, such as trialkylamines, morpholine, piperidine or pyridine, and also ammonium, alkali metal or alkaline earth metal hydroxides, carbonates and bicarbonates, in particular sodium hydroxide and potassium hydroxide, sodium carbonate and potassium carbonate and sodium bicarbonate and potassium bicarbonate. These salts are compounds in which the acidic hydrogen is replaced by an agriculturally suitable cation, for example metal salts, in particular alkali metal salts or alkaline earth metal salts, especially sodium salts and potassium salts, or else ammonium salts, salts with organic amines or quaternary ammonium salts, for example with cations of the formula [NRR*RR*]⁺ in which R, R*, R and R* independently of one another each denote an organic radical, in particular alkyl, aryl, aralkyl or alkylaryl. Also suitable are alkylsulfonium and alkylsulfoxonium salts such as $(C_1$-$C_4)$-trialkylsulfonium and $(C_1$-$C_4)$-trialkylsulfoxonium salts.

By forming an adduct with a suitable inorganic or organic acid, for example mineral acids such as HCl, HBr, $H_2SO_4$, $H_3PO_4$ or $HNO_3$ or organic acids, for example carboxylic acids such as formic acid, acetic acid, propionic acid, oxalic acid, lactic acid or salicylic acid, or sulfonic acids such as p-toluenesulfonic acid, at a basic group, such as, for example, amino, alkylamino, dialkylamino, piperidino, morpholino or pyridino, the compounds of the formula (I) are capable of forming salts. In this case, the salts contain the conjugated base of the acid as anion.

Preference is given to compounds of the formula (I) in which

Q is a radical Q1, Q2, Q3, Q4 or Q5,

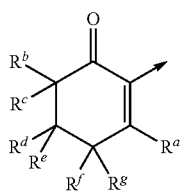

Q1

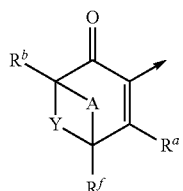

Q2

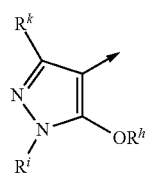

Q3

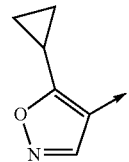

Q4

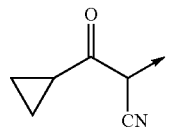

Q5

$R^a$ is hydroxyl, $R^b$, $R^c$, $R^f$ and $R^g$ independently of one another are each hydrogen or $(C_1$-$C_4)$-alkyl, $R^d$, $R^e$ independently of one another are each hydrogen or $(C_1$-$C_4)$-alkyl or together with the carbon atom to which they are attached form a carbonyl group, $R^h$ is hydrogen, $R^i$ is $(C_1$-$C_4)$-alkyl, $R^k$ is hydrogen, $(C_1$-$C_4)$-alkyl, $(C_3$-$C_7)$-cycloalkyl, A and Y independently of one another are each oxygen or $(C_1$-$C_4)$-alkylene which is substituted by n radicals $R^9$, X is nitro, halogen, cyano, $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, NC—$(C_1$-$C_6)$-alkyl, $R^1O$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, heterocyclyl-$(C_1$-$C_6)$-alkyl, where the six last-mentioned radicals are each substituted by s radicals from the group consisting of nitro, halogen, cyano, thiocyanato, $(C_1$-$C_6)$-alkyl, halo-$(C_1$-$C_6)$-alkyl, $R^1O$, $(R^1)_2N$, $R^2(O)_nS$, $R^1O(O)_2S$, $(R^1)_2N(O)_2S$ and $R^1O$—$(C_1$-$C_6)$-alkyl and where heterocyclyl carries n oxo groups, Z is hydrogen, nitro, halogen, cyano, $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, NC—$(C_1$-$C_6)$-alkyl, $R^1O$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, heterocyclyl-$(C_1$-$C_6)$-alkyl, where the six last-mentioned radicals are each substituted by s radicals from the group consisting of nitro, halogen, cyano, thiocyanato, ($C_1$-$C_6$)-alkyl, halo-($C_1$-$C_6$)-alkyl, $R^1O$, $(R^1)_2N$, $R^2(O)_nS$, $R^1O(O)_2S$, $(R^1)_2N(O)_2S$ and $R^1O$—($C_1$-$C_6$)-alkyl and where heterocyclyl carries n oxo groups, W is hydrogen, halogen, nitro, cyano, ($C_1$-$C_6$)-alkyl, halo-($C_1$-$C_6$)-alkyl, ($C_3$-$C_7$)-cycloalkyl, ($C_1$-$C_6$)-alkoxy, ($C_1$-$C_6$)-alkyl-(O)$_n$S—, $R^1O(O)C$, $(R^1)_2N$, $R^1(O)C(R^1)N$ or $R^2(O)_2S(R^1)N$, R is ($C_1$-$C_6$)-alkyl which is in each case substituted by s radicals from the group consisting of halogen, cyano, ($C_3$-$C_6$)-cycloalkyl, $R^1(O)C$, $R^1(R^1ON=)C$, $R^1O(O)C$, $(R^1)_2N(O)C$, $R^2(O)_2S(R^1)N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$ and $(R^1)_2N(O)C(R^1)N(O)_2S$ or is ($C_3$-$C_6$)-cycloalkyl which is in each case substituted by s radicals from the group consisting of halogen, ($C_1$-$C_6$)-alkyl, halo-($C_1$-$C_6$)-alkyl, ($C_3$-$C_6$)-cycloalkyl, $R^1O(O)C$ and $(R^1)_2N(O)C$, R' is hydrogen, nitro, cyano, ($C_1$-$C_6$)-alkyl, halo-($C_1$-$C_6$)-alkyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1(O)C$, $R^2O(O)C$, $(R^1)_2N(O)C$, $R^2(O)_2S$, $R^1(O)C$—($C_1$-$C_6$)-alkyl, $R^1O(O)C$—($C_1$-$C_6$)-alkyl, $(R^1)_2N(O)C$—($C_1$-$C_6$)-alkyl, $R^1O$—($C_1$-$C_6$)-alkyl, $(R^1)_2N$—($C_1$-$C_6$)-alkyl, $R^2(O)_nS$—($C_1$-$C_6$)-alkyl, $R^1$ is hydrogen, ($C_1$-$C_6$)-alkyl, halo-($C_1$-$C_6$)-alkyl, ($C_3$-$C_6$)-cycloalkyl, halo-($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, heterocyclyl-O—($C_1$-$C_6$)-alkyl, where the nine last-mentioned radicals are in each case substituted by s radicals from the group consisting of nitro, halogen, ($C_1$-$C_6$)-alkyl, halo-($C_1$-$C_6$)-alkyl, $R^3O(O)C$, $(R^3)_2N(O)C$, $R^3O$, $(R^3)_2N$, $R^4(O)_nS$ and $R^3O$—($C_1$-$C_6$)-alkyl, and where heterocyclyl carries n oxo groups, $R^2$ is ($C_1$-$C_6$)-alkyl, halo-($C_1$-$C_6$)-alkyl, ($C_3$-$C_6$)-cycloalkyl, halo-($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, heterocyclyl-O—($C_1$-$C_6$)-alkyl, where the nine last-mentioned radicals are in each case substituted by s radicals from the group consisting of nitro, halogen, ($C_1$-$C_6$)-alkyl, halo-($C_1$-$C_6$)-alkyl, $R^3O(O)C$, $(R^3)_2N(O)C$, $R^3O$, $(R^3)_2N$, $R^4(O)_nS$ and $R^3O$—($C_1$-$C_6$)-alkyl, and where heterocyclyl carries n oxo groups, $R^3$ is hydrogen or ($C_1$-$C_6$)-alkyl, $R^4$ is ($C_1$-$C_6$)-alkyl, $R^5$ is hydrogen or ($C_1$-$C_4$)-alkyl, $R^9$ is halogen, ($C_1$-$C_4$)-alkyl, ($C_1$-$C_4$)-haloalkyl, ($C_1$-$C_4$)-alkoxy, ($C_1$-$C_4$)-haloalkoxy or ($C_1$-$C_4$)-alkoxy-($C_1$-$C_4$)-alkyl, n is 0, 1 or 2, s is 0, 1, 2 or 3, t is 0 or 1.

Particular preference is given to compounds of the formula (I) in which

Q is a radical Q1, Q2, Q3, Q4 or Q5,

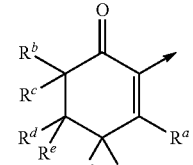
Q1

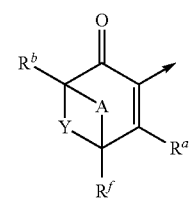
Q2

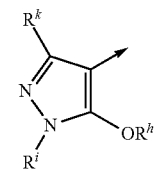
Q3

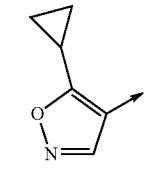
Q4

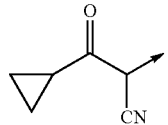
Q5

$R^a$ is hydroxyl, $R^b$, $R^c$, $R^f$ and $R^g$ independently of one another are each hydrogen or methyl, $R^d$, $R^e$ are hydrogen or together with the carbon atom to which they are attached form a carbonyl group, $R^h$ is hydrogen, $R^i$ is methyl or ethyl, $R^k$ is hydrogen, methyl or cyclopropyl, A and Y independently of one another are each $CH_2$ or $CH_2CH_2$, X is nitro, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl, methylsulfonyl, methoxymethyl, ethoxymethyl, methoxyethyl, methoxyethoxymethyl, methylthiomethyl, methylsulfinylmethyl or methylsulfonylmethyl, Z is hydrogen, nitro, cyano, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl or methylsulfonyl, W is hydrogen, chlorine or methyl, R is methyl, ethyl or n-propyl, R' is hydrogen or cyano, t is 0 or 1.

The compounds of the formula (I) according to the invention can be prepared from the corresponding thioethers of the formula (I-thioether) (Scheme 1). To this end, the thioether is converted, for example with cyanamide and an oxidizing agent (iodosobenzene diacetate, sodium hypochlorite or N-bromosuccinimide) into the corresponding sulfilimine, which can be oxidized further to the sulfoximine. Suitable for the oxidation to the sulfoximine are oxidizing agents such as, for example, meta-chlorperbenzoic acid, sodium permanganate or a mixture of sodium periodate and ruthenium trichloride. NH-Sulfoximines can be obtained, for example, from sulfoxides using sodium azide and sulfuric acid and can be functionalized at the nitrogen atom with reagents such as, for example cyanogen bromide, acid chlorides or acid anhydrides, chloroformic esters, nitric acid or other compounds. The oxidation of N-sulfonated sulfilimines to the corresponding sulfoximines can be achieved with hydrogen, for example. Alternatively, sulfoxides can be converted into N-acylated or N-sulfonated sulfoximines. The carboxamide or sulfonamide, respectively, can then be cleaved to give the NH-sulfoximine. Such synthesis methods for generating sulfilimines and sulfoximines from thioethers or for generating sulfoximines from sulfoxides or for derivatizing sulfilimines and sulfoximines, also of NH-sulfoximines, inter alia, are described, for example, in Bolm, C. Org. Lett. 2004, 6, 1305; Bolm, C. Org. Lett. 2007, 9, 3809; Bolm, C. Synthesis 2010, 17, 2922; Bolm, C. Adv. Synth. Catal. 2010, 352, 309, WO 2007/095229 A1, WO 2008/141843 A1, WO 2008/097235 A1, US 2008/0207910 A1, US 2008/0194634 A1 and US 2010/0056534 A1.

If required, protective groups have to be employed for such synthetic sequences to achieve sufficient selectivity. In particular the functionalization at the NH-sulfoximine competes in principle with the analogous functionalization at the amide nitrogen atom. The optimum procedure depends on the substitution pattern in question.

Compounds of the formula (I-thioether) and the formula (I-sulfoxide) are known and described, for example, in WO 2003/014071 A1, WO 2008/125214 A1, WO 2009/149806 A1, WO 2011012247 A1, WO 2011012247 A1, EP 0 609 798 A1 and EP 0 625 508 A1.

It may be expedient to change the order of reaction steps. Under certain conditions, sulfoximines and in particular sulfilimines are insufficiently stable (Bolm, C. Adv. Synth. Catal. 2010, 352, 309), so it may be advantageous, as shown in Scheme 1, to synthesize initially, at the thioether stage, the benzoyl derivative and to generate the sulfilimine or the sulfoximine from the thioether only at the end of the synthesis sequence. However, in the case of sufficient stability, it may, depending on the substitution pattern, also be expedient to generate first, at the benzoic acid stage (or at an even earlier stage) the sulfilimine of the sulfoximine from the thioether, and only then to convert the benzoic acid into its benzoyl derivative (Scheme 2). The conversion of benzoic acids into their benzoyl derivatives is known for numerous classes of structures not comprising a sulfilimino group or sulfoximino group and described, for example, in WO 2003/014071 A1, WO 2008/125214 A1, WO 2009/149806 A1, WO 2011012247 A1, WO 2011012247 A1, EP 0 609 798 A1 and

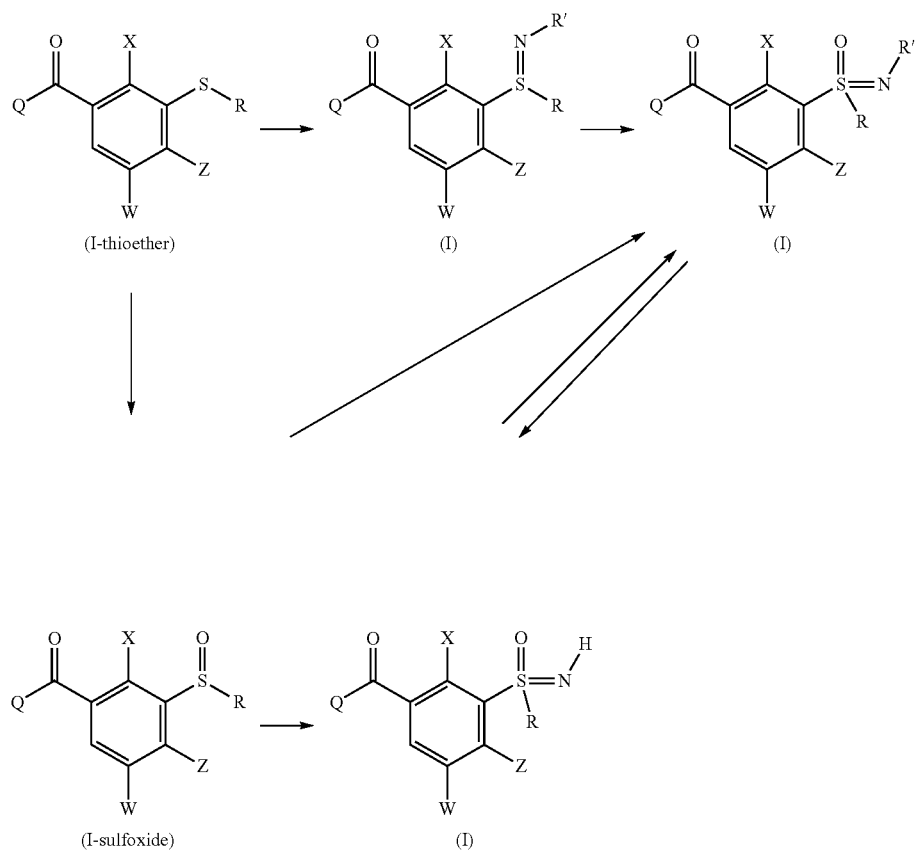

EP 0 625 508 A1. Depending on the substitution pattern, this route to the compounds of the formula (I) according to the invention may be expedient.

lar for preparing the compounds of the formula (I) according to the invention. The compounds of the formula (II) also form part of the subject matter of the present invention.

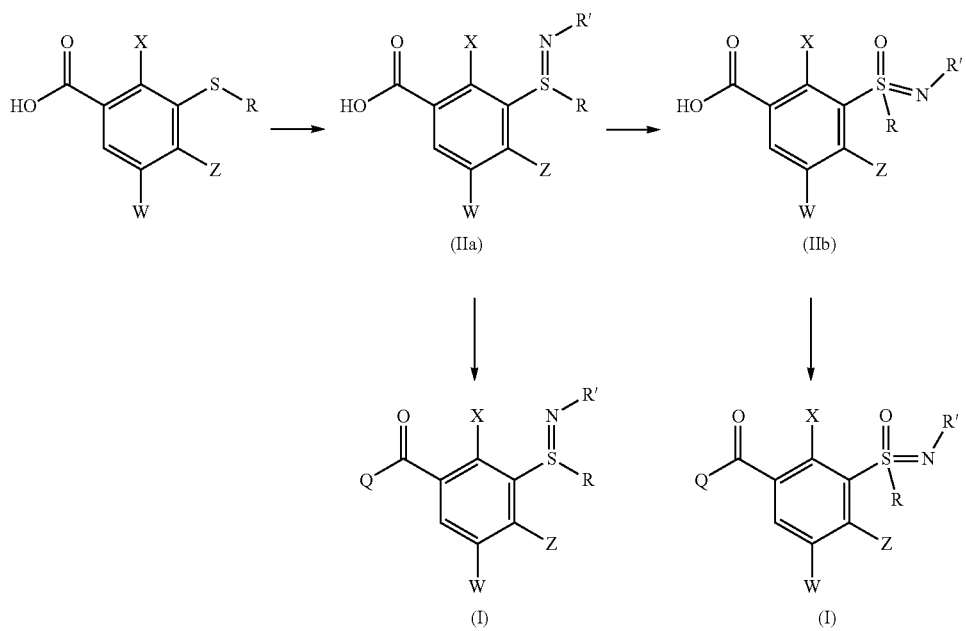

Scheme 2

In certain cases, it may be advantageous to use not the free benzoic acid but derivatives thereof for the reactions. Sometimes it is sufficient for the stability of a functional group to work only in acidic or only in basic media, that is to work only with the free benzoic acid or only with its salt. In many cases, esters such as methyl or ethyl esters are suitable. Frequently, tert-butyl esters effectively shield the carboxyl group sterically against nucleophilic reagents, and they are easily cleaved in acidic medium (T. W. Greene, P. G. M. Wuts, Protective Groups in Organic Synthesis, 2nd Edition, John Wiley & Sons, Inc. 1991, p. 227 ff.). Also suitable are radicals which are considerably more stable than carboxyl groups, which can, however, also be easily re-converted into the free carboxylic acids. These include, for example, oxazolines (T. W. Greene, P. G. M. Wuts, Protective Groups in Organic Synthesis, 2nd Edition, John Wiley & Sons, Inc. 1991, p. 265 ff.; Z. Hell et al, Tetrahedron Letters 43 (2002), 3985-3987).

The benzoic acids of the formulae (IIa) and (IIb) mentioned above and their ethyl esters, methyl esters and benzoyl chlorides are novel and are represented by the formula (II).

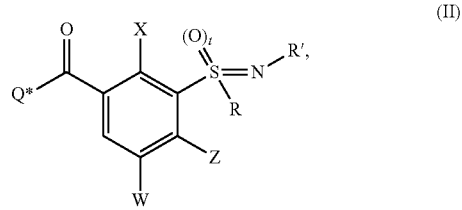

(II)

In formula (II), Q* is hydroxyl, ethoxy, methoxy or chlorine. R, R', X, W, Z and t have the meanings given for formula (I). The compounds of the formula (II) are suitable in particu- Work-up of the respective reaction mixtures is generally carried out by known methods, for example by crystallization, aqueous-extractive work-up, by chromatographic methods or by a combination of these methods.

Collections of compounds of the formula (I) and/or their salts which can be synthesized in accordance with the abovementioned reactions can also be prepared in a parallelized manner, which can be effected manually or in a partly or fully automated manner. Here, it is possible for example to automate the procedure of the reaction, the work-up or the purification of the products or intermediates. In total, this is understood as meaning a procedure as described for example by D. Tiebes in Combinatorial Chemistry—Synthesis, Analysis, Screening (Editor Günther Jung), Wiley 1999, on pages 1 to 34.

A number of commercially available apparatuses can be used for the parallelized reaction procedure and work-up, for example Calpyso reaction blocks from Barnstead International, Dubuque, Iowa 52004-0797, USA, or reaction stations from Radleys, Shirehill, Saffron Walden, Essex, CB 11 3AZ, England or MultiPROBE Automated Workstations from Perkin Elmar, Waltham, Mass. 02451, USA. Chromatographic apparatuses, for example from ISCO, Inc., 4700 Superior Street, Lincoln, Nebr. 68504, USA, are available, inter alia, for the parallelized purification of compounds of the formula (I) and their salts or of intermediates generated in the course of the preparation.

The apparatuses listed lead to a modular procedure in which the individual passes are automated, but manual operations must be carried out between the passes. This can be circumvented by the use of partly or fully integrated automation systems, where the relevant automation modules are operated by, for example, robots. Such automation systems can be obtained for example from Caliper, Hopkinton, Mass. 01748, USA.

The performance of individual, or a plurality of, synthesis steps can be aided by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) and their salts can be effected fully or in part by solid-phase-supported methods. For this purpose, individual intermediates, or all intermediates, of the synthesis or of a synthesis adapted to the relevant procedure are bound to a synthesis resin. Solid-phase-supported synthesis methods are described sufficiently in the specialist literature, for example Barry A. Bunin in "The Combinatorial Index", Academic Press, 1998 and Combinatorial Chemistry—Synthesis, Analysis, Screening (Editor Guinther Jung), Wiley, 1999. The use of solid-phase-supported synthesis methods permits a series of protocols known from the literature, which, again, can be carried out manually or in an automated manner. For example, the reactions can be carried out by means of IRORI technology in microreactors from Nexus Biosystems, 12140 Community Road, Poway, Calif. 92064, USA.

Carrying out individual or a plurality of synthesis steps, both on a solid and in the liquid phase, can be aided by the use of microwave technology. A series of experimental protocols are described in the specialist literature, for example in Microwaves in Organic and Medicinal Chemistry (Editors C. O. Kappe and A. Stadler), Wiley, 2005. The preparation in accordance with the processes described herein generates compounds of the formula (I) and their salts in the form of substance collections, which are referred to as libraries. The present invention also relates to libraries which comprise at least two compounds of the formula (I) and their salts.

The compounds of the formula (I) according to the invention (and/or their salts), hereinbelow together referred to as "compounds according to the invention", have an outstanding herbicidal activity against a broad spectrum of economically important monocotyledonous and dicotyledonous annual harmful plants. The active substances also act efficiently on perennial harmful plants which produce shoots from rhizomes, rootstocks or other perennial organs and which are difficult to control.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active substances are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of undesired plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since for example lodging can be reduced, or prevented completely, hereby.

Owing to their herbicidal and plant-growth-regulatory properties, the active substances can also be employed for controlling harmful plants in crops of genetically modified plants or plants which have been modified by conventional mutagenesis. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known.

It is preferred to use the compounds according to the invention or their salts in economically important transgenic crops of useful plants and ornamentals, for example of cereals such as wheat, barley, rye, oats, sorghum and millet, rice, cassava and maize or else crops of sugar beet, cotton, soybean, oil seed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

recombinant modifications of crop plants for the purposes of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone", V C H Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product. To do this, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances. When the active substances according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be employed in the customary preparations in the form of wettable powders, emulsifiable concentrates, sprayable solutions, dusts or granules. The invention therefore also relates to herbicidal and plant-growth-regulating compositions which comprise the compounds according to the invention.

The compounds according to the invention can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Kuichler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix. Suitable safeners are, for example, mefenpyr-diethyl, cyprosulfamide, isoxadifen-ethyl, cloquintocet-mexyl and dichlormid.

Wettable powders are preparations which are uniformly dispersible in water and which, besides the active substance, also comprise ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, besides a diluent or inert substance. To prepare the wettable powders, the herbicidally active substances are ground finely, for example in customary apparatuses such as hammer mills, blower mills and air-jet mills, and mixed with the formulation auxiliaries, either simultaneously or subsequently.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials such as, for example, talcum, natural clays such as kaolin, bentonite and pyrophyllite, or diatomaceous earth.

Suspension concentrates can be water- or oil-based. They can be prepared for example by wet-grinding by means of commercially available bead mills, if appropriate with addition of surfactants as already listed above for example in the case of the other formulation types.

Emulsions, for example oil-in-water emulsions (EW), can be prepared for example by means of stirrers, colloid mills and/or static mixers using aqueous organic solvents and, if appropriate, surfactants, as have already been mentioned for example above for the other formulation types.

Granules can be prepared either by spraying the active substance onto adsorptive, granulated inert material, or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the manner which is customary for the production of fertilizer granules, if desired as a mixture with fertilizers.

Water-dispersible granules are generally prepared by customary methods such as spray drying, fluidized-bed granulation, disk granulation, mixing with high-speed stirrers, and extrusion without solid inert material.

To prepare disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details of the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise from 0.1 to 99% by weight, in particular from 0.1 to 95% by weight, of compounds according to the invention. In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise from 1 to 30% by weight of active substance, preferably in most cases from 5 to 20% by weight of active substance, and sprayable solutions comprise approximately from 0.05 to 80, preferably from 2 to 50% by weight of active substance. In the case of water-dispersible granules, the active substance content depends partly on whether the active compound is in liquid or solid form, and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetting agents, dispersants, emulsifiers, penetrants, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Active substances which can be employed in combination with the compounds according to the invention in mixed formulations or in the tank mix are, for example, known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active substances (the compounds are either designated by the common name according to the International Organization for Standardization (ISO) or by a chemical name, if appropriate together with the code number) and always comprise all use forms such as acids, salts, esters and isomers such as stereoisomers and optical isomers.

For use, the formulations, which are present in commercially available form, if appropriate, are diluted in the customary manner, for example using water in the case of wettable powders, emulsifiable concentrates, dispersions and water-dispersible granules. Preparations in the form of dusts, soil granules, granules for broadcasting, and sprayable solutions, are usually not diluted further with further inert substances prior to use.

The application rate required of the compounds of the formula (I) varies as a function of the external conditions such as temperature, humidity, the nature of the herbicide used and the like. It can vary within wide limits, for example between 0.001 and 1.0 kg/ha and more of active substance, but it is preferably between 0.005 and 750 g/ha.

The examples which follow illustrate the invention.

A. CHEMICAL EXAMPLES

Synthesis of 5-hydroxy-1,3-dimethyl-4-[3-(N-cyano-S-methylsulfonimidoyl)-2-methoxy-4-(trifluoromethyl)benzoyl]pyrazole (Table Example No. 4-160)

Step 1: Synthesis of 3-(N-cyano-S-methylsulfonimidoyl)-2-methoxy-4-(trifluoromethyl)benzoic acid (Table Example No. 15-28)

3.71 g (33.1 mmol) of potassium tert-butoxide were added to a solution of 4.00 g (15.0 mmol) of 2-methoxy-3-(methylsulfanyl)-4-(trifluoromethyl)benzoic acid in 250 ml of methanol. The mixture was stirred for 10 minutes, and 1.07 g (25.5 mmol) of cyanamide and 4.81 g (27.0 mmol) of N-bromsuccinimide were then added in succession. The contents was then stirred at RT for 2 h. The mixture was then freed from the solvent on a rotary evaporator and the residue was taken up in a mixture of in each case 120 ml of acetonitrile and water. 7.21 g (45.1 mmol) of sodium permanganate monohydrate were added, and the mixture was stirred at RT for one week. During this week, both after one day and after a further day, in each case 3.6 g (22.5 mmol) of sodium permanganate monohydrate were added. For work-up, a 10% by weight strength solution of sodium bisulfate was added. On a rotary evaporator, at a temperature of at most 30° C., the solvent was substantially removed. The residue was cooled in an ice bath and then acidified with 1 M hydrochloric acid. The mixture was extracted three times with ice-cold dichloromethane. The combined organic phases were freed from the solvent on a rotary evaporator and the residue was purified chromatographically, which gave 1.30 g of product of a purity of 80% by weight.

Step 2: Synthesis of 5-hydroxy-1,3-dimethyl-4-[3-(N-cyano-S-methylsulfonimidoyl)-2-methoxy-4-(trifluoromethyl)benzoyl]pyrazole 165 mg (75% by weight; 0.384 mmol) of 3-(N-cyano-S-methylsulfonimidoyl)-2-methoxy-4-(trifluormethyl)benzoic acid and 68.9 mg (0.614 mmol) of 5-hydroxy-1,3-dimethylpyrazole were initially charged in 20 ml of dichlormethane, and 128 mg (0.666 mmol) of 1-(3-dimethylaminopropyl)-3-ethylcarbodiimide hydrochloride were added. The mixture was stirred at RT for 16 h and, for work-up, washed with 1 M hydrochloric acid. After phase separation, the organic phase was dried, filtered and freed from the solvent on a rotary evaporator. The residue was purified chromatographically and the intermediate obtained was then dissolved in 15 ml of acetonitrile. 104 mg (1.02 mmol) of triethylamine, eight drops of trimethylcyanide and a spatula tip of potassium cyanide were then added. The mixture was stirred at RT for 16 h and, for work-up, freed from the solvent. The residue was taken up in dichloromethane and washed with 3 ml of 1M hydrochloric acid. After phase separation, the organic phase was freed from the solvent and the residue was purified chromatographically, which gave 31.3 mg of 5-hydroxy-1,3-dimethyl-4-[3-(N-cyano-S-methylsulfonimidoyl)-2-methoxy-4-(trifluoromethyl)benzoyl]pyrazole in a purity of 85% by weight.

The examples listed in the tables hereinbelow were prepared analogously to abovementioned methods or are obtainable analogously to abovementioned methods.

These compounds are very particularly preferred.

The abbreviations used are:

Et=ethyl Me=methyl n-Pr=n-propyl i-Pr=isopropyl c-Pr=cyclopropyl Ph=phenyl

TABLE 1

Compounds according to the invention of the formula (I) in which Q is Q1, $R^a$ is a hydroxyl group, the radicals $R^b$, $R^c$, $R^d$, $R^e$, $R^f$, $R^g$ and W are each hydrogen, t = 1 and the other radicals have the meanings indicated in the table

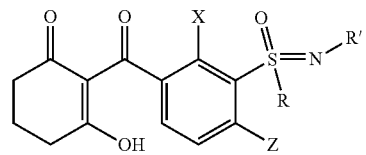

| No. | X | Z | R | R' | Physical data ($^1$H NMR) |
|---|---|---|---|---|---|
| 1-1 | Me | Me | Me | H | |
| 1-2 | Me | F | Me | H | |
| 1-3 | Me | Cl | Me | H | |
| 1-4 | Me | Br | Me | H | |
| 1-5 | Me | I | Me | H | |
| 1-6 | Me | CF$_3$ | Me | H | |
| 1-7 | Me | CHF$_2$ | Me | H | |
| 1-8 | Me | CF$_2$Cl | Me | H | |

TABLE 1-continued

Compounds according to the invention of the formula (I) in which Q is Q1, $R^a$ is a hydroxyl group, the radicals $R^b$, $R^c$, $R^d$, $R^e$, $R^f$, $R^g$ and W are each hydrogen, t = 1 and the other radicals have the meanings indicated in the table

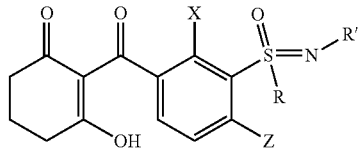

| No. | X | Z | R | R' | Physical data ($^1$H NMR) |
|---|---|---|---|---|---|
| 1-9 | Me | OMe | Me | H | |
| 1-10 | Me | NO$_2$ | Me | H | |
| 1-11 | Me | SO$_2$Me | Me | H | |
| 1-12 | Cl | Me | Me | H | |
| 1-13 | Cl | F | Me | H | |
| 1-14 | Cl | Cl | Me | H | |
| 1-15 | Cl | Br | Me | H | |
| 1-16 | Cl | I | Me | H | |
| 1-17 | Cl | CF$_3$ | Me | H | |
| 1-18 | Cl | CHF$_2$ | Me | H | |
| 1-19 | Cl | CF$_2$Cl | Me | H | |
| 1-20 | Cl | OMe | Me | H | |
| 1-21 | Cl | NO$_2$ | Me | H | |
| 1-22 | Cl | SO$_2$Me | Me | H | |
| 1-23 | OMe | Me | Me | H | |
| 1-24 | OMe | F | Me | H | |
| 1-25 | OMe | Cl | Me | H | |
| 1-26 | OMe | Br | Me | H | |
| 1-27 | OMe | I | Me | H | |
| 1-28 | OMe | CF$_3$ | Me | H | |
| 1-29 | OMe | CHF$_2$ | Me | H | |
| 1-30 | OMe | CF$_2$Cl | Me | H | |
| 1-31 | OMe | OMe | Me | H | |
| 1-32 | OMe | NO$_2$ | Me | H | |
| 1-33 | OMe | SO$_2$Me | Me | H | |
| 1-34 | SO$_2$Me | Me | Me | H | |
| 1-35 | SO$_2$Me | F | Me | H | |
| 1-36 | SO$_2$Me | Cl | Me | H | |
| 1-37 | SO$_2$Me | Br | Me | H | |
| 1-38 | SO$_2$Me | I | Me | H | |
| 1-39 | SO$_2$Me | CF$_3$ | Me | H | |
| 1-40 | SO$_2$Me | CHF$_2$ | Me | H | |
| 1-41 | SO$_2$Me | CF$_2$Cl | Me | H | |
| 1-42 | SO$_2$Me | OMe | Me | H | |
| 1-43 | SO$_2$Me | NO$_2$ | Me | H | |
| 1-44 | SO$_2$Me | SO$_2$Me | Me | H | |
| 1-45 | Me | Me | Et | H | |
| 1-46 | Me | F | Et | H | |
| 1-47 | Me | Cl | Et | H | |
| 1-48 | Me | Br | Et | H | |
| 1-49 | Me | I | Et | H | |
| 1-50 | Me | CF$_3$ | Et | H | |
| 1-51 | Me | CHF$_2$ | Et | H | |
| 1-52 | Me | CF$_2$Cl | Et | H | |
| 1-53 | Me | OMe | Et | H | |
| 1-54 | Me | NO$_2$ | Et | H | |
| 1-55 | Me | SO$_2$Me | Et | H | |
| 1-56 | Cl | Me | Et | H | |
| 1-57 | Cl | F | Et | H | |
| 1-58 | Cl | Cl | Et | H | |
| 1-59 | Cl | Br | Et | H | |
| 1-60 | Cl | I | Et | H | |
| 1-61 | Cl | CF$_3$ | Et | H | |
| 1-62 | Cl | CHF$_2$ | Et | H | |
| 1-63 | Cl | CF$_2$Cl | Et | H | |
| 1-64 | Cl | OMe | Et | H | |
| 1-65 | Cl | NO$_2$ | Et | H | |
| 1-66 | Cl | SO$_2$Me | Et | H | |
| 1-67 | OMe | Me | Et | H | |
| 1-68 | OMe | F | Et | H | |
| 1-69 | OMe | Cl | Et | H | |
| 1-70 | OMe | Br | Et | H | |
| 1-71 | OMe | I | Et | H | |
| 1-72 | OMe | CF$_3$ | Et | H | |
| 1-73 | OMe | CHF$_2$ | Et | H | |

TABLE 1-continued

Compounds according to the invention of the formula (I) in which Q is Q1, $R^a$ is a hydroxyl group, the radicals $R^b$, $R^c$, $R^d$, $R^e$, $R^f$, $R^g$ and W are each hydrogen, t = 1 and the other radicals have the meanings indicated in the table

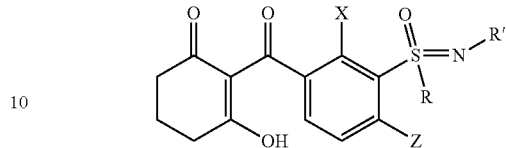

| No. | X | Z | R | R' | Physical data ($^1$H NMR) |
|---|---|---|---|---|---|
| 1-74 | OMe | CF$_2$Cl | Et | H | |
| 1-75 | OMe | OMe | Et | H | |
| 1-76 | OMe | NO$_2$ | Et | H | |
| 1-77 | OMe | SO$_2$Me | Et | H | |
| 1-78 | SO$_2$Me | Me | Et | H | |
| 1-79 | SO$_2$Me | F | Et | H | |
| 1-80 | SO$_2$Me | Cl | Et | H | |
| 1-81 | SO$_2$Me | Br | Et | H | |
| 1-82 | SO$_2$Me | I | Et | H | |
| 1-83 | SO$_2$Me | CF$_3$ | Et | H | |
| 1-84 | SO$_2$Me | CHF$_2$ | Et | H | |
| 1-85 | SO$_2$Me | CF$_2$Cl | Et | H | |
| 1-86 | SO$_2$Me | OMe | Et | H | |
| 1-87 | SO$_2$Me | NO$_2$ | Et | H | |
| 1-88 | SO$_2$Me | SO$_2$Me | Et | H | |
| 1-89 | Me | Me | CH$_2$CH$_2$OMe | H | |
| 1-90 | Me | F | CH$_2$CH$_2$OMe | H | |
| 1-91 | Me | Cl | CH$_2$CH$_2$OMe | H | |
| 1-92 | Me | Br | CH$_2$CH$_2$OMe | H | |
| 1-93 | Me | I | CH$_2$CH$_2$OMe | H | |
| 1-94 | Me | CF$_3$ | CH$_2$CH$_2$OMe | H | |
| 1-95 | Me | CHF$_2$ | CH$_2$CH$_2$OMe | H | |
| 1-96 | Me | CF$_2$Cl | CH$_2$CH$_2$OMe | H | |
| 1-97 | Me | OMe | CH$_2$CH$_2$OMe | H | |
| 1-98 | Me | NO$_2$ | CH$_2$CH$_2$OMe | H | |
| 1-99 | Me | SO$_2$Me | CH$_2$CH$_2$OMe | H | |
| 1-100 | Cl | Me | CH$_2$CH$_2$OMe | H | |
| 1-101 | Cl | F | CH$_2$CH$_2$OMe | H | |
| 1-102 | Cl | Cl | CH$_2$CH$_2$OMe | H | |
| 1-103 | Cl | Br | CH$_2$CH$_2$OMe | H | |
| 1-104 | Cl | I | CH$_2$CH$_2$OMe | H | |
| 1-105 | Cl | CF$_3$ | CH$_2$CH$_2$OMe | H | |
| 1-106 | Cl | CHF$_2$ | CH$_2$CH$_2$OMe | H | |
| 1-107 | Cl | CF$_2$Cl | CH$_2$CH$_2$OMe | H | |
| 1-108 | Cl | OMe | CH$_2$CH$_2$OMe | H | |
| 1-109 | Cl | NO$_2$ | CH$_2$CH$_2$OMe | H | |
| 1-110 | Cl | SO$_2$Me | CH$_2$CH$_2$OMe | H | |
| 1-111 | OMe | Me | CH$_2$CH$_2$OMe | H | |
| 1-112 | OMe | F | CH$_2$CH$_2$OMe | H | |
| 1-113 | OMe | Cl | CH$_2$CH$_2$OMe | H | |
| 1-114 | OMe | Br | CH$_2$CH$_2$OMe | H | |
| 1-115 | OMe | I | CH$_2$CH$_2$OMe | H | |
| 1-116 | OMe | CF$_3$ | CH$_2$CH$_2$OMe | H | |
| 1-117 | OMe | CHF$_2$ | CH$_2$CH$_2$OMe | H | |
| 1-118 | OMe | CF$_2$Cl | CH$_2$CH$_2$OMe | H | |
| 1-119 | OMe | OMe | CH$_2$CH$_2$OMe | H | |
| 1-120 | OMe | NO$_2$ | CH$_2$CH$_2$OMe | H | |
| 1-121 | OMe | SO$_2$Me | CH$_2$CH$_2$OMe | H | |
| 1-122 | SO$_2$Me | Me | CH$_2$CH$_2$OMe | H | |
| 1-123 | SO$_2$Me | F | CH$_2$CH$_2$OMe | H | |
| 1-124 | SO$_2$Me | Cl | CH$_2$CH$_2$OMe | H | |
| 1-125 | SO$_2$Me | Br | CH$_2$CH$_2$OMe | H | |
| 1-126 | SO$_2$Me | I | CH$_2$CH$_2$OMe | H | |
| 1-127 | SO$_2$Me | CF$_3$ | CH$_2$CH$_2$OMe | H | |
| 1-128 | SO$_2$Me | CHF$_2$ | CH$_2$CH$_2$OMe | H | |
| 1-129 | SO$_2$Me | CF$_2$Cl | CH$_2$CH$_2$OMe | H | |
| 1-130 | SO$_2$Me | OMe | CH$_2$CH$_2$OMe | H | |
| 1-131 | SO$_2$Me | NO$_2$ | CH$_2$CH$_2$OMe | H | |
| 1-132 | SO$_2$Me | SO$_2$Me | CH$_2$CH$_2$OMe | H | |
| 1-133 | Me | Me | Me | CN | |
| 1-134 | Me | F | Me | CN | |
| 1-135 | Me | Cl | Me | CN | |
| 1-136 | Me | Br | Me | CN | |
| 1-137 | Me | I | Me | CN | |
| 1-138 | Me | CF$_3$ | Me | CN | |

TABLE 1-continued

Compounds according to the invention of the formula (I) in which Q is Q1, $R^a$ is a hydroxyl group, the radicals $R^b$, $R^c$, $R^d$, $R^e$, $R^f$, $R^g$ and W are each hydrogen, t = 1 and the other radicals have the meanings indicated in the table

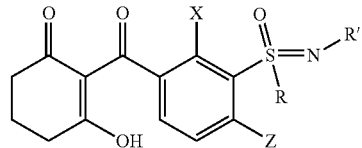

| No. | X | Z | R | R' | Physical data ($^1$H NMR) |
|---|---|---|---|---|---|
| 1-139 | Me | CHF$_2$ | Me | CN | |
| 1-140 | Me | CF$_2$Cl | Me | CN | |
| 1-141 | Me | OMe | Me | CN | |
| 1-142 | Me | NO$_2$ | Me | CN | |
| 1-143 | Me | SO$_2$Me | Me | CN | |
| 1-144 | Cl | Me | Me | CN | |
| 1-145 | Cl | F | Me | CN | |
| 1-146 | Cl | Cl | Me | CN | |
| 1-147 | Cl | Br | Me | CN | |
| 1-148 | Cl | I | Me | CN | |
| 1-149 | Cl | CF$_3$ | Me | CN | |
| 1-150 | Cl | CHF$_2$ | Me | CN | |
| 1-151 | Cl | CF$_2$Cl | Me | CN | |
| 1-152 | Cl | OMe | Me | CN | |
| 1-153 | Cl | NO$_2$ | Me | CN | |
| 1-154 | Cl | SO$_2$Me | Me | CN | |
| 1-155 | OMe | Me | Me | CN | |
| 1-156 | OMe | F | Me | CN | |
| 1-157 | OMe | Cl | Me | CN | |
| 1-158 | OMe | Br | Me | CN | |
| 1-159 | OMe | I | Me | CN | |
| 1-160 | OMe | CF$_3$ | Me | CN | |
| 1-161 | OMe | CHF$_2$ | Me | CN | |
| 1-162 | OMe | CF$_2$Cl | Me | CN | |
| 1-163 | OMe | OMe | Me | CN | |
| 1-164 | OMe | NO$_2$ | Me | CN | |
| 1-165 | OMe | SO$_2$Me | Me | CN | |
| 1-166 | SO$_2$Me | Me | Me | CN | |
| 1-167 | SO$_2$Me | F | Me | CN | |
| 1-168 | SO$_2$Me | Cl | Me | CN | |
| 1-169 | SO$_2$Me | Br | Me | CN | |
| 1-170 | SO$_2$Me | I | Me | CN | |
| 1-171 | SO$_2$Me | CF$_3$ | Me | CN | |
| 1-172 | SO$_2$Me | CHF$_2$ | Me | CN | |
| 1-173 | SO$_2$Me | CF$_2$Cl | Me | CN | |
| 1-174 | SO$_2$Me | OMe | Me | CN | |
| 1-175 | SO$_2$Me | NO$_2$ | Me | CN | |
| 1-176 | SO$_2$Me | SO$_2$Me | Me | CN | |
| 1-177 | Me | Me | Et | CN | |
| 1-178 | Me | F | Et | CN | |
| 1-179 | Me | Cl | Et | CN | |
| 1-180 | Me | Br | Et | CN | |
| 1-181 | Me | I | Et | CN | |
| 1-182 | Me | CF$_3$ | Et | CN | |
| 1-183 | Me | CHF$_2$ | Et | CN | |
| 1-184 | Me | CF$_2$Cl | Et | CN | |
| 1-185 | Me | OMe | Et | CN | |
| 1-186 | Me | NO$_2$ | Et | CN | |
| 1-187 | Me | SO$_2$Me | Et | CN | |
| 1-188 | Cl | Me | Et | CN | |
| 1-189 | Cl | F | Et | CN | |
| 1-190 | Cl | Cl | Et | CN | |
| 1-191 | Cl | Br | Et | CN | |
| 1-192 | Cl | I | Et | CN | |
| 1-193 | Cl | CF$_3$ | Et | CN | |
| 1-194 | Cl | CHF$_2$ | Et | CN | |
| 1-195 | Cl | CF$_2$Cl | Et | CN | |
| 1-196 | Cl | OMe | Et | CN | |
| 1-197 | Cl | NO$_2$ | Et | CN | |
| 1-198 | Cl | SO$_2$Me | Et | CN | |
| 1-199 | OMe | Me | Et | CN | |
| 1-200 | OMe | F | Et | CN | |
| 1-201 | OMe | Cl | Et | CN | |
| 1-202 | OMe | Br | Et | CN | |
| 1-203 | OMe | I | Et | CN | |
| 1-204 | OMe | CF$_3$ | Et | CN | |
| 1-205 | OMe | CHF$_2$ | Et | CN | |
| 1-206 | OMe | CF$_2$Cl | Et | CN | |
| 1-207 | OMe | OMe | Et | CN | |
| 1-208 | OMe | NO$_2$ | Et | CN | |
| 1-209 | OMe | SO$_2$Me | Et | CN | |
| 1-210 | SO$_2$Me | Me | Et | CN | |
| 1-211 | SO$_2$Me | F | Et | CN | |
| 1-212 | SO$_2$Me | Cl | Et | CN | |
| 1-213 | SO$_2$Me | Br | Et | CN | |
| 1-214 | SO$_2$Me | I | Et | CN | |
| 1-215 | SO$_2$Me | CF$_3$ | Et | CN | |
| 1-216 | SO$_2$Me | CHF$_2$ | Et | CN | |
| 1-217 | SO$_2$Me | CF$_2$Cl | Et | CN | |
| 1-218 | SO$_2$Me | OMe | Et | CN | |
| 1-219 | SO$_2$Me | NO$_2$ | Et | CN | |
| 1-220 | SO$_2$Me | SO$_2$Me | Et | CN | |
| 1-221 | Me | Me | CH$_2$CH$_2$OMe | CN | |
| 1-222 | Me | F | CH$_2$CH$_2$OMe | CN | |
| 1-223 | Me | Cl | CH$_2$CH$_2$OMe | CN | |
| 1-224 | Me | Br | CH$_2$CH$_2$OMe | CN | |
| 1-225 | Me | I | CH$_2$CH$_2$OMe | CN | |
| 1-226 | Me | CF$_3$ | CH$_2$CH$_2$OMe | CN | |
| 1-227 | Me | CHF$_2$ | CH$_2$CH$_2$OMe | CN | |
| 1-228 | Me | CF$_2$Cl | CH$_2$CH$_2$OMe | CN | |
| 1-229 | Me | OMe | CH$_2$CH$_2$OMe | CN | |
| 1-230 | Me | NO$_2$ | CH$_2$CH$_2$OMe | CN | |
| 1-231 | Me | SO$_2$Me | CH$_2$CH$_2$OMe | CN | |
| 1-232 | Cl | Me | CH$_2$CH$_2$OMe | CN | |
| 1-233 | Cl | F | CH$_2$CH$_2$OMe | CN | |
| 1-234 | Cl | Cl | CH$_2$CH$_2$OMe | CN | |
| 1-235 | Cl | Br | CH$_2$CH$_2$OMe | CN | |
| 1-236 | Cl | I | CH$_2$CH$_2$OMe | CN | |
| 1-237 | Cl | CF$_3$ | CH$_2$CH$_2$OMe | CN | |
| 1-238 | Cl | CHF$_2$ | CH$_2$CH$_2$OMe | CN | |
| 1-239 | Cl | CF$_2$Cl | CH$_2$CH$_2$OMe | CN | |
| 1-240 | Cl | OMe | CH$_2$CH$_2$OMe | CN | |
| 1-241 | Cl | NO$_2$ | CH$_2$CH$_2$OMe | CN | |
| 1-242 | Cl | SO$_2$Me | CH$_2$CH$_2$OMe | CN | |
| 1-243 | OMe | Me | CH$_2$CH$_2$OMe | CN | |
| 1-244 | OMe | F | CH$_2$CH$_2$OMe | CN | |
| 1-245 | OMe | Cl | CH$_2$CH$_2$OMe | CN | |
| 1-246 | OMe | Br | CH$_2$CH$_2$OMe | CN | |
| 1-247 | OMe | I | CH$_2$CH$_2$OMe | CN | |
| 1-248 | OMe | CF$_3$ | CH$_2$CH$_2$OMe | CN | |
| 1-249 | OMe | CHF$_2$ | CH$_2$CH$_2$OMe | CN | |
| 1-250 | OMe | CF$_2$Cl | CH$_2$CH$_2$OMe | CN | |
| 1-251 | OMe | OMe | CH$_2$CH$_2$OMe | CN | |
| 1-252 | OMe | NO$_2$ | CH$_2$CH$_2$OMe | CN | |
| 1-253 | OMe | SO$_2$Me | CH$_2$CH$_2$OMe | CN | |
| 1-254 | SO$_2$Me | Me | CH$_2$CH$_2$OMe | CN | |
| 1-255 | SO$_2$Me | F | CH$_2$CH$_2$OMe | CN | |
| 1-256 | SO$_2$Me | Cl | CH$_2$CH$_2$OMe | CN | |
| 1-257 | SO$_2$Me | Br | CH$_2$CH$_2$OMe | CN | |
| 1-258 | SO$_2$Me | I | CH$_2$CH$_2$OMe | CN | |
| 1-259 | SO$_2$Me | CF$_3$ | CH$_2$CH$_2$OMe | CN | |
| 1-260 | SO$_2$Me | CHF$_2$ | CH$_2$CH$_2$OMe | CN | |
| 1-261 | SO$_2$Me | CF$_2$Cl | CH$_2$CH$_2$OMe | CN | |
| 1-262 | SO$_2$Me | OMe | CH$_2$CH$_2$OMe | CN | |
| 1-263 | SO$_2$Me | NO$_2$ | CH$_2$CH$_2$OMe | CN | |
| 1-264 | SO$_2$Me | SO$_2$Me | CH$_2$CH$_2$OMe | CN | |

TABLE 2

Compounds according to the invention of the formula (I) in which Q is Q2, $R^a$ is a hydroxyl group, $R^b$, $R^f$ and W are each hydrogen, A is $CH_2CH_2$, Y is $CH_2$, t = 1 and the other radicals have the meanings indicated in the table

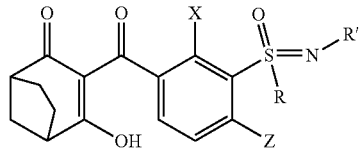

| No. | X | Z | R | R' | Physical data ($^1$H NMR) |
|---|---|---|---|---|---|
| 2-1 | Me | Me | Me | H | |
| 2-2 | Me | F | Me | H | |
| 2-3 | Me | Cl | Me | H | |
| 2-4 | Me | Br | Me | H | |
| 2-5 | Me | I | Me | H | |
| 2-6 | Me | $CF_3$ | Me | H | |
| 2-7 | Me | $CHF_2$ | Me | H | |
| 2-8 | Me | $CF_2Cl$ | Me | H | |
| 2-9 | Me | OMe | Me | H | |
| 2-10 | Me | $NO_2$ | Me | H | |
| 2-11 | Me | $SO_2Me$ | Me | H | |
| 2-12 | Cl | Me | Me | H | |
| 2-13 | Cl | F | Me | H | |
| 2-14 | Cl | Cl | Me | H | |
| 2-15 | Cl | Br | Me | H | |
| 2-16 | Cl | I | Me | H | |
| 2-17 | Cl | $CF_3$ | Me | H | |
| 2-18 | Cl | $CHF_2$ | Me | H | |
| 2-19 | Cl | $CF_2Cl$ | Me | H | |
| 2-20 | Cl | OMe | Me | H | |
| 2-21 | Cl | $NO_2$ | Me | H | |
| 2-22 | Cl | $SO_2Me$ | Me | H | |
| 2-23 | OMe | Me | Me | H | |
| 2-24 | OMe | F | Me | H | |
| 2-25 | OMe | Cl | Me | H | |
| 2-26 | OMe | Br | Me | H | |
| 2-27 | OMe | I | Me | H | |
| 2-28 | OMe | $CF_3$ | Me | H | |
| 2-29 | OMe | $CHF_2$ | Me | H | |
| 2-30 | OMe | $CF_2Cl$ | Me | H | |
| 2-31 | OMe | OMe | Me | H | |
| 2-32 | OMe | $NO_2$ | Me | H | |
| 2-33 | OMe | $SO_2Me$ | Me | H | |
| 2-34 | $SO_2Me$ | Me | Me | H | |
| 2-35 | $SO_2Me$ | F | Me | H | |
| 2-36 | $SO_2Me$ | Cl | Me | H | |
| 2-37 | $SO_2Me$ | Br | Me | H | |
| 2-38 | $SO_2Me$ | I | Me | H | |
| 2-39 | $SO_2Me$ | $CF_3$ | Me | H | |
| 2-40 | $SO_2Me$ | $CHF_2$ | Me | H | |
| 2-41 | $SO_2Me$ | $CF_2Cl$ | Me | H | |
| 2-42 | $SO_2Me$ | OMe | Me | H | |
| 2-43 | $SO_2Me$ | $NO_2$ | Me | H | |
| 2-44 | $SO_2Me$ | $SO_2Me$ | Me | H | |
| 2-45 | Me | Me | Et | H | |
| 2-46 | Me | F | Et | H | |
| 2-47 | Me | Cl | Et | H | |
| 2-48 | Me | Br | Et | H | |
| 2-49 | Me | I | Et | H | |
| 2-50 | Me | $CF_3$ | Et | H | |
| 2-51 | Me | $CHF_2$ | Et | H | |
| 2-52 | Me | $CF_2Cl$ | Et | H | |
| 2-53 | Me | OMe | Et | H | |
| 2-54 | Me | $NO_2$ | Et | H | |
| 2-55 | Me | $SO_2Me$ | Et | H | |
| 2-56 | Cl | Me | Et | H | |
| 2-57 | Cl | F | Et | H | |
| 2-58 | Cl | Cl | Et | H | |
| 2-59 | Cl | Br | Et | H | |
| 2-60 | Cl | I | Et | H | |
| 2-61 | Cl | $CF_3$ | Et | H | |
| 2-62 | Cl | $CHF_2$ | Et | H | |
| 2-63 | Cl | $CF_2Cl$ | Et | H | |
| 2-64 | Cl | OMe | Et | H | |
| 2-65 | Cl | $NO_2$ | Et | H | |
| 2-66 | Cl | $SO_2Me$ | Et | H | |
| 2-67 | OMe | Me | Et | H | |
| 2-68 | OMe | F | Et | H | |
| 2-69 | OMe | Cl | Et | H | |
| 2-70 | OMe | Br | Et | H | |
| 2-71 | OMe | I | Et | H | |
| 2-72 | OMe | $CF_3$ | Et | H | |
| 2-73 | OMe | $CHF_2$ | Et | H | |
| 2-74 | OMe | $CF_2Cl$ | Et | H | |
| 2-75 | OMe | OMe | Et | H | |
| 2-76 | OMe | $NO_2$ | Et | H | |
| 2-77 | OMe | $SO_2Me$ | Et | H | |
| 2-78 | $SO_2Me$ | Me | Et | H | |
| 2-79 | $SO_2Me$ | F | Et | H | |
| 2-80 | $SO_2Me$ | Cl | Et | H | |
| 2-81 | $SO_2Me$ | Br | Et | H | |
| 2-82 | $SO_2Me$ | I | Et | H | |
| 2-83 | $SO_2Me$ | $CF_3$ | Et | H | |
| 2-84 | $SO_2Me$ | $CHF_2$ | Et | H | |
| 2-85 | $SO_2Me$ | $CF_2Cl$ | Et | H | |
| 2-86 | $SO_2Me$ | OMe | Et | H | |
| 2-87 | $SO_2Me$ | $NO_2$ | Et | H | |
| 2-88 | $SO_2Me$ | $SO_2Me$ | Et | H | |
| 2-89 | Me | Me | $CH_2CH_2OMe$ | H | |
| 2-90 | Me | F | $CH_2CH_2OMe$ | H | |
| 2-91 | Me | Cl | $CH_2CH_2OMe$ | H | |
| 2-92 | Me | Br | $CH_2CH_2OMe$ | H | |
| 2-93 | Me | I | $CH_2CH_2OMe$ | H | |
| 2-94 | Me | $CF_3$ | $CH_2CH_2OMe$ | H | |
| 2-95 | Me | $CHF_2$ | $CH_2CH_2OMe$ | H | |
| 2-96 | Me | $CF_2Cl$ | $CH_2CH_2OMe$ | H | |
| 2-97 | Me | OMe | $CH_2CH_2OMe$ | H | |
| 2-98 | Me | $NO_2$ | $CH_2CH_2OMe$ | H | |
| 2-99 | Me | $SO_2Me$ | $CH_2CH_2OMe$ | H | |
| 2-100 | Cl | Me | $CH_2CH_2OMe$ | H | |
| 2-101 | Cl | F | $CH_2CH_2OMe$ | H | |
| 2-102 | Cl | Cl | $CH_2CH_2OMe$ | H | |
| 2-103 | Cl | Br | $CH_2CH_2OMe$ | H | |
| 2-104 | Cl | I | $CH_2CH_2OMe$ | H | |
| 2-105 | Cl | $CF_3$ | $CH_2CH_2OMe$ | H | |
| 2-106 | Cl | $CHF_2$ | $CH_2CH_2OMe$ | H | |
| 2-107 | Cl | $CF_2Cl$ | $CH_2CH_2OMe$ | H | |
| 2-108 | Cl | OMe | $CH_2CH_2OMe$ | H | |
| 2-109 | Cl | $NO_2$ | $CH_2CH_2OMe$ | H | |
| 2-110 | Cl | $SO_2Me$ | $CH_2CH_2OMe$ | H | |
| 2-111 | OMe | Me | $CH_2CH_2OMe$ | H | |
| 2-112 | OMe | F | $CH_2CH_2OMe$ | H | |
| 2-113 | OMe | Cl | $CH_2CH_2OMe$ | H | |
| 2-114 | OMe | Br | $CH_2CH_2OMe$ | H | |
| 2-115 | OMe | I | $CH_2CH_2OMe$ | H | |
| 2-116 | OMe | $CF_3$ | $CH_2CH_2OMe$ | H | |
| 2-117 | OMe | $CHF_2$ | $CH_2CH_2OMe$ | H | |
| 2-118 | OMe | $CF_2Cl$ | $CH_2CH_2OMe$ | H | |
| 2-119 | OMe | OMe | $CH_2CH_2OMe$ | H | |
| 2-120 | OMe | $NO_2$ | $CH_2CH_2OMe$ | H | |
| 2-121 | OMe | $SO_2Me$ | $CH_2CH_2OMe$ | H | |
| 2-122 | $SO_2Me$ | Me | $CH_2CH_2OMe$ | H | |
| 2-123 | $SO_2Me$ | F | $CH_2CH_2OMe$ | H | |
| 2-124 | $SO_2Me$ | Cl | $CH_2CH_2OMe$ | H | |
| 2-125 | $SO_2Me$ | Br | $CH_2CH_2OMe$ | H | |
| 2-126 | $SO_2Me$ | I | $CH_2CH_2OMe$ | H | |
| 2-127 | $SO_2Me$ | $CF_3$ | $CH_2CH_2OMe$ | H | |
| 2-128 | $SO_2Me$ | $CHF_2$ | $CH_2CH_2OMe$ | H | |
| 2-129 | $SO_2Me$ | $CF_2Cl$ | $CH_2CH_2OMe$ | H | |
| 2-130 | $SO_2Me$ | OMe | $CH_2CH_2OMe$ | H | |

TABLE 2-continued

Compounds according to the invention of the formula (I) in which Q is Q2, $R^a$ is a hydroxyl group, $R^b$, $R^f$ and W are each hydrogen, A is $CH_2CH_2$, Y is $CH_2$, t = 1 and the other radicals have the meanings indicated in the table

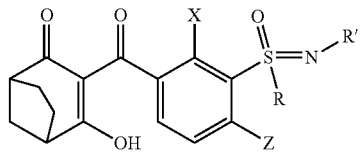

| No. | X | Z | R | R' | Physical data ($^1$H NMR) |
|---|---|---|---|---|---|
| 2-131 | SO$_2$Me | NO$_2$ | CH$_2$CH$_2$OMe | H | |
| 2-132 | SO$_2$Me | SO$_2$Me | CH$_2$CH$_2$OMe | H | |
| 2-133 | Me | Me | Me | CN | |
| 2-134 | Me | F | Me | CN | |
| 2-135 | Me | Cl | Me | CN | |
| 2-136 | Me | Br | Me | CN | |
| 2-137 | Me | I | Me | CN | |
| 2-138 | Me | CF$_3$ | Me | CN | |
| 2-139 | Me | CHF$_2$ | Me | CN | |
| 2-140 | Me | CF$_2$Cl | Me | CN | |
| 2-141 | Me | OMe | Me | CN | |
| 2-142 | Me | NO$_2$ | Me | CN | |
| 2-143 | Me | SO$_2$Me | Me | CN | |
| 2-144 | Cl | Me | Me | CN | |
| 2-145 | Cl | F | Me | CN | |
| 2-146 | Cl | Cl | Me | CN | |
| 2-147 | Cl | Br | Me | CN | |
| 2-148 | Cl | I | Me | CN | |
| 2-149 | Cl | CF$_3$ | Me | CN | |
| 2-150 | Cl | CHF$_2$ | Me | CN | |
| 2-151 | Cl | CF$_2$Cl | Me | CN | |
| 2-152 | Cl | OMe | Me | CN | |
| 2-153 | Cl | NO$_2$ | Me | CN | |
| 2-154 | Cl | SO$_2$Me | Me | CN | |
| 2-155 | OMe | Me | Me | CN | |
| 2-156 | OMe | F | Me | CN | |
| 2-157 | OMe | Cl | Me | CN | |
| 2-158 | OMe | Br | Me | CN | |
| 2-159 | OMe | I | Me | CN | |
| 2-160 | OMe | CF$_3$ | Me | CN | (400 MHz, CDCl$_3$ δ, ppm) 7.81 (m, 1H), 7.65 (d, 1H), 3.91 + 3.88 (s + s, 3H), 3.65 + 3.62 (s + s, 3H), 3.21 (m, 1H), 2.91 (m, 1H) |
| 2-161 | OMe | CHF$_2$ | Me | CN | |
| 2-162 | OMe | CF$_2$Cl | Me | CN | |
| 2-163 | OMe | OMe | Me | CN | |
| 2-164 | OMe | NO$_2$ | Me | CN | |
| 2-165 | OMe | SO$_2$Me | Me | CN | |
| 2-166 | SO$_2$Me | Me | Me | CN | |
| 2-167 | SO$_2$Me | F | Me | CN | |
| 2-168 | SO$_2$Me | Cl | Me | CN | |
| 2-169 | SO$_2$Me | Br | Me | CN | |
| 2-170 | SO$_2$Me | I | Me | CN | |
| 2-171 | SO$_2$Me | CF$_3$ | Me | CN | |
| 2-172 | SO$_2$Me | CHF$_2$ | Me | CN | |
| 2-173 | SO$_2$Me | CF$_2$Cl | Me | CN | |
| 2-174 | SO$_2$Me | OMe | Me | CN | |
| 2-175 | SO$_2$Me | NO$_2$ | Me | CN | |
| 2-176 | SO$_2$Me | SO$_2$Me | Me | CN | |
| 2-177 | Me | Me | Et | CN | |
| 2-178 | Me | F | Et | CN | |
| 2-179 | Me | Cl | Et | CN | |
| 2-180 | Me | Br | Et | CN | |
| 2-181 | Me | I | Et | CN | |
| 2-182 | Me | CF$_3$ | Et | CN | |
| 2-183 | Me | CHF$_2$ | Et | CN | |
| 2-184 | Me | CF$_2$Cl | Et | CN | |
| 2-185 | Me | OMe | Et | CN | |
| 2-186 | Me | NO$_2$ | Et | CN | |
| 2-187 | Me | SO$_2$Me | Et | CN | |
| 2-188 | Cl | Me | Et | CN | |
| 2-189 | Cl | F | Et | CN | |
| 2-190 | Cl | Cl | Et | CN | |
| 2-191 | Cl | Br | Et | CN | |

TABLE 2-continued

Compounds according to the invention of the formula (I) in which Q is Q2, $R^a$ is a hydroxyl group, $R^b$, $R^f$ and W are each hydrogen, A is $CH_2CH_2$, Y is $CH_2$, t = 1 and the other radicals have the meanings indicated in the table

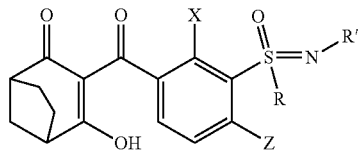

| No. | X | Z | R | R' | Physical data ($^1$H NMR) |
|---|---|---|---|---|---|
| 2-192 | Cl | I | Et | CN | |
| 2-193 | Cl | CF$_3$ | Et | CN | |
| 2-194 | Cl | CHF$_2$ | Et | CN | |
| 2-195 | Cl | CF$_2$Cl | Et | CN | |
| 2-196 | Cl | OMe | Et | CN | |
| 2-197 | Cl | NO$_2$ | Et | CN | |
| 2-198 | Cl | SO$_2$Me | Et | CN | |
| 2-199 | OMe | Me | Et | CN | |
| 2-200 | OMe | F | Et | CN | |
| 2-201 | OMe | Cl | Et | CN | |
| 2-202 | OMe | Br | Et | CN | |
| 2-203 | OMe | I | Et | CN | |
| 2-204 | OMe | CF$_3$ | Et | CN | |
| 2-205 | OMe | CHF$_2$ | Et | CN | |
| 2-206 | OMe | CF$_2$Cl | Et | CN | |
| 2-207 | OMe | OMe | Et | CN | |
| 2-208 | OMe | NO$_2$ | Et | CN | |
| 2-209 | OMe | SO$_2$Me | Et | CN | |
| 2-210 | SO$_2$Me | Me | Et | CN | |
| 2-211 | SO$_2$Me | F | Et | CN | |
| 2-212 | SO$_2$Me | Cl | Et | CN | |
| 2-213 | SO$_2$Me | Br | Et | CN | |
| 2-214 | SO$_2$Me | I | Et | CN | |
| 2-215 | SO$_2$Me | CF$_3$ | Et | CN | |
| 2-216 | SO$_2$Me | CHF$_2$ | Et | CN | |
| 2-217 | SO$_2$Me | CF$_2$Cl | Et | CN | |
| 2-218 | SO$_2$Me | OMe | Et | CN | |
| 2-219 | SO$_2$Me | NO$_2$ | Et | CN | |
| 2-220 | SO$_2$Me | SO$_2$Me | Et | CN | |
| 2-221 | Me | Me | CH$_2$CH$_2$OMe | CN | |
| 2-222 | Me | F | CH$_2$CH$_2$OMe | CN | |
| 2-223 | Me | Cl | CH$_2$CH$_2$OMe | CN | |
| 2-224 | Me | Br | CH$_2$CH$_2$OMe | CN | |
| 2-225 | Me | I | CH$_2$CH$_2$OMe | CN | |
| 2-226 | Me | CF$_3$ | CH$_2$CH$_2$OMe | CN | |
| 2-227 | Me | CHF$_2$ | CH$_2$CH$_2$OMe | CN | |
| 2-228 | Me | CF$_2$Cl | CH$_2$CH$_2$OMe | CN | |
| 2-229 | Me | OMe | CH$_2$CH$_2$OMe | CN | |
| 2-230 | Me | NO$_2$ | CH$_2$CH$_2$OMe | CN | |
| 2-231 | Me | SO$_2$Me | CH$_2$CH$_2$OMe | CN | |
| 2-232 | Cl | Me | CH$_2$CH$_2$OMe | CN | |
| 2-233 | Cl | F | CH$_2$CH$_2$OMe | CN | |
| 2-234 | Cl | Cl | CH$_2$CH$_2$OMe | CN | |
| 2-235 | Cl | Br | CH$_2$CH$_2$OMe | CN | |
| 2-236 | Cl | I | CH$_2$CH$_2$OMe | CN | |
| 2-237 | Cl | CF$_3$ | CH$_2$CH$_2$OMe | CN | |
| 2-238 | Cl | CHF$_2$ | CH$_2$CH$_2$OMe | CN | |
| 2-239 | Cl | CF$_2$Cl | CH$_2$CH$_2$OMe | CN | |
| 2-240 | Cl | OMe | CH$_2$CH$_2$OMe | CN | |
| 2-241 | Cl | NO$_2$ | CH$_2$CH$_2$OMe | CN | |
| 2-242 | Cl | SO$_2$Me | CH$_2$CH$_2$OMe | CN | |
| 2-243 | OMe | Me | CH$_2$CH$_2$OMe | CN | |
| 2-244 | OMe | F | CH$_2$CH$_2$OMe | CN | |
| 2-245 | OMe | Cl | CH$_2$CH$_2$OMe | CN | |
| 2-246 | OMe | Br | CH$_2$CH$_2$OMe | CN | |
| 2-247 | OMe | I | CH$_2$CH$_2$OMe | CN | |
| 2-248 | OMe | CF$_3$ | CH$_2$CH$_2$OMe | CN | |
| 2-249 | OMe | CHF$_2$ | CH$_2$CH$_2$OMe | CN | |
| 2-250 | OMe | CF$_2$Cl | CH$_2$CH$_2$OMe | CN | |
| 2-251 | OMe | OMe | CH$_2$CH$_2$OMe | CN | |
| 2-252 | OMe | NO$_2$ | CH$_2$CH$_2$OMe | CN | |
| 2-253 | OMe | SO$_2$Me | CH$_2$CH$_2$OMe | CN | |
| 2-254 | SO$_2$Me | Me | CH$_2$CH$_2$OMe | CN | |
| 2-255 | SO$_2$Me | F | CH$_2$CH$_2$OMe | CN | |
| 2-256 | SO$_2$Me | Cl | CH$_2$CH$_2$OMe | CN | |

TABLE 2-continued

Compounds according to the invention of the formula (I) in which Q is Q2, $R^a$ is a hydroxyl group, $R^b$, $R^f$ and W are each hydrogen, A is $CH_2CH_2$, Y is $CH_2$, t = 1 and the other radicals have the meanings indicated in the table

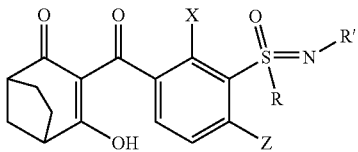

| No. | X | Z | R | R' | Physical data ($^1$H NMR) |
|---|---|---|---|---|---|
| 2-257 | SO$_2$Me | Br | CH$_2$CH$_2$OMe | CN | |
| 2-258 | SO$_2$Me | I | CH$_2$CH$_2$OMe | CN | |
| 2-259 | SO$_2$Me | CF$_3$ | CH$_2$CH$_2$OMe | CN | |
| 2-260 | SO$_2$Me | CHF$_2$ | CH$_2$CH$_2$OMe | CN | |
| 2-261 | SO$_2$Me | CF$_2$Cl | CH$_2$CH$_2$OMe | CN | |
| 2-262 | SO$_2$Me | OMe | CH$_2$CH$_2$OMe | CN | |
| 2-263 | SO$_2$Me | NO$_2$ | CH$_2$CH$_2$OMe | CN | |
| 2-264 | SO$_2$Me | SO$_2$Me | CH$_2$CH$_2$OMe | CN | |

TABLE 3

Compounds according to the invention of the formula (I) in which Q is Q3, $R^i$ is methyl and $R^h$, $R^k$ and W are each hydrogen, t = 1 and the other radicals have the meanings indicated in the table

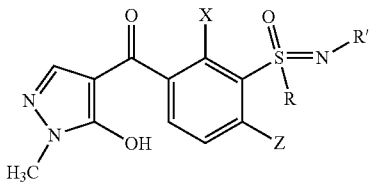

| No. | X | Z | R | R' | Physical data ($^1$H NMR) |
|---|---|---|---|---|---|
| 3-1 | Me | Me | Me | H | |
| 3-2 | Me | F | Me | H | |
| 3-3 | Me | Cl | Me | H | |
| 3-4 | Me | Br | Me | H | |
| 3-5 | Me | I | Me | H | |
| 3-6 | Me | CF$_3$ | Me | H | |
| 3-7 | Me | CHF$_2$ | Me | H | |
| 3-8 | Me | CF$_2$Cl | Me | H | |
| 3-9 | Me | OMe | Me | H | |
| 3-10 | Me | NO$_2$ | Me | H | |
| 3-11 | Me | SO$_2$Me | Me | H | |
| 3-12 | Cl | Me | Me | H | |
| 3-13 | Cl | F | Me | H | |
| 3-14 | Cl | Cl | Me | H | |
| 3-15 | Cl | Br | Me | H | |
| 3-16 | Cl | I | Me | H | |
| 3-17 | Cl | CF$_3$ | Me | H | |
| 3-18 | Cl | CHF$_2$ | Me | H | |
| 3-19 | Cl | CF$_2$Cl | Me | H | |
| 3-20 | Cl | OMe | Me | H | |
| 3-21 | Cl | NO$_2$ | Me | H | |
| 3-22 | Cl | SO$_2$Me | Me | H | |
| 3-23 | OMe | Me | Me | H | |
| 3-24 | OMe | F | Me | H | |
| 3-25 | OMe | Cl | Me | H | |
| 3-26 | OMe | Br | Me | H | |
| 3-27 | OMe | I | Me | H | |
| 3-28 | OMe | CF$_3$ | Me | H | |
| 3-29 | OMe | CHF$_2$ | Me | H | |
| 3-30 | OMe | CF$_2$Cl | Me | H | |
| 3-31 | OMe | OMe | Me | H | |
| 3-32 | OMe | NO$_2$ | Me | H | |
| 3-33 | OMe | SO$_2$Me | Me | H | |
| 3-34 | SO$_2$Me | Me | Me | H | |
| 3-35 | SO$_2$Me | F | Me | H | |
| 3-36 | SO$_2$Me | Cl | Me | H | |

TABLE 3-continued

Compounds according to the invention of the formula (I) in which Q is Q3, $R^i$ is methyl and $R^h$, $R^k$ and W are each hydrogen, t = 1 and the other radicals have the meanings indicated in the table

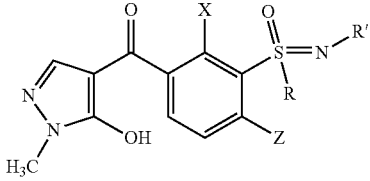

| No. | X | Z | R | R' | Physical data ($^1$H NMR) |
|---|---|---|---|---|---|
| 3-37 | SO$_2$Me | Br | Me | H | |
| 3-38 | SO$_2$Me | I | Me | H | |
| 3-39 | SO$_2$Me | CF$_3$ | Me | H | |
| 3-40 | SO$_2$Me | CHF$_2$ | Me | H | |
| 3-41 | SO$_2$Me | CF$_2$Cl | Me | H | |
| 3-42 | SO$_2$Me | OMe | Me | H | |
| 3-43 | SO$_2$Me | NO$_2$ | Me | H | |
| 3-44 | SO$_2$Me | SO$_2$Me | Me | H | |
| 3-45 | Me | Me | Et | H | |
| 3-46 | Me | F | Et | H | |
| 3-47 | Me | Cl | Et | H | |
| 3-48 | Me | Br | Et | H | |
| 3-49 | Me | I | Et | H | |
| 3-50 | Me | CF$_3$ | Et | H | |
| 3-51 | Me | CHF$_2$ | Et | H | |
| 3-52 | Me | CF$_2$Cl | Et | H | |
| 3-53 | Me | OMe | Et | H | |
| 3-54 | Me | NO$_2$ | Et | H | |
| 3-55 | Me | SO$_2$Me | Et | H | |
| 3-56 | Cl | Me | Et | H | |
| 3-57 | Cl | F | Et | H | |
| 3-58 | Cl | Cl | Et | H | |
| 3-59 | Cl | Br | Et | H | |
| 3-60 | Cl | I | Et | H | |
| 3-61 | Cl | CF$_3$ | Et | H | |
| 3-62 | Cl | CHF$_2$ | Et | H | |
| 3-63 | Cl | CF$_2$Cl | Et | H | |
| 3-64 | Cl | OMe | Et | H | |
| 3-65 | Cl | NO$_2$ | Et | H | |
| 3-66 | Cl | SO$_2$Me | Et | H | |
| 3-67 | OMe | Me | Et | H | |
| 3-68 | OMe | F | Et | H | |
| 3-69 | OMe | Cl | Et | H | |
| 3-70 | OMe | Br | Et | H | |
| 3-71 | OMe | I | Et | H | |
| 3-72 | OMe | CF$_3$ | Et | H | |
| 3-73 | OMe | CHF$_2$ | Et | H | |
| 3-74 | OMe | CF$_2$Cl | Et | H | |
| 3-75 | OMe | OMe | Et | H | |
| 3-76 | OMe | NO$_2$ | Et | H | |
| 3-77 | OMe | SO$_2$Me | Et | H | |
| 3-78 | SO$_2$Me | Me | Et | H | |
| 3-79 | SO$_2$Me | F | Et | H | |
| 3-80 | SO$_2$Me | Cl | Et | H | |
| 3-81 | SO$_2$Me | Br | Et | H | |
| 3-82 | SO$_2$Me | I | Et | H | |
| 3-83 | SO$_2$Me | CF$_3$ | Et | H | |
| 3-84 | SO$_2$Me | CHF$_2$ | Et | H | |
| 3-85 | SO$_2$Me | CF$_2$Cl | Et | H | |
| 3-86 | SO$_2$Me | OMe | Et | H | |
| 3-87 | SO$_2$Me | NO$_2$ | Et | H | |
| 3-88 | SO$_2$Me | SO$_2$Me | Et | H | |
| 3-89 | Me | Me | CH$_2$CH$_2$OMe | H | |
| 3-90 | Me | F | CH$_2$CH$_2$OMe | H | |
| 3-91 | Me | Cl | CH$_2$CH$_2$OMe | H | |
| 3-92 | Me | Br | CH$_2$CH$_2$OMe | H | |
| 3-93 | Me | I | CH$_2$CH$_2$OMe | H | |
| 3-94 | Me | CF$_3$ | CH$_2$CH$_2$OMe | H | |
| 3-95 | Me | CHF$_2$ | CH$_2$CH$_2$OMe | H | |
| 3-96 | Me | CF$_2$Cl | CH$_2$CH$_2$OMe | H | |
| 3-97 | Me | OMe | CH$_2$CH$_2$OMe | H | |
| 3-98 | Me | NO$_2$ | CH$_2$CH$_2$OMe | H | |
| 3-99 | Me | SO$_2$Me | CH$_2$CH$_2$OMe | H | |
| 3-100 | Cl | Me | CH$_2$CH$_2$OMe | H | |

TABLE 3-continued

Compounds according to the invention of the formula (I) in which Q is Q3, $R^i$ is methyl and $R^h$, $R^k$ and W are each hydrogen, t = 1 and the other radicals have the meanings indicated in the table

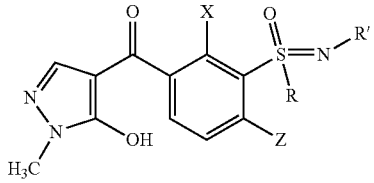

| No. | X | Z | R | R' | Physical data ($^1$H NMR) |
|---|---|---|---|---|---|
| 3-101 | Cl | F | CH$_2$CH$_2$OMe | H | |
| 3-102 | Cl | Cl | CH$_2$CH$_2$OMe | H | |
| 3-103 | Cl | Br | CH$_2$CH$_2$OMe | H | |
| 3-104 | Cl | I | CH$_2$CH$_2$OMe | H | |
| 3-105 | Cl | CF$_3$ | CH$_2$CH$_2$OMe | H | |
| 3-106 | Cl | CHF$_2$ | CH$_2$CH$_2$OMe | H | |
| 3-107 | Cl | CF$_2$Cl | CH$_2$CH$_2$OMe | H | |
| 3-108 | Cl | OMe | CH$_2$CH$_2$OMe | H | |
| 3-109 | Cl | NO$_2$ | CH$_2$CH$_2$OMe | H | |
| 3-110 | Cl | SO$_2$Me | CH$_2$CH$_2$OMe | H | |
| 3-111 | OMe | Me | CH$_2$CH$_2$OMe | H | |
| 3-112 | OMe | F | CH$_2$CH$_2$OMe | H | |
| 3-113 | OMe | Cl | CH$_2$CH$_2$OMe | H | |
| 3-114 | OMe | Br | CH$_2$CH$_2$OMe | H | |
| 3-115 | OMe | I | CH$_2$CH$_2$OMe | H | |
| 3-116 | OMe | CF$_3$ | CH$_2$CH$_2$OMe | H | |
| 3-117 | OMe | CHF$_2$ | CH$_2$CH$_2$OMe | H | |
| 3-118 | OMe | CF$_2$Cl | CH$_2$CH$_2$OMe | H | |
| 3-119 | OMe | OMe | CH$_2$CH$_2$OMe | H | |
| 3-120 | OMe | NO$_2$ | CH$_2$CH$_2$OMe | H | |
| 3-121 | OMe | SO$_2$Me | CH$_2$CH$_2$OMe | H | |
| 3-122 | SO$_2$Me | Me | CH$_2$CH$_2$OMe | H | |
| 3-123 | SO$_2$Me | F | CH$_2$CH$_2$OMe | H | |
| 3-124 | SO$_2$Me | Cl | CH$_2$CH$_2$OMe | H | |
| 3-125 | SO$_2$Me | Br | CH$_2$CH$_2$OMe | H | |
| 3-126 | SO$_2$Me | I | CH$_2$CH$_2$OMe | H | |
| 3-127 | SO$_2$Me | CF$_3$ | CH$_2$CH$_2$OMe | H | |
| 3-128 | SO$_2$Me | CHF$_2$ | CH$_2$CH$_2$OMe | H | |
| 3-129 | SO$_2$Me | CF$_2$Cl | CH$_2$CH$_2$OMe | H | |
| 3-130 | SO$_2$Me | OMe | CH$_2$CH$_2$OMe | H | |
| 3-131 | SO$_2$Me | NO$_2$ | CH$_2$CH$_2$OMe | H | |
| 3-132 | SO$_2$Me | SO$_2$Me | CH$_2$CH$_2$OMe | H | |
| 3-133 | Me | Me | Me | CN | |
| 3-134 | Me | F | Me | CN | |
| 3-135 | Me | Cl | Me | CN | |
| 3-136 | Me | Br | Me | CN | |
| 3-137 | Me | I | Me | CN | |
| 3-138 | Me | CF$_3$ | Me | CN | |
| 3-139 | Me | CHF$_2$ | Me | CN | |
| 3-140 | Me | CF$_2$Cl | Me | CN | |
| 3-141 | Me | OMe | Me | CN | |
| 3-142 | Me | NO$_2$ | Me | CN | |
| 3-143 | Me | SO$_2$Me | Me | CN | |
| 3-144 | Cl | Me | Me | CN | |
| 3-145 | Cl | F | Me | CN | |
| 3-146 | Cl | Cl | Me | CN | |
| 3-147 | Cl | Br | Me | CN | |
| 3-148 | Cl | I | Me | CN | |
| 3-149 | Cl | CF$_3$ | Me | CN | |
| 3-150 | Cl | CHF$_2$ | Me | CN | |
| 3-151 | Cl | CF$_2$Cl | Me | CN | |
| 3-152 | Cl | OMe | Me | CN | |
| 3-153 | Cl | NO$_2$ | Me | CN | |
| 3-154 | Cl | SO$_2$Me | Me | CN | |
| 3-155 | OMe | Me | Me | CN | |
| 3-156 | OMe | F | Me | CN | |
| 3-157 | OMe | Cl | Me | CN | |
| 3-158 | OMe | Br | Me | CN | |
| 3-159 | OMe | I | Me | CN | |
| 3-160 | OMe | CF$_3$ | Me | CN | (400 MHz, CDCl$_3$ δ, ppm) 7.94 (d, 1H), 7.86 (d, 1H), 7.52 (s, 1H), 3.99 (s, 3H), 3.75 (s, 3H), 3.69 (s, 3H) |

TABLE 3-continued

Compounds according to the invention of the formula (I) in which Q is Q3, $R^i$ is methyl and $R^h$, $R^k$ and W are each hydrogen, t = 1 and the other radicals have the meanings indicated in the table

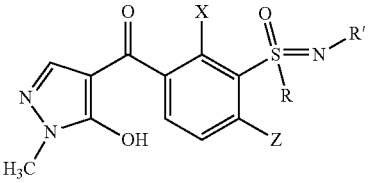

| No. | X | Z | R | R' | Physical data ($^1$H NMR) |
|---|---|---|---|---|---|
| 3-161 | OMe | CHF$_2$ | Me | CN | |
| 3-162 | OMe | CF$_2$Cl | Me | CN | |
| 3-163 | OMe | OMe | Me | CN | |
| 3-164 | OMe | NO$_2$ | Me | CN | |
| 3-165 | OMe | SO$_2$Me | Me | CN | |
| 3-166 | SO$_2$Me | Me | Me | CN | |
| 3-167 | SO$_2$Me | F | Me | CN | |
| 3-168 | SO$_2$Me | Cl | Me | CN | |
| 3-169 | SO$_2$Me | Br | Me | CN | |
| 3-170 | SO$_2$Me | I | Me | CN | |
| 3-171 | SO$_2$Me | CF$_3$ | Me | CN | |
| 3-172 | SO$_2$Me | CHF$_2$ | Me | CN | |
| 3-173 | SO$_2$Me | CF$_2$Cl | Me | CN | |
| 3-174 | SO$_2$Me | OMe | Me | CN | |
| 3-175 | SO$_2$Me | NO$_2$ | Me | CN | |
| 3-176 | SO$_2$Me | SO$_2$Me | Me | CN | |
| 3-177 | Me | Me | Et | CN | |
| 3-178 | Me | F | Et | CN | |
| 3-179 | Me | Cl | Et | CN | |
| 3-180 | Me | Br | Et | CN | |
| 3-181 | Me | I | Et | CN | |
| 3-182 | Me | CF$_3$ | Et | CN | |
| 3-183 | Me | CHF$_2$ | Et | CN | |
| 3-184 | Me | CF$_2$Cl | Et | CN | |
| 3-185 | Me | OMe | Et | CN | |
| 3-186 | Me | NO$_2$ | Et | CN | |
| 3-187 | Me | SO$_2$Me | Et | CN | |
| 3-188 | Cl | Me | Et | CN | |
| 3-189 | Cl | F | Et | CN | |
| 3-190 | Cl | Cl | Et | CN | |
| 3-191 | Cl | Br | Et | CN | |
| 3-192 | Cl | I | Et | CN | |
| 3-193 | Cl | CF$_3$ | Et | CN | |
| 3-194 | Cl | CHF$_2$ | Et | CN | |
| 3-195 | Cl | CF$_2$Cl | Et | CN | |
| 3-196 | Cl | OMe | Et | CN | |
| 3-197 | Cl | NO$_2$ | Et | CN | |
| 3-198 | Cl | SO$_2$Me | Et | CN | |
| 3-199 | OMe | Me | Et | CN | |
| 3-200 | OMe | F | Et | CN | |
| 3-201 | OMe | Cl | Et | CN | |
| 3-202 | OMe | Br | Et | CN | |
| 3-203 | OMe | I | Et | CN | |
| 3-204 | OMe | CF$_3$ | Et | CN | |
| 3-205 | OMe | CHF$_2$ | Et | CN | |
| 3-206 | OMe | CF$_2$Cl | Et | CN | |
| 3-207 | OMe | OMe | Et | CN | |
| 3-208 | OMe | NO$_2$ | Et | CN | |
| 3-209 | OMe | SO$_2$Me | Et | CN | |
| 3-210 | SO$_2$Me | Me | Et | CN | |
| 3-211 | SO$_2$Me | F | Et | CN | |
| 3-212 | SO$_2$Me | Cl | Et | CN | |
| 3-213 | SO$_2$Me | Br | Et | CN | |
| 3-214 | SO$_2$Me | I | Et | CN | |
| 3-215 | SO$_2$Me | CF$_3$ | Et | CN | |
| 3-216 | SO$_2$Me | CHF$_2$ | Et | CN | |
| 3-217 | SO$_2$Me | CF$_2$Cl | Et | CN | |
| 3-218 | SO$_2$Me | OMe | Et | CN | |
| 3-219 | SO$_2$Me | NO$_2$ | Et | CN | |
| 3-220 | SO$_2$Me | SO$_2$Me | Et | CN | |
| 3-221 | Me | Me | CH$_2$CH$_2$OMe | CN | |
| 3-222 | Me | F | CH$_2$CH$_2$OMe | CN | |
| 3-223 | Me | Cl | CH$_2$CH$_2$OMe | CN | |
| 3-224 | Me | Br | CH$_2$CH$_2$OMe | CN | |

TABLE 3-continued

Compounds according to the invention of the formula (I) in which Q is Q3, $R^i$ is methyl and $R^h$, $R^k$ and W are each hydrogen, t = 1 and the other radicals have the meanings indicated in the table

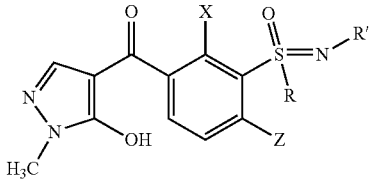

| No. | X | Z | R | R' | Physical data ($^1$H NMR) |
|---|---|---|---|---|---|
| 3-225 | Me | I | CH$_2$CH$_2$OMe | CN | |
| 3-226 | Me | CF$_3$ | CH$_2$CH$_2$OMe | CN | |
| 3-227 | Me | CHF$_2$ | CH$_2$CH$_2$OMe | CN | |
| 3-228 | Me | CF$_2$Cl | CH$_2$CH$_2$OMe | CN | |
| 3-229 | Me | OMe | CH$_2$CH$_2$OMe | CN | |
| 3-230 | Me | NO$_2$ | CH$_2$CH$_2$OMe | CN | |
| 3-231 | Me | SO$_2$Me | CH$_2$CH$_2$OMe | CN | |
| 3-232 | Cl | Me | CH$_2$CH$_2$OMe | CN | |
| 3-233 | Cl | F | CH$_2$CH$_2$OMe | CN | |
| 3-234 | Cl | Cl | CH$_2$CH$_2$OMe | CN | |
| 3-235 | Cl | Br | CH$_2$CH$_2$OMe | CN | |
| 3-236 | Cl | I | CH$_2$CH$_2$OMe | CN | |
| 3-237 | Cl | CF$_3$ | CH$_2$CH$_2$OMe | CN | |
| 3-238 | Cl | CHF$_2$ | CH$_2$CH$_2$OMe | CN | |
| 3-239 | Cl | CF$_2$Cl | CH$_2$CH$_2$OMe | CN | |
| 3-240 | Cl | OMe | CH$_2$CH$_2$OMe | CN | |
| 3-241 | Cl | NO$_2$ | CH$_2$CH$_2$OMe | CN | |
| 3-242 | Cl | SO$_2$Me | CH$_2$CH$_2$OMe | CN | |
| 3-243 | OMe | Me | CH$_2$CH$_2$OMe | CN | |
| 3-244 | OMe | F | CH$_2$CH$_2$OMe | CN | |
| 3-245 | OMe | Cl | CH$_2$CH$_2$OMe | CN | |
| 3-246 | OMe | Br | CH$_2$CH$_2$OMe | CN | |
| 3-247 | OMe | I | CH$_2$CH$_2$OMe | CN | |
| 3-248 | OMe | CF$_3$ | CH$_2$CH$_2$OMe | CN | |
| 3-249 | OMe | CHF$_2$ | CH$_2$CH$_2$OMe | CN | |
| 3-250 | OMe | CF$_2$Cl | CH$_2$CH$_2$OMe | CN | |
| 3-251 | OMe | OMe | CH$_2$CH$_2$OMe | CN | |
| 3-252 | OMe | NO$_2$ | CH$_2$CH$_2$OMe | CN | |
| 3-253 | OMe | SO$_2$Me | CH$_2$CH$_2$OMe | CN | |
| 3-254 | SO$_2$Me | Me | CH$_2$CH$_2$OMe | CN | |
| 3-255 | SO$_2$Me | F | CH$_2$CH$_2$OMe | CN | |
| 3-256 | SO$_2$Me | Cl | CH$_2$CH$_2$OMe | CN | |
| 3-257 | SO$_2$Me | Br | CH$_2$CH$_2$OMe | CN | |
| 3-258 | SO$_2$Me | I | CH$_2$CH$_2$OMe | CN | |
| 3-259 | SO$_2$Me | CF$_3$ | CH$_2$CH$_2$OMe | CN | |
| 3-260 | SO$_2$Me | CHF$_2$ | CH$_2$CH$_2$OMe | CN | |
| 3-261 | SO$_2$Me | CF$_2$Cl | CH$_2$CH$_2$OMe | CN | |
| 3-262 | SO$_2$Me | OMe | CH$_2$CH$_2$OMe | CN | |
| 3-263 | SO$_2$Me | NO$_2$ | CH$_2$CH$_2$OMe | CN | |
| 3-264 | SO$_2$Me | SO$_2$Me | CH$_2$CH$_2$OMe | CN | |

TABLE 3a

Compounds according to the invention of the formula (I) in which Q is Q3, $R^i$ is ethyl and $R^h$, $R^k$ and W are each hydrogen, t = 1 and the other radicals have the meanings indicated in the table

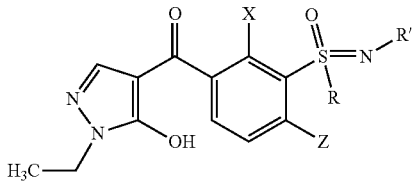

| No. | X | Z | R | R' | Physical data ($^1$H NMR) |
|---|---|---|---|---|---|
| 3a-1 | Me | Me | Me | H | |
| 3a-2 | Me | F | Me | H | |
| 3a-3 | Me | Cl | Me | H | |

TABLE 3a-continued

Compounds according to the invention of the formula (I) in which Q is Q3, $R^i$ is ethyl and $R^h$, $R^k$ and W are each hydrogen, t = 1 and the other radicals have the meanings indicated in the table

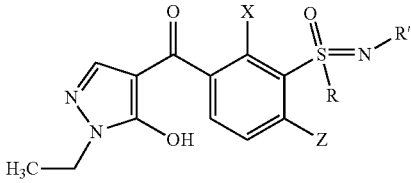

| No. | X | Z | R | R' | Physical data ($^1$H NMR) |
|---|---|---|---|---|---|
| 3a-4 | Me | Br | Me | H | |
| 3a-5 | Me | I | Me | H | |
| 3a-6 | Me | CF$_3$ | Me | H | |
| 3a-7 | Me | CHF$_2$ | Me | H | |
| 3a-8 | Me | CF$_2$Cl | Me | H | |
| 3a-9 | Me | OMe | Me | H | |
| 3a-10 | Me | NO$_2$ | Me | H | |
| 3a-11 | Me | SO$_2$Me | Me | H | |
| 3a-12 | Cl | Me | Me | H | |
| 3a-13 | Cl | F | Me | H | |
| 3a-14 | Cl | Cl | Me | H | |
| 3a-15 | Cl | Br | Me | H | |
| 3a-16 | Cl | I | Me | H | |
| 3a-17 | Cl | CF$_3$ | Me | H | |
| 3a-18 | Cl | CHF$_2$ | Me | H | |
| 3a-19 | Cl | CF$_2$Cl | Me | H | |
| 3a-20 | Cl | OMe | Me | H | |
| 3a-21 | Cl | NO$_2$ | Me | H | |
| 3a-22 | Cl | SO$_2$Me | Me | H | |
| 3a-23 | OMe | Me | Me | H | |
| 3a-24 | OMe | F | Me | H | |
| 3a-25 | OMe | Cl | Me | H | |
| 3a-26 | OMe | Br | Me | H | |
| 3a-27 | OMe | I | Me | H | |
| 3a-28 | OMe | CF$_3$ | Me | H | |
| 3a-29 | OMe | CHF$_2$ | Me | H | |
| 3a-30 | OMe | CF$_2$Cl | Me | H | |
| 3a-31 | OMe | OMe | Me | H | |
| 3a-32 | OMe | NO$_2$ | Me | H | |
| 3a-33 | OMe | SO$_2$Me | Me | H | |
| 3a-34 | SO$_2$Me | Me | Me | H | |
| 3a-35 | SO$_2$Me | F | Me | H | |
| 3a-36 | SO$_2$Me | Cl | Me | H | |
| 3a-37 | SO$_2$Me | Br | Me | H | |
| 3a-38 | SO$_2$Me | I | Me | H | |
| 3a-39 | SO$_2$Me | CF$_3$ | Me | H | |
| 3a-40 | SO$_2$Me | CHF$_2$ | Me | H | |
| 3a-41 | SO$_2$Me | CF$_2$Cl | Me | H | |
| 3a-42 | SO$_2$Me | OMe | Me | H | |
| 3a-43 | SO$_2$Me | NO$_2$ | Me | H | |
| 3a-44 | SO$_2$Me | SO$_2$Me | Me | H | |
| 3a-45 | Me | Me | Et | H | |
| 3a-46 | Me | F | Et | H | |
| 3a-47 | Me | Cl | Et | H | |
| 3a-48 | Me | Br | Et | H | |
| 3a-49 | Me | I | Et | H | |
| 3a-50 | Me | CF$_3$ | Et | H | |
| 3a-51 | Me | CHF$_2$ | Et | H | |
| 3a-52 | Me | CF$_2$Cl | Et | H | |
| 3a-53 | Me | OMe | Et | H | |
| 3a-54 | Me | NO$_2$ | Et | H | |
| 3a-55 | Me | SO$_2$Me | Et | H | |
| 3a-56 | Cl | Me | Et | H | |
| 3a-57 | Cl | F | Et | H | |
| 3a-58 | Cl | Cl | Et | H | |
| 3a-59 | Cl | Br | Et | H | |
| 3a-60 | Cl | I | Et | H | |
| 3a-61 | Cl | CF$_3$ | Et | H | |
| 3a-62 | Cl | CHF$_2$ | Et | H | |
| 3a-63 | Cl | CF$_2$Cl | Et | H | |
| 3a-64 | Cl | OMe | Et | H | |
| 3a-65 | Cl | NO$_2$ | Et | H | |
| 3a-66 | Cl | SO$_2$Me | Et | H | |
| 3a-67 | OMe | Me | Et | H | |

TABLE 3a-continued

Compounds according to the invention of the formula (I) in which Q is Q3, $R^i$ is ethyl and $R^h$, $R^k$ and W are each hydrogen, t = 1 and the other radicals have the meanings indicated in the table

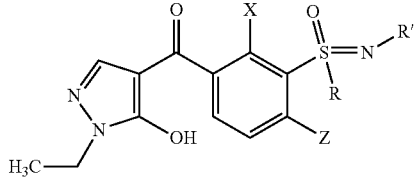

| No. | X | Z | R | R' | Physical data ($^1$H NMR) |
|---|---|---|---|---|---|
| 3a-68 | OMe | F | Et | H | |
| 3a-69 | OMe | Cl | Et | H | |
| 3a-70 | OMe | Br | Et | H | |
| 3a-71 | OMe | I | Et | H | |
| 3a-72 | OMe | CF$_3$ | Et | H | |
| 3a-73 | OMe | CHF$_2$ | Et | H | |
| 3a-74 | OMe | CF$_2$Cl | Et | H | |
| 3a-75 | OMe | OMe | Et | H | |
| 3a-76 | OMe | NO$_2$ | Et | H | |
| 3a-77 | OMe | SO$_2$Me | Et | H | |
| 3a-78 | SO$_2$Me | Me | Et | H | |
| 3a-79 | SO$_2$Me | F | Et | H | |
| 3a-80 | SO$_2$Me | Cl | Et | H | |
| 3a-81 | SO$_2$Me | Br | Et | H | |
| 3a-82 | SO$_2$Me | I | Et | H | |
| 3a-83 | SO$_2$Me | CF$_3$ | Et | H | |
| 3a-84 | SO$_2$Me | CHF$_2$ | Et | H | |
| 3a-85 | SO$_2$Me | CF$_2$Cl | Et | H | |
| 3a-86 | SO$_2$Me | OMe | Et | H | |
| 3a-87 | SO$_2$Me | NO$_2$ | Et | H | |
| 3a-88 | SO$_2$Me | SO$_2$Me | Et | H | |
| 3a-89 | Me | Me | CH$_2$CH$_2$OMe | H | |
| 3a-90 | Me | F | CH$_2$CH$_2$OMe | H | |
| 3a-91 | Me | Cl | CH$_2$CH$_2$OMe | H | |
| 3a-92 | Me | Br | CH$_2$CH$_2$OMe | H | |
| 3a-93 | Me | I | CH$_2$CH$_2$OMe | H | |
| 3a-94 | Me | CF$_3$ | CH$_2$CH$_2$OMe | H | |
| 3a-95 | Me | CHF$_2$ | CH$_2$CH$_2$OMe | H | |
| 3a-96 | Me | CF$_2$Cl | CH$_2$CH$_2$OMe | H | |
| 3a-97 | Me | OMe | CH$_2$CH$_2$OMe | H | |
| 3a-98 | Me | NO$_2$ | CH$_2$CH$_2$OMe | H | |
| 3a-99 | Me | SO$_2$Me | CH$_2$CH$_2$OMe | H | |
| 3a-100 | Cl | Me | CH$_2$CH$_2$OMe | H | |
| 3a-101 | Cl | F | CH$_2$CH$_2$OMe | H | |
| 3a-102 | Cl | Cl | CH$_2$CH$_2$OMe | H | |
| 3a-103 | Cl | Br | CH$_2$CH$_2$OMe | H | |
| 3a-104 | Cl | I | CH$_2$CH$_2$OMe | H | |
| 3a-105 | Cl | CF$_3$ | CH$_2$CH$_2$OMe | H | |
| 3a-106 | Cl | CHF$_2$ | CH$_2$CH$_2$OMe | H | |
| 3a-107 | Cl | CF$_2$Cl | CH$_2$CH$_2$OMe | H | |
| 3a-108 | Cl | OMe | CH$_2$CH$_2$OMe | H | |
| 3a-109 | Cl | NO$_2$ | CH$_2$CH$_2$OMe | H | |
| 3a-110 | Cl | SO$_2$Me | CH$_2$CH$_2$OMe | H | |
| 3a-111 | OMe | Me | CH$_2$CH$_2$OMe | H | |
| 3a-112 | OMe | F | CH$_2$CH$_2$OMe | H | |
| 3a-113 | OMe | Cl | CH$_2$CH$_2$OMe | H | |
| 3a-114 | OMe | Br | CH$_2$CH$_2$OMe | H | |
| 3a-115 | OMe | I | CH$_2$CH$_2$OMe | H | |
| 3a-116 | OMe | CF$_3$ | CH$_2$CH$_2$OMe | H | |
| 3a-117 | OMe | CHF$_2$ | CH$_2$CH$_2$OMe | H | |
| 3a-118 | OMe | CF$_2$Cl | CH$_2$CH$_2$OMe | H | |
| 3a-119 | OMe | OMe | CH$_2$CH$_2$OMe | H | |
| 3a-120 | OMe | NO$_2$ | CH$_2$CH$_2$OMe | H | |
| 3a-121 | OMe | SO$_2$Me | CH$_2$CH$_2$OMe | H | |
| 3a-122 | SO$_2$Me | Me | CH$_2$CH$_2$OMe | H | |
| 3a-123 | SO$_2$Me | F | CH$_2$CH$_2$OMe | H | |
| 3a-124 | SO$_2$Me | Cl | CH$_2$CH$_2$OMe | H | |
| 3a-125 | SO$_2$Me | Br | CH$_2$CH$_2$OMe | H | |
| 3a-126 | SO$_2$Me | I | CH$_2$CH$_2$OMe | H | |
| 3a-127 | SO$_2$Me | CF$_3$ | CH$_2$CH$_2$OMe | H | |
| 3a-128 | SO$_2$Me | CHF$_2$ | CH$_2$CH$_2$OMe | H | |
| 3a-129 | SO$_2$Me | CF$_2$Cl | CH$_2$CH$_2$OMe | H | |
| 3a-130 | SO$_2$Me | OMe | CH$_2$CH$_2$OMe | H | |
| 3a-131 | SO$_2$Me | NO$_2$ | CH$_2$CH$_2$OMe | H | |
| 3a-132 | SO$_2$Me | SO$_2$Me | CH$_2$CH$_2$OMe | H | |
| 3a-133 | Me | Me | Me | CN | |
| 3a-134 | Me | F | Me | CN | |
| 3a-135 | Me | Cl | Me | CN | |
| 3a-136 | Me | Br | Me | CN | |
| 3a-137 | Me | I | Me | CN | |
| 3a-138 | Me | CF$_3$ | Me | CN | |
| 3a-139 | Me | CHF$_2$ | Me | CN | |
| 3a-140 | Me | CF$_2$Cl | Me | CN | |
| 3a-141 | Me | OMe | Me | CN | |
| 3a-142 | Me | NO$_2$ | Me | CN | |
| 3a-143 | Me | SO$_2$Me | Me | CN | |
| 3a-144 | Cl | Me | Me | CN | |
| 3a-145 | Cl | F | Me | CN | |
| 3a-146 | Cl | Cl | Me | CN | |
| 3a-147 | Cl | Br | Me | CN | |
| 3a-148 | Cl | I | Me | CN | |
| 3a-149 | Cl | CF$_3$ | Me | CN | |
| 3a-150 | Cl | CHF$_2$ | Me | CN | |
| 3a-151 | Cl | CF$_2$Cl | Me | CN | |
| 3a-152 | Cl | OMe | Me | CN | |
| 3a-153 | Cl | NO$_2$ | Me | CN | |
| 3a-154 | Cl | SO$_2$Me | Me | CN | |
| 3a-155 | OMe | Me | Me | CN | |
| 3a-156 | OMe | F | Me | CN | |
| 3a-157 | OMe | Cl | Me | CN | |
| 3a-158 | OMe | Br | Me | CN | |
| 3a-159 | OMe | I | Me | CN | |
| 3a-160 | OMe | CF$_3$ | Me | CN | |
| 3a-161 | OMe | CHF$_2$ | Me | CN | |
| 3a-162 | OMe | CF$_2$Cl | Me | CN | |
| 3a-163 | OMe | OMe | Me | CN | |
| 3a-164 | OMe | NO$_2$ | Me | CN | |
| 3a-165 | OMe | SO$_2$Me | Me | CN | |
| 3a-166 | SO$_2$Me | Me | Me | CN | |
| 3a-167 | SO$_2$Me | F | Me | CN | |
| 3a-168 | SO$_2$Me | Cl | Me | CN | |
| 3a-169 | SO$_2$Me | Br | Me | CN | |
| 3a-170 | SO$_2$Me | I | Me | CN | |
| 3a-171 | SO$_2$Me | CF$_3$ | Me | CN | |
| 3a-172 | SO$_2$Me | CHF$_2$ | Me | CN | |
| 3a-173 | SO$_2$Me | CF$_2$Cl | Me | CN | |
| 3a-174 | SO$_2$Me | OMe | Me | CN | |
| 3a-175 | SO$_2$Me | NO$_2$ | Me | CN | |
| 3a-176 | SO$_2$Me | SO$_2$Me | Me | CN | |
| 3a-177 | Me | Me | Et | CN | |
| 3a-178 | Me | F | Et | CN | |
| 3a-179 | Me | Cl | Et | CN | |
| 3a-180 | Me | Br | Et | CN | |
| 3a-181 | Me | I | Et | CN | |
| 3a-182 | Me | CF$_3$ | Et | CN | |
| 3a-183 | Me | CHF$_2$ | Et | CN | |
| 3a-184 | Me | CF$_2$Cl | Et | CN | |
| 3a-185 | Me | OMe | Et | CN | |
| 3a-186 | Me | NO$_2$ | Et | CN | |
| 3a-187 | Me | SO$_2$Me | Et | CN | |
| 3a-188 | Cl | Me | Et | CN | |
| 3a-189 | Cl | F | Et | CN | |
| 3a-190 | Cl | Cl | Et | CN | |
| 3a-191 | Cl | Br | Et | CN | |
| 3a-192 | Cl | I | Et | CN | |
| 3a-193 | Cl | CF$_3$ | Et | CN | |
| 3a-194 | Cl | CHF$_2$ | Et | CN | |
| 3a-195 | Cl | CF$_2$Cl | Et | CN | |

TABLE 3a-continued

Compounds according to the invention of the formula (I) in which Q is Q3, $R^i$ is ethyl and $R^h$, $R^k$ and W are each hydrogen, t = 1 and the other radicals have the meanings indicated in the table

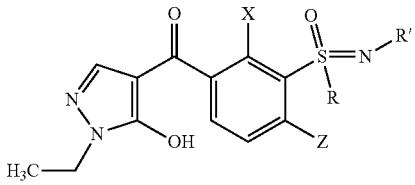

| No. | X | Z | R | R' | Physical data ($^1$H NMR) |
|---|---|---|---|---|---|
| 3a-196 | Cl | OMe | Et | CN | |
| 3a-197 | Cl | NO$_2$ | Et | CN | |
| 3a-198 | Cl | SO$_2$Me | Et | CN | |
| 3a-199 | OMe | Me | Et | CN | |
| 3a-200 | OMe | F | Et | CN | |
| 3a-201 | OMe | Cl | Et | CN | |
| 3a-202 | OMe | Br | Et | CN | |
| 3a-203 | OMe | I | Et | CN | |
| 3a-204 | OMe | CF$_3$ | Et | CN | |
| 3a-205 | OMe | CHF$_2$ | Et | CN | |
| 3a-206 | OMe | CF$_2$Cl | Et | CN | |
| 3a-207 | OMe | OMe | Et | CN | |
| 3a-208 | OMe | NO$_2$ | Et | CN | |
| 3a-209 | OMe | SO$_2$Me | Et | CN | |
| 3a-210 | SO$_2$Me | Me | Et | CN | |
| 3a-211 | SO$_2$Me | F | Et | CN | |
| 3a-212 | SO$_2$Me | Cl | Et | CN | |
| 3a-213 | SO$_2$Me | Br | Et | CN | |
| 3a-214 | SO$_2$Me | I | Et | CN | |
| 3a-215 | SO$_2$Me | CF$_3$ | Et | CN | |
| 3a-216 | SO$_2$Me | CHF$_2$ | Et | CN | |
| 3a-217 | SO$_2$Me | CF$_2$Cl | Et | CN | |
| 3a-218 | SO$_2$Me | OMe | Et | CN | |
| 3a-219 | SO$_2$Me | NO$_2$ | Et | CN | |
| 3a-220 | SO$_2$Me | SO$_2$Me | Et | CN | |
| 3a-221 | Me | Me | CH$_2$CH$_2$OMe | CN | |
| 3a-222 | Me | F | CH$_2$CH$_2$OMe | CN | |
| 3a-223 | Me | Cl | CH$_2$CH$_2$OMe | CN | |
| 3a-224 | Me | Br | CH$_2$CH$_2$OMe | CN | |
| 3a-225 | Me | I | CH$_2$CH$_2$OMe | CN | |
| 3a-226 | Me | CF$_3$ | CH$_2$CH$_2$OMe | CN | |
| 3a-227 | Me | CHF$_2$ | CH$_2$CH$_2$OMe | CN | |
| 3a-228 | Me | CF$_2$Cl | CH$_2$CH$_2$OMe | CN | |
| 3a-229 | Me | OMe | CH$_2$CH$_2$OMe | CN | |
| 3a-230 | Me | NO$_2$ | CH$_2$CH$_2$OMe | CN | |
| 3a-231 | Me | SO$_2$Me | CH$_2$CH$_2$OMe | CN | |
| 3a-232 | Cl | Me | CH$_2$CH$_2$OMe | CN | |
| 3a-233 | Cl | F | CH$_2$CH$_2$OMe | CN | |
| 3a-234 | Cl | Cl | CH$_2$CH$_2$OMe | CN | |
| 3a-235 | Cl | Br | CH$_2$CH$_2$OMe | CN | |
| 3a-236 | Cl | I | CH$_2$CH$_2$OMe | CN | |
| 3a-237 | Cl | CF$_3$ | CH$_2$CH$_2$OMe | CN | |
| 3a-238 | Cl | CHF$_2$ | CH$_2$CH$_2$OMe | CN | |
| 3a-239 | Cl | CF$_2$Cl | CH$_2$CH$_2$OMe | CN | |
| 3a-240 | Cl | OMe | CH$_2$CH$_2$OMe | CN | |
| 3a-241 | Cl | NO$_2$ | CH$_2$CH$_2$OMe | CN | |
| 3a-242 | Cl | SO$_2$Me | CH$_2$CH$_2$OMe | CN | |
| 3a-243 | OMe | Me | CH$_2$CH$_2$OMe | CN | |
| 3a-244 | OMe | F | CH$_2$CH$_2$OMe | CN | |
| 3a-245 | OMe | Cl | CH$_2$CH$_2$OMe | CN | |
| 3a-246 | OMe | Br | CH$_2$CH$_2$OMe | CN | |
| 3a-247 | OMe | I | CH$_2$CH$_2$OMe | CN | |
| 3a-248 | OMe | CF$_3$ | CH$_2$CH$_2$OMe | CN | |
| 3a-249 | OMe | CHF$_2$ | CH$_2$CH$_2$OMe | CN | |
| 3a-250 | OMe | CF$_2$Cl | CH$_2$CH$_2$OMe | CN | |
| 3a-251 | OMe | OMe | CH$_2$CH$_2$OMe | CN | |
| 3a-252 | OMe | NO$_2$ | CH$_2$CH$_2$OMe | CN | |
| 3a-253 | OMe | SO$_2$Me | CH$_2$CH$_2$OMe | CN | |
| 3a-254 | SO$_2$Me | Me | CH$_2$CH$_2$OMe | CN | |
| 3a-255 | SO$_2$Me | F | CH$_2$CH$_2$OMe | CN | |
| 3a-256 | SO$_2$Me | Cl | CH$_2$CH$_2$OMe | CN | |
| 3a-257 | SO$_2$Me | Br | CH$_2$CH$_2$OMe | CN | |
| 3a-258 | SO$_2$Me | I | CH$_2$CH$_2$OMe | CN | |
| 3a-259 | SO$_2$Me | CF$_3$ | CH$_2$CH$_2$OMe | CN | |
| 3a-260 | SO$_2$Me | CHF$_2$ | CH$_2$CH$_2$OMe | CN | |
| 3a-261 | SO$_2$Me | CF$_2$Cl | CH$_2$CH$_2$OMe | CN | |
| 3a-262 | SO$_2$Me | OMe | CH$_2$CH$_2$OMe | CN | |
| 3a-263 | SO$_2$Me | NO$_2$ | CH$_2$CH$_2$OMe | CN | |
| 3a-264 | SO$_2$Me | SO$_2$Me | CH$_2$CH$_2$OMe | CN | |

TABLE 4

Compounds according to the invention of the formula (I) in which Q is Q3, $R^i$ and $R^k$ are each methyl, $R^h$ and W are each hydrogen, t = 1 and the other radicals have the meanings indicated in the table

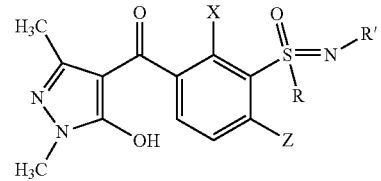

| No. | X | Z | R | R' | Physical data (1H NMR) |
|---|---|---|---|---|---|
| 4-1 | Me | Me | Me | H | |
| 4-2 | Me | F | Me | H | |
| 4-3 | Me | Cl | Me | H | |
| 4-4 | Me | Br | Me | H | |
| 4-5 | Me | I | Me | H | |
| 4-6 | Me | CF$_3$ | Me | H | |
| 4-7 | Me | CHF$_2$ | Me | H | |
| 4-8 | Me | CF$_2$Cl | Me | H | |
| 4-9 | Me | OMe | Me | H | |
| 4-10 | Me | NO$_2$ | Me | H | |
| 4-11 | Me | SO$_2$Me | Me | H | |
| 4-12 | Cl | Me | Me | H | |
| 4-13 | Cl | F | Me | H | |
| 4-14 | Cl | Cl | Me | H | |
| 4-15 | Cl | Br | Me | H | |
| 4-16 | Cl | I | Me | H | |
| 4-17 | Cl | CF$_3$ | Me | H | |
| 4-18 | Cl | CHF$_2$ | Me | H | |
| 4-19 | Cl | CF$_2$Cl | Me | H | |
| 4-20 | Cl | OMe | Me | H | |
| 4-21 | Cl | NO$_2$ | Me | H | |
| 4-22 | Cl | SO$_2$Me | Me | H | |
| 4-23 | OMe | Me | Me | H | |
| 4-24 | OMe | F | Me | H | |
| 4-25 | OMe | Cl | Me | H | |
| 4-26 | OMe | Br | Me | H | |
| 4-27 | OMe | I | Me | H | |
| 4-28 | OMe | CF$_3$ | Me | H | |
| 4-29 | OMe | CHF$_2$ | Me | H | |
| 4-30 | OMe | CF$_2$Cl | Me | H | |
| 4-31 | OMe | OMe | Me | H | |
| 4-32 | OMe | NO$_2$ | Me | H | |
| 4-33 | OMe | SO$_2$Me | Me | H | |
| 4-34 | SO$_2$Me | Me | Me | H | |
| 4-35 | SO$_2$Me | F | Me | H | |
| 4-36 | SO$_2$Me | Cl | Me | H | |
| 4-37 | SO$_2$Me | Br | Me | H | |
| 4-38 | SO$_2$Me | I | Me | H | |

TABLE 4-continued

Compounds according to the invention of the formula (I) in which Q is Q3, $R^i$ and $R^k$ are each methyl, $R^h$ and W are each hydrogen, t = 1 and the other radicals have the meanings indicated in the table

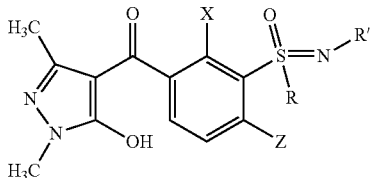

| No. | X | Z | R | R' | Physical data (1H NMR) |
|---|---|---|---|---|---|
| 4-39 | SO$_2$Me | CF$_3$ | Me | H | |
| 4-40 | SO$_2$Me | CHF$_2$ | Me | H | |
| 4-41 | SO$_2$Me | CF$_2$Cl | Me | H | |
| 4-42 | SO$_2$Me | OMe | Me | H | |
| 4-43 | SO$_2$Me | NO$_2$ | Me | H | |
| 4-44 | SO$_2$Me | SO$_2$Me | Me | H | |
| 4-45 | Me | Me | Et | H | |
| 4-46 | Me | F | Et | H | |
| 4-47 | Me | Cl | Et | H | |
| 4-48 | Me | Br | Et | H | |
| 4-49 | Me | I | Et | H | |
| 4-50 | Me | CF$_3$ | Et | H | |
| 4-51 | Me | CHF$_2$ | Et | H | |
| 4-52 | Me | CF$_2$Cl | Et | H | |
| 4-53 | Me | OMe | Et | H | |
| 4-54 | Me | NO$_2$ | Et | H | |
| 4-55 | Me | SO$_2$Me | Et | H | |
| 4-56 | Cl | Me | Et | H | |
| 4-57 | Cl | F | Et | H | |
| 4-58 | Cl | Cl | Et | H | |
| 4-59 | Cl | Br | Et | H | |
| 4-60 | Cl | I | Et | H | |
| 4-61 | Cl | CF$_3$ | Et | H | |
| 4-62 | Cl | CHF$_2$ | Et | H | |
| 4-63 | Cl | CF$_2$Cl | Et | H | |
| 4-64 | Cl | OMe | Et | H | |
| 4-65 | Cl | NO$_2$ | Et | H | |
| 4-66 | Cl | SO$_2$Me | Et | H | |
| 4-67 | OMe | Me | Et | H | |
| 4-68 | OMe | F | Et | H | |
| 4-69 | OMe | Cl | Et | H | |
| 4-70 | OMe | Br | Et | H | |
| 4-71 | OMe | I | Et | H | |
| 4-72 | OMe | CF$_3$ | Et | H | |
| 4-73 | OMe | CHF$_2$ | Et | H | |
| 4-74 | OMe | CF$_2$Cl | Et | H | |
| 4-75 | OMe | OMe | Et | H | |
| 4-76 | OMe | NO$_2$ | Et | H | |
| 4-77 | OMe | SO$_2$Me | Et | H | |
| 4-78 | SO$_2$Me | Me | Et | H | |
| 4-79 | SO$_2$Me | F | Et | H | |
| 4-80 | SO$_2$Me | Cl | Et | H | |
| 4-81 | SO$_2$Me | Br | Et | H | |
| 4-82 | SO$_2$Me | I | Et | H | |
| 4-83 | SO$_2$Me | CF$_3$ | Et | H | |
| 4-84 | SO$_2$Me | CHF$_2$ | Et | H | |
| 4-85 | SO$_2$Me | CF$_2$Cl | Et | H | |
| 4-86 | SO$_2$Me | OMe | Et | H | |
| 4-87 | SO$_2$Me | NO$_2$ | Et | H | |
| 4-88 | SO$_2$Me | SO$_2$Me | Et | H | |
| 4-89 | Me | Me | CH$_2$CH$_2$OMe | H | |
| 4-90 | Me | F | CH$_2$CH$_2$OMe | H | |
| 4-91 | Me | Cl | CH$_2$CH$_2$OMe | H | |
| 4-92 | Me | Br | CH$_2$CH$_2$OMe | H | |
| 4-93 | Me | I | CH$_2$CH$_2$OMe | H | |
| 4-94 | Me | CF$_3$ | CH$_2$CH$_2$OMe | H | |
| 4-95 | Me | CHF$_2$ | CH$_2$CH$_2$OMe | H | |
| 4-96 | Me | CF$_2$Cl | CH$_2$CH$_2$OMe | H | |
| 4-97 | Me | OMe | CH$_2$CH$_2$OMe | H | |
| 4-98 | Me | NO$_2$ | CH$_2$CH$_2$OMe | H | |
| 4-99 | Me | SO$_2$Me | CH$_2$CH$_2$OMe | H | |
| 4-100 | Cl | Me | CH$_2$CH$_2$OMe | H | |
| 4-101 | Cl | F | CH$_2$CH$_2$OMe | H | |
| 4-102 | Cl | Cl | CH$_2$CH$_2$OMe | H | |

TABLE 4-continued

Compounds according to the invention of the formula (I) in which Q is Q3, $R^i$ and $R^k$ are each methyl, $R^h$ and W are each hydrogen, t = 1 and the other radicals have the meanings indicated in the table

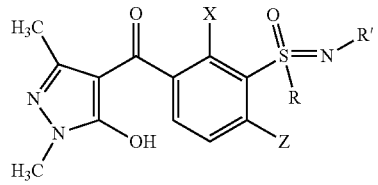

| No. | X | Z | R | R' | Physical data (1H NMR) |
|---|---|---|---|---|---|
| 4-103 | Cl | Br | CH$_2$CH$_2$OMe | H | |
| 4-104 | Cl | I | CH$_2$CH$_2$OMe | H | |
| 4-105 | Cl | CF$_3$ | CH$_2$CH$_2$OMe | H | |
| 4-106 | Cl | CHF$_2$ | CH$_2$CH$_2$OMe | H | |
| 4-107 | Cl | CF$_2$Cl | CH$_2$CH$_2$OMe | H | |
| 4-108 | Cl | OMe | CH$_2$CH$_2$OMe | H | |
| 4-109 | Cl | NO$_2$ | CH$_2$CH$_2$OMe | H | |
| 4-110 | Cl | SO$_2$Me | CH$_2$CH$_2$OMe | H | |
| 4-111 | OMe | Me | CH$_2$CH$_2$OMe | H | |
| 4-112 | OMe | F | CH$_2$CH$_2$OMe | H | |
| 4-113 | OMe | Cl | CH$_2$CH$_2$OMe | H | |
| 4-114 | OMe | Br | CH$_2$CH$_2$OMe | H | |
| 4-115 | OMe | I | CH$_2$CH$_2$OMe | H | |
| 4-116 | OMe | CF$_3$ | CH$_2$CH$_2$OMe | H | |
| 4-117 | OMe | CHF$_2$ | CH$_2$CH$_2$OMe | H | |
| 4-118 | OMe | CF$_2$Cl | CH$_2$CH$_2$OMe | H | |
| 4-119 | OMe | OMe | CH$_2$CH$_2$OMe | H | |
| 4-120 | OMe | NO$_2$ | CH$_2$CH$_2$OMe | H | |
| 4-121 | OMe | SO$_2$Me | CH$_2$CH$_2$OMe | H | |
| 4-122 | SO$_2$Me | Me | CH$_2$CH$_2$OMe | H | |
| 4-123 | SO$_2$Me | F | CH$_2$CH$_2$OMe | H | |
| 4-124 | SO$_2$Me | Cl | CH$_2$CH$_2$OMe | H | |
| 4-125 | SO$_2$Me | Br | CH$_2$CH$_2$OMe | H | |
| 4-126 | SO$_2$Me | I | CH$_2$CH$_2$OMe | H | |
| 4-127 | SO$_2$Me | CF$_3$ | CH$_2$CH$_2$OMe | H | |
| 4-128 | SO$_2$Me | CHF$_2$ | CH$_2$CH$_2$OMe | H | |
| 4-129 | SO$_2$Me | CF$_2$Cl | CH$_2$CH$_2$OMe | H | |
| 4-130 | SO$_2$Me | OMe | CH$_2$CH$_2$OMe | H | |
| 4-131 | SO$_2$Me | NO$_2$ | CH$_2$CH$_2$OMe | H | |
| 4-132 | SO$_2$Me | SO$_2$Me | CH$_2$CH$_2$OMe | H | |
| 4-133 | Me | Me | Me | CN | |
| 4-134 | Me | F | Me | CN | |
| 4-135 | Me | Cl | Me | CN | |
| 4-136 | Me | Br | Me | CN | |
| 4-137 | Me | I | Me | CN | |
| 4-138 | Me | CF$_3$ | Me | CN | |
| 4-139 | Me | CHF$_2$ | Me | CN | |
| 4-140 | Me | CF$_2$Cl | Me | CN | |
| 4-141 | Me | OMe | Me | CN | |
| 4-142 | Me | NO$_2$ | Me | CN | |
| 4-143 | Me | SO$_2$Me | Me | CN | |
| 4-144 | Cl | Me | Me | CN | |
| 4-145 | Cl | F | Me | CN | |
| 4-146 | Cl | Cl | Me | CN | |
| 4-147 | Cl | Br | Me | CN | |
| 4-148 | Cl | I | Me | CN | |
| 4-149 | Cl | CF$_3$ | Me | CN | |
| 4-150 | Cl | CHF$_2$ | Me | CN | |
| 4-151 | Cl | CF$_2$Cl | Me | CN | |
| 4-152 | Cl | OMe | Me | CN | |
| 4-153 | Cl | NO$_2$ | Me | CN | |
| 4-154 | Cl | SO$_2$Me | Me | CN | |
| 4-155 | OMe | Me | Me | CN | |
| 4-156 | OMe | F | Me | CN | |
| 4-157 | OMe | Cl | Me | CN | |
| 4-158 | OMe | Br | Me | CN | |
| 4-159 | OMe | I | Me | CN | |
| 4-160 | OMe | CF$_3$ | Me | CN | (400 MHz, CDCl$_3$ δ, ppm) 7.85 (d, 1H), 7.75 (d, 1H), 4.03 (s, 3H), 3.68 (s, 3H), 3.65 (s, 3H), 1.90 (s, 3H) |
| 4-161 | OMe | CHF$_2$ | Me | CN | |
| 4-162 | OMe | CF$_2$Cl | Me | CN | |

TABLE 4-continued

Compounds according to the invention of the formula (I) in which Q is Q3, $R^i$ and $R^k$ are each methyl, $R^h$ and W are each hydrogen, t = 1 and the other radicals have the meanings indicated in the table

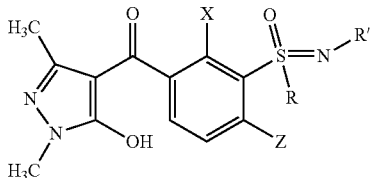

| No. | X | Z | R | R' | Physical data (1H NMR) |
|---|---|---|---|---|---|
| 4-163 | OMe | OMe | Me | CN | |
| 4-164 | OMe | NO$_2$ | Me | CN | |
| 4-165 | OMe | SO$_2$Me | Me | CN | |
| 4-166 | SO$_2$Me | Me | Me | CN | |
| 4-167 | SO$_2$Me | F | Me | CN | |
| 4-168 | SO$_2$Me | Cl | Me | CN | |
| 4-169 | SO$_2$Me | Br | Me | CN | |
| 4-170 | SO$_2$Me | I | Me | CN | |
| 4-171 | SO$_2$Me | CF$_3$ | Me | CN | |
| 4-172 | SO$_2$Me | CHF$_2$ | Me | CN | |
| 4-173 | SO$_2$Me | CF$_2$Cl | Me | CN | |
| 4-174 | SO$_2$Me | OMe | Me | CN | |
| 4-175 | SO$_2$Me | NO$_2$ | Me | CN | |
| 4-176 | SO$_2$Me | SO$_2$Me | Me | CN | |
| 4-177 | Me | Me | Et | CN | |
| 4-178 | Me | F | Et | CN | |
| 4-179 | Me | Cl | Et | CN | |
| 4-180 | Me | Br | Et | CN | |
| 4-181 | Me | I | Et | CN | |
| 4-182 | Me | CF$_3$ | Et | CN | |
| 4-183 | Me | CHF$_2$ | Et | CN | |
| 4-184 | Me | CF$_2$Cl | Et | CN | |
| 4-185 | Me | OMe | Et | CN | |
| 4-186 | Me | NO$_2$ | Et | CN | |
| 4-187 | Me | SO$_2$Me | Et | CN | |
| 4-188 | Cl | Me | Et | CN | |
| 4-189 | Cl | F | Et | CN | |
| 4-190 | Cl | Cl | Et | CN | |
| 4-191 | Cl | Br | Et | CN | |
| 4-192 | Cl | I | Et | CN | |
| 4-193 | Cl | CF$_3$ | Et | CN | |
| 4-194 | Cl | CHF$_2$ | Et | CN | |
| 4-195 | Cl | CF$_2$Cl | Et | CN | |
| 4-196 | Cl | OMe | Et | CN | |
| 4-197 | Cl | NO$_2$ | Et | CN | |
| 4-198 | Cl | SO$_2$Me | Et | CN | |
| 4-199 | OMe | Me | Et | CN | |
| 4-200 | OMe | F | Et | CN | |
| 4-201 | OMe | Cl | Et | CN | |
| 4-202 | OMe | Br | Et | CN | |
| 4-203 | OMe | I | Et | CN | |
| 4-204 | OMe | CF$_3$ | Et | CN | |
| 4-205 | OMe | CHF$_2$ | Et | CN | |
| 4-206 | OMe | CF$_2$Cl | Et | CN | |
| 4-207 | OMe | OMe | Et | CN | |
| 4-208 | OMe | NO$_2$ | Et | CN | |
| 4-209 | OMe | SO$_2$Me | Et | CN | |
| 4-210 | SO$_2$Me | Me | Et | CN | |
| 4-211 | SO$_2$Me | F | Et | CN | |
| 4-212 | SO$_2$Me | Cl | Et | CN | |
| 4-213 | SO$_2$Me | Br | Et | CN | |
| 4-214 | SO$_2$Me | I | Et | CN | |
| 4-215 | SO$_2$Me | CF$_3$ | Et | CN | |
| 4-216 | SO$_2$Me | CHF$_2$ | Et | CN | |
| 4-217 | SO$_2$Me | CF$_2$Cl | Et | CN | |
| 4-218 | SO$_2$Me | OMe | Et | CN | |
| 4-219 | SO$_2$Me | NO$_2$ | Et | CN | |
| 4-220 | SO$_2$Me | SO$_2$Me | Et | CN | |
| 4-221 | Me | Me | CH$_2$CH$_2$OMe | CN | |
| 4-222 | Me | F | CH$_2$CH$_2$OMe | CN | |
| 4-223 | Me | Cl | CH$_2$CH$_2$OMe | CN | |
| 4-224 | Me | Br | CH$_2$CH$_2$OMe | CN | |
| 4-225 | Me | I | CH$_2$CH$_2$OMe | CN | |
| 4-226 | Me | CF$_3$ | CH$_2$CH$_2$OMe | CN | |

TABLE 4-continued

Compounds according to the invention of the formula (I) in which Q is Q3, $R^i$ and $R^k$ are each methyl, $R^h$ and W are each hydrogen, t = 1 and the other radicals have the meanings indicated in the table

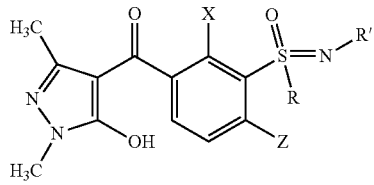

| No. | X | Z | R | R' | Physical data (1H NMR) |
|---|---|---|---|---|---|
| 4-227 | Me | CHF$_2$ | CH$_2$CH$_2$OMe | CN | |
| 4-228 | Me | CF$_2$Cl | CH$_2$CH$_2$OMe | CN | |
| 4-229 | Me | OMe | CH$_2$CH$_2$OMe | CN | |
| 4-230 | Me | NO$_2$ | CH$_2$CH$_2$OMe | CN | |
| 4-231 | Me | SO$_2$Me | CH$_2$CH$_2$OMe | CN | |
| 4-232 | Cl | Me | CH$_2$CH$_2$OMe | CN | |
| 4-233 | Cl | F | CH$_2$CH$_2$OMe | CN | |
| 4-234 | Cl | Cl | CH$_2$CH$_2$OMe | CN | |
| 4-235 | Cl | Br | CH$_2$CH$_2$OMe | CN | |
| 4-236 | Cl | I | CH$_2$CH$_2$OMe | CN | |
| 4-237 | Cl | CF$_3$ | CH$_2$CH$_2$OMe | CN | |
| 4-238 | Cl | CHF$_2$ | CH$_2$CH$_2$OMe | CN | |
| 4-239 | Cl | CF$_2$Cl | CH$_2$CH$_2$OMe | CN | |
| 4-240 | Cl | OMe | CH$_2$CH$_2$OMe | CN | |
| 4-241 | Cl | NO$_2$ | CH$_2$CH$_2$OMe | CN | |
| 4-242 | Cl | SO$_2$Me | CH$_2$CH$_2$OMe | CN | |
| 4-243 | OMe | Me | CH$_2$CH$_2$OMe | CN | |
| 4-244 | OMe | F | CH$_2$CH$_2$OMe | CN | |
| 4-245 | OMe | Cl | CH$_2$CH$_2$OMe | CN | |
| 4-246 | OMe | Br | CH$_2$CH$_2$OMe | CN | |
| 4-247 | OMe | I | CH$_2$CH$_2$OMe | CN | |
| 4-248 | OMe | CF$_3$ | CH$_2$CH$_2$OMe | CN | |
| 4-249 | OMe | CHF$_2$ | CH$_2$CH$_2$OMe | CN | |
| 4-250 | OMe | CF$_2$Cl | CH$_2$CH$_2$OMe | CN | |
| 4-251 | OMe | OMe | CH$_2$CH$_2$OMe | CN | |
| 4-252 | OMe | NO$_2$ | CH$_2$CH$_2$OMe | CN | |
| 4-253 | OMe | SO$_2$Me | CH$_2$CH$_2$OMe | CN | |
| 4-254 | SO$_2$Me | Me | CH$_2$CH$_2$OMe | CN | |
| 4-255 | SO$_2$Me | F | CH$_2$CH$_2$OMe | CN | |
| 4-256 | SO$_2$Me | Cl | CH$_2$CH$_2$OMe | CN | |
| 4-257 | SO$_2$Me | Br | CH$_2$CH$_2$OMe | CN | |
| 4-258 | SO$_2$Me | I | CH$_2$CH$_2$OMe | CN | |
| 4-259 | SO$_2$Me | CF$_3$ | CH$_2$CH$_2$OMe | CN | |
| 4-260 | SO$_2$Me | CHF$_2$ | CH$_2$CH$_2$OMe | CN | |
| 4-261 | SO$_2$Me | CF$_2$Cl | CH$_2$CH$_2$OMe | CN | |
| 4-262 | SO$_2$Me | OMe | CH$_2$CH$_2$OMe | CN | |
| 4-263 | SO$_2$Me | NO$_2$ | CH$_2$CH$_2$OMe | CN | |
| 4-264 | SO$_2$Me | SO$_2$Me | CH$_2$CH$_2$OMe | CN | |

TABLE 5

Compounds according to the invention of the formula (I) in which Q is Q4, W is hydrogen, t = 1 and the other radicals have the meanings indicated in the table

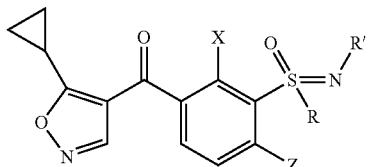

| No. | X | Z | R | R' | Physical data (1H NMR) |
|---|---|---|---|---|---|
| 5-1 | Me | Me | Me | H | |
| 5-2 | Me | F | Me | H | |
| 5-3 | Me | Cl | Me | H | |
| 5-4 | Me | Br | Me | H | |
| 5-5 | Me | I | Me | H | |
| 5-6 | Me | CF$_3$ | Me | H | |

TABLE 5-continued

Compounds according to the invention of the formula (I) in which Q is Q4, W is hydrogen, t = 1 and the other radicals have the meanings indicated in the table

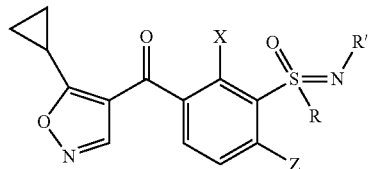

| No. | X | Z | R | R' | Physical data (1H NMR) |
|---|---|---|---|---|---|
| 5-7 | Me | CHF$_2$ | Me | H | |
| 5-8 | Me | CF$_2$Cl | Me | H | |
| 5-9 | Me | OMe | Me | H | |
| 5-10 | Me | NO$_2$ | Me | H | |
| 5-11 | Me | SO$_2$Me | Me | H | |
| 5-12 | Cl | Me | Me | H | |
| 5-13 | Cl | F | Me | H | |
| 5-14 | Cl | Cl | Me | H | |
| 5-15 | Cl | Br | Me | H | |
| 5-16 | Cl | I | Me | H | |
| 5-17 | Cl | CF$_3$ | Me | H | |
| 5-18 | Cl | CHF$_2$ | Me | H | |
| 5-19 | Cl | CF$_2$Cl | Me | H | |
| 5-20 | Cl | OMe | Me | H | |
| 5-21 | Cl | NO$_2$ | Me | H | |
| 5-22 | Cl | SO$_2$Me | Me | H | |
| 5-23 | OMe | Me | Me | H | |
| 5-24 | OMe | F | Me | H | |
| 5-25 | OMe | Cl | Me | H | |
| 5-26 | OMe | Br | Me | H | |
| 5-27 | OMe | I | Me | H | |
| 5-28 | OMe | CF$_3$ | Me | H | |
| 5-29 | OMe | CHF$_2$ | Me | H | |
| 5-30 | OMe | CF$_2$Cl | Me | H | |
| 5-31 | OMe | OMe | Me | H | |
| 5-32 | OMe | NO$_2$ | Me | H | |
| 5-33 | OMe | SO$_2$Me | Me | H | |
| 5-34 | SO$_2$Me | Me | Me | H | |
| 5-35 | SO$_2$Me | F | Me | H | |
| 5-36 | SO$_2$Me | Cl | Me | H | |
| 5-37 | SO$_2$Me | Br | Me | H | |
| 5-38 | SO$_2$Me | I | Me | H | |
| 5-39 | SO$_2$Me | CF$_3$ | Me | H | |
| 5-40 | SO$_2$Me | CHF$_2$ | Me | H | |
| 5-41 | SO$_2$Me | CF$_2$Cl | Me | H | |
| 5-42 | SO$_2$Me | OMe | Me | H | |
| 5-43 | SO$_2$Me | NO$_2$ | Me | H | |
| 5-44 | SO$_2$Me | SO$_2$Me | Me | H | |
| 5-45 | Me | Me | Et | H | |
| 5-46 | Me | F | Et | H | |
| 5-47 | Me | Cl | Et | H | |
| 5-48 | Me | Br | Et | H | |
| 5-49 | Me | I | Et | H | |
| 5-50 | Me | CF$_3$ | Et | H | |
| 5-51 | Me | CHF$_2$ | Et | H | |
| 5-52 | Me | CF$_2$Cl | Et | H | |
| 5-53 | Me | OMe | Et | H | |
| 5-54 | Me | NO$_2$ | Et | H | |
| 5-55 | Me | SO$_2$Me | Et | H | |
| 5-56 | Cl | Me | Et | H | |
| 5-57 | Cl | F | Et | H | |
| 5-58 | Cl | Cl | Et | H | |
| 5-59 | Cl | Br | Et | H | |
| 5-60 | Cl | I | Et | H | |
| 5-61 | Cl | CF$_3$ | Et | H | |
| 5-62 | Cl | CHF$_2$ | Et | H | |
| 5-63 | Cl | CF$_2$Cl | Et | H | |
| 5-64 | Cl | OMe | Et | H | |
| 5-65 | Cl | NO$_2$ | Et | H | |
| 5-66 | Cl | SO$_2$Me | Et | H | |
| 5-67 | OMe | Me | Et | H | |
| 5-68 | OMe | F | Et | H | |
| 5-69 | OMe | Cl | Et | H | |
| 5-70 | OMe | Br | Et | H | |
| 5-71 | OMe | I | Et | H | |

TABLE 5-continued

Compounds according to the invention of the formula (I) in which Q is Q4, W is hydrogen, t = 1 and the other radicals have the meanings indicated in the table

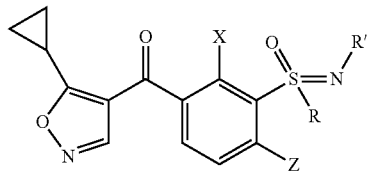

| No. | X | Z | R | R' | Physical data (1H NMR) |
|---|---|---|---|---|---|
| 5-72 | OMe | CF$_3$ | Et | H | |
| 5-73 | OMe | CHF$_2$ | Et | H | |
| 5-74 | OMe | CF$_2$Cl | Et | H | |
| 5-75 | OMe | OMe | Et | H | |
| 5-76 | OMe | NO$_2$ | Et | H | |
| 5-77 | OMe | SO$_2$Me | Et | H | |
| 5-78 | SO$_2$Me | Me | Et | H | |
| 5-79 | SO$_2$Me | F | Et | H | |
| 5-80 | SO$_2$Me | Cl | Et | H | |
| 5-81 | SO$_2$Me | Br | Et | H | |
| 5-82 | SO$_2$Me | I | Et | H | |
| 5-83 | SO$_2$Me | CF$_3$ | Et | H | |
| 5-84 | SO$_2$Me | CHF$_2$ | Et | H | |
| 5-85 | SO$_2$Me | CF$_2$Cl | Et | H | |
| 5-86 | SO$_2$Me | OMe | Et | H | |
| 5-87 | SO$_2$Me | NO$_2$ | Et | H | |
| 5-88 | SO$_2$Me | SO$_2$Me | Et | H | |
| 5-89 | Me | Me | CH$_2$CH$_2$OMe | H | |
| 5-90 | Me | F | CH$_2$CH$_2$OMe | H | |
| 5-91 | Me | Cl | CH$_2$CH$_2$OMe | H | |
| 5-92 | Me | Br | CH$_2$CH$_2$OMe | H | |
| 5-93 | Me | I | CH$_2$CH$_2$OMe | H | |
| 5-94 | Me | CF$_3$ | CH$_2$CH$_2$OMe | H | |
| 5-95 | Me | CHF$_2$ | CH$_2$CH$_2$OMe | H | |
| 5-96 | Me | CF$_2$Cl | CH$_2$CH$_2$OMe | H | |
| 5-97 | Me | OMe | CH$_2$CH$_2$OMe | H | |
| 5-98 | Me | NO$_2$ | CH$_2$CH$_2$OMe | H | |
| 5-99 | Me | SO$_2$Me | CH$_2$CH$_2$OMe | H | |
| 5-100 | Cl | Me | CH$_2$CH$_2$OMe | H | |
| 5-101 | Cl | F | CH$_2$CH$_2$OMe | H | |
| 5-102 | Cl | Cl | CH$_2$CH$_2$OMe | H | |
| 5-103 | Cl | Br | CH$_2$CH$_2$OMe | H | |
| 5-104 | Cl | I | CH$_2$CH$_2$OMe | H | |
| 5-105 | Cl | CF$_3$ | CH$_2$CH$_2$OMe | H | |
| 5-106 | Cl | CHF$_2$ | CH$_2$CH$_2$OMe | H | |
| 5-107 | Cl | CF$_2$Cl | CH$_2$CH$_2$OMe | H | |
| 5-108 | Cl | OMe | CH$_2$CH$_2$OMe | H | |
| 5-109 | Cl | NO$_2$ | CH$_2$CH$_2$OMe | H | |
| 5-110 | Cl | SO$_2$Me | CH$_2$CH$_2$OMe | H | |
| 5-111 | OMe | Me | CH$_2$CH$_2$OMe | H | |
| 5-112 | OMe | F | CH$_2$CH$_2$OMe | H | |
| 5-113 | OMe | Cl | CH$_2$CH$_2$OMe | H | |
| 5-114 | OMe | Br | CH$_2$CH$_2$OMe | H | |
| 5-115 | OMe | I | CH$_2$CH$_2$OMe | H | |
| 5-116 | OMe | CF$_3$ | CH$_2$CH$_2$OMe | H | |
| 5-117 | OMe | CHF$_2$ | CH$_2$CH$_2$OMe | H | |
| 5-118 | OMe | CF$_2$Cl | CH$_2$CH$_2$OMe | H | |
| 5-119 | OMe | OMe | CH$_2$CH$_2$OMe | H | |
| 5-120 | OMe | NO$_2$ | CH$_2$CH$_2$OMe | H | |
| 5-121 | OMe | SO$_2$Me | CH$_2$CH$_2$OMe | H | |
| 5-122 | SO$_2$Me | Me | CH$_2$CH$_2$OMe | H | |
| 5-123 | SO$_2$Me | F | CH$_2$CH$_2$OMe | H | |
| 5-124 | SO$_2$Me | Cl | CH$_2$CH$_2$OMe | H | |
| 5-125 | SO$_2$Me | Br | CH$_2$CH$_2$OMe | H | |
| 5-126 | SO$_2$Me | I | CH$_2$CH$_2$OMe | H | |
| 5-127 | SO$_2$Me | CF$_3$ | CH$_2$CH$_2$OMe | H | |
| 5-128 | SO$_2$Me | CHF$_2$ | CH$_2$CH$_2$OMe | H | |
| 5-129 | SO$_2$Me | CF$_2$Cl | CH$_2$CH$_2$OMe | H | |
| 5-130 | SO$_2$Me | OMe | CH$_2$CH$_2$OMe | H | |
| 5-131 | SO$_2$Me | NO$_2$ | CH$_2$CH$_2$OMe | H | |
| 5-132 | SO$_2$Me | SO$_2$Me | CH$_2$CH$_2$OMe | H | |
| 5-133 | Me | Me | Me | CN | |
| 5-134 | Me | F | Me | CN | |
| 5-135 | Me | Cl | Me | CN | |
| 5-136 | Me | Br | Me | CN | |

TABLE 5-continued

Compounds according to the invention of the formula (I) in which Q is Q4, W is hydrogen, t = 1 and the other radicals have the meanings indicated in the table

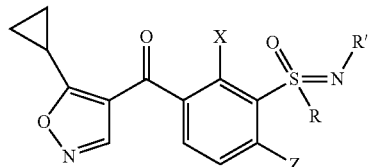

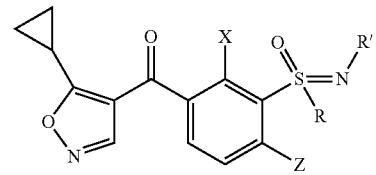

| No. | X | Z | R | R' | Physical data (1H NMR) |
|---|---|---|---|---|---|
| 5-137 | Me | I | Me | CN | |
| 5-138 | Me | CF$_3$ | Me | CN | |
| 5-139 | Me | CHF$_2$ | Me | CN | |
| 5-140 | Me | CF$_2$Cl | Me | CN | |
| 5-141 | Me | OMe | Me | CN | |
| 5-142 | Me | NO$_2$ | Me | CN | |
| 5-143 | Me | SO$_2$Me | Me | CN | |
| 5-144 | Cl | Me | Me | CN | |
| 5-145 | Cl | F | Me | CN | |
| 5-146 | Cl | Cl | Me | CN | |
| 5-147 | Cl | Br | Me | CN | |
| 5-148 | Cl | I | Me | CN | |
| 5-149 | Cl | CF$_3$ | Me | CN | |
| 5-150 | Cl | CHF$_2$ | Me | CN | |
| 5-151 | Cl | CF$_2$Cl | Me | CN | |
| 5-152 | Cl | OMe | Me | CN | |
| 5-153 | Cl | NO$_2$ | Me | CN | |
| 5-154 | Cl | SO$_2$Me | Me | CN | |
| 5-155 | OMe | Me | Me | CN | |
| 5-156 | OMe | F | Me | CN | |
| 5-157 | OMe | Cl | Me | CN | |
| 5-158 | OMe | Br | Me | CN | |
| 5-159 | OMe | I | Me | CN | |
| 5-160 | OMe | CF$_3$ | Me | CN | |
| 5-161 | OMe | CHF$_2$ | Me | CN | |
| 5-162 | OMe | CF$_2$Cl | Me | CN | |
| 5-163 | OMe | OMe | Me | CN | |
| 5-164 | OMe | NO$_2$ | Me | CN | |
| 5-165 | OMe | SO$_2$Me | Me | CN | |
| 5-166 | SO$_2$Me | Me | Me | CN | |
| 5-167 | SO$_2$Me | F | Me | CN | |
| 5-168 | SO$_2$Me | Cl | Me | CN | |
| 5-169 | SO$_2$Me | Br | Me | CN | |
| 5-170 | SO$_2$Me | I | Me | CN | |
| 5-171 | SO$_2$Me | CF$_3$ | Me | CN | |
| 5-172 | SO$_2$Me | CHF$_2$ | Me | CN | |
| 5-173 | SO$_2$Me | CF$_2$Cl | Me | CN | |
| 5-174 | SO$_2$Me | OMe | Me | CN | |
| 5-175 | SO$_2$Me | NO$_2$ | Me | CN | |
| 5-176 | SO$_2$Me | SO$_2$Me | Me | CN | |
| 5-177 | Me | Me | Et | CN | |
| 5-178 | Me | F | Et | CN | |
| 5-179 | Me | Cl | Et | CN | |
| 5-180 | Me | Br | Et | CN | |
| 5-181 | Me | I | Et | CN | |
| 5-182 | Me | CF$_3$ | Et | CN | |
| 5-183 | Me | CHF$_2$ | Et | CN | |
| 5-184 | Me | CF$_2$Cl | Et | CN | |
| 5-185 | Me | OMe | Et | CN | |
| 5-186 | Me | NO$_2$ | Et | CN | |
| 5-187 | Me | SO$_2$Me | Et | CN | |
| 5-188 | Cl | Me | Et | CN | |
| 5-189 | Cl | F | Et | CN | |
| 5-190 | Cl | Cl | Et | CN | |
| 5-191 | Cl | Br | Et | CN | |
| 5-192 | Cl | I | Et | CN | |
| 5-193 | Cl | CF$_3$ | Et | CN | |
| 5-194 | Cl | CHF$_2$ | Et | CN | |
| 5-195 | Cl | CF$_2$Cl | Et | CN | |
| 5-196 | Cl | OMe | Et | CN | |
| 5-197 | Cl | NO$_2$ | Et | CN | |
| 5-198 | Cl | SO$_2$Me | Et | CN | |
| 5-199 | OMe | Me | Et | CN | |
| 5-200 | OMe | F | Et | CN | |
| 5-201 | OMe | Cl | Et | CN | |
| 5-202 | OMe | Br | Et | CN | |
| 5-203 | OMe | I | Et | CN | |
| 5-204 | OMe | CF$_3$ | Et | CN | |
| 5-205 | OMe | CHF$_2$ | Et | CN | |
| 5-206 | OMe | CF$_2$Cl | Et | CN | |
| 5-207 | OMe | OMe | Et | CN | |
| 5-208 | OMe | NO$_2$ | Et | CN | |
| 5-209 | OMe | SO$_2$Me | Et | CN | |
| 5-210 | SO$_2$Me | Me | Et | CN | |
| 5-211 | SO$_2$Me | F | Et | CN | |
| 5-212 | SO$_2$Me | Cl | Et | CN | |
| 5-213 | SO$_2$Me | Br | Et | CN | |
| 5-214 | SO$_2$Me | I | Et | CN | |
| 5-215 | SO$_2$Me | CF$_3$ | Et | CN | |
| 5-216 | SO$_2$Me | CHF$_2$ | Et | CN | |
| 5-217 | SO$_2$Me | CF$_2$Cl | Et | CN | |
| 5-218 | SO$_2$Me | OMe | Et | CN | |
| 5-219 | SO$_2$Me | NO$_2$ | Et | CN | |
| 5-220 | SO$_2$Me | SO$_2$Me | Et | CN | |
| 5-221 | Me | Me | CH$_2$CH$_2$OMe | CN | |
| 5-222 | Me | F | CH$_2$CH$_2$OMe | CN | |
| 5-223 | Me | Cl | CH$_2$CH$_2$OMe | CN | |
| 5-224 | Me | Br | CH$_2$CH$_2$OMe | CN | |
| 5-225 | Me | I | CH$_2$CH$_2$OMe | CN | |
| 5-226 | Me | CF$_3$ | CH$_2$CH$_2$OMe | CN | |
| 5-227 | Me | CHF$_2$ | CH$_2$CH$_2$OMe | CN | |
| 5-228 | Me | CF$_2$Cl | CH$_2$CH$_2$OMe | CN | |
| 5-229 | Me | OMe | CH$_2$CH$_2$OMe | CN | |
| 5-230 | Me | NO$_2$ | CH$_2$CH$_2$OMe | CN | |
| 5-231 | Me | SO$_2$Me | CH$_2$CH$_2$OMe | CN | |
| 5-232 | Cl | Me | CH$_2$CH$_2$OMe | CN | |
| 5-233 | Cl | F | CH$_2$CH$_2$OMe | CN | |
| 5-234 | Cl | Cl | CH$_2$CH$_2$OMe | CN | |
| 5-235 | Cl | Br | CH$_2$CH$_2$OMe | CN | |
| 5-236 | Cl | I | CH$_2$CH$_2$OMe | CN | |
| 5-237 | Cl | CF$_3$ | CH$_2$CH$_2$OMe | CN | |
| 5-238 | Cl | CHF$_2$ | CH$_2$CH$_2$OMe | CN | |
| 5-239 | Cl | CF$_2$Cl | CH$_2$CH$_2$OMe | CN | |
| 5-240 | Cl | OMe | CH$_2$CH$_2$OMe | CN | |
| 5-241 | Cl | NO$_2$ | CH$_2$CH$_2$OMe | CN | |
| 5-242 | Cl | SO$_2$Me | CH$_2$CH$_2$OMe | CN | |
| 5-243 | OMe | Me | CH$_2$CH$_2$OMe | CN | |
| 5-244 | OMe | F | CH$_2$CH$_2$OMe | CN | |
| 5-245 | OMe | Cl | CH$_2$CH$_2$OMe | CN | |
| 5-246 | OMe | Br | CH$_2$CH$_2$OMe | CN | |
| 5-247 | OMe | I | CH$_2$CH$_2$OMe | CN | |
| 5-248 | OMe | CF$_3$ | CH$_2$CH$_2$OMe | CN | |
| 5-249 | OMe | CHF$_2$ | CH$_2$CH$_2$OMe | CN | |
| 5-250 | OMe | CF$_2$Cl | CH$_2$CH$_2$OMe | CN | |
| 5-251 | OMe | OMe | CH$_2$CH$_2$OMe | CN | |
| 5-252 | OMe | NO$_2$ | CH$_2$CH$_2$OMe | CN | |
| 5-253 | OMe | SO$_2$Me | CH$_2$CH$_2$OMe | CN | |
| 5-254 | SO$_2$Me | Me | CH$_2$CH$_2$OMe | CN | |
| 5-255 | SO$_2$Me | F | CH$_2$CH$_2$OMe | CN | |
| 5-256 | SO$_2$Me | Cl | CH$_2$CH$_2$OMe | CN | |
| 5-257 | SO$_2$Me | Br | CH$_2$CH$_2$OMe | CN | |
| 5-258 | SO$_2$Me | I | CH$_2$CH$_2$OMe | CN | |
| 5-259 | SO$_2$Me | CF$_3$ | CH$_2$CH$_2$OMe | CN | |
| 5-260 | SO$_2$Me | CHF$_2$ | CH$_2$CH$_2$OMe | CN | |
| 5-261 | SO$_2$Me | CF$_2$Cl | CH$_2$CH$_2$OMe | CN | |
| 5-262 | SO$_2$Me | OMe | CH$_2$CH$_2$OMe | CN | |
| 5-263 | SO$_2$Me | NO$_2$ | CH$_2$CH$_2$OMe | CN | |
| 5-264 | SO$_2$Me | SO$_2$Me | CH$_2$CH$_2$OMe | CN | |

TABLE 6

Compounds according to the invention of the formula (I) in which Q is Q5, W is hydrogen, t = 1 and the other radicals have the meanings indicated in the table

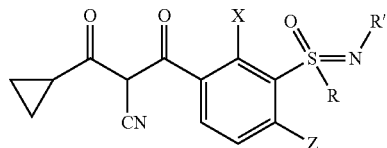

| No. | X | Z | R | R' | Physical data (1H NMR) |
|---|---|---|---|---|---|
| 6-1 | Me | Me | Me | H | |
| 6-2 | Me | F | Me | H | |
| 6-3 | Me | Cl | Me | H | |
| 6-4 | Me | Br | Me | H | |
| 6-5 | Me | I | Me | H | |
| 6-6 | Me | CF$_3$ | Me | H | |
| 6-7 | Me | CHF$_2$ | Me | H | |
| 6-8 | Me | CF$_2$Cl | Me | H | |
| 6-9 | Me | OMe | Me | H | |
| 6-10 | Me | NO$_2$ | Me | H | |
| 6-11 | Me | SO$_2$Me | Me | H | |
| 6-12 | Cl | Me | Me | H | |
| 6-13 | Cl | F | Me | H | |
| 6-14 | Cl | Cl | Me | H | |
| 6-15 | Cl | Br | Me | H | |
| 6-16 | Cl | I | Me | H | |
| 6-17 | Cl | CF$_3$ | Me | H | |
| 6-18 | Cl | CHF$_2$ | Me | H | |
| 6-19 | Cl | CF$_2$Cl | Me | H | |
| 6-20 | Cl | OMe | Me | H | |
| 6-21 | Cl | NO$_2$ | Me | H | |
| 6-22 | Cl | SO$_2$Me | Me | H | |
| 6-23 | OMe | Me | Me | H | |
| 6-24 | OMe | F | Me | H | |
| 6-25 | OMe | Cl | Me | H | |
| 6-26 | OMe | Br | Me | H | |
| 6-27 | OMe | I | Me | H | |
| 6-28 | OMe | CF$_3$ | Me | H | |
| 6-29 | OMe | CHF$_2$ | Me | H | |
| 6-30 | OMe | CF$_2$Cl | Me | H | |
| 6-31 | OMe | OMe | Me | H | |
| 6-32 | OMe | NO$_2$ | Me | H | |
| 6-33 | OMe | SO$_2$Me | Me | H | |
| 6-34 | SO$_2$Me | Me | Me | H | |
| 6-35 | SO$_2$Me | F | Me | H | |
| 6-36 | SO$_2$Me | Cl | Me | H | |
| 6-37 | SO$_2$Me | Br | Me | H | |
| 6-38 | SO$_2$Me | I | Me | H | |
| 6-39 | SO$_2$Me | CF$_3$ | Me | H | |
| 6-40 | SO$_2$Me | CHF$_2$ | Me | H | |
| 6-41 | SO$_2$Me | CF$_2$Cl | Me | H | |
| 6-42 | SO$_2$Me | OMe | Me | H | |
| 6-43 | SO$_2$Me | NO$_2$ | Me | H | |
| 6-44 | SO$_2$Me | SO$_2$Me | Me | H | |
| 6-45 | Me | Me | Et | H | |
| 6-46 | Me | F | Et | H | |
| 6-47 | Me | Cl | Et | H | |
| 6-48 | Me | Br | Et | H | |
| 6-49 | Me | I | Et | H | |
| 6-50 | Me | CF$_3$ | Et | H | |
| 6-51 | Me | CHF$_2$ | Et | H | |
| 6-52 | Me | CF$_2$Cl | Et | H | |
| 6-53 | Me | OMe | Et | H | |
| 6-54 | Me | NO$_2$ | Et | H | |
| 6-55 | Me | SO$_2$Me | Et | H | |
| 6-56 | Cl | Me | Et | H | |
| 6-57 | Cl | F | Et | H | |
| 6-58 | Cl | Cl | Et | H | |
| 6-59 | Cl | Br | Et | H | |
| 6-60 | Cl | I | Et | H | |
| 6-61 | Cl | CF$_3$ | Et | H | |
| 6-62 | Cl | CHF$_2$ | Et | H | |
| 6-63 | Cl | CF$_2$Cl | Et | H | |
| 6-64 | Cl | OMe | Et | H | |
| 6-65 | Cl | NO$_2$ | Et | H | |
| 6-66 | Cl | SO$_2$Me | Et | H | |

TABLE 6-continued

Compounds according to the invention of the formula (I) in which Q is Q5, W is hydrogen, t = 1 and the other radicals have the meanings indicated in the table

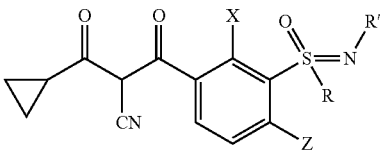

| No. | X | Z | R | R' | Physical data (1H NMR) |
|---|---|---|---|---|---|
| 6-67 | OMe | Me | Et | H | |
| 6-68 | OMe | F | Et | H | |
| 6-69 | OMe | Cl | Et | H | |
| 6-70 | OMe | Br | Et | H | |
| 6-71 | OMe | I | Et | H | |
| 6-72 | OMe | CF$_3$ | Et | H | |
| 6-73 | OMe | CHF$_2$ | Et | H | |
| 6-74 | OMe | CF$_2$Cl | Et | H | |
| 6-75 | OMe | OMe | Et | H | |
| 6-76 | OMe | NO$_2$ | Et | H | |
| 6-77 | OMe | SO$_2$Me | Et | H | |
| 6-78 | SO$_2$Me | Me | Et | H | |
| 6-79 | SO$_2$Me | F | Et | H | |
| 6-80 | SO$_2$Me | Cl | Et | H | |
| 6-81 | SO$_2$Me | Br | Et | H | |
| 6-82 | SO$_2$Me | I | Et | H | |
| 6-83 | SO$_2$Me | CF$_3$ | Et | H | |
| 6-84 | SO$_2$Me | CHF$_2$ | Et | H | |
| 6-85 | SO$_2$Me | CF$_2$Cl | Et | H | |
| 6-86 | SO$_2$Me | OMe | Et | H | |
| 6-87 | SO$_2$Me | NO$_2$ | Et | H | |
| 6-88 | SO$_2$Me | SO$_2$Me | Et | H | |
| 6-89 | Me | Me | CH$_2$CH$_2$OMe | H | |
| 6-90 | Me | F | CH$_2$CH$_2$OMe | H | |
| 6-91 | Me | Cl | CH$_2$CH$_2$OMe | H | |
| 6-92 | Me | Br | CH$_2$CH$_2$OMe | H | |
| 6-93 | Me | I | CH$_2$CH$_2$OMe | H | |
| 6-94 | Me | CF$_3$ | CH$_2$CH$_2$OMe | H | |
| 6-95 | Me | CHF$_2$ | CH$_2$CH$_2$OMe | H | |
| 6-96 | Me | CF$_2$Cl | CH$_2$CH$_2$OMe | H | |
| 6-97 | Me | OMe | CH$_2$CH$_2$OMe | H | |
| 6-98 | Me | NO$_2$ | CH$_2$CH$_2$OMe | H | |
| 6-99 | Me | SO$_2$Me | CH$_2$CH$_2$OMe | H | |
| 6-100 | Cl | Me | CH$_2$CH$_2$OMe | H | |
| 6-101 | Cl | F | CH$_2$CH$_2$OMe | H | |
| 6-102 | Cl | Cl | CH$_2$CH$_2$OMe | H | |
| 6-103 | Cl | Br | CH$_2$CH$_2$OMe | H | |
| 6-104 | Cl | I | CH$_2$CH$_2$OMe | H | |
| 6-105 | Cl | CF$_3$ | CH$_2$CH$_2$OMe | H | |
| 6-106 | Cl | CHF$_2$ | CH$_2$CH$_2$OMe | H | |
| 6-107 | Cl | CF$_2$Cl | CH$_2$CH$_2$OMe | H | |
| 6-108 | Cl | OMe | CH$_2$CH$_2$OMe | H | |
| 6-109 | Cl | NO$_2$ | CH$_2$CH$_2$OMe | H | |
| 6-110 | Cl | SO$_2$Me | CH$_2$CH$_2$OMe | H | |
| 6-111 | OMe | Me | CH$_2$CH$_2$OMe | H | |
| 6-112 | OMe | F | CH$_2$CH$_2$OMe | H | |
| 6-113 | OMe | Cl | CH$_2$CH$_2$OMe | H | |
| 6-114 | OMe | Br | CH$_2$CH$_2$OMe | H | |
| 6-115 | OMe | I | CH$_2$CH$_2$OMe | H | |
| 6-116 | OMe | CF$_3$ | CH$_2$CH$_2$OMe | H | |
| 6-117 | OMe | CHF$_2$ | CH$_2$CH$_2$OMe | H | |
| 6-118 | OMe | CF$_2$Cl | CH$_2$CH$_2$OMe | H | |
| 6-119 | OMe | OMe | CH$_2$CH$_2$OMe | H | |
| 6-120 | OMe | NO$_2$ | CH$_2$CH$_2$OMe | H | |
| 6-121 | OMe | SO$_2$Me | CH$_2$CH$_2$OMe | H | |
| 6-122 | SO$_2$Me | Me | CH$_2$CH$_2$OMe | H | |
| 6-123 | SO$_2$Me | F | CH$_2$CH$_2$OMe | H | |
| 6-124 | SO$_2$Me | Cl | CH$_2$CH$_2$OMe | H | |
| 6-125 | SO$_2$Me | Br | CH$_2$CH$_2$OMe | H | |
| 6-126 | SO$_2$Me | I | CH$_2$CH$_2$OMe | H | |
| 6-127 | SO$_2$Me | CF$_3$ | CH$_2$CH$_2$OMe | H | |
| 6-128 | SO$_2$Me | CHF$_2$ | CH$_2$CH$_2$OMe | H | |
| 6-129 | SO$_2$Me | CF$_2$Cl | CH$_2$CH$_2$OMe | H | |
| 6-130 | SO$_2$Me | OMe | CH$_2$CH$_2$OMe | H | |
| 6-131 | SO$_2$Me | NO$_2$ | CH$_2$CH$_2$OMe | H | |
| 6-132 | SO$_2$Me | SO$_2$Me | CH$_2$CH$_2$OMe | H | |

TABLE 6-continued

Compounds according to the invention of the formula (I) in which Q is Q5, W is hydrogen, t = 1 and the other radicals have the meanings indicated in the table

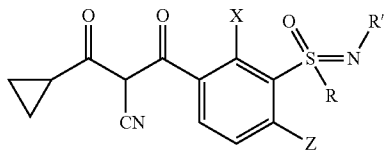

| No. | X | Z | R | R' | Physical data (1H NMR) |
|---|---|---|---|---|---|
| 6-133 | Me | Me | Me | CN | |
| 6-134 | Me | F | Me | CN | |
| 6-135 | Me | Cl | Me | CN | |
| 6-136 | Me | Br | Me | CN | |
| 6-137 | Me | I | Me | CN | |
| 6-138 | Me | CF$_3$ | Me | CN | |
| 6-139 | Me | CHF$_2$ | Me | CN | |
| 6-140 | Me | CF$_2$Cl | Me | CN | |
| 6-141 | Me | OMe | Me | CN | |
| 6-142 | Me | NO$_2$ | Me | CN | |
| 6-143 | Me | SO$_2$Me | Me | CN | |
| 6-144 | Cl | Me | Me | CN | |
| 6-145 | Cl | F | Me | CN | |
| 6-146 | Cl | Cl | Me | CN | |
| 6-147 | Cl | Br | Me | CN | |
| 6-148 | Cl | I | Me | CN | |
| 6-149 | Cl | CF$_3$ | Me | CN | |
| 6-150 | Cl | CHF$_2$ | Me | CN | |
| 6-151 | Cl | CF$_2$Cl | Me | CN | |
| 6-152 | Cl | OMe | Me | CN | |
| 6-153 | Cl | NO$_2$ | Me | CN | |
| 6-154 | Cl | SO$_2$Me | Me | CN | |
| 6-155 | OMe | Me | Me | CN | |
| 6-156 | OMe | F | Me | CN | |
| 6-157 | OMe | Cl | Me | CN | |
| 6-158 | OMe | Br | Me | CN | |
| 6-159 | OMe | I | Me | CN | |
| 6-160 | OMe | CF$_3$ | Me | CN | |
| 6-161 | OMe | CHF$_2$ | Me | CN | |
| 6-162 | OMe | CF$_2$Cl | Me | CN | |
| 6-163 | OMe | OMe | Me | CN | |
| 6-164 | OMe | NO$_2$ | Me | CN | |
| 6-165 | OMe | SO$_2$Me | Me | CN | |
| 6-166 | SO$_2$Me | Me | Me | CN | |
| 6-167 | SO$_2$Me | F | Me | CN | |
| 6-168 | SO$_2$Me | Cl | Me | CN | |
| 6-169 | SO$_2$Me | Br | Me | CN | |
| 6-170 | SO$_2$Me | I | Me | CN | |
| 6-171 | SO$_2$Me | CF$_3$ | Me | CN | |
| 6-172 | SO$_2$Me | CHF$_2$ | Me | CN | |
| 6-173 | SO$_2$Me | CF$_2$Cl | Me | CN | |
| 6-174 | SO$_2$Me | OMe | Me | CN | |
| 6-175 | SO$_2$Me | NO$_2$ | Me | CN | |
| 6-176 | SO$_2$Me | SO$_2$Me | Me | CN | |
| 6-177 | Me | Me | Et | CN | |
| 6-178 | Me | F | Et | CN | |
| 6-179 | Me | Cl | Et | CN | |
| 6-180 | Me | Br | Et | CN | |
| 6-181 | Me | I | Et | CN | |
| 6-182 | Me | CF$_3$ | Et | CN | |
| 6-183 | Me | CHF$_2$ | Et | CN | |
| 6-184 | Me | CF$_2$Cl | Et | CN | |
| 6-185 | Me | OMe | Et | CN | |
| 6-186 | Me | NO$_2$ | Et | CN | |
| 6-187 | Me | SO$_2$Me | Et | CN | |
| 6-188 | Cl | Me | Et | CN | |
| 6-189 | Cl | F | Et | CN | |
| 6-190 | Cl | Cl | Et | CN | |
| 6-191 | Cl | Br | Et | CN | |
| 6-192 | Cl | I | Et | CN | |
| 6-193 | Cl | CF$_3$ | Et | CN | |
| 6-194 | Cl | CHF$_2$ | Et | CN | |
| 6-195 | Cl | CF$_2$Cl | Et | CN | |
| 6-196 | Cl | OMe | Et | CN | |
| 6-197 | Cl | NO$_2$ | Et | CN | |
| 6-198 | Cl | SO$_2$Me | Et | CN | |

TABLE 6-continued

Compounds according to the invention of the formula (I) in which Q is Q5, W is hydrogen, t = 1 and the other radicals have the meanings indicated in the table

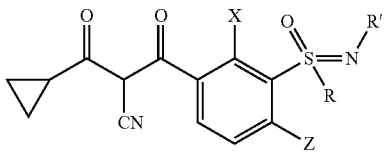

| No. | X | Z | R | R' | Physical data (1H NMR) |
|---|---|---|---|---|---|
| 6-199 | OMe | Me | Et | CN | |
| 6-200 | OMe | F | Et | CN | |
| 6-201 | OMe | Cl | Et | CN | |
| 6-202 | OMe | Br | Et | CN | |
| 6-203 | OMe | I | Et | CN | |
| 6-204 | OMe | CF$_3$ | Et | CN | |
| 6-205 | OMe | CHF$_2$ | Et | CN | |
| 6-206 | OMe | CF$_2$Cl | Et | CN | |
| 6-207 | OMe | OMe | Et | CN | |
| 6-208 | OMe | NO$_2$ | Et | CN | |
| 6-209 | OMe | SO$_2$Me | Et | CN | |
| 6-210 | SO$_2$Me | Me | Et | CN | |
| 6-211 | SO$_2$Me | F | Et | CN | |
| 6-212 | SO$_2$Me | Cl | Et | CN | |
| 6-213 | SO$_2$Me | Br | Et | CN | |
| 6-214 | SO$_2$Me | I | Et | CN | |
| 6-215 | SO$_2$Me | CF$_3$ | Et | CN | |
| 6-216 | SO$_2$Me | CHF$_2$ | Et | CN | |
| 6-217 | SO$_2$Me | CF$_2$Cl | Et | CN | |
| 6-218 | SO$_2$Me | OMe | Et | CN | |
| 6-219 | SO$_2$Me | NO$_2$ | Et | CN | |
| 6-220 | SO$_2$Me | SO$_2$Me | Et | CN | |
| 6-221 | Me | Me | CH$_2$CH$_2$OMe | CN | |
| 6-222 | Me | F | CH$_2$CH$_2$OMe | CN | |
| 6-223 | Me | Cl | CH$_2$CH$_2$OMe | CN | |
| 6-224 | Me | Br | CH$_2$CH$_2$OMe | CN | |
| 6-225 | Me | I | CH$_2$CH$_2$OMe | CN | |
| 6-226 | Me | CF$_3$ | CH$_2$CH$_2$OMe | CN | |
| 6-227 | Me | CHF$_2$ | CH$_2$CH$_2$OMe | CN | |
| 6-228 | Me | CF$_2$Cl | CH$_2$CH$_2$OMe | CN | |
| 6-229 | Me | OMe | CH$_2$CH$_2$OMe | CN | |
| 6-230 | Me | NO$_2$ | CH$_2$CH$_2$OMe | CN | |
| 6-231 | Me | SO$_2$Me | CH$_2$CH$_2$OMe | CN | |
| 6-232 | Cl | Me | CH$_2$CH$_2$OMe | CN | |
| 6-233 | Cl | F | CH$_2$CH$_2$OMe | CN | |
| 6-234 | Cl | Cl | CH$_2$CH$_2$OMe | CN | |
| 6-235 | Cl | Br | CH$_2$CH$_2$OMe | CN | |
| 6-236 | Cl | I | CH$_2$CH$_2$OMe | CN | |
| 6-237 | Cl | CF$_3$ | CH$_2$CH$_2$OMe | CN | |
| 6-238 | Cl | CHF$_2$ | CH$_2$CH$_2$OMe | CN | |
| 6-239 | Cl | CF$_2$Cl | CH$_2$CH$_2$OMe | CN | |
| 6-240 | Cl | OMe | CH$_2$CH$_2$OMe | CN | |
| 6-241 | Cl | NO$_2$ | CH$_2$CH$_2$OMe | CN | |
| 6-242 | Cl | SO$_2$Me | CH$_2$CH$_2$OMe | CN | |
| 6-243 | OMe | Me | CH$_2$CH$_2$OMe | CN | |
| 6-244 | OMe | F | CH$_2$CH$_2$OMe | CN | |
| 6-245 | OMe | Cl | CH$_2$CH$_2$OMe | CN | |
| 6-246 | OMe | Br | CH$_2$CH$_2$OMe | CN | |
| 6-247 | OMe | I | CH$_2$CH$_2$OMe | CN | |
| 6-248 | OMe | CF$_3$ | CH$_2$CH$_2$OMe | CN | |
| 6-249 | OMe | CHF$_2$ | CH$_2$CH$_2$OMe | CN | |
| 6-250 | OMe | CF$_2$Cl | CH$_2$CH$_2$OMe | CN | |
| 6-251 | OMe | OMe | CH$_2$CH$_2$OMe | CN | |
| 6-252 | OMe | NO$_2$ | CH$_2$CH$_2$OMe | CN | |
| 6-253 | OMe | SO$_2$Me | CH$_2$CH$_2$OMe | CN | |
| 6-254 | SO$_2$Me | Me | CH$_2$CH$_2$OMe | CN | |
| 6-255 | SO$_2$Me | F | CH$_2$CH$_2$OMe | CN | |
| 6-256 | SO$_2$Me | Cl | CH$_2$CH$_2$OMe | CN | |
| 6-257 | SO$_2$Me | Br | CH$_2$CH$_2$OMe | CN | |
| 6-258 | SO$_2$Me | I | CH$_2$CH$_2$OMe | CN | |
| 6-259 | SO$_2$Me | CF$_3$ | CH$_2$CH$_2$OMe | CN | |
| 6-260 | SO$_2$Me | CHF$_2$ | CH$_2$CH$_2$OMe | CN | |
| 6-261 | SO$_2$Me | CF$_2$Cl | CH$_2$CH$_2$OMe | CN | |

TABLE 6-continued

Compounds according to the invention of the formula (I) in which Q is Q5, W is hydrogen, t = 1 and the other radicals have the meanings indicated in the table

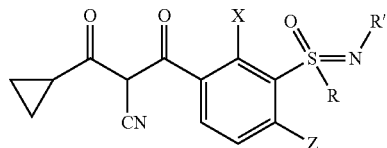

| No. | X | Z | R | R' | Physical data (1H NMR) |
|---|---|---|---|---|---|
| 6-262 | SO₂Me | OMe | CH₂CH₂OMe | CN | |
| 6-263 | SO₂Me | NO₂ | CH₂CH₂OMe | CN | |
| 6-264 | SO₂Me | SO₂Me | CH₂CH₂OMe | CN | |

TABLE 7

Compounds according to the invention of the formula (I) in the form of the sodium salts in which Q is Q3, $R^i$ is methyl, $R^k$ and W are each hydrogen, t = 1 and the other radicals have the meanings indicated in the table

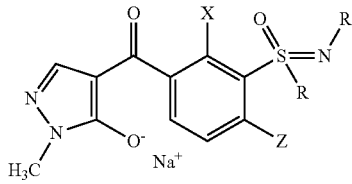

| No. | X | Z | R | R' | Physical data (1H NMR) |
|---|---|---|---|---|---|
| 7-1 | Me | Me | Me | H | |
| 7-2 | Me | Cl | Me | H | |
| 7-3 | Me | CF₃ | Me | H | |
| 7-4 | Me | CHF₂ | Me | H | |
| 7-5 | Cl | Me | Me | H | |
| 7-6 | Cl | Cl | Me | H | |
| 7-7 | Cl | CF₃ | Me | H | |
| 7-8 | Cl | CHF₂ | Me | H | |
| 7-9 | OMe | Me | Me | H | |
| 7-10 | OMe | Cl | Me | H | |
| 7-11 | OMe | CF₃ | Me | H | |
| 7-12 | OMe | CHF₂ | Me | H | |
| 7-13 | SO₂Me | Me | Me | H | |
| 7-14 | SO₂Me | Cl | Me | H | |
| 7-15 | SO₂Me | CF₃ | Me | H | |
| 7-16 | SO₂Me | CHF₂ | Me | H | |
| 7-17 | Me | Me | Et | H | |
| 7-18 | Me | Cl | Et | H | |
| 7-19 | Me | CF₃ | Et | H | |
| 7-20 | Me | CHF₂ | Et | H | |
| 7-21 | Cl | Me | Et | H | |
| 7-22 | Cl | Cl | Et | H | |
| 7-23 | Cl | CF₃ | Et | H | |
| 7-24 | Cl | CHF₂ | Et | H | |
| 7-25 | OMe | Me | Et | H | |
| 7-26 | OMe | Cl | Et | H | |
| 7-27 | OMe | CF₃ | Et | H | |
| 7-28 | OMe | CHF₂ | Et | H | |
| 7-29 | SO₂Me | Me | Et | H | |
| 7-30 | SO₂Me | Cl | Et | H | |
| 7-31 | SO₂Me | CF₃ | Et | H | |
| 7-32 | SO₂Me | CHF₂ | Et | H | |
| 7-33 | Me | Me | CH₂CH₂OMe | H | |
| 7-34 | Me | Cl | CH₂CH₂OMe | H | |
| 7-35 | Me | CF₃ | CH₂CH₂OMe | H | |
| 7-36 | Me | CHF₂ | CH₂CH₂OMe | H | |
| 7-37 | Cl | Me | CH₂CH₂OMe | H | |
| 7-38 | Cl | Cl | CH₂CH₂OMe | H | |
| 7-39 | Cl | CF₃ | CH₂CH₂OMe | H | |
| 7-40 | Cl | CHF₂ | CH₂CH₂OMe | H | |
| 7-41 | OMe | Me | CH₂CH₂OMe | H | |

TABLE 7-continued

Compounds according to the invention of the formula (I) in the form of the sodium salts in which Q is Q3, $R^i$ is methyl, $R^k$ and W are each hydrogen, t = 1 and the other radicals have the meanings indicated in the table

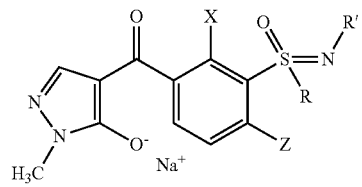

| No. | X | Z | R | R' | Physical data (1H NMR) |
|---|---|---|---|---|---|
| 7-42 | OMe | Cl | CH₂CH₂OMe | H | |
| 7-43 | OMe | CF₃ | CH₂CH₂OMe | H | |
| 7-44 | OMe | CHF₂ | CH₂CH₂OMe | H | |
| 7-45 | SO₂Me | Me | CH₂CH₂OMe | H | |
| 7-46 | SO₂Me | Cl | CH₂CH₂OMe | H | |
| 7-47 | SO₂Me | CF₃ | CH₂CH₂OMe | H | |
| 7-48 | SO₂Me | CHF₂ | CH₂CH₂OMe | H | |
| 7-49 | Me | Me | Me | CN | |
| 7-50 | Me | Cl | Me | CN | |
| 7-51 | Me | CF₃ | Me | CN | |
| 7-52 | Me | CHF₂ | Me | CN | |
| 7-53 | Cl | Me | Me | CN | |
| 7-54 | Cl | Cl | Me | CN | |
| 7-55 | Cl | CF₃ | Me | CN | |
| 7-56 | Cl | CHF₂ | Me | CN | |
| 7-57 | OMe | Me | Me | CN | |
| 7-58 | OMe | Cl | Me | CN | |
| 7-59 | OMe | CF₃ | Me | CN | |
| 7-60 | OMe | CHF₂ | Me | CN | |
| 7-61 | SO₂Me | Me | Me | CN | |
| 7-62 | SO₂Me | Cl | Me | CN | |
| 7-63 | SO₂Me | CF₃ | Me | CN | |
| 7-64 | SO₂Me | CHF₂ | Me | CN | |
| 7-65 | Me | Me | Et | CN | |
| 7-66 | Me | Cl | Et | CN | |
| 7-67 | Me | CF₃ | Et | CN | |
| 7-68 | Me | CHF₂ | Et | CN | |
| 7-69 | Cl | Me | Et | CN | |
| 7-70 | Cl | Cl | Et | CN | |
| 7-71 | Cl | CF₃ | Et | CN | |
| 7-72 | Cl | CHF₂ | Et | CN | |
| 7-73 | OMe | Me | Et | CN | |
| 7-74 | OMe | Cl | Et | CN | |
| 7-75 | OMe | CF₃ | Et | CN | |
| 7-76 | OMe | CHF₂ | Et | CN | |
| 7-77 | SO₂Me | Me | Et | CN | |
| 7-78 | SO₂Me | Cl | Et | CN | |
| 7-79 | SO₂Me | CF₃ | Et | CN | |
| 7-80 | SO₂Me | CHF₂ | Et | CN | |
| 7-81 | Me | Me | CH₂CH₂OMe | CN | |
| 7-82 | Me | Cl | CH₂CH₂OMe | CN | |
| 7-83 | Me | CF₃ | CH₂CH₂OMe | CN | |
| 7-84 | Me | CHF₂ | CH₂CH₂OMe | CN | |
| 7-85 | Cl | Me | CH₂CH₂OMe | CN | |
| 7-86 | Cl | Cl | CH₂CH₂OMe | CN | |
| 7-87 | Cl | CF₃ | CH₂CH₂OMe | CN | |
| 7-88 | Cl | CHF₂ | CH₂CH₂OMe | CN | |
| 7-89 | OMe | Me | CH₂CH₂OMe | CN | |
| 7-90 | OMe | Cl | CH₂CH₂OMe | CN | |
| 7-91 | OMe | CF₃ | CH₂CH₂OMe | CN | |
| 7-92 | OMe | CHF₂ | CH₂CH₂OMe | CN | |
| 7-93 | SO₂Me | Me | CH₂CH₂OMe | CN | |
| 7-94 | SO₂Me | Cl | CH₂CH₂OMe | CN | |
| 7-95 | SO₂Me | CF₃ | CH₂CH₂OMe | CN | |
| 7-96 | SO₂Me | CHF₂ | CH₂CH₂OMe | CN | |

TABLE 8

Compounds according to the invention of the formula (I) in which Q is Q1, $R^a$ is a hydroxyl group, the radicals $R^b$, $R^c$, $R^d$, $R^e$, $R^f$, $R^g$ and W are each hydrogen, t = 0 and the other radicals have the meanings indicated in the table

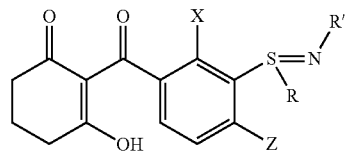

| No. | X | Z | R | R' | Physical data ($^1$H NMR) |
|---|---|---|---|---|---|
| 8-1 | Me | Me | Me | H | |
| 8-2 | Me | F | Me | H | |
| 8-3 | Me | Cl | Me | H | |
| 8-4 | Me | Br | Me | H | |
| 8-5 | Me | I | Me | H | |
| 8-6 | Me | CF$_3$ | Me | H | |
| 8-7 | Me | CHF$_2$ | Me | H | |
| 8-8 | Me | CF$_2$Cl | Me | H | |
| 8-9 | Me | OMe | Me | H | |
| 8-10 | Me | NO$_2$ | Me | H | |
| 8-11 | Me | SO$_2$Me | Me | H | |
| 8-12 | Cl | Me | Me | H | |
| 8-13 | Cl | F | Me | H | |
| 8-14 | Cl | Cl | Me | H | |
| 8-15 | Cl | Br | Me | H | |
| 8-16 | Cl | I | Me | H | |
| 8-17 | Cl | CF$_3$ | Me | H | |
| 8-18 | Cl | CHF$_2$ | Me | H | |
| 8-19 | Cl | CF$_2$Cl | Me | H | |
| 8-20 | Cl | OMe | Me | H | |
| 8-21 | Cl | NO$_2$ | Me | H | |
| 8-22 | Cl | SO$_2$Me | Me | H | |
| 8-23 | OMe | Me | Me | H | |
| 8-24 | OMe | F | Me | H | |
| 8-25 | OMe | Cl | Me | H | |
| 8-26 | OMe | Br | Me | H | |
| 8-27 | OMe | I | Me | H | |
| 8-28 | OMe | CF$_3$ | Me | H | |
| 8-29 | OMe | CHF$_2$ | Me | H | |
| 8-30 | OMe | CF$_2$Cl | Me | H | |
| 8-31 | OMe | OMe | Me | H | |
| 8-32 | OMe | NO$_2$ | Me | H | |
| 8-33 | OMe | SO$_2$Me | Me | H | |
| 8-34 | SO$_2$Me | Me | Me | H | |
| 8-35 | SO$_2$Me | F | Me | H | |
| 8-36 | SO$_2$Me | Cl | Me | H | |
| 8-37 | SO$_2$Me | Br | Me | H | |
| 8-38 | SO$_2$Me | I | Me | H | |
| 8-39 | SO$_2$Me | CF$_3$ | Me | H | |
| 8-40 | SO$_2$Me | CHF$_2$ | Me | H | |
| 8-41 | SO$_2$Me | CF$_2$Cl | Me | H | |
| 8-42 | SO$_2$Me | OMe | Me | H | |
| 8-43 | SO$_2$Me | NO$_2$ | Me | H | |
| 8-44 | SO$_2$Me | SO$_2$Me | Me | H | |
| 8-45 | Me | Me | Et | H | |
| 8-46 | Me | F | Et | H | |
| 8-47 | Me | Cl | Et | H | |
| 8-48 | Me | Br | Et | H | |
| 8-49 | Me | I | Et | H | |
| 8-50 | Me | CF$_3$ | Et | H | |
| 8-51 | Me | CHF$_2$ | Et | H | |
| 8-52 | Me | CF$_2$Cl | Et | H | |
| 8-53 | Me | OMe | Et | H | |
| 8-54 | Me | NO$_2$ | Et | H | |
| 8-55 | Me | SO$_2$Me | Et | H | |
| 8-56 | Cl | Me | Et | H | |
| 8-57 | Cl | F | Et | H | |
| 8-58 | Cl | Cl | Et | H | |
| 8-59 | Cl | Br | Et | H | |
| 8-60 | Cl | I | Et | H | |
| 8-61 | Cl | CF$_3$ | Et | H | |
| 8-62 | Cl | CHF$_2$ | Et | H | |
| 8-63 | Cl | CF$_2$Cl | Et | H | |
| 8-64 | Cl | OMe | Et | H | |
| 8-65 | Cl | NO$_2$ | Et | H | |

TABLE 8-continued

Compounds according to the invention of the formula (I) in which Q is Q1, $R^a$ is a hydroxyl group, the radicals $R^b$, $R^c$, $R^d$, $R^e$, $R^f$, $R^g$ and W are each hydrogen, t = 0 and the other radicals have the meanings indicated in the table

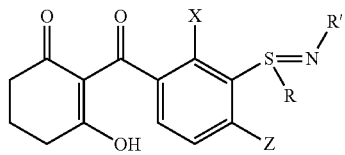

| No. | X | Z | R | R' | Physical data ($^1$H NMR) |
|---|---|---|---|---|---|
| 8-66 | Cl | SO$_2$Me | Et | H | |
| 8-67 | OMe | Me | Et | H | |
| 8-68 | OMe | F | Et | H | |
| 8-69 | OMe | Cl | Et | H | |
| 8-70 | OMe | Br | Et | H | |
| 8-71 | OMe | I | Et | H | |
| 8-72 | OMe | CF$_3$ | Et | H | |
| 8-73 | OMe | CHF$_2$ | Et | H | |
| 8-74 | OMe | CF$_2$Cl | Et | H | |
| 8-75 | OMe | OMe | Et | H | |
| 8-76 | OMe | NO$_2$ | Et | H | |
| 8-77 | OMe | SO$_2$Me | Et | H | |
| 8-78 | SO$_2$Me | Me | Et | H | |
| 8-79 | SO$_2$Me | F | Et | H | |
| 8-80 | SO$_2$Me | Cl | Et | H | |
| 8-81 | SO$_2$Me | Br | Et | H | |
| 8-82 | SO$_2$Me | I | Et | H | |
| 8-83 | SO$_2$Me | CF$_3$ | Et | H | |
| 8-84 | SO$_2$Me | CHF$_2$ | Et | H | |
| 8-85 | SO$_2$Me | CF$_2$Cl | Et | H | |
| 8-86 | SO$_2$Me | OMe | Et | H | |
| 8-87 | SO$_2$Me | NO$_2$ | Et | H | |
| 8-88 | SO$_2$Me | SO$_2$Me | Et | H | |
| 8-89 | Me | Me | CH$_2$CH$_2$OMe | H | |
| 8-90 | Me | F | CH$_2$CH$_2$OMe | H | |
| 8-91 | Me | Cl | CH$_2$CH$_2$OMe | H | |
| 8-92 | Me | Br | CH$_2$CH$_2$OMe | H | |
| 8-93 | Me | I | CH$_2$CH$_2$OMe | H | |
| 8-94 | Me | CF$_3$ | CH$_2$CH$_2$OMe | H | |
| 8-95 | Me | CHF$_2$ | CH$_2$CH$_2$OMe | H | |
| 8-96 | Me | CF$_2$Cl | CH$_2$CH$_2$OMe | H | |
| 8-97 | Me | OMe | CH$_2$CH$_2$OMe | H | |
| 8-98 | Me | NO$_2$ | CH$_2$CH$_2$OMe | H | |
| 8-99 | Me | SO$_2$Me | CH$_2$CH$_2$OMe | H | |
| 8-100 | Cl | Me | CH$_2$CH$_2$OMe | H | |
| 8-101 | Cl | F | CH$_2$CH$_2$OMe | H | |
| 8-102 | Cl | Cl | CH$_2$CH$_2$OMe | H | |
| 8-103 | Cl | Br | CH$_2$CH$_2$OMe | H | |
| 8-104 | Cl | I | CH$_2$CH$_2$OMe | H | |
| 8-105 | Cl | CF$_3$ | CH$_2$CH$_2$OMe | H | |
| 8-106 | Cl | CHF$_2$ | CH$_2$CH$_2$OMe | H | |
| 8-107 | Cl | CF$_2$Cl | CH$_2$CH$_2$OMe | H | |
| 8-108 | Cl | OMe | CH$_2$CH$_2$OMe | H | |
| 8-109 | Cl | NO$_2$ | CH$_2$CH$_2$OMe | H | |
| 8-110 | Cl | SO$_2$Me | CH$_2$CH$_2$OMe | H | |
| 8-111 | OMe | Me | CH$_2$CH$_2$OMe | H | |
| 8-112 | OMe | F | CH$_2$CH$_2$OMe | H | |
| 8-113 | OMe | Cl | CH$_2$CH$_2$OMe | H | |
| 8-114 | OMe | Br | CH$_2$CH$_2$OMe | H | |
| 8-115 | OMe | I | CH$_2$CH$_2$OMe | H | |
| 8-116 | OMe | CF$_3$ | CH$_2$CH$_2$OMe | H | |
| 8-117 | OMe | CHF$_2$ | CH$_2$CH$_2$OMe | H | |
| 8-118 | OMe | CF$_2$Cl | CH$_2$CH$_2$OMe | H | |
| 8-119 | OMe | OMe | CH$_2$CH$_2$OMe | H | |
| 8-120 | OMe | NO$_2$ | CH$_2$CH$_2$OMe | H | |
| 8-121 | OMe | SO$_2$Me | CH$_2$CH$_2$OMe | H | |
| 8-122 | SO$_2$Me | Me | CH$_2$CH$_2$OMe | H | |
| 8-123 | SO$_2$Me | F | CH$_2$CH$_2$OMe | H | |
| 8-124 | SO$_2$Me | Cl | CH$_2$CH$_2$OMe | H | |
| 8-125 | SO$_2$Me | Br | CH$_2$CH$_2$OMe | H | |
| 8-126 | SO$_2$Me | I | CH$_2$CH$_2$OMe | H | |
| 8-127 | SO$_2$Me | CF$_3$ | CH$_2$CH$_2$OMe | H | |
| 8-128 | SO$_2$Me | CHF$_2$ | CH$_2$CH$_2$OMe | H | |
| 8-129 | SO$_2$Me | CF$_2$Cl | CH$_2$CH$_2$OMe | H | |
| 8-130 | SO$_2$Me | OMe | CH$_2$CH$_2$OMe | H | |

TABLE 8-continued

Compounds according to the invention of the formula (I) in which Q is Q1, $R^a$ is a hydroxyl group, the radicals $R^b, R^c, R^d, R^e, R^f, R^g$ and W are each hydrogen, t = 0 and the other radicals have the meanings indicated in the table

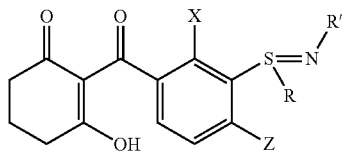

| No. | X | Z | R | R' | Physical data ($^1$H NMR) |
|---|---|---|---|---|---|
| 8-131 | SO$_2$Me | NO$_2$ | CH$_2$CH$_2$OMe | H | |
| 8-132 | SO$_2$Me | SO$_2$Me | CH$_2$CH$_2$OMe | H | |
| 8-133 | Me | Me | Me | CN | |
| 8-134 | Me | F | Me | CN | |
| 8-135 | Me | Cl | Me | CN | |
| 8-136 | Me | Br | Me | CN | |
| 8-137 | Me | I | Me | CN | |
| 8-138 | Me | CF$_3$ | Me | CN | |
| 8-139 | Me | CHF$_2$ | Me | CN | |
| 8-140 | Me | CF$_2$Cl | Me | CN | |
| 8-141 | Me | OMe | Me | CN | |
| 8-142 | Me | NO$_2$ | Me | CN | |
| 8-143 | Me | SO$_2$Me | Me | CN | |
| 8-144 | Cl | Me | Me | CN | |
| 8-145 | Cl | F | Me | CN | |
| 8-146 | Cl | Cl | Me | CN | |
| 8-147 | Cl | Br | Me | CN | |
| 8-148 | Cl | I | Me | CN | |
| 8-149 | Cl | CF$_3$ | Me | CN | |
| 8-150 | Cl | CHF$_2$ | Me | CN | |
| 8-151 | Cl | CF$_2$Cl | Me | CN | |
| 8-152 | Cl | OMe | Me | CN | |
| 8-153 | Cl | NO$_2$ | Me | CN | |
| 8-154 | Cl | SO$_2$Me | Me | CN | |
| 8-155 | OMe | Me | Me | CN | |
| 8-156 | OMe | F | Me | CN | |
| 8-157 | OMe | Cl | Me | CN | |
| 8-158 | OMe | Br | Me | CN | |
| 8-159 | OMe | I | Me | CN | |
| 8-160 | OMe | CF$_3$ | Me | CN | |
| 8-161 | OMe | CHF$_2$ | Me | CN | |
| 8-162 | OMe | CF$_2$Cl | Me | CN | |
| 8-163 | OMe | OMe | Me | CN | |
| 8-164 | OMe | NO$_2$ | Me | CN | |
| 8-165 | OMe | SO$_2$Me | Me | CN | |
| 8-166 | SO$_2$Me | Me | Me | CN | |
| 8-167 | SO$_2$Me | F | Me | CN | |
| 8-168 | SO$_2$Me | Cl | Me | CN | |
| 8-169 | SO$_2$Me | Br | Me | CN | |
| 8-170 | SO$_2$Me | I | Me | CN | |
| 8-171 | SO$_2$Me | CF$_3$ | Me | CN | |
| 8-172 | SO$_2$Me | CHF$_2$ | Me | CN | |
| 8-173 | SO$_2$Me | CF$_2$Cl | Me | CN | |
| 8-174 | SO$_2$Me | OMe | Me | CN | |
| 8-175 | SO$_2$Me | NO$_2$ | Me | CN | |
| 8-176 | SO$_2$Me | SO$_2$Me | Me | CN | |
| 8-177 | Me | Me | Et | CN | |
| 8-178 | Me | F | Et | CN | |
| 8-179 | Me | Cl | Et | CN | |
| 8-180 | Me | Br | Et | CN | |
| 8-181 | Me | I | Et | CN | |
| 8-182 | Me | CF$_3$ | Et | CN | |
| 8-183 | Me | CHF$_2$ | Et | CN | |
| 8-184 | Me | CF$_2$Cl | Et | CN | |
| 8-185 | Me | OMe | Et | CN | |
| 8-186 | Me | NO$_2$ | Et | CN | |
| 8-187 | Me | SO$_2$Me | Et | CN | |
| 8-188 | Cl | Me | Et | CN | |
| 8-189 | Cl | F | Et | CN | |
| 8-190 | Cl | Cl | Et | CN | |
| 8-191 | Cl | Br | Et | CN | |
| 8-192 | Cl | I | Et | CN | |
| 8-193 | Cl | CF$_3$ | Et | CN | |
| 8-194 | Cl | CHF$_2$ | Et | CN | |
| 8-195 | Cl | CF$_2$Cl | Et | CN | |

TABLE 8-continued

Compounds according to the invention of the formula (I) in which Q is Q1, $R^a$ is a hydroxyl group, the radicals $R^b, R^c, R^d, R^e, R^f, R^g$ and W are each hydrogen, t = 0 and the other radicals have the meanings indicated in the table

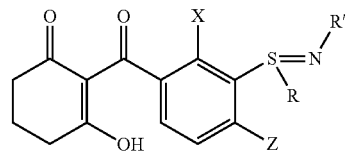

| No. | X | Z | R | R' | Physical data ($^1$H NMR) |
|---|---|---|---|---|---|
| 8-196 | Cl | OMe | Et | CN | |
| 8-197 | Cl | NO$_2$ | Et | CN | |
| 8-198 | Cl | SO$_2$Me | Et | CN | |
| 8-199 | OMe | Me | Et | CN | |
| 8-200 | OMe | F | Et | CN | |
| 8-201 | OMe | Cl | Et | CN | |
| 8-202 | OMe | Br | Et | CN | |
| 8-203 | OMe | I | Et | CN | |
| 8-204 | OMe | CF$_3$ | Et | CN | |
| 8-205 | OMe | CHF$_2$ | Et | CN | |
| 8-206 | OMe | CF$_2$Cl | Et | CN | |
| 8-207 | OMe | OMe | Et | CN | |
| 8-208 | OMe | NO$_2$ | Et | CN | |
| 8-209 | OMe | SO$_2$Me | Et | CN | |
| 8-210 | SO$_2$Me | Me | Et | CN | |
| 8-211 | SO$_2$Me | F | Et | CN | |
| 8-212 | SO$_2$Me | Cl | Et | CN | |
| 8-213 | SO$_2$Me | Br | Et | CN | |
| 8-214 | SO$_2$Me | I | Et | CN | |
| 8-215 | SO$_2$Me | CF$_3$ | Et | CN | |
| 8-216 | SO$_2$Me | CHF$_2$ | Et | CN | |
| 8-217 | SO$_2$Me | CF$_2$Cl | Et | CN | |
| 8-218 | SO$_2$Me | OMe | Et | CN | |
| 8-219 | SO$_2$Me | NO$_2$ | Et | CN | |
| 8-220 | SO$_2$Me | SO$_2$Me | Et | CN | |
| 8-221 | Me | Me | CH$_2$CH$_2$OMe | CN | |
| 8-222 | Me | F | CH$_2$CH$_2$OMe | CN | |
| 8-223 | Me | Cl | CH$_2$CH$_2$OMe | CN | |
| 8-224 | Me | Br | CH$_2$CH$_2$OMe | CN | |
| 8-225 | Me | I | CH$_2$CH$_2$OMe | CN | |
| 8-226 | Me | CF$_3$ | CH$_2$CH$_2$OMe | CN | |
| 8-227 | Me | CHF$_2$ | CH$_2$CH$_2$OMe | CN | |
| 8-228 | Me | CF$_2$Cl | CH$_2$CH$_2$OMe | CN | |
| 8-229 | Me | OMe | CH$_2$CH$_2$OMe | CN | |
| 8-230 | Me | NO$_2$ | CH$_2$CH$_2$OMe | CN | |
| 8-231 | Me | SO$_2$Me | CH$_2$CH$_2$OMe | CN | |
| 8-232 | Cl | Me | CH$_2$CH$_2$OMe | CN | |
| 8-233 | Cl | F | CH$_2$CH$_2$OMe | CN | |
| 8-234 | Cl | Cl | CH$_2$CH$_2$OMe | CN | |
| 8-235 | Cl | Br | CH$_2$CH$_2$OMe | CN | |
| 8-236 | Cl | I | CH$_2$CH$_2$OMe | CN | |
| 8-237 | Cl | CF$_3$ | CH$_2$CH$_2$OMe | CN | |
| 8-238 | Cl | CHF$_2$ | CH$_2$CH$_2$OMe | CN | |
| 8-239 | Cl | CF$_2$Cl | CH$_2$CH$_2$OMe | CN | |
| 8-240 | Cl | OMe | CH$_2$CH$_2$OMe | CN | |
| 8-241 | Cl | NO$_2$ | CH$_2$CH$_2$OMe | CN | |
| 8-242 | Cl | SO$_2$Me | CH$_2$CH$_2$OMe | CN | |
| 8-243 | OMe | Me | CH$_2$CH$_2$OMe | CN | |
| 8-244 | OMe | F | CH$_2$CH$_2$OMe | CN | |
| 8-245 | OMe | Cl | CH$_2$CH$_2$OMe | CN | |
| 8-246 | OMe | Br | CH$_2$CH$_2$OMe | CN | |
| 8-247 | OMe | I | CH$_2$CH$_2$OMe | CN | |
| 8-248 | OMe | CF$_3$ | CH$_2$CH$_2$OMe | CN | |
| 8-249 | OMe | CHF$_2$ | CH$_2$CH$_2$OMe | CN | |
| 8-250 | OMe | CF$_2$Cl | CH$_2$CH$_2$OMe | CN | |
| 8-251 | OMe | OMe | CH$_2$CH$_2$OMe | CN | |
| 8-252 | OMe | NO$_2$ | CH$_2$CH$_2$OMe | CN | |
| 8-253 | OMe | SO$_2$Me | CH$_2$CH$_2$OMe | CN | |
| 8-254 | SO$_2$Me | Me | CH$_2$CH$_2$OMe | CN | |
| 8-255 | SO$_2$Me | F | CH$_2$CH$_2$OMe | CN | |
| 8-256 | SO$_2$Me | Cl | CH$_2$CH$_2$OMe | CN | |
| 8-257 | SO$_2$Me | Br | CH$_2$CH$_2$OMe | CN | |
| 8-258 | SO$_2$Me | I | CH$_2$CH$_2$OMe | CN | |
| 8-259 | SO$_2$Me | CF$_3$ | CH$_2$CH$_2$OMe | CN | |
| 8-260 | SO$_2$Me | CHF$_2$ | CH$_2$CH$_2$OMe | CN | |

TABLE 8-continued

Compounds according to the invention of the formula (I) in which Q is Q1, $R^a$ is a hydroxyl group, the radicals $R^b$, $R^c$, $R^d$, $R^e$, $R^f$, $R^g$ and W are each hydrogen, t = 0 and the other radicals have the meanings indicated in the table

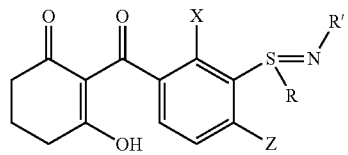

| No. | X | Z | R | R' | Physical data ($^1$H NMR) |
|---|---|---|---|---|---|
| 8-261 | SO$_2$Me | CF$_2$Cl | CH$_2$CH$_2$OMe | CN | |
| 8-262 | SO$_2$Me | OMe | CH$_2$CH$_2$OMe | CN | |
| 8-263 | SO$_2$Me | NO$_2$ | CH$_2$CH$_2$OMe | CN | |
| 8-264 | SO$_2$Me | SO$_2$Me | CH$_2$CH$_2$OMe | CN | |

TABLE 9

Compounds according to the invention of the formula (I) in which Q is Q2, $R^a$ is a hydroxyl group, $R^b$, $R^f$ and W are each hydrogen, A is CH$_2$CH$_2$, Y is CH$_2$, t = 0 and the other radicals have the meanings indicated in the table

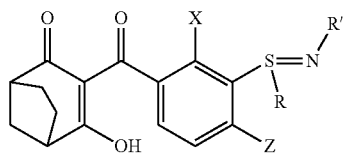

| No. | X | Z | R | R' | Physical data ($^1$H NMR) |
|---|---|---|---|---|---|
| 9-1 | Me | Me | Me | H | |
| 9-2 | Me | F | Me | H | |
| 9-3 | Me | Cl | Me | H | |
| 9-4 | Me | Br | Me | H | |
| 9-5 | Me | I | Me | H | |
| 9-6 | Me | CF$_3$ | Me | H | |
| 9-7 | Me | CHF$_2$ | Me | H | |
| 9-8 | Me | CF$_2$Cl | Me | H | |
| 9-9 | Me | OMe | Me | H | |
| 9-10 | Me | NO$_2$ | Me | H | |
| 9-11 | Me | SO$_2$Me | Me | H | |
| 9-12 | Cl | Me | Me | H | |
| 9-13 | Cl | F | Me | H | |
| 9-14 | Cl | Cl | Me | H | |
| 9-15 | Cl | Br | Me | H | |
| 9-16 | Cl | I | Me | H | |
| 9-17 | Cl | CF$_3$ | Me | H | |
| 9-18 | Cl | CHF$_2$ | Me | H | |
| 9-19 | Cl | CF$_2$Cl | Me | H | |
| 9-20 | Cl | OMe | Me | H | |
| 9-21 | Cl | NO$_2$ | Me | H | |
| 9-22 | Cl | SO$_2$Me | Me | H | |
| 9-23 | OMe | Me | Me | H | |
| 9-24 | OMe | F | Me | H | |
| 9-25 | OMe | Cl | Me | H | |
| 9-26 | OMe | Br | Me | H | |
| 9-27 | OMe | I | Me | H | |
| 9-28 | OMe | CF$_3$ | Me | H | |
| 9-29 | OMe | CHF$_2$ | Me | H | |
| 9-30 | OMe | CF$_2$Cl | Me | H | |
| 9-31 | OMe | OMe | Me | H | |
| 9-32 | OMe | NO$_2$ | Me | H | |
| 9-33 | OMe | SO$_2$Me | Me | H | |
| 9-34 | SO$_2$Me | Me | Me | H | |
| 9-35 | SO$_2$Me | F | Me | H | |
| 9-36 | SO$_2$Me | Cl | Me | H | |
| 9-37 | SO$_2$Me | Br | Me | H | |
| 9-38 | SO$_2$Me | I | Me | H | |
| 9-39 | SO$_2$Me | CF$_3$ | Me | H | |
| 9-40 | SO$_2$Me | CHF$_2$ | Me | H | |

TABLE 9-continued

Compounds according to the invention of the formula (I) in which Q is Q2, $R^a$ is a hydroxyl group, $R^b$, $R^f$ and W are each hydrogen, A is CH$_2$CH$_2$, Y is CH$_2$, t = 0 and the other radicals have the meanings indicated in the table

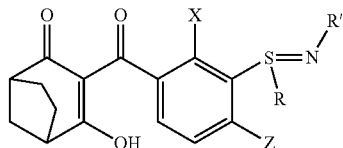

| No. | X | Z | R | R' | Physical data ($^1$H NMR) |
|---|---|---|---|---|---|
| 9-41 | SO$_2$Me | CF$_2$Cl | Me | H | |
| 9-42 | SO$_2$Me | OMe | Me | H | |
| 9-43 | SO$_2$Me | NO$_2$ | Me | H | |
| 9-44 | SO$_2$Me | SO$_2$Me | Me | H | |
| 9-45 | Me | Me | Et | H | |
| 9-46 | Me | F | Et | H | |
| 9-47 | Me | Cl | Et | H | |
| 9-48 | Me | Br | Et | H | |
| 9-49 | Me | I | Et | H | |
| 9-50 | Me | CF$_3$ | Et | H | |
| 9-51 | Me | CHF$_2$ | Et | H | |
| 9-52 | Me | CF$_2$Cl | Et | H | |
| 9-53 | Me | OMe | Et | H | |
| 9-54 | Me | NO$_2$ | Et | H | |
| 9-55 | Me | SO$_2$Me | Et | H | |
| 9-56 | Cl | Me | Et | H | |
| 9-57 | Cl | F | Et | H | |
| 9-58 | Cl | Cl | Et | H | |
| 9-59 | Cl | Br | Et | H | |
| 9-60 | Cl | I | Et | H | |
| 9-61 | Cl | CF$_3$ | Et | H | |
| 9-62 | Cl | CHF$_2$ | Et | H | |
| 9-63 | Cl | CF$_2$Cl | Et | H | |
| 9-64 | Cl | OMe | Et | H | |
| 9-65 | Cl | NO$_2$ | Et | H | |
| 9-66 | Cl | SO$_2$Me | Et | H | |
| 9-67 | OMe | Me | Et | H | |
| 9-68 | OMe | F | Et | H | |
| 9-69 | OMe | Cl | Et | H | |
| 9-70 | OMe | Br | Et | H | |
| 9-71 | OMe | I | Et | H | |
| 9-72 | OMe | CF$_3$ | Et | H | |
| 9-73 | OMe | CHF$_2$ | Et | H | |
| 9-74 | OMe | CF$_2$Cl | Et | H | |
| 9-75 | OMe | OMe | Et | H | |
| 9-76 | OMe | NO$_2$ | Et | H | |
| 9-77 | OMe | SO$_2$Me | Et | H | |
| 9-78 | SO$_2$Me | Me | Et | H | |
| 9-79 | SO$_2$Me | F | Et | H | |
| 9-80 | SO$_2$Me | Cl | Et | H | |
| 9-81 | SO$_2$Me | Br | Et | H | |
| 9-82 | SO$_2$Me | I | Et | H | |
| 9-83 | SO$_2$Me | CF$_3$ | Et | H | |
| 9-84 | SO$_2$Me | CHF$_2$ | Et | H | |
| 9-85 | SO$_2$Me | CF$_2$Cl | Et | H | |
| 9-86 | SO$_2$Me | OMe | Et | H | |
| 9-87 | SO$_2$Me | NO$_2$ | Et | H | |
| 9-88 | SO$_2$Me | SO$_2$Me | Et | H | |
| 9-89 | Me | Me | CH$_2$CH$_2$OMe | H | |
| 9-90 | Me | F | CH$_2$CH$_2$OMe | H | |
| 9-91 | Me | Cl | CH$_2$CH$_2$OMe | H | |
| 9-92 | Me | Br | CH$_2$CH$_2$OMe | H | |
| 9-93 | Me | I | CH$_2$CH$_2$OMe | H | |
| 9-94 | Me | CF$_3$ | CH$_2$CH$_2$OMe | H | |
| 9-95 | Me | CHF$_2$ | CH$_2$CH$_2$OMe | H | |
| 9-96 | Me | CF$_2$Cl | CH$_2$CH$_2$OMe | H | |
| 9-97 | Me | OMe | CH$_2$CH$_2$OMe | H | |
| 9-98 | Me | NO$_2$ | CH$_2$CH$_2$OMe | H | |
| 9-99 | Me | SO$_2$Me | CH$_2$CH$_2$OMe | H | |
| 9-100 | Cl | Me | CH$_2$CH$_2$OMe | H | |
| 9-101 | Cl | F | CH$_2$CH$_2$OMe | H | |
| 9-102 | Cl | Cl | CH$_2$CH$_2$OMe | H | |
| 9-103 | Cl | Br | CH$_2$CH$_2$OMe | H | |
| 9-104 | Cl | I | CH$_2$CH$_2$OMe | H | |

TABLE 9-continued

Compounds according to the invention of the formula (I) in which Q is Q2, $R^a$ is a hydroxyl group, $R^b$, $R^f$ and W are each hydrogen, A is $CH_2CH_2$, Y is $CH_2$, t = 0 and the other radicals have the meanings indicated in the table

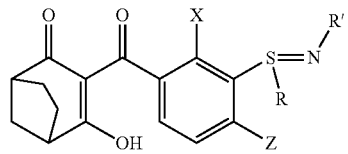
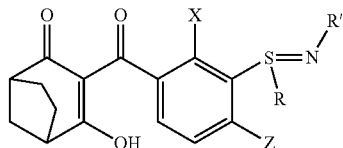

| No. | X | Z | R | R' | Physical data ($^1$H NMR) |
|---|---|---|---|---|---|
| 9-105 | Cl | $CF_3$ | $CH_2CH_2OMe$ | H | |
| 9-106 | Cl | $CHF_2$ | $CH_2CH_2OMe$ | H | |
| 9-107 | Cl | $CF_2Cl$ | $CH_2CH_2OMe$ | H | |
| 9-108 | Cl | OMe | $CH_2CH_2OMe$ | H | |
| 9-109 | Cl | $NO_2$ | $CH_2CH_2OMe$ | H | |
| 9-110 | Cl | $SO_2Me$ | $CH_2CH_2OMe$ | H | |
| 9-111 | OMe | Me | $CH_2CH_2OMe$ | H | |
| 9-112 | OMe | F | $CH_2CH_2OMe$ | H | |
| 9-113 | OMe | Cl | $CH_2CH_2OMe$ | H | |
| 9-114 | OMe | Br | $CH_2CH_2OMe$ | H | |
| 9-115 | OMe | I | $CH_2CH_2OMe$ | H | |
| 9-116 | OMe | $CF_3$ | $CH_2CH_2OMe$ | H | |
| 9-117 | OMe | $CHF_2$ | $CH_2CH_2OMe$ | H | |
| 9-118 | OMe | $CF_2Cl$ | $CH_2CH_2OMe$ | H | |
| 9-119 | OMe | OMe | $CH_2CH_2OMe$ | H | |
| 9-120 | OMe | $NO_2$ | $CH_2CH_2OMe$ | H | |
| 9-121 | OMe | $SO_2Me$ | $CH_2CH_2OMe$ | H | |
| 9-122 | $SO_2Me$ | Me | $CH_2CH_2OMe$ | H | |
| 9-123 | $SO_2Me$ | F | $CH_2CH_2OMe$ | H | |
| 9-124 | $SO_2Me$ | Cl | $CH_2CH_2OMe$ | H | |
| 9-125 | $SO_2Me$ | Br | $CH_2CH_2OMe$ | H | |
| 9-126 | $SO_2Me$ | I | $CH_2CH_2OMe$ | H | |
| 9-127 | $SO_2Me$ | $CF_3$ | $CH_2CH_2OMe$ | H | |
| 9-128 | $SO_2Me$ | $CHF_2$ | $CH_2CH_2OMe$ | H | |
| 9-129 | $SO_2Me$ | $CF_2Cl$ | $CH_2CH_2OMe$ | H | |
| 9-130 | $SO_2Me$ | OMe | $CH_2CH_2OMe$ | H | |
| 9-131 | $SO_2Me$ | $NO_2$ | $CH_2CH_2OMe$ | H | |
| 9-132 | $SO_2Me$ | $SO_2Me$ | $CH_2CH_2OMe$ | H | |
| 9-133 | Me | Me | Me | CN | |
| 9-134 | Me | F | Me | CN | |
| 9-135 | Me | Cl | Me | CN | |
| 9-136 | Me | Br | Me | CN | |
| 9-137 | Me | I | Me | CN | |
| 9-138 | Me | $CF_3$ | Me | CN | |
| 9-139 | Me | $CHF_2$ | Me | CN | |
| 9-140 | Me | $CF_2Cl$ | Me | CN | |
| 9-141 | Me | OMe | Me | CN | |
| 9-142 | Me | $NO_2$ | Me | CN | |
| 9-143 | Me | $SO_2Me$ | Me | CN | |
| 9-144 | Cl | Me | Me | CN | |
| 9-145 | Cl | F | Me | CN | |
| 9-146 | Cl | Cl | Me | CN | |
| 9-147 | Cl | Br | Me | CN | |
| 9-148 | Cl | I | Me | CN | |
| 9-149 | Cl | $CF_3$ | Me | CN | |
| 9-150 | Cl | $CHF_2$ | Me | CN | |
| 9-151 | Cl | $CF_2Cl$ | Me | CN | |
| 9-152 | Cl | OMe | Me | CN | |
| 9-153 | Cl | $NO_2$ | Me | CN | |
| 9-154 | Cl | $SO_2Me$ | Me | CN | |
| 9-155 | OMe | Me | Me | CN | |
| 9-156 | OMe | F | Me | CN | |
| 9-157 | OMe | Cl | Me | CN | |
| 9-158 | OMe | Br | Me | CN | |
| 9-159 | OMe | I | Me | CN | |
| 9-160 | OMe | $CF_3$ | Me | CN | |
| 9-161 | OMe | $CHF_2$ | Me | CN | |
| 9-162 | OMe | $CF_2Cl$ | Me | CN | |
| 9-163 | OMe | OMe | Me | CN | |
| 9-164 | OMe | $NO_2$ | Me | CN | |
| 9-165 | OMe | $SO_2Me$ | Me | CN | |
| 9-166 | $SO_2Me$ | Me | Me | CN | |
| 9-167 | $SO_2Me$ | F | Me | CN | |
| 9-168 | $SO_2Me$ | Cl | Me | CN | |
| 9-169 | $SO_2Me$ | Br | Me | CN | |
| 9-170 | $SO_2Me$ | I | Me | CN | |
| 9-171 | $SO_2Me$ | $CF_3$ | Me | CN | |
| 9-172 | $SO_2Me$ | $CHF_2$ | Me | CN | |
| 9-173 | $SO_2Me$ | $CF_2Cl$ | Me | CN | |
| 9-174 | $SO_2Me$ | OMe | Me | CN | |
| 9-175 | $SO_2Me$ | $NO_2$ | Me | CN | |
| 9-176 | $SO_2Me$ | $SO_2Me$ | Me | CN | |
| 9-177 | Me | Me | Et | CN | |
| 9-178 | Me | F | Et | CN | |
| 9-179 | Me | Cl | Et | CN | |
| 9-180 | Me | Br | Et | CN | |
| 9-181 | Me | I | Et | CN | |
| 9-182 | Me | $CF_3$ | Et | CN | |
| 9-183 | Me | $CHF_2$ | Et | CN | |
| 9-184 | Me | $CF_2Cl$ | Et | CN | |
| 9-185 | Me | OMe | Et | CN | |
| 9-186 | Me | $NO_2$ | Et | CN | |
| 9-187 | Me | $SO_2Me$ | Et | CN | |
| 9-188 | Cl | Me | Et | CN | |
| 9-189 | Cl | F | Et | CN | |
| 9-190 | Cl | Cl | Et | CN | |
| 9-191 | Cl | Br | Et | CN | |
| 9-192 | Cl | I | Et | CN | |
| 9-193 | Cl | $CF_3$ | Et | CN | |
| 9-194 | Cl | $CHF_2$ | Et | CN | |
| 9-195 | Cl | $CF_2Cl$ | Et | CN | |
| 9-196 | Cl | OMe | Et | CN | |
| 9-197 | Cl | $NO_2$ | Et | CN | |
| 9-198 | Cl | $SO_2Me$ | Et | CN | |
| 9-199 | OMe | Me | Et | CN | |
| 9-200 | OMe | F | Et | CN | |
| 9-201 | OMe | Cl | Et | CN | |
| 9-202 | OMe | Br | Et | CN | |
| 9-203 | OMe | I | Et | CN | |
| 9-204 | OMe | $CF_3$ | Et | CN | |
| 9-205 | OMe | $CHF_2$ | Et | CN | |
| 9-206 | OMe | $CF_2Cl$ | Et | CN | |
| 9-207 | OMe | OMe | Et | CN | |
| 9-208 | OMe | $NO_2$ | Et | CN | |
| 9-209 | OMe | $SO_2Me$ | Et | CN | |
| 9-210 | $SO_2Me$ | Me | Et | CN | |
| 9-211 | $SO_2Me$ | F | Et | CN | |
| 9-212 | $SO_2Me$ | Cl | Et | CN | |
| 9-213 | $SO_2Me$ | Br | Et | CN | |
| 9-214 | $SO_2Me$ | I | Et | CN | |
| 9-215 | $SO_2Me$ | $CF_3$ | Et | CN | |
| 9-216 | $SO_2Me$ | $CHF_2$ | Et | CN | |
| 9-217 | $SO_2Me$ | $CF_2Cl$ | Et | CN | |
| 9-218 | $SO_2Me$ | OMe | Et | CN | |
| 9-219 | $SO_2Me$ | $NO_2$ | Et | CN | |
| 9-220 | $SO_2Me$ | $SO_2Me$ | Et | CN | |
| 9-221 | Me | Me | $CH_2CH_2OMe$ | CN | |
| 9-222 | Me | F | $CH_2CH_2OMe$ | CN | |
| 9-223 | Me | Cl | $CH_2CH_2OMe$ | CN | |
| 9-224 | Me | Br | $CH_2CH_2OMe$ | CN | |
| 9-225 | Me | I | $CH_2CH_2OMe$ | CN | |
| 9-226 | Me | $CF_3$ | $CH_2CH_2OMe$ | CN | |
| 9-227 | Me | $CHF_2$ | $CH_2CH_2OMe$ | CN | |
| 9-228 | Me | $CF_2Cl$ | $CH_2CH_2OMe$ | CN | |
| 9-229 | Me | OMe | $CH_2CH_2OMe$ | CN | |
| 9-230 | Me | $NO_2$ | $CH_2CH_2OMe$ | CN | |
| 9-231 | Me | $SO_2Me$ | $CH_2CH_2OMe$ | CN | |
| 9-232 | Cl | Me | $CH_2CH_2OMe$ | CN | |

TABLE 9-continued

Compounds according to the invention of the formula (I) in which Q is Q2, $R^a$ is a hydroxyl group, $R^b$, $R^f$ and W are each hydrogen, A is $CH_2CH_2$, Y is $CH_2$, t = 0 and the other radicals have the meanings indicated in the table

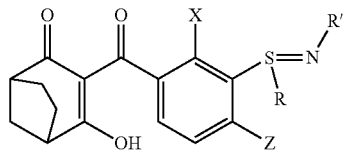

| No. | X | Z | R | R' | Physical data ($^1$H NMR) |
|---|---|---|---|---|---|
| 9-233 | Cl | F | $CH_2CH_2OMe$ | CN | |
| 9-234 | Cl | Cl | $CH_2CH_2OMe$ | CN | |
| 9-235 | Cl | Br | $CH_2CH_2OMe$ | CN | |
| 9-236 | Cl | I | $CH_2CH_2OMe$ | CN | |
| 9-237 | Cl | $CF_3$ | $CH_2CH_2OMe$ | CN | |
| 9-238 | Cl | $CHF_2$ | $CH_2CH_2OMe$ | CN | |
| 9-239 | Cl | $CF_2Cl$ | $CH_2CH_2OMe$ | CN | |
| 9-240 | Cl | OMe | $CH_2CH_2OMe$ | CN | |
| 9-241 | Cl | $NO_2$ | $CH_2CH_2OMe$ | CN | |
| 9-242 | Cl | $SO_2Me$ | $CH_2CH_2OMe$ | CN | |
| 9-243 | OMe | Me | $CH_2CH_2OMe$ | CN | |
| 9-244 | OMe | F | $CH_2CH_2OMe$ | CN | |
| 9-245 | OMe | Cl | $CH_2CH_2OMe$ | CN | |
| 9-246 | OMe | Br | $CH_2CH_2OMe$ | CN | |
| 9-247 | OMe | I | $CH_2CH_2OMe$ | CN | |
| 9-248 | OMe | $CF_3$ | $CH_2CH_2OMe$ | CN | |
| 9-249 | OMe | $CHF_2$ | $CH_2CH_2OMe$ | CN | |
| 9-250 | OMe | $CF_2Cl$ | $CH_2CH_2OMe$ | CN | |
| 9-251 | OMe | OMe | $CH_2CH_2OMe$ | CN | |
| 9-252 | OMe | $NO_2$ | $CH_2CH_2OMe$ | CN | |
| 9-253 | OMe | $SO_2Me$ | $CH_2CH_2OMe$ | CN | |
| 9-254 | $SO_2Me$ | Me | $CH_2CH_2OMe$ | CN | |
| 9-255 | $SO_2Me$ | F | $CH_2CH_2OMe$ | CN | |
| 9-256 | $SO_2Me$ | Cl | $CH_2CH_2OMe$ | CN | |
| 9-257 | $SO_2Me$ | Br | $CH_2CH_2OMe$ | CN | |
| 9-258 | $SO_2Me$ | I | $CH_2CH_2OMe$ | CN | |
| 9-259 | $SO_2Me$ | $CF_3$ | $CH_2CH_2OMe$ | CN | |
| 9-260 | $SO_2Me$ | $CHF_2$ | $CH_2CH_2OMe$ | CN | |
| 9-261 | $SO_2Me$ | $CF_2Cl$ | $CH_2CH_2OMe$ | CN | |
| 9-262 | $SO_2Me$ | OMe | $CH_2CH_2OMe$ | CN | |
| 9-263 | $SO_2Me$ | $NO_2$ | $CH_2CH_2OMe$ | CN | |
| 9-264 | $SO_2Me$ | $SO_2Me$ | $CH_2CH_2OMe$ | CN | |

TABLE 10

Compounds according to the invention of the formula (I) in which Q is Q3, $R^i$ is methyl and $R^h$, $R^k$ and W are each hydrogen, t = 0 and the other radicals have the meanings indicated in the table

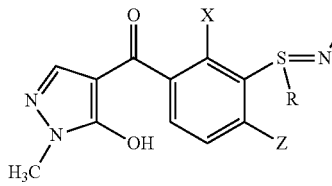

| No. | X | Z | R | R' | Physical data ($^1$H NMR) |
|---|---|---|---|---|---|
| 10-1 | Me | Me | Me | H | |
| 10-2 | Me | F | Me | H | |
| 10-3 | Me | Cl | Me | H | |
| 10-4 | Me | Br | Me | H | |
| 10-5 | Me | I | Me | H | |
| 10-6 | Me | $CF_3$ | Me | H | |
| 10-7 | Me | $CHF_2$ | Me | H | |
| 10-8 | Me | $CF_2Cl$ | Me | H | |
| 10-9 | Me | OMe | Me | H | |
| 10-10 | Me | $NO_2$ | Me | H | |

TABLE 10-continued

Compounds according to the invention of the formula (I) in which Q is Q3, $R^i$ is methyl and $R^h$, $R^k$ and W are each hydrogen, t = 0 and the other radicals have the meanings indicated in the table

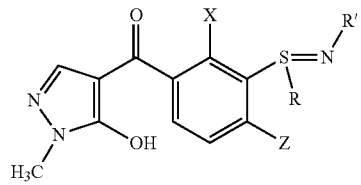

| No. | X | Z | R | R' | Physical data ($^1$H NMR) |
|---|---|---|---|---|---|
| 10-11 | Me | $SO_2Me$ | Me | H | |
| 10-12 | Cl | Me | Me | H | |
| 10-13 | Cl | F | Me | H | |
| 10-14 | Cl | Cl | Me | H | |
| 10-15 | Cl | Br | Me | H | |
| 10-16 | Cl | I | Me | H | |
| 10-17 | Cl | $CF_3$ | Me | H | |
| 10-18 | Cl | $CHF_2$ | Me | H | |
| 10-19 | Cl | $CF_2Cl$ | Me | H | |
| 10-20 | Cl | OMe | Me | H | |
| 10-21 | Cl | $NO_2$ | Me | H | |
| 10-22 | Cl | $SO_2Me$ | Me | H | |
| 10-23 | OMe | Me | Me | H | |
| 10-24 | OMe | F | Me | H | |
| 10-25 | OMe | Cl | Me | H | |
| 10-26 | OMe | Br | Me | H | |
| 10-27 | OMe | I | Me | H | |
| 10-28 | OMe | $CF_3$ | Me | H | |
| 10-29 | OMe | $CHF_2$ | Me | H | |
| 10-30 | OMe | $CF_2Cl$ | Me | H | |
| 10-31 | OMe | OMe | Me | H | |
| 10-32 | OMe | $NO_2$ | Me | H | |
| 10-33 | OMe | $SO_2Me$ | Me | H | |
| 10-34 | $SO_2Me$ | Me | Me | H | |
| 10-35 | $SO_2Me$ | F | Me | H | |
| 10-36 | $SO_2Me$ | Cl | Me | H | |
| 10-37 | $SO_2Me$ | Br | Me | H | |
| 10-38 | $SO_2Me$ | I | Me | H | |
| 10-39 | $SO_2Me$ | $CF_3$ | Me | H | |
| 10-40 | $SO_2Me$ | $CHF_2$ | Me | H | |
| 10-41 | $SO_2Me$ | $CF_2Cl$ | Me | H | |
| 10-42 | $SO_2Me$ | OMe | Me | H | |
| 10-43 | $SO_2Me$ | $NO_2$ | Me | H | |
| 10-44 | $SO_2Me$ | $SO_2Me$ | Me | H | |
| 10-45 | Me | Me | Et | H | |
| 10-46 | Me | F | Et | H | |
| 10-47 | Me | Cl | Et | H | |
| 10-48 | Me | Br | Et | H | |
| 10-49 | Me | I | Et | H | |
| 10-50 | Me | $CF_3$ | Et | H | |
| 10-51 | Me | $CHF_2$ | Et | H | |
| 10-52 | Me | $CF_2Cl$ | Et | H | |
| 10-53 | Me | OMe | Et | H | |
| 10-54 | Me | $NO_2$ | Et | H | |
| 10-55 | Me | $SO_2Me$ | Et | H | |
| 10-56 | Cl | Me | Et | H | |
| 10-57 | Cl | F | Et | H | |
| 10-58 | Cl | Cl | Et | H | |
| 10-59 | Cl | Br | Et | H | |
| 10-60 | Cl | I | Et | H | |
| 10-61 | Cl | $CF_3$ | Et | H | |
| 10-62 | Cl | $CHF_2$ | Et | H | |
| 10-63 | Cl | $CF_2Cl$ | Et | H | |
| 10-64 | Cl | OMe | Et | H | |
| 10-65 | Cl | $NO_2$ | Et | H | |
| 10-66 | Cl | $SO_2Me$ | Et | H | |
| 10-67 | OMe | Me | Et | H | |
| 10-68 | OMe | F | Et | H | |
| 10-69 | OMe | Cl | Et | H | |
| 10-70 | OMe | Br | Et | H | |
| 10-71 | OMe | I | Et | H | |
| 10-72 | OMe | $CF_3$ | Et | H | |
| 10-73 | OMe | $CHF_2$ | Et | H | |

TABLE 10-continued

Compounds according to the invention of the formula (I) in which
Q is Q3, $R^i$ is methyl and $R^h$, $R^k$ and W are each hydrogen, t = 0
and the other radicals have the meanings indicated in the table

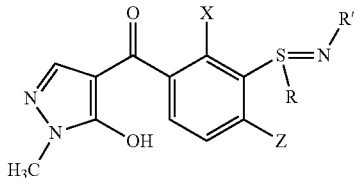

| No. | X | Z | R | R' | Physical data ($^1$H NMR) |
|---|---|---|---|---|---|
| 10-74 | OMe | CF$_2$Cl | Et | H | |
| 10-75 | OMe | OMe | Et | H | |
| 10-76 | OMe | NO$_2$ | Et | H | |
| 10-77 | OMe | SO$_2$Me | Et | H | |
| 10-78 | SO$_2$Me | Me | Et | H | |
| 10-79 | SO$_2$Me | F | Et | H | |
| 10-80 | SO$_2$Me | Cl | Et | H | |
| 10-81 | SO$_2$Me | Br | Et | H | |
| 10-82 | SO$_2$Me | I | Et | H | |
| 10-83 | SO$_2$Me | CF$_3$ | Et | H | |
| 10-84 | SO$_2$Me | CHF$_2$ | Et | H | |
| 10-85 | SO$_2$Me | CF$_2$Cl | Et | H | |
| 10-86 | SO$_2$Me | OMe | Et | H | |
| 10-87 | SO$_2$Me | NO$_2$ | Et | H | |
| 10-88 | SO$_2$Me | SO$_2$Me | Et | H | |
| 10-89 | Me | Me | CH$_2$CH$_2$OMe | H | |
| 10-90 | Me | F | CH$_2$CH$_2$OMe | H | |
| 10-91 | Me | Cl | CH$_2$CH$_2$OMe | H | |
| 10-92 | Me | Br | CH$_2$CH$_2$OMe | H | |
| 10-93 | Me | I | CH$_2$CH$_2$OMe | H | |
| 10-94 | Me | CF$_3$ | CH$_2$CH$_2$OMe | H | |
| 10-95 | Me | CHF$_2$ | CH$_2$CH$_2$OMe | H | |
| 10-96 | Me | CF$_2$Cl | CH$_2$CH$_2$OMe | H | |
| 10-97 | Me | OMe | CH$_2$CH$_2$OMe | H | |
| 10-98 | Me | NO$_2$ | CH$_2$CH$_2$OMe | H | |
| 10-99 | Me | SO$_2$Me | CH$_2$CH$_2$OMe | H | |
| 10-100 | Cl | Me | CH$_2$CH$_2$OMe | H | |
| 10-101 | Cl | F | CH$_2$CH$_2$OMe | H | |
| 10-102 | Cl | Cl | CH$_2$CH$_2$OMe | H | |
| 10-103 | Cl | Br | CH$_2$CH$_2$OMe | H | |
| 10-104 | Cl | I | CH$_2$CH$_2$OMe | H | |
| 10-105 | Cl | CF$_3$ | CH$_2$CH$_2$OMe | H | |
| 10-106 | Cl | CHF$_2$ | CH$_2$CH$_2$OMe | H | |
| 10-107 | Cl | CF$_2$Cl | CH$_2$CH$_2$OMe | H | |
| 10-108 | Cl | OMe | CH$_2$CH$_2$OMe | H | |
| 10-109 | Cl | NO$_2$ | CH$_2$CH$_2$OMe | H | |
| 10-110 | Cl | SO$_2$Me | CH$_2$CH$_2$OMe | H | |
| 10-111 | OMe | Me | CH$_2$CH$_2$OMe | H | |
| 10-112 | OMe | F | CH$_2$CH$_2$OMe | H | |
| 10-113 | OMe | Cl | CH$_2$CH$_2$OMe | H | |
| 10-114 | OMe | Br | CH$_2$CH$_2$OMe | H | |
| 10-115 | OMe | I | CH$_2$CH$_2$OMe | H | |
| 10-116 | OMe | CF$_3$ | CH$_2$CH$_2$OMe | H | |
| 10-117 | OMe | CHF$_2$ | CH$_2$CH$_2$OMe | H | |
| 10-118 | OMe | CF$_2$Cl | CH$_2$CH$_2$OMe | H | |
| 10-119 | OMe | OMe | CH$_2$CH$_2$OMe | H | |
| 10-120 | OMe | NO$_2$ | CH$_2$CH$_2$OMe | H | |
| 10-121 | OMe | SO$_2$Me | CH$_2$CH$_2$OMe | H | |
| 10-122 | SO$_2$Me | Me | CH$_2$CH$_2$OMe | H | |
| 10-123 | SO$_2$Me | F | CH$_2$CH$_2$OMe | H | |
| 10-124 | SO$_2$Me | Cl | CH$_2$CH$_2$OMe | H | |
| 10-125 | SO$_2$Me | Br | CH$_2$CH$_2$OMe | H | |
| 10-126 | SO$_2$Me | I | CH$_2$CH$_2$OMe | H | |
| 10-127 | SO$_2$Me | CF$_3$ | CH$_2$CH$_2$OMe | H | |
| 10-128 | SO$_2$Me | CHF$_2$ | CH$_2$CH$_2$OMe | H | |
| 10-129 | SO$_2$Me | CF$_2$Cl | CH$_2$CH$_2$OMe | H | |
| 10-130 | SO$_2$Me | OMe | CH$_2$CH$_2$OMe | H | |
| 10-131 | SO$_2$Me | NO$_2$ | CH$_2$CH$_2$OMe | H | |
| 10-132 | SO$_2$Me | SO$_2$Me | CH$_2$CH$_2$OMe | H | |
| 10-133 | Me | Me | Me | CN | |
| 10-134 | Me | F | Me | CN | |
| 10-135 | Me | Cl | Me | CN | |
| 10-136 | Me | Br | Me | CN | |

TABLE 10-continued

Compounds according to the invention of the formula (I) in which
Q is Q3, $R^i$ is methyl and $R^h$, $R^k$ and W are each hydrogen, t = 0
and the other radicals have the meanings indicated in the table

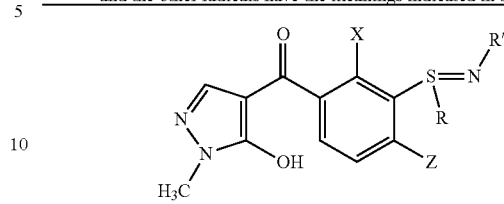

| No. | X | Z | R | R' | Physical data ($^1$H NMR) |
|---|---|---|---|---|---|
| 10-137 | Me | I | Me | CN | |
| 10-138 | Me | CF$_3$ | Me | CN | |
| 10-139 | Me | CHF$_2$ | Me | CN | |
| 10-140 | Me | CF$_2$Cl | Me | CN | |
| 10-141 | Me | OMe | Me | CN | |
| 10-142 | Me | NO$_2$ | Me | CN | |
| 10-143 | Me | SO$_2$Me | Me | CN | |
| 10-144 | Cl | Me | Me | CN | |
| 10-145 | Cl | F | Me | CN | |
| 10-146 | Cl | Cl | Me | CN | |
| 10-147 | Cl | Br | Me | CN | |
| 10-148 | Cl | I | Me | CN | |
| 10-149 | Cl | CF$_3$ | Me | CN | |
| 10-150 | Cl | CHF$_2$ | Me | CN | |
| 10-151 | Cl | CF$_2$Cl | Me | CN | |
| 10-152 | Cl | OMe | Me | CN | |
| 10-153 | Cl | NO$_2$ | Me | CN | |
| 10-154 | Cl | SO$_2$Me | Me | CN | |
| 10-155 | OMe | Me | Me | CN | |
| 10-156 | OMe | F | Me | CN | |
| 10-157 | OMe | Cl | Me | CN | |
| 10-158 | OMe | Br | Me | CN | |
| 10-159 | OMe | I | Me | CN | |
| 10-160 | OMe | CF$_3$ | Me | CN | |
| 10-161 | OMe | CHF$_2$ | Me | CN | |
| 10-162 | OMe | CF$_2$Cl | Me | CN | |
| 10-163 | OMe | OMe | Me | CN | |
| 10-164 | OMe | NO$_2$ | Me | CN | |
| 10-165 | OMe | SO$_2$Me | Me | CN | |
| 10-166 | SO$_2$Me | Me | Me | CN | |
| 10-167 | SO$_2$Me | F | Me | CN | |
| 10-168 | SO$_2$Me | Cl | Me | CN | |
| 10-169 | SO$_2$Me | Br | Me | CN | |
| 10-170 | SO$_2$Me | I | Me | CN | |
| 10-171 | SO$_2$Me | CF$_3$ | Me | CN | |
| 10-172 | SO$_2$Me | CHF$_2$ | Me | CN | |
| 10-173 | SO$_2$Me | CF$_2$Cl | Me | CN | |
| 10-174 | SO$_2$Me | OMe | Me | CN | |
| 10-175 | SO$_2$Me | NO$_2$ | Me | CN | |
| 10-176 | SO$_2$Me | SO$_2$Me | Me | CN | |
| 10-177 | Me | Me | Et | CN | |
| 10-178 | Me | F | Et | CN | |
| 10-179 | Me | Cl | Et | CN | |
| 10-180 | Me | Br | Et | CN | |
| 10-181 | Me | I | Et | CN | |
| 10-182 | Me | CF$_3$ | Et | CN | |
| 10-183 | Me | CHF$_2$ | Et | CN | |
| 10-184 | Me | CF$_2$Cl | Et | CN | |
| 10-185 | Me | OMe | Et | CN | |
| 10-186 | Me | NO$_2$ | Et | CN | |
| 10-187 | Me | SO$_2$Me | Et | CN | |
| 10-188 | Cl | Me | Et | CN | |
| 10-189 | Cl | F | Et | CN | |
| 10-190 | Cl | Cl | Et | CN | |
| 10-191 | Cl | Br | Et | CN | |
| 10-192 | Cl | I | Et | CN | |
| 10-193 | Cl | CF$_3$ | Et | CN | |
| 10-194 | Cl | CHF$_2$ | Et | CN | |
| 10-195 | Cl | CF$_2$Cl | Et | CN | |
| 10-196 | Cl | OMe | Et | CN | |
| 10-197 | Cl | NO$_2$ | Et | CN | |
| 10-198 | Cl | SO$_2$Me | Et | CN | |
| 10-199 | OMe | Me | Et | CN | |

TABLE 10-continued

Compounds according to the invention of the formula (I) in which Q is Q3, $R^i$ is methyl and $R^h$, $R^k$ and W are each hydrogen, t = 0 and the other radicals have the meanings indicated in the table

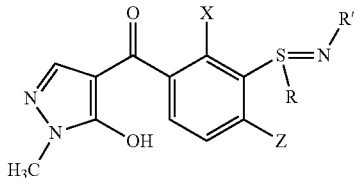

| No. | X | Z | R | R' | Physical data ($^1$H NMR) |
|---|---|---|---|---|---|
| 10-200 | OMe | F | Et | CN | |
| 10-201 | OMe | Cl | Et | CN | |
| 10-202 | OMe | Br | Et | CN | |
| 10-203 | OMe | I | Et | CN | |
| 10-204 | OMe | CF$_3$ | Et | CN | |
| 10-205 | OMe | CHF$_2$ | Et | CN | |
| 10-206 | OMe | CF$_2$Cl | Et | CN | |
| 10-207 | OMe | OMe | Et | CN | |
| 10-208 | OMe | NO$_2$ | Et | CN | |
| 10-209 | OMe | SO$_2$Me | Et | CN | |
| 10-210 | SO$_2$Me | Me | Et | CN | |
| 10-211 | SO$_2$Me | F | Et | CN | |
| 10-212 | SO$_2$Me | Cl | Et | CN | |
| 10-213 | SO$_2$Me | Br | Et | CN | |
| 10-214 | SO$_2$Me | I | Et | CN | |
| 10-215 | SO$_2$Me | CF$_3$ | Et | CN | |
| 10-216 | SO$_2$Me | CHF$_2$ | Et | CN | |
| 10-217 | SO$_2$Me | CF$_2$Cl | Et | CN | |
| 10-218 | SO$_2$Me | OMe | Et | CN | |
| 10-219 | SO$_2$Me | NO$_2$ | Et | CN | |
| 10-220 | SO$_2$Me | SO$_2$Me | Et | CN | |
| 10-221 | Me | Me | CH$_2$CH$_2$OMe | CN | |
| 10-222 | Me | F | CH$_2$CH$_2$OMe | CN | |
| 10-223 | Me | Cl | CH$_2$CH$_2$OMe | CN | |
| 10-224 | Me | Br | CH$_2$CH$_2$OMe | CN | |
| 10-225 | Me | I | CH$_2$CH$_2$OMe | CN | |
| 10-226 | Me | CF$_3$ | CH$_2$CH$_2$OMe | CN | |
| 10-227 | Me | CHF$_2$ | CH$_2$CH$_2$OMe | CN | |
| 10-228 | Me | CF$_2$Cl | CH$_2$CH$_2$OMe | CN | |
| 10-229 | Me | OMe | CH$_2$CH$_2$OMe | CN | |
| 10-230 | Me | NO$_2$ | CH$_2$CH$_2$OMe | CN | |
| 10-231 | Me | SO$_2$Me | CH$_2$CH$_2$OMe | CN | |
| 10-232 | Cl | Me | CH$_2$CH$_2$OMe | CN | |
| 10-233 | Cl | F | CH$_2$CH$_2$OMe | CN | |
| 10-234 | Cl | Cl | CH$_2$CH$_2$OMe | CN | |
| 10-235 | Cl | Br | CH$_2$CH$_2$OMe | CN | |
| 10-236 | Cl | I | CH$_2$CH$_2$OMe | CN | |
| 10-237 | Cl | CF$_3$ | CH$_2$CH$_2$OMe | CN | |
| 10-238 | Cl | CHF$_2$ | CH$_2$CH$_2$OMe | CN | |
| 10-239 | Cl | CF$_2$Cl | CH$_2$CH$_2$OMe | CN | |
| 10-240 | Cl | OMe | CH$_2$CH$_2$OMe | CN | |
| 10-241 | Cl | NO$_2$ | CH$_2$CH$_2$OMe | CN | |
| 10-242 | Cl | SO$_2$Me | CH$_2$CH$_2$OMe | CN | |
| 10-243 | OMe | Me | CH$_2$CH$_2$OMe | CN | |
| 10-244 | OMe | F | CH$_2$CH$_2$OMe | CN | |
| 10-245 | OMe | Cl | CH$_2$CH$_2$OMe | CN | |
| 10-246 | OMe | Br | CH$_2$CH$_2$OMe | CN | |
| 10-247 | OMe | I | CH$_2$CH$_2$OMe | CN | |
| 10-248 | OMe | CF$_3$ | CH$_2$CH$_2$OMe | CN | |
| 10-249 | OMe | CHF$_2$ | CH$_2$CH$_2$OMe | CN | |
| 10-250 | OMe | CF$_2$Cl | CH$_2$CH$_2$OMe | CN | |
| 10-251 | OMe | OMe | CH$_2$CH$_2$OMe | CN | |
| 10-252 | OMe | NO$_2$ | CH$_2$CH$_2$OMe | CN | |
| 10-253 | OMe | SO$_2$Me | CH$_2$CH$_2$OMe | CN | |
| 10-254 | SO$_2$Me | Me | CH$_2$CH$_2$OMe | CN | |
| 10-255 | SO$_2$Me | F | CH$_2$CH$_2$OMe | CN | |
| 10-256 | SO$_2$Me | Cl | CH$_2$CH$_2$OMe | CN | |
| 10-257 | SO$_2$Me | Br | CH$_2$CH$_2$OMe | CN | |
| 10-258 | SO$_2$Me | I | CH$_2$CH$_2$OMe | CN | |
| 10-259 | SO$_2$Me | CF$_3$ | CH$_2$CH$_2$OMe | CN | |
| 10-260 | SO$_2$Me | CHF$_2$ | CH$_2$CH$_2$OMe | CN | |
| 10-261 | SO$_2$Me | CF$_2$Cl | CH$_2$CH$_2$OMe | CN | |
| 10-262 | SO$_2$Me | OMe | CH$_2$CH$_2$OMe | CN | |
| 10-263 | SO$_2$Me | NO$_2$ | CH$_2$CH$_2$OMe | CN | |
| 10-264 | SO$_2$Me | SO$_2$Me | CH$_2$CH$_2$OMe | CN | |

TABLE 10a

Compounds according to the invention of the formula (I) in which Q is Q3, $R^i$ is ethyl and $R^h$, $R^k$ and W are each hydrogen, t = 0 and the other radicals have the meanings indicated in the table

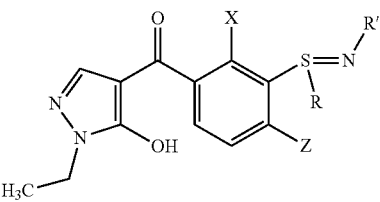

| No. | X | Z | R | R' | Physical data ($^1$H NMR) |
|---|---|---|---|---|---|
| 10a-1 | Me | Me | Me | H | |
| 10a-2 | Me | F | Me | H | |
| 10a-3 | Me | Cl | Me | H | |
| 10a-4 | Me | Br | Me | H | |
| 10a-5 | Me | I | Me | H | |
| 10a-6 | Me | CF$_3$ | Me | H | |
| 10a-7 | Me | CHF$_2$ | Me | H | |
| 10a-8 | Me | CF$_2$Cl | Me | H | |
| 10a-9 | Me | OMe | Me | H | |
| 10a-10 | Me | NO$_2$ | Me | H | |
| 10a-11 | Me | SO$_2$Me | Me | H | |
| 10a-12 | Cl | Me | Me | H | |
| 10a-13 | Cl | F | Me | H | |
| 10a-14 | Cl | Cl | Me | H | |
| 10a-15 | Cl | Br | Me | H | |
| 10a-16 | Cl | I | Me | H | |
| 10a-17 | Cl | CF$_3$ | Me | H | |
| 10a-18 | Cl | CHF$_2$ | Me | H | |
| 10a-19 | Cl | CF$_2$Cl | Me | H | |
| 10a-20 | Cl | OMe | Me | H | |
| 10a-21 | Cl | NO$_2$ | Me | H | |
| 10a-22 | Cl | SO$_2$Me | Me | H | |
| 10a-23 | OMe | Me | Me | H | |
| 10a-24 | OMe | F | Me | H | |
| 10a-25 | OMe | Cl | Me | H | |
| 10a-26 | OMe | Br | Me | H | |
| 10a-27 | OMe | I | Me | H | |
| 10a-28 | OMe | CF$_3$ | Me | H | |
| 10a-29 | OMe | CHF$_2$ | Me | H | |
| 10a-30 | OMe | CF$_2$Cl | Me | H | |
| 10a-31 | OMe | OMe | Me | H | |
| 10a-32 | OMe | NO$_2$ | Me | H | |
| 10a-33 | OMe | SO$_2$Me | Me | H | |
| 10a-34 | SO$_2$Me | Me | Me | H | |
| 10a-35 | SO$_2$Me | F | Me | H | |
| 10a-36 | SO$_2$Me | Cl | Me | H | |
| 10a-37 | SO$_2$Me | Br | Me | H | |
| 10a-38 | SO$_2$Me | I | Me | H | |
| 10a-39 | SO$_2$Me | CF$_3$ | Me | H | |
| 10a-40 | SO$_2$Me | CHF$_2$ | Me | H | |

TABLE 10a-continued

Compounds according to the invention of the formula (I) in which Q is Q3, $R^i$ is ethyl and $R^h$, $R^k$ and W are each hydrogen, t = 0 and the other radicals have the meanings indicated in the table

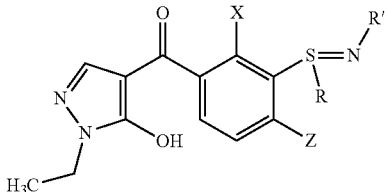

| No. | X | Z | R | R' | Physical data ($^1$H NMR) |
|---|---|---|---|---|---|
| 10a-41 | SO$_2$Me | CF$_2$Cl | Me | H | |
| 10a-42 | SO$_2$Me | OMe | Me | H | |
| 10a-43 | SO$_2$Me | NO$_2$ | Me | H | |
| 10a-44 | SO$_2$Me | SO$_2$Me | Me | H | |
| 10a-45 | Me | Me | Et | H | |
| 10a-46 | Me | F | Et | H | |
| 10a-47 | Me | Cl | Et | H | |
| 10a-48 | Me | Br | Et | H | |
| 10a-49 | Me | I | Et | H | |
| 10a-50 | Me | CF$_3$ | Et | H | |
| 10a-51 | Me | CHF$_2$ | Et | H | |
| 10a-52 | Me | CF$_2$Cl | Et | H | |
| 10a-53 | Me | OMe | Et | H | |
| 10a-54 | Me | NO$_2$ | Et | H | |
| 10a-55 | Me | SO$_2$Me | Et | H | |
| 10a-56 | Cl | Me | Et | H | |
| 10a-57 | Cl | F | Et | H | |
| 10a-58 | Cl | Cl | Et | H | |
| 10a-59 | Cl | Br | Et | H | |
| 10a-60 | Cl | I | Et | H | |
| 10a-61 | Cl | CF$_3$ | Et | H | |
| 10a-62 | Cl | CHF$_2$ | Et | H | |
| 10a-63 | Cl | CF$_2$Cl | Et | H | |
| 10a-64 | Cl | OMe | Et | H | |
| 10a-65 | Cl | NO$_2$ | Et | H | |
| 10a-66 | Cl | SO$_2$Me | Et | H | |
| 10a-67 | OMe | Me | Et | H | |
| 10a-68 | OMe | F | Et | H | |
| 10a-69 | OMe | Cl | Et | H | |
| 10a-70 | OMe | Br | Et | H | |
| 10a-71 | OMe | I | Et | H | |
| 10a-72 | OMe | CF$_3$ | Et | H | |
| 10a-73 | OMe | CHF$_2$ | Et | H | |
| 10a-74 | OMe | CF$_2$Cl | Et | H | |
| 10a-75 | OMe | OMe | Et | H | |
| 10a-76 | OMe | NO$_2$ | Et | H | |
| 10a-77 | OMe | SO$_2$Me | Et | H | |
| 10a-78 | SO$_2$Me | Me | Et | H | |
| 10a-79 | SO$_2$Me | F | Et | H | |
| 10a-80 | SO$_2$Me | Cl | Et | H | |
| 10a-81 | SO$_2$Me | Br | Et | H | |
| 10a-82 | SO$_2$Me | I | Et | H | |
| 10a-83 | SO$_2$Me | CF$_3$ | Et | H | |
| 10a-84 | SO$_2$Me | CHF$_2$ | Et | H | |
| 10a-85 | SO$_2$Me | CF$_2$Cl | Et | H | |
| 10a-86 | SO$_2$Me | OMe | Et | H | |
| 10a-87 | SO$_2$Me | NO$_2$ | Et | H | |
| 10a-88 | SO$_2$Me | SO$_2$Me | Et | H | |
| 10a-89 | Me | Me | CH$_2$CH$_2$OMe | H | |
| 10a-90 | Me | F | CH$_2$CH$_2$OMe | H | |
| 10a-91 | Me | Cl | CH$_2$CH$_2$OMe | H | |
| 10a-92 | Me | Br | CH$_2$CH$_2$OMe | H | |
| 10a-93 | Me | I | CH$_2$CH$_2$OMe | H | |
| 10a-94 | Me | CF$_3$ | CH$_2$CH$_2$OMe | H | |
| 10a-95 | Me | CHF$_2$ | CH$_2$CH$_2$OMe | H | |
| 10a-96 | Me | CF$_2$Cl | CH$_2$CH$_2$OMe | H | |
| 10a-97 | Me | OMe | CH$_2$CH$_2$OMe | H | |
| 10a-98 | Me | NO$_2$ | CH$_2$CH$_2$OMe | H | |
| 10a-99 | Me | SO$_2$Me | CH$_2$CH$_2$OMe | H | |
| 10a-100 | Cl | Me | CH$_2$CH$_2$OMe | H | |
| 10a-101 | Cl | F | CH$_2$CH$_2$OMe | H | |
| 10a-102 | Cl | Cl | CH$_2$CH$_2$OMe | H | |
| 10a-103 | Cl | Br | CH$_2$CH$_2$OMe | H | |
| 10a-104 | Cl | I | CH$_2$CH$_2$OMe | H | |
| 10a-105 | Cl | CF$_3$ | CH$_2$CH$_2$OMe | H | |
| 10a-106 | Cl | CHF$_2$ | CH$_2$CH$_2$OMe | H | |
| 10a-107 | Cl | CF$_2$Cl | CH$_2$CH$_2$OMe | H | |
| 10a-108 | Cl | OMe | CH$_2$CH$_2$OMe | H | |
| 10a-109 | Cl | NO$_2$ | CH$_2$CH$_2$OMe | H | |
| 10a-110 | Cl | SO$_2$Me | CH$_2$CH$_2$OMe | H | |
| 10a-111 | OMe | Me | CH$_2$CH$_2$OMe | H | |
| 10a-112 | OMe | F | CH$_2$CH$_2$OMe | H | |
| 10a-113 | OMe | Cl | CH$_2$CH$_2$OMe | H | |
| 10a-114 | OMe | Br | CH$_2$CH$_2$OMe | H | |
| 10a-115 | OMe | I | CH$_2$CH$_2$OMe | H | |
| 10a-116 | OMe | CF$_3$ | CH$_2$CH$_2$OMe | H | |
| 10a-117 | OMe | CHF$_2$ | CH$_2$CH$_2$OMe | H | |
| 10a-118 | OMe | CF$_2$Cl | CH$_2$CH$_2$OMe | H | |
| 10a-119 | OMe | OMe | CH$_2$CH$_2$OMe | H | |
| 10a-120 | OMe | NO$_2$ | CH$_2$CH$_2$OMe | H | |
| 10a-121 | OMe | SO$_2$Me | CH$_2$CH$_2$OMe | H | |
| 10a-122 | SO$_2$Me | Me | CH$_2$CH$_2$OMe | H | |
| 10a-123 | SO$_2$Me | F | CH$_2$CH$_2$OMe | H | |
| 10a-124 | SO$_2$Me | Cl | CH$_2$CH$_2$OMe | H | |
| 10a-125 | SO$_2$Me | Br | CH$_2$CH$_2$OMe | H | |
| 10a-126 | SO$_2$Me | I | CH$_2$CH$_2$OMe | H | |
| 10a-127 | SO$_2$Me | CF$_3$ | CH$_2$CH$_2$OMe | H | |
| 10a-128 | SO$_2$Me | CHF$_2$ | CH$_2$CH$_2$OMe | H | |
| 10a-129 | SO$_2$Me | CF$_2$Cl | CH$_2$CH$_2$OMe | H | |
| 10a-130 | SO$_2$Me | OMe | CH$_2$CH$_2$OMe | H | |
| 10a-131 | SO$_2$Me | NO$_2$ | CH$_2$CH$_2$OMe | H | |
| 10a-132 | SO$_2$Me | SO$_2$Me | CH$_2$CH$_2$OMe | H | |
| 10a-133 | Me | Me | Me | CN | |
| 10a-134 | Me | F | Me | CN | |
| 10a-135 | Me | Cl | Me | CN | |
| 10a-136 | Me | Br | Me | CN | |
| 10a-137 | Me | I | Me | CN | |
| 10a-138 | Me | CF$_3$ | Me | CN | |
| 10a-139 | Me | CHF$_2$ | Me | CN | |
| 10a-140 | Me | CF$_2$Cl | Me | CN | |
| 10a-141 | Me | OMe | Me | CN | |
| 10a-142 | Me | NO$_2$ | Me | CN | |
| 10a-143 | Me | SO$_2$Me | Me | CN | |
| 10a-144 | Cl | Me | Me | CN | |
| 10a-145 | Cl | F | Me | CN | |
| 10a-146 | Cl | Cl | Me | CN | |
| 10a-147 | Cl | Br | Me | CN | |
| 10a-148 | Cl | I | Me | CN | |
| 10a-149 | Cl | CF$_3$ | Me | CN | |
| 10a-150 | Cl | CHF$_2$ | Me | CN | |
| 10a-151 | Cl | CF$_2$Cl | Me | CN | |
| 10a-152 | Cl | OMe | Me | CN | |
| 10a-153 | Cl | NO$_2$ | Me | CN | |
| 10a-154 | Cl | SO$_2$Me | Me | CN | |
| 10a-155 | OMe | Me | Me | CN | |
| 10a-156 | OMe | F | Me | CN | |
| 10a-157 | OMe | Cl | Me | CN | |
| 10a-158 | OMe | Br | Me | CN | |
| 10a-159 | OMe | I | Me | CN | |
| 10a-160 | OMe | CF$_3$ | Me | CN | (400 MHz, CDCl$_3$ δ, ppm) 7.82 (d, 1H), 7.61 (d, 1H), 7.48 (s, 1H), 4.12 (q, 2H), 4.06 (s, 3H), 3.36 (s, 3H), 1.48 (t, 3H) |
| 10a-161 | OMe | CHF$_2$ | Me | CN | |

TABLE 10a-continued

Compounds according to the invention of the formula (I) in which Q is Q3, $R^i$ is ethyl and $R^h$, $R^k$ and W are each hydrogen, t = 0 and the other radicals have the meanings indicated in the table

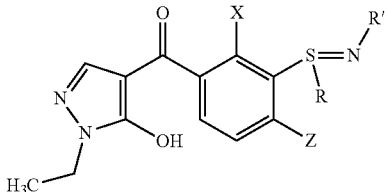

| No. | X | Z | R | R' | Physical data ($^1$H NMR) |
|---|---|---|---|---|---|
| 10a-162 | OMe | CF$_2$Cl | Me | CN | |
| 10a-163 | OMe | OMe | Me | CN | |
| 10a-164 | OMe | NO$_2$ | Me | CN | |
| 10a-165 | OMe | SO$_2$Me | Me | CN | |
| 10a-166 | SO$_2$Me | Me | Me | CN | |
| 10a-167 | SO$_2$Me | F | Me | CN | |
| 10a-168 | SO$_2$Me | Cl | Me | CN | |
| 10a-169 | SO$_2$Me | Br | Me | CN | |
| 10a-170 | SO$_2$Me | I | Me | CN | |
| 10a-171 | SO$_2$Me | CF$_3$ | Me | CN | |
| 10a-172 | SO$_2$Me | CHF$_2$ | Me | CN | |
| 10a-173 | SO$_2$Me | CF$_2$Cl | Me | CN | |
| 10a-174 | SO$_2$Me | OMe | Me | CN | |
| 10a-175 | SO$_2$Me | NO$_2$ | Me | CN | |
| 10a-176 | SO$_2$Me | SO$_2$Me | Me | CN | |
| 10a-177 | Me | Me | Et | CN | |
| 10a-178 | Me | F | Et | CN | |
| 10a-179 | Me | Cl | Et | CN | |
| 10a-180 | Me | Br | Et | CN | |
| 10a-181 | Me | I | Et | CN | |
| 10a-182 | Me | CF$_3$ | Et | CN | |
| 10a-183 | Me | CHF$_2$ | Et | CN | |
| 10a-184 | Me | CF$_2$Cl | Et | CN | |
| 10a-185 | Me | OMe | Et | CN | |
| 10a-186 | Me | NO$_2$ | Et | CN | |
| 10a-187 | Me | SO$_2$Me | Et | CN | |
| 10a-188 | Cl | Me | Et | CN | |
| 10a-189 | Cl | F | Et | CN | |
| 10a-190 | Cl | Cl | Et | CN | |
| 10a-191 | Cl | Br | Et | CN | |
| 10a-192 | Cl | I | Et | CN | |
| 10a-193 | Cl | CF$_3$ | Et | CN | |
| 10a-194 | Cl | CHF$_2$ | Et | CN | |
| 10a-195 | Cl | CF$_2$Cl | Et | CN | |
| 10a-196 | Cl | OMe | Et | CN | |
| 10a-197 | Cl | NO$_2$ | Et | CN | |
| 10a-198 | Cl | SO$_2$Me | Et | CN | |
| 10a-199 | OMe | Me | Et | CN | |
| 10a-200 | OMe | F | Et | CN | |
| 10a-201 | OMe | Cl | Et | CN | |
| 10a-202 | OMe | Br | Et | CN | |
| 10a-203 | OMe | I | Et | CN | |
| 10a-204 | OMe | CF$_3$ | Et | CN | |
| 10a-205 | OMe | CHF$_2$ | Et | CN | |
| 10a-206 | OMe | CF$_2$Cl | Et | CN | |
| 10a-207 | OMe | OMe | Et | CN | |
| 10a-208 | OMe | NO$_2$ | Et | CN | |
| 10a-209 | OMe | SO$_2$Me | Et | CN | |
| 10a-210 | SO$_2$Me | Me | Et | CN | |
| 10a-211 | SO$_2$Me | F | Et | CN | |
| 10a-212 | SO$_2$Me | Cl | Et | CN | |
| 10a-213 | SO$_2$Me | Br | Et | CN | |
| 10a-214 | SO$_2$Me | I | Et | CN | |
| 10a-215 | SO$_2$Me | CF$_3$ | Et | CN | |
| 10a-216 | SO$_2$Me | CHF$_2$ | Et | CN | |
| 10a-217 | SO$_2$Me | CF$_2$Cl | Et | CN | |
| 10a-218 | SO$_2$Me | OMe | Et | CN | |
| 10a-219 | SO$_2$Me | NO$_2$ | Et | CN | |
| 10a-220 | SO$_2$Me | SO$_2$Me | Et | CN | |
| 10a-221 | Me | Me | CH$_2$CH$_2$OMe | CN | |
| 10a-222 | Me | F | CH$_2$CH$_2$OMe | CN | |
| 10a-223 | Me | Cl | CH$_2$CH$_2$OMe | CN | |
| 10a-224 | Me | Br | CH$_2$CH$_2$OMe | CN | |

TABLE 10a-continued

Compounds according to the invention of the formula (I) in which Q is Q3, $R^i$ is ethyl and $R^h$, $R^k$ and W are each hydrogen, t = 0 and the other radicals have the meanings indicated in the table

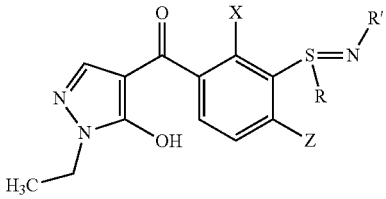

| No. | X | Z | R | R' | Physical data ($^1$H NMR) |
|---|---|---|---|---|---|
| 10a-225 | Me | I | CH$_2$CH$_2$OMe | CN | |
| 10a-226 | Me | CF$_3$ | CH$_2$CH$_2$OMe | CN | |
| 10a-227 | Me | CHF$_2$ | CH$_2$CH$_2$OMe | CN | |
| 10a-228 | Me | CF$_2$Cl | CH$_2$CH$_2$OMe | CN | |
| 10a-229 | Me | OMe | CH$_2$CH$_2$OMe | CN | |
| 10a-230 | Me | NO$_2$ | CH$_2$CH$_2$OMe | CN | |
| 10a-231 | Me | SO$_2$Me | CH$_2$CH$_2$OMe | CN | |
| 10a-232 | Cl | Me | CH$_2$CH$_2$OMe | CN | |
| 10a-233 | Cl | F | CH$_2$CH$_2$OMe | CN | |
| 10a-234 | Cl | Cl | CH$_2$CH$_2$OMe | CN | |
| 10a-235 | Cl | Br | CH$_2$CH$_2$OMe | CN | |
| 10a-236 | Cl | I | CH$_2$CH$_2$OMe | CN | |
| 10a-237 | Cl | CF$_3$ | CH$_2$CH$_2$OMe | CN | |
| 10a-238 | Cl | CHF$_2$ | CH$_2$CH$_2$OMe | CN | |
| 10a-239 | Cl | CF$_2$Cl | CH$_2$CH$_2$OMe | CN | |
| 10a-240 | Cl | OMe | CH$_2$CH$_2$OMe | CN | |
| 10a-241 | Cl | NO$_2$ | CH$_2$CH$_2$OMe | CN | |
| 10a-242 | Cl | SO$_2$Me | CH$_2$CH$_2$OMe | CN | |
| 10a-243 | OMe | Me | CH$_2$CH$_2$OMe | CN | |
| 10a-244 | OMe | F | CH$_2$CH$_2$OMe | CN | |
| 10a-245 | OMe | Cl | CH$_2$CH$_2$OMe | CN | |
| 10a-246 | OMe | Br | CH$_2$CH$_2$OMe | CN | |
| 10a-247 | OMe | I | CH$_2$CH$_2$OMe | CN | |
| 10a-248 | OMe | CF$_3$ | CH$_2$CH$_2$OMe | CN | |
| 10a-249 | OMe | CHF$_2$ | CH$_2$CH$_2$OMe | CN | |
| 10a-250 | OMe | CF$_2$Cl | CH$_2$CH$_2$OMe | CN | |
| 10a-251 | OMe | OMe | CH$_2$CH$_2$OMe | CN | |
| 10a-252 | OMe | NO$_2$ | CH$_2$CH$_2$OMe | CN | |
| 10a-253 | OMe | SO$_2$Me | CH$_2$CH$_2$OMe | CN | |
| 10a-254 | SO$_2$Me | Me | CH$_2$CH$_2$OMe | CN | |
| 10a-255 | SO$_2$Me | F | CH$_2$CH$_2$OMe | CN | |
| 10a-256 | SO$_2$Me | Cl | CH$_2$CH$_2$OMe | CN | |
| 10a-257 | SO$_2$Me | Br | CH$_2$CH$_2$OMe | CN | |
| 10a-258 | SO$_2$Me | I | CH$_2$CH$_2$OMe | CN | |
| 10a-259 | SO$_2$Me | CF$_3$ | CH$_2$CH$_2$OMe | CN | |
| 10a-260 | SO$_2$Me | CHF$_2$ | CH$_2$CH$_2$OMe | CN | |
| 10a-261 | SO$_2$Me | CF$_2$Cl | CH$_2$CH$_2$OMe | CN | |
| 10a-262 | SO$_2$Me | OMe | CH$_2$CH$_2$OMe | CN | |
| 10a-263 | SO$_2$Me | NO$_2$ | CH$_2$CH$_2$OMe | CN | |
| 10a-264 | SO$_2$Me | SO$_2$Me | CH$_2$CH$_2$OMe | CN | |

TABLE 11

Compounds according to the invention of the formula (I) in which Q is Q3, $R^i$ and $R^k$ is in each case methyl, $R^h$ and W are each hydrogen, t = 0 and the other radicals have the meanings indicated in the table

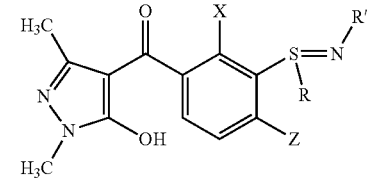

| No. | X | Z | R | R' | Physical data (1H NMR) |
|---|---|---|---|---|---|
| 11-1 | Me | Me | Me | H | |
| 11-2 | Me | F | Me | H | |

TABLE 11-continued

Compounds according to the invention of the formula (I) in which Q is Q3, $R^i$ and $R^k$ is in each case methyl, $R^h$ and W are each hydrogen, t = 0 and the other radicals have the meanings indicated in the table

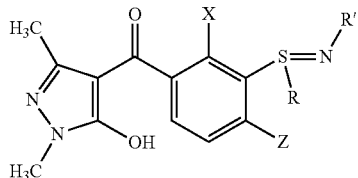
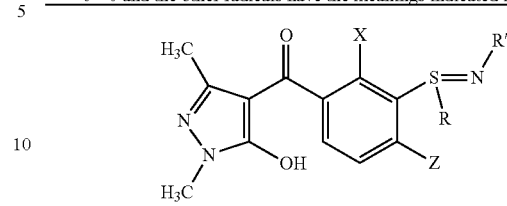

| No. | X | Z | R | R' | Physical data (1H NMR) |
|---|---|---|---|---|---|
| 11-3 | Me | Cl | Me | H | |
| 11-4 | Me | Br | Me | H | |
| 11-5 | Me | I | Me | H | |
| 11-6 | Me | CF$_3$ | Me | H | |
| 11-7 | Me | CHF$_2$ | Me | H | |
| 11-8 | Me | CF$_2$Cl | Me | H | |
| 11-9 | Me | OMe | Me | H | |
| 11-10 | Me | NO$_2$ | Me | H | |
| 11-11 | Me | SO$_2$Me | Me | H | |
| 11-12 | Cl | Me | Me | H | |
| 11-13 | Cl | F | Me | H | |
| 11-14 | Cl | Cl | Me | H | |
| 11-15 | Cl | Br | Me | H | |
| 11-16 | Cl | I | Me | H | |
| 11-17 | Cl | CF$_3$ | Me | H | |
| 11-18 | Cl | CHF$_2$ | Me | H | |
| 11-19 | Cl | CF$_2$Cl | Me | H | |
| 11-20 | Cl | OMe | Me | H | |
| 11-21 | Cl | NO$_2$ | Me | H | |
| 11-22 | Cl | SO$_2$Me | Me | H | |
| 11-23 | OMe | Me | Me | H | |
| 11-24 | OMe | F | Me | H | |
| 11-25 | OMe | Cl | Me | H | |
| 11-26 | OMe | Br | Me | H | |
| 11-27 | OMe | I | Me | H | |
| 11-28 | OMe | CF$_3$ | Me | H | |
| 11-29 | OMe | CHF$_2$ | Me | H | |
| 11-30 | OMe | CF$_2$Cl | Me | H | |
| 11-31 | OMe | OMe | Me | H | |
| 11-32 | OMe | NO$_2$ | Me | H | |
| 11-33 | OMe | SO$_2$Me | Me | H | |
| 11-34 | SO$_2$Me | Me | Me | H | |
| 11-35 | SO$_2$Me | F | Me | H | |
| 11-36 | SO$_2$Me | Cl | Me | H | |
| 11-37 | SO$_2$Me | Br | Me | H | |
| 11-38 | SO$_2$Me | I | Me | H | |
| 11-39 | SO$_2$Me | CF$_3$ | Me | H | |
| 11-40 | SO$_2$Me | CHF$_2$ | Me | H | |
| 11-41 | SO$_2$Me | CF$_2$Cl | Me | H | |
| 11-42 | SO$_2$Me | OMe | Me | H | |
| 11-43 | SO$_2$Me | NO$_2$ | Me | H | |
| 11-44 | SO$_2$Me | SO$_2$Me | Me | H | |
| 11-45 | Me | Me | Et | H | |
| 11-46 | Me | F | Et | H | |
| 11-47 | Me | Cl | Et | H | |
| 11-48 | Me | Br | Et | H | |
| 11-49 | Me | I | Et | H | |
| 11-50 | Me | CF$_3$ | Et | H | |
| 11-51 | Me | CHF$_2$ | Et | H | |
| 11-52 | Me | CF$_2$Cl | Et | H | |
| 11-53 | Me | OMe | Et | H | |
| 11-54 | Me | NO$_2$ | Et | H | |
| 11-55 | Me | SO$_2$Me | Et | H | |
| 11-56 | Cl | Me | Et | H | |
| 11-57 | Cl | F | Et | H | |
| 11-58 | Cl | Cl | Et | H | |
| 11-59 | Cl | Br | Et | H | |
| 11-60 | Cl | I | Et | H | |
| 11-61 | Cl | CF$_3$ | Et | H | |
| 11-62 | Cl | CHF$_2$ | Et | H | |
| 11-63 | Cl | CF$_2$Cl | Et | H | |
| 11-64 | Cl | OMe | Et | H | |
| 11-65 | Cl | NO$_2$ | Et | H | |
| 11-66 | Cl | SO$_2$Me | Et | H | |
| 11-67 | OMe | Me | Et | H | |
| 11-68 | OMe | F | Et | H | |
| 11-69 | OMe | Cl | Et | H | |
| 11-70 | OMe | Br | Et | H | |
| 11-71 | OMe | I | Et | H | |
| 11-72 | OMe | CF$_3$ | Et | H | |
| 11-73 | OMe | CHF$_2$ | Et | H | |
| 11-74 | OMe | CF$_2$Cl | Et | H | |
| 11-75 | OMe | OMe | Et | H | |
| 11-76 | OMe | NO$_2$ | Et | H | |
| 11-77 | OMe | SO$_2$Me | Et | H | |
| 11-78 | SO$_2$Me | Me | Et | H | |
| 11-79 | SO$_2$Me | F | Et | H | |
| 11-80 | SO$_2$Me | Cl | Et | H | |
| 11-81 | SO$_2$Me | Br | Et | H | |
| 11-82 | SO$_2$Me | I | Et | H | |
| 11-83 | SO$_2$Me | CF$_3$ | Et | H | |
| 11-84 | SO$_2$Me | CHF$_2$ | Et | H | |
| 11-85 | SO$_2$Me | CF$_2$Cl | Et | H | |
| 11-86 | SO$_2$Me | OMe | Et | H | |
| 11-87 | SO$_2$Me | NO$_2$ | Et | H | |
| 11-88 | SO$_2$Me | SO$_2$Me | Et | H | |
| 11-89 | Me | Me | CH$_2$CH$_2$OMe | H | |
| 11-90 | Me | F | CH$_2$CH$_2$OMe | H | |
| 11-91 | Me | Cl | CH$_2$CH$_2$OMe | H | |
| 11-92 | Me | Br | CH$_2$CH$_2$OMe | H | |
| 11-93 | Me | I | CH$_2$CH$_2$OMe | H | |
| 11-94 | Me | CF$_3$ | CH$_2$CH$_2$OMe | H | |
| 11-95 | Me | CHF$_2$ | CH$_2$CH$_2$OMe | H | |
| 11-96 | Me | CF$_2$Cl | CH$_2$CH$_2$OMe | H | |
| 11-97 | Me | OMe | CH$_2$CH$_2$OMe | H | |
| 11-98 | Me | NO$_2$ | CH$_2$CH$_2$OMe | H | |
| 11-99 | Me | SO$_2$Me | CH$_2$CH$_2$OMe | H | |
| 11-100 | Cl | Me | CH$_2$CH$_2$OMe | H | |
| 11-101 | Cl | F | CH$_2$CH$_2$OMe | H | |
| 11-102 | Cl | Cl | CH$_2$CH$_2$OMe | H | |
| 11-103 | Cl | Br | CH$_2$CH$_2$OMe | H | |
| 11-104 | Cl | I | CH$_2$CH$_2$OMe | H | |
| 11-105 | Cl | CF$_3$ | CH$_2$CH$_2$OMe | H | |
| 11-106 | Cl | CHF$_2$ | CH$_2$CH$_2$OMe | H | |
| 11-107 | Cl | CF$_2$Cl | CH$_2$CH$_2$OMe | H | |
| 11-108 | Cl | OMe | CH$_2$CH$_2$OMe | H | |
| 11-109 | Cl | NO$_2$ | CH$_2$CH$_2$OMe | H | |
| 11-110 | Cl | SO$_2$Me | CH$_2$CH$_2$OMe | H | |
| 11-111 | OMe | Me | CH$_2$CH$_2$OMe | H | |
| 11-112 | OMe | F | CH$_2$CH$_2$OMe | H | |
| 11-113 | OMe | Cl | CH$_2$CH$_2$OMe | H | |
| 11-114 | OMe | Br | CH$_2$CH$_2$OMe | H | |
| 11-115 | OMe | I | CH$_2$CH$_2$OMe | H | |
| 11-116 | OMe | CF$_3$ | CH$_2$CH$_2$OMe | H | |
| 11-117 | OMe | CHF$_2$ | CH$_2$CH$_2$OMe | H | |
| 11-118 | OMe | CF$_2$Cl | CH$_2$CH$_2$OMe | H | |
| 11-119 | OMe | OMe | CH$_2$CH$_2$OMe | H | |
| 11-120 | OMe | NO$_2$ | CH$_2$CH$_2$OMe | H | |
| 11-121 | OMe | SO$_2$Me | CH$_2$CH$_2$OMe | H | |
| 11-122 | SO$_2$Me | Me | CH$_2$CH$_2$OMe | H | |
| 11-123 | SO$_2$Me | F | CH$_2$CH$_2$OMe | H | |
| 11-124 | SO$_2$Me | Cl | CH$_2$CH$_2$OMe | H | |
| 11-125 | SO$_2$Me | Br | CH$_2$CH$_2$OMe | H | |
| 11-126 | SO$_2$Me | I | CH$_2$CH$_2$OMe | H | |
| 11-127 | SO$_2$Me | CF$_3$ | CH$_2$CH$_2$OMe | H | |
| 11-128 | SO$_2$Me | CHF$_2$ | CH$_2$CH$_2$OMe | H | |

TABLE 11-continued

Compounds according to the invention of the formula (I) in which Q is Q3, $R^i$ and $R^k$ is in each case methyl, $R^h$ and W are each hydrogen, t = 0 and the other radicals have the meanings indicated in the table

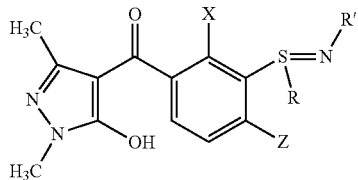

| No. | X | Z | R | R' | Physical data (1H NMR) |
|---|---|---|---|---|---|
| 11-129 | SO$_2$Me | CF$_2$Cl | CH$_2$CH$_2$OMe | H | |
| 11-130 | SO$_2$Me | OMe | CH$_2$CH$_2$OMe | H | |
| 11-131 | SO$_2$Me | NO$_2$ | CH$_2$CH$_2$OMe | H | |
| 11-132 | SO$_2$Me | SO$_2$Me | CH$_2$CH$_2$OMe | H | |
| 11-133 | Me | Me | Me | CN | |
| 11-134 | Me | F | Me | CN | |
| 11-135 | Me | Cl | Me | CN | |
| 11-136 | Me | Br | Me | CN | |
| 11-137 | Me | I | Me | CN | |
| 11-138 | Me | CF$_3$ | Me | CN | |
| 11-139 | Me | CHF$_2$ | Me | CN | |
| 11-140 | Me | CF$_2$Cl | Me | CN | |
| 11-141 | Me | OMe | Me | CN | |
| 11-142 | Me | NO$_2$ | Me | CN | |
| 11-143 | Me | SO$_2$Me | Me | CN | |
| 11-144 | Cl | Me | Me | CN | |
| 11-145 | Cl | F | Me | CN | |
| 11-146 | Cl | Cl | Me | CN | |
| 11-147 | Cl | Br | Me | CN | |
| 11-148 | Cl | I | Me | CN | |
| 11-149 | Cl | CF$_3$ | Me | CN | |
| 11-150 | Cl | CHF$_2$ | Me | CN | |
| 11-151 | Cl | CF$_2$Cl | Me | CN | |
| 11-152 | Cl | OMe | Me | CN | |
| 11-153 | Cl | NO$_2$ | Me | CN | |
| 11-154 | Cl | SO$_2$Me | Me | CN | |
| 11-155 | OMe | Me | Me | CN | |
| 11-156 | OMe | F | Me | CN | |
| 11-157 | OMe | Cl | Me | CN | |
| 11-158 | OMe | Br | Me | CN | |
| 11-159 | OMe | I | Me | CN | |
| 11-160 | OMe | CF$_3$ | Me | CN | |
| 11-161 | OMe | CHF$_2$ | Me | CN | |
| 11-162 | OMe | CF$_2$Cl | Me | CN | |
| 11-163 | OMe | OMe | Me | CN | |
| 11-164 | OMe | NO$_2$ | Me | CN | |
| 11-165 | OMe | SO$_2$Me | Me | CN | |
| 11-166 | SO$_2$Me | Me | Me | CN | |
| 11-167 | SO$_2$Me | F | Me | CN | |
| 11-168 | SO$_2$Me | Cl | Me | CN | |
| 11-169 | SO$_2$Me | Br | Me | CN | |
| 11-170 | SO$_2$Me | I | Me | CN | |
| 11-171 | SO$_2$Me | CF$_3$ | Me | CN | |
| 11-172 | SO$_2$Me | CHF$_2$ | Me | CN | |
| 11-173 | SO$_2$Me | CF$_2$Cl | Me | CN | |
| 11-174 | SO$_2$Me | OMe | Me | CN | |
| 11-175 | SO$_2$Me | NO$_2$ | Me | CN | |
| 11-176 | SO$_2$Me | SO$_2$Me | Me | CN | |
| 11-177 | Me | Me | Et | CN | |
| 11-178 | Me | F | Et | CN | |
| 11-179 | Me | Cl | Et | CN | |
| 11-180 | Me | Br | Et | CN | |
| 11-181 | Me | I | Et | CN | |
| 11-182 | Me | CF$_3$ | Et | CN | |
| 11-183 | Me | CHF$_2$ | Et | CN | |
| 11-184 | Me | CF$_2$Cl | Et | CN | |
| 11-185 | Me | OMe | Et | CN | |
| 11-186 | Me | NO$_2$ | Et | CN | |
| 11-187 | Me | SO$_2$Me | Et | CN | |
| 11-188 | Cl | Me | Et | CN | |
| 11-189 | Cl | F | Et | CN | |
| 11-190 | Cl | Cl | Et | CN | |
| 11-191 | Cl | Br | Et | CN | |
| 11-192 | Cl | I | Et | CN | |
| 11-193 | Cl | CF$_3$ | Et | CN | |
| 11-194 | Cl | CHF$_2$ | Et | CN | |
| 11-195 | Cl | CF$_2$Cl | Et | CN | |
| 11-196 | Cl | OMe | Et | CN | |
| 11-197 | Cl | NO$_2$ | Et | CN | |
| 11-198 | Cl | SO$_2$Me | Et | CN | |
| 11-199 | OMe | Me | Et | CN | |
| 11-200 | OMe | F | Et | CN | |
| 11-201 | OMe | Cl | Et | CN | |
| 11-202 | OMe | Br | Et | CN | |
| 11-203 | OMe | I | Et | CN | |
| 11-204 | OMe | CF$_3$ | Et | CN | |
| 11-205 | OMe | CHF$_2$ | Et | CN | |
| 11-206 | OMe | CF$_2$Cl | Et | CN | |
| 11-207 | OMe | OMe | Et | CN | |
| 11-208 | OMe | NO$_2$ | Et | CN | |
| 11-209 | OMe | SO$_2$Me | Et | CN | |
| 11-210 | SO$_2$Me | Me | Et | CN | |
| 11-211 | SO$_2$Me | F | Et | CN | |
| 11-212 | SO$_2$Me | Cl | Et | CN | |
| 11-213 | SO$_2$Me | Br | Et | CN | |
| 11-214 | SO$_2$Me | I | Et | CN | |
| 11-215 | SO$_2$Me | CF$_3$ | Et | CN | |
| 11-216 | SO$_2$Me | CHF$_2$ | Et | CN | |
| 11-217 | SO$_2$Me | CF$_2$Cl | Et | CN | |
| 11-218 | SO$_2$Me | OMe | Et | CN | |
| 11-219 | SO$_2$Me | NO$_2$ | Et | CN | |
| 11-220 | SO$_2$Me | SO$_2$Me | Et | CN | |
| 11-221 | Me | Me | CH$_2$CH$_2$OMe | CN | |
| 11-222 | Me | F | CH$_2$CH$_2$OMe | CN | |
| 11-223 | Me | Cl | CH$_2$CH$_2$OMe | CN | |
| 11-224 | Me | Br | CH$_2$CH$_2$OMe | CN | |
| 11-225 | Me | I | CH$_2$CH$_2$OMe | CN | |
| 11-226 | Me | CF$_3$ | CH$_2$CH$_2$OMe | CN | |
| 11-227 | Me | CHF$_2$ | CH$_2$CH$_2$OMe | CN | |
| 11-228 | Me | CF$_2$Cl | CH$_2$CH$_2$OMe | CN | |
| 11-229 | Me | OMe | CH$_2$CH$_2$OMe | CN | |
| 11-230 | Me | NO$_2$ | CH$_2$CH$_2$OMe | CN | |
| 11-231 | Me | SO$_2$Me | CH$_2$CH$_2$OMe | CN | |
| 11-232 | Cl | Me | CH$_2$CH$_2$OMe | CN | |
| 11-233 | Cl | F | CH$_2$CH$_2$OMe | CN | |
| 11-234 | Cl | Cl | CH$_2$CH$_2$OMe | CN | |
| 11-235 | Cl | Br | CH$_2$CH$_2$OMe | CN | |
| 11-236 | Cl | I | CH$_2$CH$_2$OMe | CN | |
| 11-237 | Cl | CF$_3$ | CH$_2$CH$_2$OMe | CN | |
| 11-238 | Cl | CHF$_2$ | CH$_2$CH$_2$OMe | CN | |
| 11-239 | Cl | CF$_2$Cl | CH$_2$CH$_2$OMe | CN | |
| 11-240 | Cl | OMe | CH$_2$CH$_2$OMe | CN | |
| 11-241 | Cl | NO$_2$ | CH$_2$CH$_2$OMe | CN | |
| 11-242 | Cl | SO$_2$Me | CH$_2$CH$_2$OMe | CN | |
| 11-243 | OMe | Me | CH$_2$CH$_2$OMe | CN | |
| 11-244 | OMe | F | CH$_2$CH$_2$OMe | CN | |
| 11-245 | OMe | Cl | CH$_2$CH$_2$OMe | CN | |
| 11-246 | OMe | Br | CH$_2$CH$_2$OMe | CN | |
| 11-247 | OMe | I | CH$_2$CH$_2$OMe | CN | |
| 11-248 | OMe | CF$_3$ | CH$_2$CH$_2$OMe | CN | |
| 11-249 | OMe | CHF$_2$ | CH$_2$CH$_2$OMe | CN | |
| 11-250 | OMe | CF$_2$Cl | CH$_2$CH$_2$OMe | CN | |
| 11-251 | OMe | OMe | CH$_2$CH$_2$OMe | CN | |
| 11-252 | OMe | NO$_2$ | CH$_2$CH$_2$OMe | CN | |
| 11-253 | OMe | SO$_2$Me | CH$_2$CH$_2$OMe | CN | |
| 11-254 | SO$_2$Me | Me | CH$_2$CH$_2$OMe | CN | |

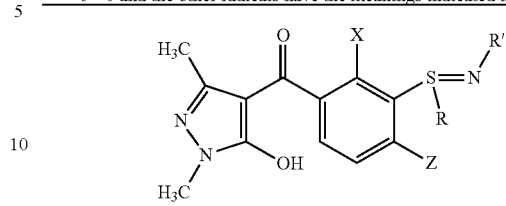

TABLE 11-continued

Compounds according to the invention of the formula (I) in which Q is Q3, $R^i$ and $R^k$ is in each case methyl, $R^h$ and W are each hydrogen, t = 0 and the other radicals have the meanings indicated in the table

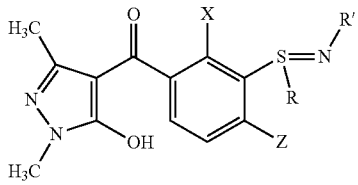

| No. | X | Z | R | R' | Physical data (1H NMR) |
|---|---|---|---|---|---|
| 11-255 | SO$_2$Me | F | CH$_2$CH$_2$OMe | CN | |
| 11-256 | SO$_2$Me | Cl | CH$_2$CH$_2$OMe | CN | |
| 11-257 | SO$_2$Me | Br | CH$_2$CH$_2$OMe | CN | |
| 11-258 | SO$_2$Me | I | CH$_2$CH$_2$OMe | CN | |
| 11-259 | SO$_2$Me | CF$_3$ | CH$_2$CH$_2$OMe | CN | |
| 11-260 | SO$_2$Me | CHF$_2$ | CH$_2$CH$_2$OMe | CN | |
| 11-261 | SO$_2$Me | CF$_2$Cl | CH$_2$CH$_2$OMe | CN | |
| 11-262 | SO$_2$Me | OMe | CH$_2$CH$_2$OMe | CN | |
| 11-263 | SO$_2$Me | NO$_2$ | CH$_2$CH$_2$OMe | CN | |
| 11-264 | SO$_2$Me | SO$_2$Me | CH$_2$CH$_2$OMe | CN | |

TABLE 12

Compounds according to the invention of the formula (I) in which Q is Q4, W is hydrogen, t = 0 and the other radicals have the meanings indicated in the table

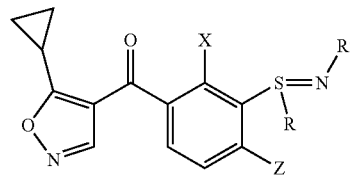

| No. | X | Z | R | R' | Physical data (1H NMR) |
|---|---|---|---|---|---|
| 12-1 | Me | Me | Me | H | |
| 12-2 | Me | F | Me | H | |
| 12-3 | Me | Cl | Me | H | |
| 12-4 | Me | Br | Me | H | |
| 12-5 | Me | I | Me | H | |
| 12-6 | Me | CF$_3$ | Me | H | |
| 12-7 | Me | CHF$_2$ | Me | H | |
| 12-8 | Me | CF$_2$Cl | Me | H | |
| 12-9 | Me | OMe | Me | H | |
| 12-10 | Me | NO$_2$ | Me | H | |
| 12-11 | Me | SO$_2$Me | Me | H | |
| 12-12 | Cl | Me | Me | H | |
| 12-13 | Cl | F | Me | H | |
| 12-14 | Cl | Cl | Me | H | |
| 12-15 | Cl | Br | Me | H | |
| 12-16 | Cl | I | Me | H | |
| 12-17 | Cl | CF$_3$ | Me | H | |
| 12-18 | Cl | CHF$_2$ | Me | H | |
| 12-19 | Cl | CF$_2$Cl | Me | H | |
| 12-20 | Cl | OMe | Me | H | |
| 12-21 | Cl | NO$_2$ | Me | H | |
| 12-22 | Cl | SO$_2$Me | Me | H | |
| 12-23 | OMe | Me | Me | H | |
| 12-24 | OMe | F | Me | H | |
| 12-25 | OMe | Cl | Me | H | |
| 12-26 | OMe | Br | Me | H | |
| 12-27 | OMe | I | Me | H | |
| 12-28 | OMe | CF$_3$ | Me | H | |
| 12-29 | OMe | CHF$_2$ | Me | H | |
| 12-30 | OMe | CF$_2$Cl | Me | H | |
| 12-31 | OMe | OMe | Me | H | |
| 12-32 | OMe | NO$_2$ | Me | H | |
| 12-33 | OMe | SO$_2$Me | Me | H | |

TABLE 12-continued

Compounds according to the invention of the formula (I) in which Q is Q4, W is hydrogen, t = 0 and the other radicals have the meanings indicated in the table

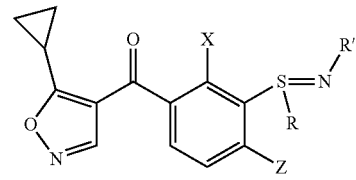

| No. | X | Z | R | R' | Physical data (1H NMR) |
|---|---|---|---|---|---|
| 12-34 | SO$_2$Me | Me | Me | H | |
| 12-35 | SO$_2$Me | F | Me | H | |
| 12-36 | SO$_2$Me | Cl | Me | H | |
| 12-37 | SO$_2$Me | Br | Me | H | |
| 12-38 | SO$_2$Me | I | Me | H | |
| 12-39 | SO$_2$Me | CF$_3$ | Me | H | |
| 12-40 | SO$_2$Me | CHF$_2$ | Me | H | |
| 12-41 | SO$_2$Me | CF$_2$Cl | Me | H | |
| 12-42 | SO$_2$Me | OMe | Me | H | |
| 12-43 | SO$_2$Me | NO$_2$ | Me | H | |
| 12-44 | SO$_2$Me | SO$_2$Me | Me | H | |
| 12-45 | Me | Me | Et | H | |
| 12-46 | Me | F | Et | H | |
| 12-47 | Me | Cl | Et | H | |
| 12-48 | Me | Br | Et | H | |
| 12-49 | Me | I | Et | H | |
| 12-50 | Me | CF$_3$ | Et | H | |
| 12-51 | Me | CHF$_2$ | Et | H | |
| 12-52 | Me | CF$_2$Cl | Et | H | |
| 12-53 | Me | OMe | Et | H | |
| 12-54 | Me | NO$_2$ | Et | H | |
| 12-55 | Me | SO$_2$Me | Et | H | |
| 12-56 | Cl | Me | Et | H | |
| 12-57 | Cl | F | Et | H | |
| 12-58 | Cl | Cl | Et | H | |
| 12-59 | Cl | Br | Et | H | |
| 12-60 | Cl | I | Et | H | |
| 12-61 | Cl | CF$_3$ | Et | H | |
| 12-62 | Cl | CHF$_2$ | Et | H | |
| 12-63 | Cl | CF$_2$Cl | Et | H | |
| 12-64 | Cl | OMe | Et | H | |
| 12-65 | Cl | NO$_2$ | Et | H | |
| 12-66 | Cl | SO$_2$Me | Et | H | |
| 12-67 | OMe | Me | Et | H | |
| 12-68 | OMe | F | Et | H | |
| 12-69 | OMe | Cl | Et | H | |
| 12-70 | OMe | Br | Et | H | |
| 12-71 | OMe | I | Et | H | |
| 12-72 | OMe | CF$_3$ | Et | H | |
| 12-73 | OMe | CHF$_2$ | Et | H | |
| 12-74 | OMe | CF$_2$Cl | Et | H | |
| 12-75 | OMe | OMe | Et | H | |
| 12-76 | OMe | NO$_2$ | Et | H | |
| 12-77 | OMe | SO$_2$Me | Et | H | |
| 12-78 | SO$_2$Me | Me | Et | H | |
| 12-79 | SO$_2$Me | F | Et | H | |
| 12-80 | SO$_2$Me | Cl | Et | H | |
| 12-81 | SO$_2$Me | Br | Et | H | |
| 12-82 | SO$_2$Me | I | Et | H | |
| 12-83 | SO$_2$Me | CF$_3$ | Et | H | |
| 12-84 | SO$_2$Me | CHF$_2$ | Et | H | |
| 12-85 | SO$_2$Me | CF$_2$Cl | Et | H | |
| 12-86 | SO$_2$Me | OMe | Et | H | |
| 12-87 | SO$_2$Me | NO$_2$ | Et | H | |
| 12-88 | SO$_2$Me | SO$_2$Me | Et | H | |
| 12-89 | Me | Me | CH$_2$CH$_2$OMe | H | |
| 12-90 | Me | F | CH$_2$CH$_2$OMe | H | |
| 12-91 | Me | Cl | CH$_2$CH$_2$OMe | H | |
| 12-92 | Me | Br | CH$_2$CH$_2$OMe | H | |
| 12-93 | Me | I | CH$_2$CH$_2$OMe | H | |
| 12-94 | Me | CF$_3$ | CH$_2$CH$_2$OMe | H | |
| 12-95 | Me | CHF$_2$ | CH$_2$CH$_2$OMe | H | |
| 12-96 | Me | CF$_2$Cl | CH$_2$CH$_2$OMe | H | |
| 12-97 | Me | OMe | CH$_2$CH$_2$OMe | H | |
| 12-98 | Me | NO$_2$ | CH$_2$CH$_2$OMe | H | |

TABLE 12-continued

Compounds according to the invention of the formula (I) in which Q is Q4, W is hydrogen, t = 0 and the other radicals have the meanings indicated in the table

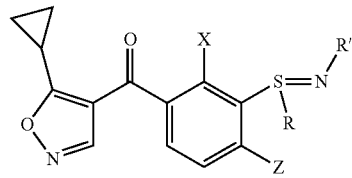

| No. | X | Z | R | R' | Physical data (1H NMR) |
|---|---|---|---|---|---|
| 12-99 | Me | SO$_2$Me | CH$_2$CH$_2$OMe | H | |
| 12-100 | Cl | Me | CH$_2$CH$_2$OMe | H | |
| 12-101 | Cl | F | CH$_2$CH$_2$OMe | H | |
| 12-102 | Cl | Cl | CH$_2$CH$_2$OMe | H | |
| 12-103 | Cl | Br | CH$_2$CH$_2$OMe | H | |
| 12-104 | Cl | I | CH$_2$CH$_2$OMe | H | |
| 12-105 | Cl | CF$_3$ | CH$_2$CH$_2$OMe | H | |
| 12-106 | Cl | CHF$_2$ | CH$_2$CH$_2$OMe | H | |
| 12-107 | Cl | CF$_2$Cl | CH$_2$CH$_2$OMe | H | |
| 12-108 | Cl | OMe | CH$_2$CH$_2$OMe | H | |
| 12-109 | Cl | NO$_2$ | CH$_2$CH$_2$OMe | H | |
| 12-110 | Cl | SO$_2$Me | CH$_2$CH$_2$OMe | H | |
| 12-111 | OMe | Me | CH$_2$CH$_2$OMe | H | |
| 12-112 | OMe | F | CH$_2$CH$_2$OMe | H | |
| 12-113 | OMe | Cl | CH$_2$CH$_2$OMe | H | |
| 12-114 | OMe | Br | CH$_2$CH$_2$OMe | H | |
| 12-115 | OMe | I | CH$_2$CH$_2$OMe | H | |
| 12-116 | OMe | CF$_3$ | CH$_2$CH$_2$OMe | H | |
| 12-117 | OMe | CHF$_2$ | CH$_2$CH$_2$OMe | H | |
| 12-118 | OMe | CF$_2$Cl | CH$_2$CH$_2$OMe | H | |
| 12-119 | OMe | OMe | CH$_2$CH$_2$OMe | H | |
| 12-120 | OMe | NO$_2$ | CH$_2$CH$_2$OMe | H | |
| 12-121 | OMe | SO$_2$Me | CH$_2$CH$_2$OMe | H | |
| 12-122 | SO$_2$Me | Me | CH$_2$CH$_2$OMe | H | |
| 12-123 | SO$_2$Me | F | CH$_2$CH$_2$OMe | H | |
| 12-124 | SO$_2$Me | Cl | CH$_2$CH$_2$OMe | H | |
| 12-125 | SO$_2$Me | Br | CH$_2$CH$_2$OMe | H | |
| 12-126 | SO$_2$Me | I | CH$_2$CH$_2$OMe | H | |
| 12-127 | SO$_2$Me | CF$_3$ | CH$_2$CH$_2$OMe | H | |
| 12-128 | SO$_2$Me | CHF$_2$ | CH$_2$CH$_2$OMe | H | |
| 12-129 | SO$_2$Me | CF$_2$Cl | CH$_2$CH$_2$OMe | H | |
| 12-130 | SO$_2$Me | OMe | CH$_2$CH$_2$OMe | H | |
| 12-131 | SO$_2$Me | NO$_2$ | CH$_2$CH$_2$OMe | H | |
| 12-132 | SO$_2$Me | SO$_2$Me | CH$_2$CH$_2$OMe | H | |
| 12-133 | Me | Me | Me | CN | |
| 12-134 | Me | F | Me | CN | |
| 12-135 | Me | Cl | Me | CN | |
| 12-136 | Me | Br | Me | CN | |
| 12-137 | Me | I | Me | CN | |
| 12-138 | Me | CF$_3$ | Me | CN | |
| 12-139 | Me | CHF$_2$ | Me | CN | |
| 12-140 | Me | CF$_2$Cl | Me | CN | |
| 12-141 | Me | OMe | Me | CN | |
| 12-142 | Me | NO$_2$ | Me | CN | |
| 12-143 | Me | SO$_2$Me | Me | CN | |
| 12-144 | Cl | Me | Me | CN | |
| 12-145 | Cl | F | Me | CN | |
| 12-146 | Cl | Cl | Me | CN | |
| 12-147 | Cl | Br | Me | CN | |
| 12-148 | Cl | I | Me | CN | |
| 12-149 | Cl | CF$_3$ | Me | CN | |
| 12-150 | Cl | CHF$_2$ | Me | CN | |
| 12-151 | Cl | CF$_2$Cl | Me | CN | |
| 12-152 | Cl | OMe | Me | CN | |
| 12-153 | Cl | NO$_2$ | Me | CN | |
| 12-154 | Cl | SO$_2$Me | Me | CN | |
| 12-155 | OMe | Me | Me | CN | |
| 12-156 | OMe | F | Me | CN | |
| 12-157 | OMe | Cl | Me | CN | |
| 12-158 | OMe | Br | Me | CN | |
| 12-159 | OMe | I | Me | CN | |
| 12-160 | OMe | CF$_3$ | Me | CN | |
| 12-161 | OMe | CHF$_2$ | Me | CN | |
| 12-162 | OMe | CF$_2$Cl | Me | CN | |
| 12-163 | OMe | OMe | Me | CN | |
| 12-164 | OMe | NO$_2$ | Me | CN | |
| 12-165 | OMe | SO$_2$Me | Me | CN | |
| 12-166 | SO$_2$Me | Me | Me | CN | |
| 12-167 | SO$_2$Me | F | Me | CN | |
| 12-168 | SO$_2$Me | Cl | Me | CN | |
| 12-169 | SO$_2$Me | Br | Me | CN | |
| 12-170 | SO$_2$Me | I | Me | CN | |
| 12-171 | SO$_2$Me | CF$_3$ | Me | CN | |
| 12-172 | SO$_2$Me | CHF$_2$ | Me | CN | |
| 12-173 | SO$_2$Me | CF$_2$Cl | Me | CN | |
| 12-174 | SO$_2$Me | OMe | Me | CN | |
| 12-175 | SO$_2$Me | NO$_2$ | Me | CN | |
| 12-176 | SO$_2$Me | SO$_2$Me | Me | CN | |
| 12-177 | Me | Me | Et | CN | |
| 12-178 | Me | F | Et | CN | |
| 12-179 | Me | Cl | Et | CN | |
| 12-180 | Me | Br | Et | CN | |
| 12-181 | Me | I | Et | CN | |
| 12-182 | Me | CF$_3$ | Et | CN | |
| 12-183 | Me | CHF$_2$ | Et | CN | |
| 12-184 | Me | CF$_2$Cl | Et | CN | |
| 12-185 | Me | OMe | Et | CN | |
| 12-186 | Me | NO$_2$ | Et | CN | |
| 12-187 | Me | SO$_2$Me | Et | CN | |
| 12-188 | Cl | Me | Et | CN | |
| 12-189 | Cl | F | Et | CN | |
| 12-190 | Cl | Cl | Et | CN | |
| 12-191 | Cl | Br | Et | CN | |
| 12-192 | Cl | I | Et | CN | |
| 12-193 | Cl | CF$_3$ | Et | CN | |
| 12-194 | Cl | CHF$_2$ | Et | CN | |
| 12-195 | Cl | CF$_2$Cl | Et | CN | |
| 12-196 | Cl | OMe | Et | CN | |
| 12-197 | Cl | NO$_2$ | Et | CN | |
| 12-198 | Cl | SO$_2$Me | Et | CN | |
| 12-199 | OMe | Me | Et | CN | |
| 12-200 | OMe | F | Et | CN | |
| 12-201 | OMe | Cl | Et | CN | |
| 12-202 | OMe | Br | Et | CN | |
| 12-203 | OMe | I | Et | CN | |
| 12-204 | OMe | CF$_3$ | Et | CN | |
| 12-205 | OMe | CHF$_2$ | Et | CN | |
| 12-206 | OMe | CF$_2$Cl | Et | CN | |
| 12-207 | OMe | OMe | Et | CN | |
| 12-208 | OMe | NO$_2$ | Et | CN | |
| 12-209 | OMe | SO$_2$Me | Et | CN | |
| 12-210 | SO$_2$Me | Me | Et | CN | |
| 12-211 | SO$_2$Me | F | Et | CN | |
| 12-212 | SO$_2$Me | Cl | Et | CN | |
| 12-213 | SO$_2$Me | Br | Et | CN | |
| 12-214 | SO$_2$Me | I | Et | CN | |
| 12-215 | SO$_2$Me | CF$_3$ | Et | CN | |
| 12-216 | SO$_2$Me | CHF$_2$ | Et | CN | |
| 12-217 | SO$_2$Me | CF$_2$Cl | Et | CN | |
| 12-218 | SO$_2$Me | OMe | Et | CN | |
| 12-219 | SO$_2$Me | NO$_2$ | Et | CN | |
| 12-220 | SO$_2$Me | SO$_2$Me | Et | CN | |
| 12-221 | Me | Me | CH$_2$CH$_2$OMe | CN | |
| 12-222 | Me | F | CH$_2$CH$_2$OMe | CN | |
| 12-223 | Me | Cl | CH$_2$CH$_2$OMe | CN | |
| 12-224 | Me | Br | CH$_2$CH$_2$OMe | CN | |
| 12-225 | Me | I | CH$_2$CH$_2$OMe | CN | |
| 12-226 | Me | CF$_3$ | CH$_2$CH$_2$OMe | CN | |
| 12-227 | Me | CHF$_2$ | CH$_2$CH$_2$OMe | CN | |
| 12-228 | Me | CF$_2$Cl | CH$_2$CH$_2$OMe | CN | |

TABLE 12-continued

Compounds according to the invention of the formula (I) in which Q is Q4, W is hydrogen, t = 0 and the other radicals have the meanings indicated in the table

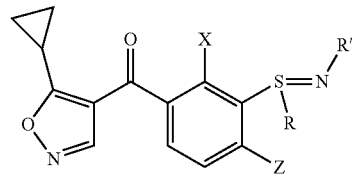

| No. | X | Z | R | R' | Physical data (1H NMR) |
|---|---|---|---|---|---|
| 12-229 | Me | OMe | CH₂CH₂OMe | CN | |
| 12-230 | Me | NO₂ | CH₂CH₂OMe | CN | |
| 12-231 | Me | SO₂Me | CH₂CH₂OMe | CN | |
| 12-232 | Cl | Me | CH₂CH₂OMe | CN | |
| 12-233 | Cl | F | CH₂CH₂OMe | CN | |
| 12-234 | Cl | Cl | CH₂CH₂OMe | CN | |
| 12-235 | Cl | Br | CH₂CH₂OMe | CN | |
| 12-236 | Cl | I | CH₂CH₂OMe | CN | |
| 12-237 | Cl | CF₃ | CH₂CH₂OMe | CN | |
| 12-238 | Cl | CHF₂ | CH₂CH₂OMe | CN | |
| 12-239 | Cl | CF₂Cl | CH₂CH₂OMe | CN | |
| 12-240 | Cl | OMe | CH₂CH₂OMe | CN | |
| 12-241 | Cl | NO₂ | CH₂CH₂OMe | CN | |
| 12-242 | Cl | SO₂Me | CH₂CH₂OMe | CN | |
| 12-243 | OMe | Me | CH₂CH₂OMe | CN | |
| 12-244 | OMe | F | CH₂CH₂OMe | CN | |
| 12-245 | OMe | Cl | CH₂CH₂OMe | CN | |
| 12-246 | OMe | Br | CH₂CH₂OMe | CN | |
| 12-247 | OMe | I | CH₂CH₂OMe | CN | |
| 12-248 | OMe | CF₃ | CH₂CH₂OMe | CN | |
| 12-249 | OMe | CHF₂ | CH₂CH₂OMe | CN | |
| 12-250 | OMe | CF₂Cl | CH₂CH₂OMe | CN | |
| 12-251 | OMe | OMe | CH₂CH₂OMe | CN | |
| 12-252 | OMe | NO₂ | CH₂CH₂OMe | CN | |
| 12-253 | OMe | SO₂Me | CH₂CH₂OMe | CN | |
| 12-254 | SO₂Me | Me | CH₂CH₂OMe | CN | |
| 12-255 | SO₂Me | F | CH₂CH₂OMe | CN | |
| 12-256 | SO₂Me | Cl | CH₂CH₂OMe | CN | |
| 12-257 | SO₂Me | Br | CH₂CH₂OMe | CN | |
| 12-258 | SO₂Me | I | CH₂CH₂OMe | CN | |
| 12-259 | SO₂Me | CF₃ | CH₂CH₂OMe | CN | |
| 12-260 | SO₂Me | CHF₂ | CH₂CH₂OMe | CN | |
| 12-261 | SO₂Me | CF₂Cl | CH₂CH₂OMe | CN | |
| 12-262 | SO₂Me | OMe | CH₂CH₂OMe | CN | |
| 12-263 | SO₂Me | NO₂ | CH₂CH₂OMe | CN | |
| 12-264 | SO₂Me | SO₂Me | CH₂CH₂OMe | CN | |

TABLE 13

Compounds according to the invention of the formula (I) in which Q is Q5, W is hydrogen, t = 0 and the other radicals have the meanings indicated in the table

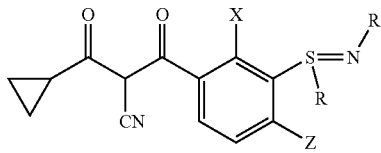

| No. | X | Z | R | R' | Physical data (1H NMR) |
|---|---|---|---|---|---|
| 13-1 | Me | Me | Me | H | |
| 13-2 | Me | F | Me | H | |
| 13-3 | Me | Cl | Me | H | |
| 13-4 | Me | Br | Me | H | |
| 13-5 | Me | I | Me | H | |
| 13-6 | Me | CF₃ | Me | H | |
| 13-7 | Me | CHF₂ | Me | H | |
| 13-8 | Me | CF₂Cl | Me | H | |
| 13-9 | Me | OMe | Me | H | |
| 13-10 | Me | NO₂ | Me | H | |
| 13-11 | Me | SO₂Me | Me | H | |
| 13-12 | Cl | Me | Me | H | |
| 13-13 | Cl | F | Me | H | |
| 13-14 | Cl | Cl | Me | H | |
| 13-15 | Cl | Br | Me | H | |
| 13-16 | Cl | I | Me | H | |
| 13-17 | Cl | CF₃ | Me | H | |
| 13-18 | Cl | CHF₂ | Me | H | |
| 13-19 | Cl | CF₂Cl | Me | H | |
| 13-20 | Cl | OMe | Me | H | |
| 13-21 | Cl | NO₂ | Me | H | |
| 13-22 | Cl | SO₂Me | Me | H | |
| 13-23 | OMe | Me | Me | H | |
| 13-24 | OMe | F | Me | H | |
| 13-25 | OMe | Cl | Me | H | |
| 13-26 | OMe | Br | Me | H | |
| 13-27 | OMe | I | Me | H | |
| 13-28 | OMe | CF₃ | Me | H | |
| 13-29 | OMe | CHF₂ | Me | H | |
| 13-30 | OMe | CF₂Cl | Me | H | |
| 13-31 | OMe | OMe | Me | H | |
| 13-32 | OMe | NO₂ | Me | H | |
| 13-33 | OMe | SO₂Me | Me | H | |
| 13-34 | SO₂Me | Me | Me | H | |
| 13-35 | SO₂Me | F | Me | H | |
| 13-36 | SO₂Me | Cl | Me | H | |
| 13-37 | SO₂Me | Br | Me | H | |
| 13-38 | SO₂Me | I | Me | H | |
| 13-39 | SO₂Me | CF₃ | Me | H | |
| 13-40 | SO₂Me | CHF₂ | Me | H | |
| 13-41 | SO₂Me | CF₂Cl | Me | H | |
| 13-42 | SO₂Me | OMe | Me | H | |
| 13-43 | SO₂Me | NO₂ | Me | H | |
| 13-44 | SO₂Me | SO₂Me | Me | H | |
| 13-45 | Me | Me | Et | H | |
| 13-46 | Me | F | Et | H | |
| 13-47 | Me | Cl | Et | H | |
| 13-48 | Me | Br | Et | H | |
| 13-49 | Me | I | Et | H | |
| 13-50 | Me | CF₃ | Et | H | |
| 13-51 | Me | CHF₂ | Et | H | |
| 13-52 | Me | CF₂Cl | Et | H | |
| 13-53 | Me | OMe | Et | H | |
| 13-54 | Me | NO₂ | Et | H | |
| 13-55 | Me | SO₂Me | Et | H | |
| 13-56 | Cl | Me | Et | H | |
| 13-57 | Cl | F | Et | H | |
| 13-58 | Cl | Cl | Et | H | |
| 13-59 | Cl | Br | Et | H | |
| 13-60 | Cl | I | Et | H | |
| 13-61 | Cl | CF₃ | Et | H | |
| 13-62 | Cl | CHF₂ | Et | H | |
| 13-63 | Cl | CF₂Cl | Et | H | |
| 13-64 | Cl | OMe | Et | H | |
| 13-65 | Cl | NO₂ | Et | H | |
| 13-66 | Cl | SO₂Me | Et | H | |
| 13-67 | OMe | Me | Et | H | |
| 13-68 | OMe | F | Et | H | |
| 13-69 | OMe | Cl | Et | H | |
| 13-70 | OMe | Br | Et | H | |
| 13-71 | OMe | I | Et | H | |
| 13-72 | OMe | CF₃ | Et | H | |
| 13-73 | OMe | CHF₂ | Et | H | |
| 13-74 | OMe | CF₂Cl | Et | H | |
| 13-75 | OMe | OMe | Et | H | |

TABLE 13-continued

Compounds according to the invention of the formula (I) in which Q is Q5, W is hydrogen, t = 0 and the other radicals have the meanings indicated in the table

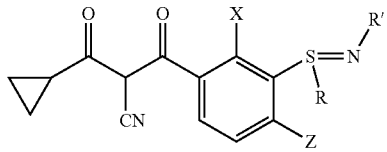
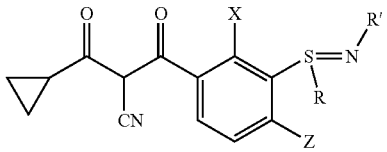

| No. | X | Z | R | R' | Physical data (1H NMR) |
|---|---|---|---|---|---|
| 13-76 | OMe | NO₂ | Et | H | |
| 13-77 | OMe | SO₂Me | Et | H | |
| 13-78 | SO₂Me | Me | Et | H | |
| 13-79 | SO₂Me | F | Et | H | |
| 13-80 | SO₂Me | Cl | Et | H | |
| 13-81 | SO₂Me | Br | Et | H | |
| 13-82 | SO₂Me | I | Et | H | |
| 13-83 | SO₂Me | CF₃ | Et | H | |
| 13-84 | SO₂Me | CHF₂ | Et | H | |
| 13-85 | SO₂Me | CF₂Cl | Et | H | |
| 13-86 | SO₂Me | OMe | Et | H | |
| 13-87 | SO₂Me | NO₂ | Et | H | |
| 13-88 | SO₂Me | SO₂Me | Et | H | |
| 13-89 | Me | Me | CH₂CH₂OMe | H | |
| 13-90 | Me | F | CH₂CH₂OMe | H | |
| 13-91 | Me | Cl | CH₂CH₂OMe | H | |
| 13-92 | Me | Br | CH₂CH₂OMe | H | |
| 13-93 | Me | I | CH₂CH₂OMe | H | |
| 13-94 | Me | CF₃ | CH₂CH₂OMe | H | |
| 13-95 | Me | CHF₂ | CH₂CH₂OMe | H | |
| 13-96 | Me | CF₂Cl | CH₂CH₂OMe | H | |
| 13-97 | Me | OMe | CH₂CH₂OMe | H | |
| 13-98 | Me | NO₂ | CH₂CH₂OMe | H | |
| 13-99 | Me | SO₂Me | CH₂CH₂OMe | H | |
| 13-100 | Cl | Me | CH₂CH₂OMe | H | |
| 13-101 | Cl | F | CH₂CH₂OMe | H | |
| 13-102 | Cl | Cl | CH₂CH₂OMe | H | |
| 13-103 | Cl | Br | CH₂CH₂OMe | H | |
| 13-104 | Cl | I | CH₂CH₂OMe | H | |
| 13-105 | Cl | CF₃ | CH₂CH₂OMe | H | |
| 13-106 | Cl | CHF₂ | CH₂CH₂OMe | H | |
| 13-107 | Cl | CF₂Cl | CH₂CH₂OMe | H | |
| 13-108 | Cl | OMe | CH₂CH₂OMe | H | |
| 13-109 | Cl | NO₂ | CH₂CH₂OMe | H | |
| 13-110 | Cl | SO₂Me | CH₂CH₂OMe | H | |
| 13-111 | OMe | Me | CH₂CH₂OMe | H | |
| 13-112 | OMe | F | CH₂CH₂OMe | H | |
| 13-113 | OMe | Cl | CH₂CH₂OMe | H | |
| 13-114 | OMe | Br | CH₂CH₂OMe | H | |
| 13-115 | OMe | I | CH₂CH₂OMe | H | |
| 13-116 | OMe | CF₃ | CH₂CH₂OMe | H | |
| 13-117 | OMe | CHF₂ | CH₂CH₂OMe | H | |
| 13-118 | OMe | CF₂Cl | CH₂CH₂OMe | H | |
| 13-119 | OMe | OMe | CH₂CH₂OMe | H | |
| 13-120 | OMe | NO₂ | CH₂CH₂OMe | H | |
| 13-121 | OMe | SO₂Me | CH₂CH₂OMe | H | |
| 13-122 | SO₂Me | Me | CH₂CH₂OMe | H | |
| 13-123 | SO₂Me | F | CH₂CH₂OMe | H | |
| 13-124 | SO₂Me | Cl | CH₂CH₂OMe | H | |
| 13-125 | SO₂Me | Br | CH₂CH₂OMe | H | |
| 13-126 | SO₂Me | I | CH₂CH₂OMe | H | |
| 13-127 | SO₂Me | CF₃ | CH₂CH₂OMe | H | |
| 13-128 | SO₂Me | CHF₂ | CH₂CH₂OMe | H | |
| 13-129 | SO₂Me | CF₂Cl | CH₂CH₂OMe | H | |
| 13-130 | SO₂Me | OMe | CH₂CH₂OMe | H | |
| 13-131 | SO₂Me | NO₂ | CH₂CH₂OMe | H | |
| 13-132 | SO₂Me | SO₂Me | CH₂CH₂OMe | H | |
| 13-133 | Me | Me | Me | CN | |
| 13-134 | Me | F | Me | CN | |
| 13-135 | Me | Cl | Me | CN | |
| 13-136 | Me | Br | Me | CN | |
| 13-137 | Me | I | Me | CN | |
| 13-138 | Me | CF₃ | Me | CN | |
| 13-139 | Me | CHF₂ | Me | CN | |
| 13-140 | Me | CF₂Cl | Me | CN | |
| 13-141 | Me | OMe | Me | CN | |
| 13-142 | Me | NO₂ | Me | CN | |
| 13-143 | Me | SO₂Me | Me | CN | |
| 13-144 | Cl | Me | Me | CN | |
| 13-145 | Cl | F | Me | CN | |
| 13-146 | Cl | Cl | Me | CN | |
| 13-147 | Cl | Br | Me | CN | |
| 13-148 | Cl | I | Me | CN | |
| 13-149 | Cl | CF₃ | Me | CN | |
| 13-150 | Cl | CHF₂ | Me | CN | |
| 13-151 | Cl | CF₂Cl | Me | CN | |
| 13-152 | Cl | OMe | Me | CN | |
| 13-153 | Cl | NO₂ | Me | CN | |
| 13-154 | Cl | SO₂Me | Me | CN | |
| 13-155 | OMe | Me | Me | CN | |
| 13-156 | OMe | F | Me | CN | |
| 13-157 | OMe | Cl | Me | CN | |
| 13-158 | OMe | Br | Me | CN | |
| 13-159 | OMe | I | Me | CN | |
| 13-160 | OMe | CF₃ | Me | CN | |
| 13-161 | OMe | CHF₂ | Me | CN | |
| 13-162 | OMe | CF₂Cl | Me | CN | |
| 13-163 | OMe | OMe | Me | CN | |
| 13-164 | OMe | NO₂ | Me | CN | |
| 13-165 | OMe | SO₂Me | Me | CN | |
| 13-166 | SO₂Me | Me | Me | CN | |
| 13-167 | SO₂Me | F | Me | CN | |
| 13-168 | SO₂Me | Cl | Me | CN | |
| 13-169 | SO₂Me | Br | Me | CN | |
| 13-170 | SO₂Me | I | Me | CN | |
| 13-171 | SO₂Me | CF₃ | Me | CN | |
| 13-172 | SO₂Me | CHF₂ | Me | CN | |
| 13-173 | SO₂Me | CF₂Cl | Me | CN | |
| 13-174 | SO₂Me | OMe | Me | CN | |
| 13-175 | SO₂Me | NO₂ | Me | CN | |
| 13-176 | SO₂Me | SO₂Me | Me | CN | |
| 13-177 | Me | Me | Et | CN | |
| 13-178 | Me | F | Et | CN | |
| 13-179 | Me | Cl | Et | CN | |
| 13-180 | Me | Br | Et | CN | |
| 13-181 | Me | I | Et | CN | |
| 13-182 | Me | CF₃ | Et | CN | |
| 13-183 | Me | CHF₂ | Et | CN | |
| 13-184 | Me | CF₂Cl | Et | CN | |
| 13-185 | Me | OMe | Et | CN | |
| 13-186 | Me | NO₂ | Et | CN | |
| 13-187 | Me | SO₂Me | Et | CN | |
| 13-188 | Cl | Me | Et | CN | |
| 13-189 | Cl | F | Et | CN | |
| 13-190 | Cl | Cl | Et | CN | |
| 13-191 | Cl | Br | Et | CN | |
| 13-192 | Cl | I | Et | CN | |
| 13-193 | Cl | CF₃ | Et | CN | |
| 13-194 | Cl | CHF₂ | Et | CN | |
| 13-195 | Cl | CF₂Cl | Et | CN | |
| 13-196 | Cl | OMe | Et | CN | |
| 13-197 | Cl | NO₂ | Et | CN | |
| 13-198 | Cl | SO₂Me | Et | CN | |
| 13-199 | OMe | Me | Et | CN | |
| 13-200 | OMe | F | Et | CN | |
| 13-201 | OMe | Cl | Et | CN | |
| 13-202 | OMe | Br | Et | CN | |
| 13-203 | OMe | I | Et | CN | |
| 13-204 | OMe | CF₃ | Et | CN | |
| 13-205 | OMe | CHF₂ | Et | CN | |
| 13-206 | OMe | CF₂Cl | Et | CN | |
| 13-207 | OMe | OMe | Et | CN | |

TABLE 13-continued

Compounds according to the invention of the formula (I) in which Q is Q5, W is hydrogen, t = 0 and the other radicals have the meanings indicated in the table

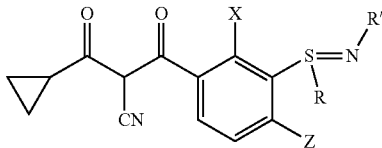

| No. | X | Z | R | R' | Physical data (1H NMR) |
|---|---|---|---|---|---|
| 13-208 | OMe | NO₂ | Et | CN | |
| 13-209 | OMe | SO₂Me | Et | CN | |
| 13-210 | SO₂Me | Me | Et | CN | |
| 13-211 | SO₂Me | F | Et | CN | |
| 13-212 | SO₂Me | Cl | Et | CN | |
| 13-213 | SO₂Me | Br | Et | CN | |
| 13-214 | SO₂Me | I | Et | CN | |
| 13-215 | SO₂Me | CF₃ | Et | CN | |
| 13-216 | SO₂Me | CHF₂ | Et | CN | |
| 13-217 | SO₂Me | CF₂Cl | Et | CN | |
| 13-218 | SO₂Me | OMe | Et | CN | |
| 13-219 | SO₂Me | NO₂ | Et | CN | |
| 13-220 | SO₂Me | SO₂Me | Et | CN | |
| 13-221 | Me | Me | CH₂CH₂OMe | CN | |
| 13-222 | Me | F | CH₂CH₂OMe | CN | |
| 13-223 | Me | Cl | CH₂CH₂OMe | CN | |
| 13-224 | Me | Br | CH₂CH₂OMe | CN | |
| 13-225 | Me | I | CH₂CH₂OMe | CN | |
| 13-226 | Me | CF₃ | CH₂CH₂OMe | CN | |
| 13-227 | Me | CHF₂ | CH₂CH₂OMe | CN | |
| 13-228 | Me | CF₂Cl | CH₂CH₂OMe | CN | |
| 13-229 | Me | OMe | CH₂CH₂OMe | CN | |
| 13-230 | Me | NO₂ | CH₂CH₂OMe | CN | |
| 13-231 | Me | SO₂Me | CH₂CH₂OMe | CN | |
| 13-232 | Cl | Me | CH₂CH₂OMe | CN | |
| 13-233 | Cl | F | CH₂CH₂OMe | CN | |
| 13-234 | Cl | Cl | CH₂CH₂OMe | CN | |
| 13-235 | Cl | Br | CH₂CH₂OMe | CN | |
| 13-236 | Cl | I | CH₂CH₂OMe | CN | |
| 13-237 | Cl | CF₃ | CH₂CH₂OMe | CN | |
| 13-238 | Cl | CHF₂ | CH₂CH₂OMe | CN | |
| 13-239 | Cl | CF₂Cl | CH₂CH₂OMe | CN | |
| 13-240 | Cl | OMe | CH₂CH₂OMe | CN | |
| 13-241 | Cl | NO₂ | CH₂CH₂OMe | CN | |
| 13-242 | Cl | SO₂Me | CH₂CH₂OMe | CN | |
| 13-243 | OMe | Me | CH₂CH₂OMe | CN | |
| 13-244 | OMe | F | CH₂CH₂OMe | CN | |
| 13-245 | OMe | Cl | CH₂CH₂OMe | CN | |
| 13-246 | OMe | Br | CH₂CH₂OMe | CN | |
| 13-247 | OMe | I | CH₂CH₂OMe | CN | |
| 13-248 | OMe | CF₃ | CH₂CH₂OMe | CN | |
| 13-249 | OMe | CHF₂ | CH₂CH₂OMe | CN | |
| 13-250 | OMe | CF₂Cl | CH₂CH₂OMe | CN | |
| 13-251 | OMe | OMe | CH₂CH₂OMe | CN | |
| 13-252 | OMe | NO₂ | CH₂CH₂OMe | CN | |
| 13-253 | OMe | SO₂Me | CH₂CH₂OMe | CN | |
| 13-254 | SO₂Me | Me | CH₂CH₂OMe | CN | |
| 13-255 | SO₂Me | F | CH₂CH₂OMe | CN | |
| 13-256 | SO₂Me | Cl | CH₂CH₂OMe | CN | |
| 13-257 | SO₂Me | Br | CH₂CH₂OMe | CN | |
| 13-258 | SO₂Me | I | CH₂CH₂OMe | CN | |
| 13-259 | SO₂Me | CF₃ | CH₂CH₂OMe | CN | |
| 13-260 | SO₂Me | CHF₂ | CH₂CH₂OMe | CN | |
| 13-261 | SO₂Me | CF₂Cl | CH₂CH₂OMe | CN | |
| 13-262 | SO₂Me | OMe | CH₂CH₂OMe | CN | |
| 13-263 | SO₂Me | NO₂ | CH₂CH₂OMe | CN | |
| 13-264 | SO₂Me | SO₂Me | CH₂CH₂OMe | CN | |

TABLE 14

Compounds according to the invention of the formula (I) in the form of the sodium salts in which Q is Q3, $R^i$ is methyl, $R^k$ and W are each hydrogen, t = 0 and the other radicals have the meanings indicated in the table

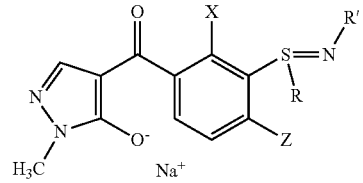

| No. | X | Z | R | R' | Physical data (1H NMR) |
|---|---|---|---|---|---|
| 14-1 | Me | Me | Me | H | |
| 14-2 | Me | Cl | Me | H | |
| 14-3 | Me | CF₃ | Me | H | |
| 14-4 | Me | CHF₂ | Me | H | |
| 14-5 | Cl | Me | Me | H | |
| 14-6 | Cl | Cl | Me | H | |
| 14-7 | Cl | CF₃ | Me | H | |
| 14-8 | Cl | CHF₂ | Me | H | |
| 14-9 | OMe | Me | Me | H | |
| 14-10 | OMe | Cl | Me | H | |
| 14-11 | OMe | CF₃ | Me | H | |
| 14-12 | OMe | CHF₂ | Me | H | |
| 14-13 | SO₂Me | Me | Me | H | |
| 14-14 | SO₂Me | Cl | Me | H | |
| 14-15 | SO₂Me | CF₃ | Me | H | |
| 14-16 | SO₂Me | CHF₂ | Me | H | |
| 14-17 | Me | Me | Et | H | |
| 14-18 | Me | Cl | Et | H | |
| 14-19 | Me | CF₃ | Et | H | |
| 14-20 | Me | CHF₂ | Et | H | |
| 14-21 | Cl | Me | Et | H | |
| 14-22 | Cl | Cl | Et | H | |
| 14-23 | Cl | CF₃ | Et | H | |
| 14-24 | Cl | CHF₂ | Et | H | |
| 14-25 | OMe | Me | Et | H | |
| 14-26 | OMe | Cl | Et | H | |
| 14-27 | OMe | CF₃ | Et | H | |
| 14-28 | OMe | CHF₂ | Et | H | |
| 14-29 | SO₂Me | Me | Et | H | |
| 14-30 | SO₂Me | Cl | Et | H | |
| 14-31 | SO₂Me | CF₃ | Et | H | |
| 14-32 | SO₂Me | CHF₂ | Et | H | |
| 14-33 | Me | Me | CH₂CH₂OMe | H | |
| 14-34 | Me | Cl | CH₂CH₂OMe | H | |
| 14-35 | Me | CF₃ | CH₂CH₂OMe | H | |
| 14-36 | Me | CHF₂ | CH₂CH₂OMe | H | |
| 14-37 | Cl | Me | CH₂CH₂OMe | H | |
| 14-38 | Cl | Cl | CH₂CH₂OMe | H | |
| 14-39 | Cl | CF₃ | CH₂CH₂OMe | H | |
| 14-40 | Cl | CHF₂ | CH₂CH₂OMe | H | |
| 14-41 | OMe | Me | CH₂CH₂OMe | H | |
| 14-42 | OMe | Cl | CH₂CH₂OMe | H | |
| 14-43 | OMe | CF₃ | CH₂CH₂OMe | H | |
| 14-44 | OMe | CHF₂ | CH₂CH₂OMe | H | |
| 14-45 | SO₂Me | Me | CH₂CH₂OMe | H | |
| 14-46 | SO₂Me | Cl | CH₂CH₂OMe | H | |
| 14-47 | SO₂Me | CF₃ | CH₂CH₂OMe | H | |
| 14-48 | SO₂Me | CHF₂ | CH₂CH₂OMe | H | |
| 14-49 | Me | Me | Me | CN | |
| 14-50 | Me | Cl | Me | CN | |
| 14-51 | Me | CF₃ | Me | CN | |
| 14-52 | Me | CHF₂ | Me | CN | |
| 14-53 | Cl | Me | Me | CN | |
| 14-54 | Cl | Cl | Me | CN | |
| 14-55 | Cl | CF₃ | Me | CN | |
| 14-56 | Cl | CHF₂ | Me | CN | |
| 14-57 | OMe | Me | Me | CN | |
| 14-58 | OMe | Cl | Me | CN | |
| 14-59 | OMe | CF₃ | Me | CN | |
| 14-60 | OMe | CHF₂ | Me | CN | |
| 14-61 | SO₂Me | Me | Me | CN | |
| 14-62 | SO₂Me | Cl | Me | CN | |
| 14-63 | SO₂Me | CF₃ | Me | CN | |

TABLE 14-continued

Compounds according to the invention of the formula (I) in the form of the sodium salts in which Q is Q3, $R^i$ is methyl, $R^k$ and W are each hydrogen, t = 0 and the other radicals have the meanings indicated in the table

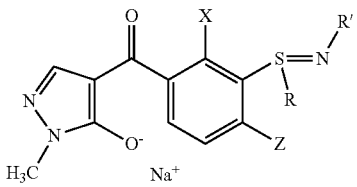

| No. | X | Z | R | R' | Physical data (1H NMR) |
|---|---|---|---|---|---|
| 14-64 | SO$_2$Me | CHF$_2$ | Me | CN | |
| 14-65 | Me | Me | Et | CN | |
| 14-66 | Me | Cl | Et | CN | |
| 14-67 | Me | CF$_3$ | Et | CN | |
| 14-68 | Me | CHF$_2$ | Et | CN | |
| 14-69 | Cl | Me | Et | CN | |
| 14-70 | Cl | Cl | Et | CN | |
| 14-71 | Cl | CF$_3$ | Et | CN | |
| 14-72 | Cl | CHF$_2$ | Et | CN | |
| 14-73 | OMe | Me | Et | CN | |
| 14-74 | OMe | Cl | Et | CN | |
| 14-75 | OMe | CF$_3$ | Et | CN | |
| 14-76 | OMe | CHF$_2$ | Et | CN | |
| 14-77 | SO$_2$Me | Me | Et | CN | |
| 14-78 | SO$_2$Me | Cl | Et | CN | |
| 14-79 | SO$_2$Me | CF$_3$ | Et | CN | |
| 14-80 | SO$_2$Me | CHF$_2$ | Et | CN | |
| 14-81 | Me | Me | CH$_2$CH$_2$OMe | CN | |
| 14-82 | Me | Cl | CH$_2$CH$_2$OMe | CN | |
| 14-83 | Me | CF$_3$ | CH$_2$CH$_2$OMe | CN | |
| 14-84 | Me | CHF$_2$ | CH$_2$CH$_2$OMe | CN | |
| 14-85 | Cl | Me | CH$_2$CH$_2$OMe | CN | |
| 14-86 | Cl | Cl | CH$_2$CH$_2$OMe | CN | |
| 14-87 | Cl | CF$_3$ | CH$_2$CH$_2$OMe | CN | |
| 14-88 | Cl | CHF$_2$ | CH$_2$CH$_2$OMe | CN | |
| 14-89 | OMe | Me | CH$_2$CH$_2$OMe | CN | |
| 14-90 | OMe | Cl | CH$_2$CH$_2$OMe | CN | |
| 14-91 | OMe | CF$_3$ | CH$_2$CH$_2$OMe | CN | |
| 14-92 | OMe | CHF$_2$ | CH$_2$CH$_2$OMe | CN | |
| 14-93 | SO$_2$Me | Me | CH$_2$CH$_2$OMe | CN | |
| 14-94 | SO$_2$Me | Cl | CH$_2$CH$_2$OMe | CN | |
| 14-95 | SO$_2$Me | CF$_3$ | CH$_2$CH$_2$OMe | CN | |
| 14-96 | SO$_2$Me | CHF$_2$ | CH$_2$CH$_2$OMe | CN | |

TABLE 15

Compounds according to the invention of the formula (II) in which Q* is hydroxyl and R' is cyano, t is 1, and the other radicals have the meanings indicated in the table

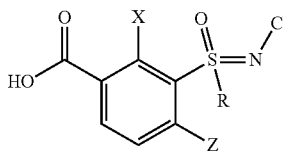

| No. | X | Z | R | Physical data ($^1$H NMR) |
|---|---|---|---|---|
| 15-1 | Me | Me | Me | |
| 15-2 | Me | F | Me | |
| 15-3 | Me | Cl | Me | |
| 15-4 | Me | Br | Me | |
| 15-5 | Me | I | Me | |
| 15-6 | Me | CF$_3$ | Me | |
| 15-7 | Me | CHF$_2$ | Me | |
| 15-8 | Me | CF$_2$Cl | Me | |
| 15-9 | Me | OMe | Me | |
| 15-10 | Me | NO$_2$ | Me | |
| 15-11 | Me | SO$_2$Me | Me | |
| 15-12 | Cl | Me | Me | |
| 15-13 | Cl | F | Me | |
| 15-14 | Cl | Cl | Me | |
| 15-15 | Cl | Br | Me | |
| 15-16 | Cl | I | Me | |
| 15-17 | Cl | CF$_3$ | Me | |
| 15-18 | Cl | CHF$_2$ | Me | |
| 15-19 | Cl | CF$_2$Cl | Me | |
| 15-20 | Cl | OMe | Me | |
| 15-21 | Cl | NO$_2$ | Me | |
| 15-22 | Cl | SO$_2$Me | Me | |
| 15-23 | OMe | Me | Me | |
| 15-24 | OMe | F | Me | |
| 15-25 | OMe | Cl | Me | |
| 15-26 | OMe | Br | Me | |
| 15-27 | OMe | I | Me | |
| 15-28 | OMe | CF$_3$ | Me | (400 MHz, CDCl$_3$ δ, ppm) 8.34 (d, 1H), 7.84 (d, 1H), 4.16 (s, 3H), 3.68 (s, 3H) |
| 15-29 | OMe | CHF$_2$ | Me | |
| 15-30 | OMe | CF$_2$Cl | Me | |
| 15-31 | OMe | OMe | Me | |
| 15-32 | OMe | NO$_2$ | Me | |
| 15-33 | OMe | SO$_2$Me | Me | |
| 15-34 | SO$_2$Me | Me | Me | |
| 15-35 | SO$_2$Me | F | Me | |
| 15-36 | SO$_2$Me | Cl | Me | |
| 15-37 | SO$_2$Me | Br | Me | |
| 15-38 | SO$_2$Me | I | Me | |
| 15-39 | SO$_2$Me | CF$_3$ | Me | |
| 15-40 | SO$_2$Me | CHF$_2$ | Me | |
| 15-41 | SO$_2$Me | CF$_2$Cl | Me | |
| 15-42 | SO$_2$Me | OMe | Me | |
| 15-43 | SO$_2$Me | NO$_2$ | Me | |
| 15-44 | SO$_2$Me | SO$_2$Me | Me | |
| 15-45 | Me | Me | Et | |
| 15-46 | Me | F | Et | |
| 15-47 | Me | Cl | Et | |
| 15-48 | Me | Br | Et | |
| 15-49 | Me | I | Et | |
| 15-50 | Me | CF$_3$ | Et | |
| 15-51 | Me | CHF$_2$ | Et | |
| 15-52 | Me | CF$_2$Cl | Et | |
| 15-53 | Me | OMe | Et | |
| 15-54 | Me | NO$_2$ | Et | |
| 15-55 | Me | SO$_2$Me | Et | |
| 15-56 | Cl | Me | Et | |
| 15-57 | Cl | F | Et | |
| 15-58 | Cl | Cl | Et | |
| 15-59 | Cl | Br | Et | |
| 15-60 | Cl | I | Et | |
| 15-61 | Cl | CF$_3$ | Et | |
| 15-62 | Cl | CHF$_2$ | Et | |
| 15-63 | Cl | CF$_2$Cl | Et | |
| 15-64 | Cl | OMe | Et | |
| 15-65 | Cl | NO$_2$ | Et | |
| 15-66 | Cl | SO$_2$Me | Et | |
| 15-67 | OMe | Me | Et | |
| 15-68 | OMe | F | Et | |
| 15-69 | OMe | Cl | Et | |
| 15-70 | OMe | Br | Et | |
| 15-71 | OMe | I | Et | |
| 15-72 | OMe | CF$_3$ | Et | |
| 15-73 | OMe | CHF$_2$ | Et | |
| 15-74 | OMe | CF$_2$Cl | Et | |
| 15-75 | OMe | OMe | Et | |

TABLE 15-continued

Compounds according to the invention of the formula (II) in which Q* is hydroxyl and R' is cyano, t is 1, and the other radicals have the meanings indicated in the table

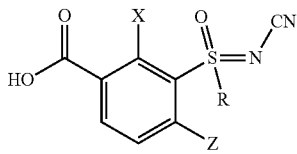

| No. | X | Z | R | Physical data ($^1$H NMR) |
|---|---|---|---|---|
| 15-76 | OMe | NO$_2$ | Et | |
| 15-77 | OMe | SO$_2$Me | Et | |
| 15-78 | SO$_2$Me | Me | Et | |
| 15-79 | SO$_2$Me | F | Et | |
| 15-80 | SO$_2$Me | Cl | Et | |
| 15-81 | SO$_2$Me | Br | Et | |
| 15-82 | SO$_2$Me | I | Et | |
| 15-83 | SO$_2$Me | CF$_3$ | Et | |
| 15-84 | SO$_2$Me | CHF$_2$ | Et | |
| 15-85 | SO$_2$Me | CF$_2$Cl | Et | |
| 15-86 | SO$_2$Me | OMe | Et | |
| 15-87 | SO$_2$Me | NO$_2$ | Et | |
| 15-88 | SO$_2$Me | SO$_2$Me | Et | |
| 15-89 | Me | Me | CH$_2$CH$_2$OMe | |
| 15-90 | Me | F | CH$_2$CH$_2$OMe | |
| 15-91 | Me | Cl | CH$_2$CH$_2$OMe | |
| 15-92 | Me | Br | CH$_2$CH$_2$OMe | |
| 15-93 | Me | I | CH$_2$CH$_2$OMe | |
| 15-94 | Me | CF$_3$ | CH$_2$CH$_2$OMe | |
| 15-95 | Me | CHF$_2$ | CH$_2$CH$_2$OMe | |
| 15-96 | Me | CF$_2$Cl | CH$_2$CH$_2$OMe | |
| 15-97 | Me | OMe | CH$_2$CH$_2$OMe | |
| 15-98 | Me | NO$_2$ | CH$_2$CH$_2$OMe | |
| 15-99 | Me | SO$_2$Me | CH$_2$CH$_2$OMe | |
| 15-100 | Cl | Me | CH$_2$CH$_2$OMe | |
| 15-101 | Cl | F | CH$_2$CH$_2$OMe | |
| 15-102 | Cl | Cl | CH$_2$CH$_2$OMe | |
| 15-103 | Cl | Br | CH$_2$CH$_2$OMe | |
| 15-104 | Cl | I | CH$_2$CH$_2$OMe | |
| 15-105 | Cl | CF$_3$ | CH$_2$CH$_2$OMe | |
| 15-106 | Cl | CHF$_2$ | CH$_2$CH$_2$OMe | |
| 15-107 | Cl | CF$_2$Cl | CH$_2$CH$_2$OMe | |
| 15-108 | Cl | OMe | CH$_2$CH$_2$OMe | |
| 15-109 | Cl | NO$_2$ | CH$_2$CH$_2$OMe | |
| 15-110 | Cl | SO$_2$Me | CH$_2$CH$_2$OMe | |
| 15-111 | OMe | Me | CH$_2$CH$_2$OMe | |
| 15-112 | OMe | F | CH$_2$CH$_2$OMe | |
| 15-113 | OMe | Cl | CH$_2$CH$_2$OMe | |
| 15-114 | OMe | Br | CH$_2$CH$_2$OMe | |
| 15-115 | OMe | I | CH$_2$CH$_2$OMe | |
| 15-116 | OMe | CF$_3$ | CH$_2$CH$_2$OMe | |
| 15-117 | OMe | CHF$_2$ | CH$_2$CH$_2$OMe | |
| 15-118 | OMe | CF$_2$Cl | CH$_2$CH$_2$OMe | |
| 15-119 | OMe | OMe | CH$_2$CH$_2$OMe | |
| 15-120 | OMe | NO$_2$ | CH$_2$CH$_2$OMe | |
| 15-121 | OMe | SO$_2$Me | CH$_2$CH$_2$OMe | |
| 15-122 | SO$_2$Me | Me | CH$_2$CH$_2$OMe | |
| 15-123 | SO$_2$Me | F | CH$_2$CH$_2$OMe | |
| 15-124 | SO$_2$Me | Cl | CH$_2$CH$_2$OMe | |
| 15-125 | SO$_2$Me | Br | CH$_2$CH$_2$OMe | |
| 15-126 | SO$_2$Me | I | CH$_2$CH$_2$OMe | |
| 15-127 | SO$_2$Me | CF$_3$ | CH$_2$CH$_2$OMe | |
| 15-128 | SO$_2$Me | CHF$_2$ | CH$_2$CH$_2$OMe | |
| 15-129 | SO$_2$Me | CF$_2$Cl | CH$_2$CH$_2$OMe | |
| 15-130 | SO$_2$Me | OMe | CH$_2$CH$_2$OMe | |
| 15-131 | SO$_2$Me | NO$_2$ | CH$_2$CH$_2$OMe | |
| 15-132 | SO$_2$Me | SO$_2$Me | CH$_2$CH$_2$OMe | |

TABLE 16

Compounds according to the invention of the formula (II) in which Q* is hydroxyl and R' is cyano, t is 0, and the other radicals have the meanings indicated in the table

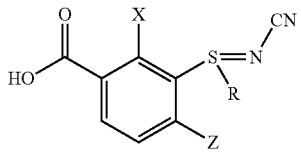

| No. | X | Z | R | Physical data ($^1$H NMR) |
|---|---|---|---|---|
| 16-1 | Me | Me | Me | |
| 16-2 | Me | F | Me | |
| 16-3 | Me | Cl | Me | |
| 16-4 | Me | Br | Me | |
| 16-5 | Me | I | Me | |
| 16-6 | Me | CF$_3$ | Me | |
| 16-7 | Me | CHF$_2$ | Me | |
| 16-8 | Me | CF$_2$Cl | Me | |
| 16-9 | Me | OMe | Me | |
| 16-10 | Me | NO$_2$ | Me | |
| 16-11 | Me | SO$_2$Me | Me | |
| 16-12 | Cl | Me | Me | |
| 16-13 | Cl | F | Me | |
| 16-14 | Cl | Cl | Me | |
| 16-15 | Cl | Br | Me | |
| 16-16 | Cl | I | Me | |
| 16-17 | Cl | CF$_3$ | Me | |
| 16-18 | Cl | CHF$_2$ | Me | |
| 16-19 | Cl | CF$_2$Cl | Me | |
| 16-20 | Cl | OMe | Me | |
| 16-21 | Cl | NO$_2$ | Me | |
| 16-22 | Cl | SO$_2$Me | Me | |
| 16-23 | OMe | Me | Me | |
| 16-24 | OMe | F | Me | |
| 16-25 | OMe | Cl | Me | |
| 16-26 | OMe | Br | Me | |
| 16-27 | OMe | I | Me | |
| 16-28 | OMe | CF$_3$ | Me | |
| 16-29 | OMe | CHF$_2$ | Me | |
| 16-30 | OMe | CF$_2$Cl | Me | |
| 16-31 | OMe | OMe | Me | |
| 16-32 | OMe | NO$_2$ | Me | |
| 16-33 | OMe | SO$_2$Me | Me | |
| 16-34 | SO$_2$Me | Me | Me | |
| 16-35 | SO$_2$Me | F | Me | |
| 16-36 | SO$_2$Me | Cl | Me | |
| 16-37 | SO$_2$Me | Br | Me | |
| 16-38 | SO$_2$Me | I | Me | |
| 16-39 | SO$_2$Me | CF$_3$ | Me | |
| 16-40 | SO$_2$Me | CHF$_2$ | Me | |
| 16-41 | SO$_2$Me | CF$_2$Cl | Me | |
| 16-42 | SO$_2$Me | OMe | Me | |
| 16-43 | SO$_2$Me | NO$_2$ | Me | |
| 16-44 | SO$_2$Me | SO$_2$Me | Me | |
| 16-45 | Me | Me | Et | |
| 16-46 | Me | F | Et | |
| 16-47 | Me | Cl | Et | |
| 16-48 | Me | Br | Et | |
| 16-49 | Me | I | Et | |
| 16-50 | Me | CF$_3$ | Et | |
| 16-51 | Me | CHF$_2$ | Et | |
| 16-52 | Me | CF$_2$Cl | Et | |
| 16-53 | Me | OMe | Et | |
| 16-54 | Me | NO$_2$ | Et | |
| 16-55 | Me | SO$_2$Me | Et | |
| 16-56 | Cl | Me | Et | |
| 16-57 | Cl | F | Et | |
| 16-58 | Cl | Cl | Et | |
| 16-59 | Cl | Br | Et | |
| 16-60 | Cl | I | Et | |
| 16-61 | Cl | CF$_3$ | Et | |
| 16-62 | Cl | CHF$_2$ | Et | |
| 16-63 | Cl | CF$_2$Cl | Et | |
| 16-64 | Cl | OMe | Et | |
| 16-65 | Cl | NO$_2$ | Et | |
| 16-66 | Cl | SO$_2$Me | Et | |

TABLE 16-continued

Compounds according to the invention of the formula (II) in which Q* is hydroxyl and R' is cyano, t is 0, and the other radicals have the meanings indicated in the table

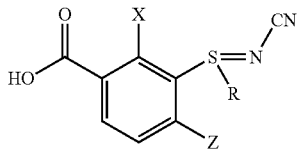

| No. | X | Z | R | Physical data (¹H NMR) |
|---|---|---|---|---|
| 16-67 | OMe | Me | Et | |
| 16-68 | OMe | F | Et | |
| 16-69 | OMe | Cl | Et | |
| 16-70 | OMe | Br | Et | |
| 16-71 | OMe | I | Et | |
| 16-72 | OMe | $CF_3$ | Et | |
| 16-73 | OMe | $CHF_2$ | Et | |
| 16-74 | OMe | $CF_2Cl$ | Et | |
| 16-75 | OMe | OMe | Et | |
| 16-76 | OMe | $NO_2$ | Et | |
| 16-77 | OMe | $SO_2Me$ | Et | |
| 16-78 | $SO_2Me$ | Me | Et | |
| 16-79 | $SO_2Me$ | F | Et | |
| 16-80 | $SO_2Me$ | Cl | Et | |
| 16-81 | $SO_2Me$ | Br | Et | |
| 16-82 | $SO_2Me$ | I | Et | |
| 16-83 | $SO_2Me$ | $CF_3$ | Et | |
| 16-84 | $SO_2Me$ | $CHF_2$ | Et | |
| 16-85 | $SO_2Me$ | $CF_2Cl$ | Et | |
| 16-86 | $SO_2Me$ | OMe | Et | |
| 16-87 | $SO_2Me$ | $NO_2$ | Et | |
| 16-88 | $SO_2Me$ | $SO_2Me$ | Et | |
| 16-89 | Me | Me | $CH_2CH_2OMe$ | |
| 16-90 | Me | F | $CH_2CH_2OMe$ | |
| 16-91 | Me | Cl | $CH_2CH_2OMe$ | |
| 16-92 | Me | Br | $CH_2CH_2OMe$ | |
| 16-93 | Me | I | $CH_2CH_2OMe$ | |
| 16-94 | Me | $CF_3$ | $CH_2CH_2OMe$ | |
| 16-95 | Me | $CHF_2$ | $CH_2CH_2OMe$ | |
| 16-96 | Me | $CF_2Cl$ | $CH_2CH_2OMe$ | |
| 16-97 | Me | OMe | $CH_2CH_2OMe$ | |
| 16-98 | Me | $NO_2$ | $CH_2CH_2OMe$ | |
| 16-99 | Me | $SO_2Me$ | $CH_2CH_2OMe$ | |
| 16-100 | Cl | Me | $CH_2CH_2OMe$ | |
| 16-101 | Cl | F | $CH_2CH_2OMe$ | |
| 16-102 | Cl | Cl | $CH_2CH_2OMe$ | |
| 16-103 | Cl | Br | $CH_2CH_2OMe$ | |
| 16-104 | Cl | I | $CH_2CH_2OMe$ | |
| 16-105 | Cl | $CF_3$ | $CH_2CH_2OMe$ | |
| 16-106 | Cl | $CHF_2$ | $CH_2CH_2OMe$ | |
| 16-107 | Cl | $CF_2Cl$ | $CH_2CH_2OMe$ | |
| 16-108 | Cl | OMe | $CH_2CH_2OMe$ | |
| 16-109 | Cl | $NO_2$ | $CH_2CH_2OMe$ | |
| 16-110 | Cl | $SO_2Me$ | $CH_2CH_2OMe$ | |
| 16-111 | OMe | Me | $CH_2CH_2OMe$ | |
| 16-112 | OMe | F | $CH_2CH_2OMe$ | |
| 16-113 | OMe | Cl | $CH_2CH_2OMe$ | |
| 16-114 | OMe | Br | $CH_2CH_2OMe$ | |
| 16-115 | OMe | I | $CH_2CH_2OMe$ | |
| 16-116 | OMe | $CF_3$ | $CH_2CH_2OMe$ | |
| 16-117 | OMe | $CHF_2$ | $CH_2CH_2OMe$ | |
| 16-118 | OMe | $CF_2Cl$ | $CH_2CH_2OMe$ | |
| 16-119 | OMe | OMe | $CH_2CH_2OMe$ | |
| 16-120 | OMe | $NO_2$ | $CH_2CH_2OMe$ | |
| 16-121 | OMe | $SO_2Me$ | $CH_2CH_2OMe$ | |
| 16-122 | $SO_2Me$ | Me | $CH_2CH_2OMe$ | |
| 16-123 | $SO_2Me$ | F | $CH_2CH_2OMe$ | |
| 16-124 | $SO_2Me$ | Cl | $CH_2CH_2OMe$ | |
| 16-125 | $SO_2Me$ | Br | $CH_2CH_2OMe$ | |
| 16-126 | $SO_2Me$ | I | $CH_2CH_2OMe$ | |
| 16-127 | $SO_2Me$ | $CF_3$ | $CH_2CH_2OMe$ | |
| 16-128 | $SO_2Me$ | $CHF_2$ | $CH_2CH_2OMe$ | |
| 16-129 | $SO_2Me$ | $CF_2Cl$ | $CH_2CH_2OMe$ | |
| 16-130 | $SO_2Me$ | OMe | $CH_2CH_2OMe$ | |

TABLE 16-continued

Compounds according to the invention of the formula (II) in which Q* is hydroxyl and R' is cyano, t is 0, and the other radicals have the meanings indicated in the table

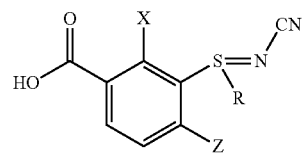

| No. | X | Z | R | Physical data (¹H NMR) |
|---|---|---|---|---|
| 16-131 | $SO_2Me$ | $NO_2$ | $CH_2CH_2OMe$ | |
| 16-132 | $SO_2Me$ | $SO_2Me$ | $CH_2CH_2OMe$ | |

TABLE 17

Compounds according to the invention of the formula (II) in which Q* is chlorine and R' is cyano, t is 1, and the other radicals have the meanings indicated in the table

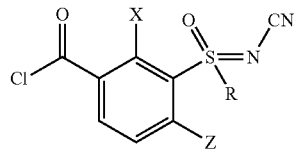

| No. | X | Z | R | Physical data (¹H NMR) |
|---|---|---|---|---|
| 17-1 | Me | Me | Me | |
| 17-2 | Me | F | Me | |
| 17-3 | Me | Cl | Me | |
| 17-4 | Me | Br | Me | |
| 17-5 | Me | I | Me | |
| 17-6 | Me | $CF_3$ | Me | |
| 17-7 | Me | $CHF_2$ | Me | |
| 17-8 | Me | $CF_2Cl$ | Me | |
| 17-9 | Me | OMe | Me | |
| 17-10 | Me | $NO_2$ | Me | |
| 17-11 | Me | $SO_2Me$ | Me | |
| 17-12 | Cl | Me | Me | |
| 17-13 | Cl | F | Me | |
| 17-14 | Cl | Cl | Me | |
| 17-15 | Cl | Br | Me | |
| 17-16 | Cl | I | Me | |
| 17-17 | Cl | $CF_3$ | Me | |
| 17-18 | Cl | $CHF_2$ | Me | |
| 17-19 | Cl | $CF_2Cl$ | Me | |
| 17-20 | Cl | OMe | Me | |
| 17-21 | Cl | $NO_2$ | Me | |
| 17-22 | Cl | $SO_2Me$ | Me | |
| 17-23 | OMe | Me | Me | |
| 17-24 | OMe | F | Me | |
| 17-25 | OMe | Cl | Me | |
| 17-26 | OMe | Br | Me | |
| 17-27 | OMe | I | Me | |
| 17-28 | OMe | $CF_3$ | Me | |
| 17-29 | OMe | $CHF_2$ | Me | |
| 17-30 | OMe | $CF_2Cl$ | Me | |
| 17-31 | OMe | OMe | Me | |
| 17-32 | OMe | $NO_2$ | Me | |
| 17-33 | OMe | $SO_2Me$ | Me | |
| 17-34 | $SO_2Me$ | Me | Me | |
| 17-35 | $SO_2Me$ | F | Me | |
| 17-36 | $SO_2Me$ | Cl | Me | |
| 17-37 | $SO_2Me$ | Br | Me | |
| 17-38 | $SO_2Me$ | I | Me | |
| 17-39 | $SO_2Me$ | $CF_3$ | Me | |
| 17-40 | $SO_2Me$ | $CHF_2$ | Me | |
| 17-41 | $SO_2Me$ | $CF_2Cl$ | Me | |
| 17-42 | $SO_2Me$ | OMe | Me | |
| 17-43 | $SO_2Me$ | $NO_2$ | Me | |
| 17-44 | $SO_2Me$ | $SO_2Me$ | Me | |

TABLE 17-continued

Compounds according to the invention of the formula (II) in which Q* is chlorine and R' is cyano, t is 1, and the other radicals have the meanings indicated in the table

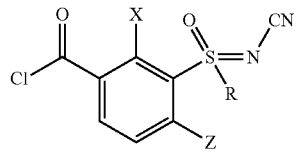

| No. | X | Z | R | Physical data ($^1$H NMR) |
|---|---|---|---|---|
| 17-45 | Me | Me | Et | |
| 17-46 | Me | F | Et | |
| 17-47 | Me | Cl | Et | |
| 17-48 | Me | Br | Et | |
| 17-49 | Me | I | Et | |
| 17-50 | Me | CF$_3$ | Et | |
| 17-51 | Me | CHF$_2$ | Et | |
| 17-52 | Me | CF$_2$Cl | Et | |
| 17-53 | Me | OMe | Et | |
| 17-54 | Me | NO$_2$ | Et | |
| 17-55 | Me | SO$_2$Me | Et | |
| 17-56 | Cl | Me | Et | |
| 17-57 | Cl | F | Et | |
| 17-58 | Cl | Cl | Et | |
| 17-59 | Cl | Br | Et | |
| 17-60 | Cl | I | Et | |
| 17-61 | Cl | CF$_3$ | Et | |
| 17-62 | Cl | CHF$_2$ | Et | |
| 17-63 | Cl | CF$_2$Cl | Et | |
| 17-64 | Cl | OMe | Et | |
| 17-65 | Cl | NO$_2$ | Et | |
| 17-66 | Cl | SO$_2$Me | Et | |
| 17-67 | OMe | Me | Et | |
| 17-68 | OMe | F | Et | |
| 17-69 | OMe | Cl | Et | |
| 17-70 | OMe | Br | Et | |
| 17-71 | OMe | I | Et | |
| 17-72 | OMe | CF$_3$ | Et | |
| 17-73 | OMe | CHF$_2$ | Et | |
| 17-74 | OMe | CF$_2$Cl | Et | |
| 17-75 | OMe | OMe | Et | |
| 17-76 | OMe | NO$_2$ | Et | |
| 17-77 | OMe | SO$_2$Me | Et | |
| 17-78 | SO$_2$Me | Me | Et | |
| 17-79 | SO$_2$Me | F | Et | |
| 17-80 | SO$_2$Me | Cl | Et | |
| 17-81 | SO$_2$Me | Br | Et | |
| 17-82 | SO$_2$Me | I | Et | |
| 17-83 | SO$_2$Me | CF$_3$ | Et | |
| 17-84 | SO$_2$Me | CHF$_2$ | Et | |
| 17-85 | SO$_2$Me | CF$_2$Cl | Et | |
| 17-86 | SO$_2$Me | OMe | Et | |
| 17-87 | SO$_2$Me | NO$_2$ | Et | |
| 17-88 | SO$_2$Me | SO$_2$Me | Et | |
| 17-89 | Me | Me | CH$_2$CH$_2$OMe | |
| 17-90 | Me | F | CH$_2$CH$_2$OMe | |
| 17-91 | Me | Cl | CH$_2$CH$_2$OMe | |
| 17-92 | Me | Br | CH$_2$CH$_2$OMe | |
| 17-93 | Me | I | CH$_2$CH$_2$OMe | |
| 17-94 | Me | CF$_3$ | CH$_2$CH$_2$OMe | |
| 17-95 | Me | CHF$_2$ | CH$_2$CH$_2$OMe | |
| 17-96 | Me | CF$_2$Cl | CH$_2$CH$_2$OMe | |
| 17-97 | Me | OMe | CH$_2$CH$_2$OMe | |
| 17-98 | Me | NO$_2$ | CH$_2$CH$_2$OMe | |
| 17-99 | Me | SO$_2$Me | CH$_2$CH$_2$OMe | |
| 17-100 | Cl | Me | CH$_2$CH$_2$OMe | |
| 17-101 | Cl | F | CH$_2$CH$_2$OMe | |
| 17-102 | Cl | Cl | CH$_2$CH$_2$OMe | |
| 17-103 | Cl | Br | CH$_2$CH$_2$OMe | |
| 17-104 | Cl | I | CH$_2$CH$_2$OMe | |
| 17-105 | Cl | CF$_3$ | CH$_2$CH$_2$OMe | |
| 17-106 | Cl | CHF$_2$ | CH$_2$CH$_2$OMe | |
| 17-107 | Cl | CF$_2$Cl | CH$_2$CH$_2$OMe | |
| 17-108 | Cl | OMe | CH$_2$CH$_2$OMe | |
| 17-109 | Cl | NO$_2$ | CH$_2$CH$_2$OMe | |
| 17-110 | Cl | SO$_2$Me | CH$_2$CH$_2$OMe | |

TABLE 17-continued

Compounds according to the invention of the formula (II) in which Q* is chlorine and R' is cyano, t is 1, and the other radicals have the meanings indicated in the table

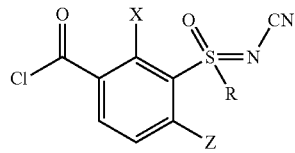

| No. | X | Z | R | Physical data ($^1$H NMR) |
|---|---|---|---|---|
| 17-111 | OMe | Me | CH$_2$CH$_2$OMe | |
| 17-112 | OMe | F | CH$_2$CH$_2$OMe | |
| 17-113 | OMe | Cl | CH$_2$CH$_2$OMe | |
| 17-114 | OMe | Br | CH$_2$CH$_2$OMe | |
| 17-115 | OMe | I | CH$_2$CH$_2$OMe | |
| 17-116 | OMe | CF$_3$ | CH$_2$CH$_2$OMe | |
| 17-117 | OMe | CHF$_2$ | CH$_2$CH$_2$OMe | |
| 17-118 | OMe | CF$_2$Cl | CH$_2$CH$_2$OMe | |
| 17-119 | OMe | OMe | CH$_2$CH$_2$OMe | |
| 17-120 | OMe | NO$_2$ | CH$_2$CH$_2$OMe | |
| 17-121 | OMe | SO$_2$Me | CH$_2$CH$_2$OMe | |
| 17-122 | SO$_2$Me | Me | CH$_2$CH$_2$OMe | |
| 17-123 | SO$_2$Me | F | CH$_2$CH$_2$OMe | |
| 17-124 | SO$_2$Me | Cl | CH$_2$CH$_2$OMe | |
| 17-125 | SO$_2$Me | Br | CH$_2$CH$_2$OMe | |
| 17-126 | SO$_2$Me | I | CH$_2$CH$_2$OMe | |
| 17-127 | SO$_2$Me | CF$_3$ | CH$_2$CH$_2$OMe | |
| 17-128 | SO$_2$Me | CHF$_2$ | CH$_2$CH$_2$OMe | |
| 17-129 | SO$_2$Me | CF$_2$Cl | CH$_2$CH$_2$OMe | |
| 17-130 | SO$_2$Me | OMe | CH$_2$CH$_2$OMe | |
| 17-131 | SO$_2$Me | NO$_2$ | CH$_2$CH$_2$OMe | |
| 17-132 | SO$_2$Me | SO$_2$Me | CH$_2$CH$_2$OMe | |

TABLE 18

Compounds accordng to the invention of the formula (II) in which Q* is chlorine and R' is cyano, t is 0, and the other radicals have the meanings indicated in the table

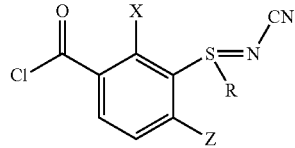

| No. | X | Z | R | Physical data ($^1$H NMR) |
|---|---|---|---|---|
| 18-1 | Me | Me | Me | |
| 18-2 | Me | F | Me | |
| 18-3 | Me | Cl | Me | |
| 18-4 | Me | Br | Me | |
| 18-5 | Me | I | Me | |
| 18-6 | Me | CF$_3$ | Me | |
| 18-7 | Me | CHF$_2$ | Me | |
| 18-8 | Me | CF$_2$Cl | Me | |
| 18-9 | Me | OMe | Me | |
| 18-10 | Me | NO$_2$ | Me | |
| 18-11 | Me | SO$_2$Me | Me | |
| 18-12 | Cl | Me | Me | |
| 18-13 | Cl | F | Me | |
| 18-14 | Cl | Cl | Me | |
| 18-15 | Cl | Br | Me | |
| 18-16 | Cl | I | Me | |
| 18-17 | Cl | CF$_3$ | Me | |
| 18-18 | Cl | CHF$_2$ | Me | |
| 18-19 | Cl | CF$_2$Cl | Me | |
| 18-20 | Cl | OMe | Me | |
| 18-21 | Cl | NO$_2$ | Me | |
| 18-22 | Cl | SO$_2$Me | Me | |
| 18-23 | OMe | Me | Me | |
| 18-24 | OMe | F | Me | |

TABLE 18-continued

Compounds according to the invention of the formula (II) in which Q* is chlorine and R' is cyano, t is 0, and the other radicals have the meanings indicated in the table

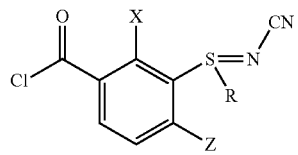

| No. | X | Z | R | Physical data ($^1$H NMR) |
|---|---|---|---|---|
| 18-25 | OMe | Cl | Me | |
| 18-26 | OMe | Br | Me | |
| 18-27 | OMe | I | Me | |
| 18-28 | OMe | $CF_3$ | Me | |
| 18-29 | OMe | $CHF_2$ | Me | |
| 18-30 | OMe | $CF_2Cl$ | Me | |
| 18-31 | OMe | OMe | Me | |
| 18-32 | OMe | $NO_2$ | Me | |
| 18-33 | OMe | $SO_2Me$ | Me | |
| 18-34 | $SO_2Me$ | Me | Me | |
| 18-35 | $SO_2Me$ | F | Me | |
| 18-36 | $SO_2Me$ | Cl | Me | |
| 18-37 | $SO_2Me$ | Br | Me | |
| 18-38 | $SO_2Me$ | I | Me | |
| 18-39 | $SO_2Me$ | $CF_3$ | Me | |
| 18-40 | $SO_2Me$ | $CHF_2$ | Me | |
| 18-41 | $SO_2Me$ | $CF_2Cl$ | Me | |
| 18-42 | $SO_2Me$ | OMe | Me | |
| 18-43 | $SO_2Me$ | $NO_2$ | Me | |
| 18-44 | $SO_2Me$ | $SO_2Me$ | Me | |
| 18-45 | Me | Me | Et | |
| 18-46 | Me | F | Et | |
| 18-47 | Me | Cl | Et | |
| 18-48 | Me | Br | Et | |
| 18-49 | Me | I | Et | |
| 18-50 | Me | $CF_3$ | Et | |
| 18-51 | Me | $CHF_2$ | Et | |
| 18-52 | Me | $CF_2Cl$ | Et | |
| 18-53 | Me | OMe | Et | |
| 18-54 | Me | $NO_2$ | Et | |
| 18-55 | Me | $SO_2Me$ | Et | |
| 18-56 | Cl | Me | Et | |
| 18-57 | Cl | F | Et | |
| 18-58 | Cl | Cl | Et | |
| 18-59 | Cl | Br | Et | |
| 18-60 | Cl | I | Et | |
| 18-61 | Cl | $CF_3$ | Et | |
| 18-62 | Cl | $CHF_2$ | Et | |
| 18-63 | Cl | $CF_2Cl$ | Et | |
| 18-64 | Cl | OMe | Et | |
| 18-65 | Cl | $NO_2$ | Et | |
| 18-66 | Cl | $SO_2Me$ | Et | |
| 18-67 | OMe | Me | Et | |
| 18-68 | OMe | F | Et | |
| 18-69 | OMe | Cl | Et | |
| 18-70 | OMe | Br | Et | |
| 18-71 | OMe | I | Et | |
| 18-72 | OMe | $CF_3$ | Et | |
| 18-73 | OMe | $CHF_2$ | Et | |
| 18-74 | OMe | $CF_2Cl$ | Et | |
| 18-75 | OMe | OMe | Et | |
| 18-76 | OMe | $NO_2$ | Et | |
| 18-77 | OMe | $SO_2Me$ | Et | |
| 18-78 | $SO_2Me$ | Me | Et | |
| 18-79 | $SO_2Me$ | F | Et | |
| 18-80 | $SO_2Me$ | Cl | Et | |
| 18-81 | $SO_2Me$ | Br | Et | |
| 18-82 | $SO_2Me$ | I | Et | |
| 18-83 | $SO_2Me$ | $CF_3$ | Et | |
| 18-84 | $SO_2Me$ | $CHF_2$ | Et | |
| 18-85 | $SO_2Me$ | $CF_2Cl$ | Et | |
| 18-86 | $SO_2Me$ | OMe | Et | |
| 18-87 | $SO_2Me$ | $NO_2$ | Et | |
| 18-88 | $SO_2Me$ | $SO_2Me$ | Et | |
| 18-89 | Me | Me | $CH_2CH_2OMe$ | |
| 18-90 | Me | F | $CH_2CH_2OMe$ | |

TABLE 18-continued

Compounds according to the invention of the formula (II) in which Q* is chlorine and R' is cyano, t is 0, and the other radicals have the meanings indicated in the table

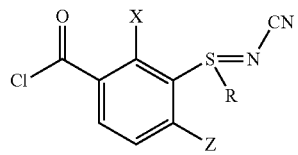

| No. | X | Z | R | Physical data ($^1$H NMR) |
|---|---|---|---|---|
| 18-91 | Me | Cl | $CH_2CH_2OMe$ | |
| 18-92 | Me | Br | $CH_2CH_2OMe$ | |
| 18-93 | Me | I | $CH_2CH_2OMe$ | |
| 18-94 | Me | $CF_3$ | $CH_2CH_2OMe$ | |
| 18-95 | Me | $CHF_2$ | $CH_2CH_2OMe$ | |
| 18-96 | Me | $CF_2Cl$ | $CH_2CH_2OMe$ | |
| 18-97 | Me | OMe | $CH_2CH_2OMe$ | |
| 18-98 | Me | $NO_2$ | $CH_2CH_2OMe$ | |
| 18-99 | Me | $SO_2Me$ | $CH_2CH_2OMe$ | |
| 18-100 | Cl | Me | $CH_2CH_2OMe$ | |
| 18-101 | Cl | F | $CH_2CH_2OMe$ | |
| 18-102 | Cl | Cl | $CH_2CH_2OMe$ | |
| 18-103 | Cl | Br | $CH_2CH_2OMe$ | |
| 18-104 | Cl | I | $CH_2CH_2OMe$ | |
| 18-105 | Cl | $CF_3$ | $CH_2CH_2OMe$ | |
| 18-106 | Cl | $CHF_2$ | $CH_2CH_2OMe$ | |
| 18-107 | Cl | $CF_2Cl$ | $CH_2CH_2OMe$ | |
| 18-108 | Cl | OMe | $CH_2CH_2OMe$ | |
| 18-109 | Cl | $NO_2$ | $CH_2CH_2OMe$ | |
| 18-110 | Cl | $SO_2Me$ | $CH_2CH_2OMe$ | |
| 18-111 | OMe | Me | $CH_2CH_2OMe$ | |
| 18-112 | OMe | F | $CH_2CH_2OMe$ | |
| 18-113 | OMe | Cl | $CH_2CH_2OMe$ | |
| 18-114 | OMe | Br | $CH_2CH_2OMe$ | |
| 18-115 | OMe | I | $CH_2CH_2OMe$ | |
| 18-116 | OMe | $CF_3$ | $CH_2CH_2OMe$ | |
| 18-117 | OMe | $CHF_2$ | $CH_2CH_2OMe$ | |
| 18-118 | OMe | $CF_2Cl$ | $CH_2CH_2OMe$ | |
| 18-119 | OMe | OMe | $CH_2CH_2OMe$ | |
| 18-120 | OMe | $NO_2$ | $CH_2CH_2OMe$ | |
| 18-121 | OMe | $SO_2Me$ | $CH_2CH_2OMe$ | |
| 18-122 | $SO_2Me$ | Me | $CH_2CH_2OMe$ | |
| 18-123 | $SO_2Me$ | F | $CH_2CH_2OMe$ | |
| 18-124 | $SO_2Me$ | Cl | $CH_2CH_2OMe$ | |
| 18-125 | $SO_2Me$ | Br | $CH_2CH_2OMe$ | |
| 18-126 | $SO_2Me$ | I | $CH_2CH_2OMe$ | |
| 18-127 | $SO_2Me$ | $CF_3$ | $CH_2CH_2OMe$ | |
| 18-128 | $SO_2Me$ | $CHF_2$ | $CH_2CH_2OMe$ | |
| 18-129 | $SO_2Me$ | $CF_2Cl$ | $CH_2CH_2OMe$ | |
| 18-130 | $SO_2Me$ | OMe | $CH_2CH_2OMe$ | |
| 18-131 | $SO_2Me$ | $NO_2$ | $CH_2CH_2OMe$ | |
| 18-132 | $SO_2Me$ | $SO_2Me$ | $CH_2CH_2OMe$ | |

TABLE 19

Compounds according to the invention of the formula (II) in which Q* is methoxy and R' is cyano, t is 1, and the other radicals have the meanings indicated in the table

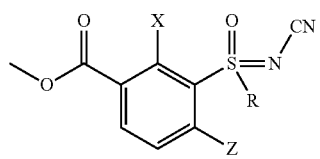

| No. | X | Z | R | Physical data ($^1$H NMR) |
|---|---|---|---|---|
| 19-1 | Me | Me | Me | |
| 19-2 | Me | F | Me | |
| 19-3 | Me | Cl | Me | |
| 19-4 | Me | Br | Me | |

TABLE 19-continued

Compounds according to the invention of the formula (II) in which Q* is methoxy and R' is cyano, t is 1, and the other radicals have the meanings indicated in the table

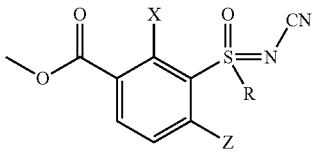

| No. | X | Z | R | Physical data ($^1$H NMR) |
|---|---|---|---|---|
| 19-5 | Me | I | Me | |
| 19-6 | Me | CF$_3$ | Me | |
| 19-7 | Me | CHF$_2$ | Me | |
| 19-8 | Me | CF$_2$Cl | Me | |
| 19-9 | Me | OMe | Me | |
| 19-10 | Me | NO$_2$ | Me | |
| 19-11 | Me | SO$_2$Me | Me | |
| 19-12 | Cl | Me | Me | |
| 19-13 | Cl | F | Me | |
| 19-14 | Cl | Cl | Me | |
| 19-15 | Cl | Br | Me | |
| 19-16 | Cl | I | Me | |
| 19-17 | Cl | CF$_3$ | Me | |
| 19-18 | Cl | CHF$_2$ | Me | |
| 19-19 | Cl | CF$_2$Cl | Me | |
| 19-20 | Cl | OMe | Me | |
| 19-21 | Cl | NO$_2$ | Me | |
| 19-22 | Cl | SO$_2$Me | Me | |
| 19-23 | OMe | Me | Me | |
| 19-24 | OMe | F | Me | |
| 19-25 | OMe | Cl | Me | |
| 19-26 | OMe | Br | Me | |
| 19-27 | OMe | I | Me | |
| 19-28 | OMe | CF$_3$ | Me | |
| 19-29 | OMe | CHF$_2$ | Me | |
| 19-30 | OMe | CF$_2$Cl | Me | |
| 19-31 | OMe | OMe | Me | |
| 19-32 | OMe | NO$_2$ | Me | |
| 19-33 | OMe | SO$_2$Me | Me | |
| 19-34 | SO$_2$Me | Me | Me | |
| 19-35 | SO$_2$Me | F | Me | |
| 19-36 | SO$_2$Me | Cl | Me | |
| 19-37 | SO$_2$Me | Br | Me | |
| 19-38 | SO$_2$Me | I | Me | |
| 19-39 | SO$_2$Me | CF$_3$ | Me | |
| 19-40 | SO$_2$Me | CHF$_2$ | Me | |
| 19-41 | SO$_2$Me | CF$_2$Cl | Me | |
| 19-42 | SO$_2$Me | OMe | Me | |
| 19-43 | SO$_2$Me | NO$_2$ | Me | |
| 19-44 | SO$_2$Me | SO$_2$Me | Me | |
| 19-45 | Me | Me | Et | |
| 19-46 | Me | F | Et | |
| 19-47 | Me | Cl | Et | |
| 19-48 | Me | Br | Et | |
| 19-49 | Me | I | Et | |
| 19-50 | Me | CF$_3$ | Et | |
| 19-51 | Me | CHF$_2$ | Et | |
| 19-52 | Me | CF$_2$Cl | Et | |
| 19-53 | Me | OMe | Et | |
| 19-54 | Me | NO$_2$ | Et | |
| 19-55 | Me | SO$_2$Me | Et | |
| 19-56 | Cl | Me | Et | |
| 19-57 | Cl | F | Et | |
| 19-58 | Cl | Cl | Et | |
| 19-59 | Cl | Br | Et | |
| 19-60 | Cl | I | Et | |
| 19-61 | Cl | CF$_3$ | Et | |
| 19-62 | Cl | CHF$_2$ | Et | |
| 19-63 | Cl | CF$_2$Cl | Et | |
| 19-64 | Cl | OMe | Et | |
| 19-65 | Cl | NO$_2$ | Et | |
| 19-66 | Cl | SO$_2$Me | Et | |
| 19-67 | OMe | Me | Et | |
| 19-68 | OMe | F | Et | |
| 19-69 | OMe | Cl | Et | |
| 19-70 | OMe | Br | Et | |

TABLE 19-continued

Compounds according to the invention of the formula (II) in which Q* is methoxy and R' is cyano, t is 1, and the other radicals have the meanings indicated in the table

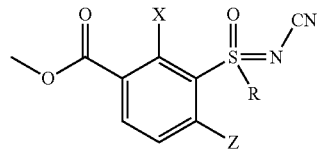

| No. | X | Z | R | Physical data ($^1$H NMR) |
|---|---|---|---|---|
| 19-71 | OMe | I | Et | |
| 19-72 | OMe | CF$_3$ | Et | |
| 19-73 | OMe | CHF$_2$ | Et | |
| 19-74 | OMe | CF$_2$Cl | Et | |
| 19-75 | OMe | OMe | Et | |
| 19-76 | OMe | NO$_2$ | Et | |
| 19-77 | OMe | SO$_2$Me | Et | |
| 19-78 | SO$_2$Me | Me | Et | |
| 19-79 | SO$_2$Me | F | Et | |
| 19-80 | SO$_2$Me | Cl | Et | |
| 19-81 | SO$_2$Me | Br | Et | |
| 19-82 | SO$_2$Me | I | Et | |
| 19-83 | SO$_2$Me | CF$_3$ | Et | |
| 19-84 | SO$_2$Me | CHF$_2$ | Et | |
| 19-85 | SO$_2$Me | CF$_2$Cl | Et | |
| 19-86 | SO$_2$Me | OMe | Et | |
| 19-87 | SO$_2$Me | NO$_2$ | Et | |
| 19-88 | SO$_2$Me | SO$_2$Me | Et | |
| 19-89 | Me | Me | CH$_2$CH$_2$OMe | |
| 19-90 | Me | F | CH$_2$CH$_2$OMe | |
| 19-91 | Me | Cl | CH$_2$CH$_2$OMe | |
| 19-92 | Me | Br | CH$_2$CH$_2$OMe | |
| 19-93 | Me | I | CH$_2$CH$_2$OMe | |
| 19-94 | Me | CF$_3$ | CH$_2$CH$_2$OMe | |
| 19-95 | Me | CHF$_2$ | CH$_2$CH$_2$OMe | |
| 19-96 | Me | CF$_2$Cl | CH$_2$CH$_2$OMe | |
| 19-97 | Me | OMe | CH$_2$CH$_2$OMe | |
| 19-98 | Me | NO$_2$ | CH$_2$CH$_2$OMe | |
| 19-99 | Me | SO$_2$Me | CH$_2$CH$_2$OMe | |
| 19-100 | Cl | Me | CH$_2$CH$_2$OMe | |
| 19-101 | Cl | F | CH$_2$CH$_2$OMe | |
| 19-102 | Cl | Cl | CH$_2$CH$_2$OMe | |
| 19-103 | Cl | Br | CH$_2$CH$_2$OMe | |
| 19-104 | Cl | I | CH$_2$CH$_2$OMe | |
| 19-105 | Cl | CF$_3$ | CH$_2$CH$_2$OMe | |
| 19-106 | Cl | CHF$_2$ | CH$_2$CH$_2$OMe | |
| 19-107 | Cl | CF$_2$Cl | CH$_2$CH$_2$OMe | |
| 19-108 | Cl | OMe | CH$_2$CH$_2$OMe | |
| 19-109 | Cl | NO$_2$ | CH$_2$CH$_2$OMe | |
| 19-110 | Cl | SO$_2$Me | CH$_2$CH$_2$OMe | |
| 19-111 | OMe | Me | CH$_2$CH$_2$OMe | |
| 19-112 | OMe | F | CH$_2$CH$_2$OMe | |
| 19-113 | OMe | Cl | CH$_2$CH$_2$OMe | |
| 19-114 | OMe | Br | CH$_2$CH$_2$OMe | |
| 19-115 | OMe | I | CH$_2$CH$_2$OMe | |
| 19-116 | OMe | CF$_3$ | CH$_2$CH$_2$OMe | |
| 19-117 | OMe | CHF$_2$ | CH$_2$CH$_2$OMe | |
| 19-118 | OMe | CF$_2$Cl | CH$_2$CH$_2$OMe | |
| 19-119 | OMe | OMe | CH$_2$CH$_2$OMe | |
| 19-120 | OMe | NO$_2$ | CH$_2$CH$_2$OMe | |
| 19-121 | OMe | SO$_2$Me | CH$_2$CH$_2$OMe | |
| 19-122 | SO$_2$Me | Me | CH$_2$CH$_2$OMe | |
| 19-123 | SO$_2$Me | F | CH$_2$CH$_2$OMe | |
| 19-124 | SO$_2$Me | Cl | CH$_2$CH$_2$OMe | |
| 19-125 | SO$_2$Me | Br | CH$_2$CH$_2$OMe | |
| 19-126 | SO$_2$Me | I | CH$_2$CH$_2$OMe | |
| 19-127 | SO$_2$Me | CF$_3$ | CH$_2$CH$_2$OMe | |
| 19-128 | SO$_2$Me | CHF$_2$ | CH$_2$CH$_2$OMe | |
| 19-129 | SO$_2$Me | CF$_2$Cl | CH$_2$CH$_2$OMe | |
| 19-130 | SO$_2$Me | OMe | CH$_2$CH$_2$OMe | |
| 19-131 | SO$_2$Me | NO$_2$ | CH$_2$CH$_2$OMe | |
| 19-132 | SO$_2$Me | SO$_2$Me | CH$_2$CH$_2$OMe | |

TABLE 20

Compounds according to the invention of the formula (II) in which Q* is methoxy and R' is cyano, t is 0, and the other radicals have the meanings indicated in the table

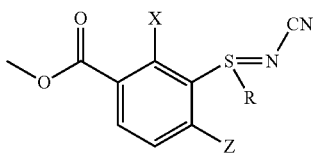

| No. | X | Z | R | Physical data ($^1$H NMR) |
|---|---|---|---|---|
| 20-1 | Me | Me | Me | |
| 20-2 | Me | F | Me | |
| 20-3 | Me | Cl | Me | |
| 20-4 | Me | Br | Me | |
| 20-5 | Me | I | Me | |
| 20-6 | Me | CF$_3$ | Me | (400 MHz, CDCl$_3$ δ, ppm) 8.01 (d, 1H), 7.75 (d, 1H), 3.98 (s, 3H), 3.18 (s, 3H), 3.08 (s, 3H) |
| 20-7 | Me | CHF$_2$ | Me | |
| 20-8 | Me | CF$_2$Cl | Me | |
| 20-9 | Me | OMe | Me | |
| 20-10 | Me | NO$_2$ | Me | |
| 20-11 | Me | SO$_2$Me | Me | |
| 20-12 | Cl | Me | Me | |
| 20-13 | Cl | F | Me | |
| 20-14 | Cl | Cl | Me | |
| 20-15 | Cl | Br | Me | |
| 20-16 | Cl | I | Me | |
| 20-17 | Cl | CF$_3$ | Me | |
| 20-18 | Cl | CHF$_2$ | Me | |
| 20-19 | Cl | CF$_2$Cl | Me | |
| 20-20 | Cl | OMe | Me | |
| 20-21 | Cl | NO$_2$ | Me | |
| 20-22 | Cl | SO$_2$Me | Me | |
| 20-23 | OMe | Me | Me | |
| 20-24 | OMe | F | Me | |
| 20-25 | OMe | Cl | Me | |
| 20-26 | OMe | Br | Me | |
| 20-27 | OMe | I | Me | |
| 20-28 | OMe | CF$_3$ | Me | |
| 20-29 | OMe | CHF$_2$ | Me | |
| 20-30 | OMe | CF$_2$Cl | Me | |
| 20-31 | OMe | OMe | Me | |
| 20-32 | OMe | NO$_2$ | Me | |
| 20-33 | OMe | SO$_2$Me | Me | |
| 20-34 | SO$_2$Me | Me | Me | |
| 20-35 | SO$_2$Me | F | Me | |
| 20-36 | SO$_2$Me | Cl | Me | |
| 20-37 | SO$_2$Me | Br | Me | |
| 20-38 | SO$_2$Me | I | Me | |
| 20-39 | SO$_2$Me | CF$_3$ | Me | |
| 20-40 | SO$_2$Me | CHF$_2$ | Me | |
| 20-41 | SO$_2$Me | CF$_2$Cl | Me | |
| 20-42 | SO$_2$Me | OMe | Me | |
| 20-43 | SO$_2$Me | NO$_2$ | Me | |
| 20-44 | SO$_2$Me | SO$_2$Me | Me | |
| 20-45 | Me | Me | Et | |
| 20-46 | Me | F | Et | |
| 20-47 | Me | Cl | Et | |
| 20-48 | Me | Br | Et | |
| 20-49 | Me | I | Et | |
| 20-50 | Me | CF$_3$ | Et | |
| 20-51 | Me | CHF$_2$ | Et | |
| 20-52 | Me | CF$_2$Cl | Et | |
| 20-53 | Me | OMe | Et | |
| 20-54 | Me | NO$_2$ | Et | |
| 20-55 | Me | SO$_2$Me | Et | |
| 20-56 | Cl | Me | Et | |
| 20-57 | Cl | F | Et | |
| 20-58 | Cl | Cl | Et | |
| 20-59 | Cl | Br | Et | |
| 20-60 | Cl | I | Et | |
| 20-61 | Cl | CF$_3$ | Et | |
| 20-62 | Cl | CHF$_2$ | Et | |
| 20-63 | Cl | CF$_2$Cl | Et | |
| 20-64 | Cl | OMe | Et | |
| 20-65 | Cl | NO$_2$ | Et | |

TABLE 20-continued

Compounds according to the invention of the formula (II) in which Q* is methoxy and R' is cyano, t is 0, and the other radicals have the meanings indicated in the table

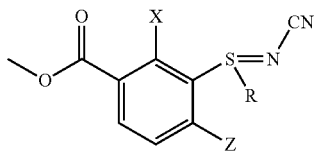

| No. | X | Z | R | Physical data ($^1$H NMR) |
|---|---|---|---|---|
| 20-66 | Cl | SO$_2$Me | Et | |
| 20-67 | OMe | Me | Et | |
| 20-68 | OMe | F | Et | |
| 20-69 | OMe | Cl | Et | |
| 20-70 | OMe | Br | Et | |
| 20-71 | OMe | I | Et | |
| 20-72 | OMe | CF$_3$ | Et | |
| 20-73 | OMe | CHF$_2$ | Et | |
| 20-74 | OMe | CF$_2$Cl | Et | |
| 20-75 | OMe | OMe | Et | |
| 20-76 | OMe | NO$_2$ | Et | |
| 20-77 | OMe | SO$_2$Me | Et | |
| 20-78 | SO$_2$Me | Me | Et | |
| 20-79 | SO$_2$Me | F | Et | |
| 20-80 | SO$_2$Me | Cl | Et | |
| 20-81 | SO$_2$Me | Br | Et | |
| 20-82 | SO$_2$Me | I | Et | |
| 20-83 | SO$_2$Me | CF$_3$ | Et | |
| 20-84 | SO$_2$Me | CHF$_2$ | Et | |
| 20-85 | SO$_2$Me | CF$_2$Cl | Et | |
| 20-86 | SO$_2$Me | OMe | Et | |
| 20-87 | SO$_2$Me | NO$_2$ | Et | |
| 20-88 | SO$_2$Me | SO$_2$Me | Et | |
| 20-89 | Me | Me | CH$_2$CH$_2$OMe | |
| 20-90 | Me | F | CH$_2$CH$_2$OMe | |
| 20-91 | Me | Cl | CH$_2$CH$_2$OMe | |
| 20-92 | Me | Br | CH$_2$CH$_2$OMe | |
| 20-93 | Me | I | CH$_2$CH$_2$OMe | |
| 20-94 | Me | CF$_3$ | CH$_2$CH$_2$OMe | |
| 20-95 | Me | CHF$_2$ | CH$_2$CH$_2$OMe | |
| 20-96 | Me | CF$_2$Cl | CH$_2$CH$_2$OMe | |
| 20-97 | Me | OMe | CH$_2$CH$_2$OMe | |
| 29-98 | Me | NO$_2$ | CH$_2$CH$_2$OMe | |
| 29-99 | Me | SO$_2$Me | CH$_2$CH$_2$OMe | |
| 20-100 | Cl | Me | CH$_2$CH$_2$OMe | |
| 20-101 | Cl | F | CH$_2$CH$_2$OMe | |
| 20-102 | Cl | Cl | CH$_2$CH$_2$OMe | |
| 20-103 | Cl | Br | CH$_2$CH$_2$OMe | |
| 20-104 | Cl | I | CH$_2$CH$_2$OMe | |
| 20-105 | Cl | CF$_3$ | CH$_2$CH$_2$OMe | |
| 20-106 | Cl | CHF$_2$ | CH$_2$CH$_2$OMe | |
| 20-107 | Cl | CF$_2$Cl | CH$_2$CH$_2$OMe | |
| 20-108 | Cl | OMe | CH$_2$CH$_2$OMe | |
| 20-109 | Cl | NO$_2$ | CH$_2$CH$_2$OMe | |
| 20-110 | Cl | SO$_2$Me | CH$_2$CH$_2$OMe | |
| 20-111 | OMe | Me | CH$_2$CH$_2$OMe | |
| 20-112 | OMe | F | CH$_2$CH$_2$OMe | |
| 20-113 | OMe | Cl | CH$_2$CH$_2$OMe | |
| 20-114 | OMe | Br | CH$_2$CH$_2$OMe | |
| 20-115 | OMe | I | CH$_2$CH$_2$OMe | |
| 20-116 | OMe | CF$_3$ | CH$_2$CH$_2$OMe | |
| 20-117 | OMe | CHF$_2$ | CH$_2$CH$_2$OMe | |
| 20-118 | OMe | CF$_2$Cl | CH$_2$CH$_2$OMe | |
| 20-119 | OMe | OMe | CH$_2$CH$_2$OMe | |
| 20-120 | OMe | NO$_2$ | CH$_2$CH$_2$OMe | |
| 20-121 | OMe | SO$_2$Me | CH$_2$CH$_2$OMe | |
| 20-122 | SO$_2$Me | Me | CH$_2$CH$_2$OMe | |
| 20-123 | SO$_2$Me | F | CH$_2$CH$_2$OMe | |
| 20-124 | SO$_2$Me | Cl | CH$_2$CH$_2$OMe | |
| 20-125 | SO$_2$Me | Br | CH$_2$CH$_2$OMe | |
| 20-126 | SO$_2$Me | I | CH$_2$CH$_2$OMe | |
| 20-127 | SO$_2$Me | CF$_3$ | CH$_2$CH$_2$OMe | |
| 20-128 | SO$_2$Me | CHF$_2$ | CH$_2$CH$_2$OMe | |
| 20-129 | SO$_2$Me | CF$_2$Cl | CH$_2$CH$_2$OMe | |

TABLE 20-continued

Compounds according to the invention of the formula (II) in which Q* is methoxy and R' is cyano, t is 0, and the other radicals have the meanings indicated in the table

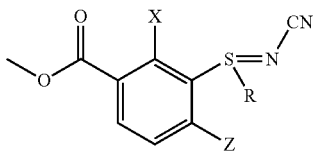

| No. | X | Z | R | Physical data ($^1$H NMR) |
|---|---|---|---|---|
| 20-130 | SO$_2$Me | OMe | CH$_2$CH$_2$OMe | |
| 20-131 | SO$_2$Me | NO$_2$ | CH$_2$CH$_2$OMe | |
| 20-132 | SO$_2$Me | SO$_2$Me | CH$_2$CH$_2$OMe | |

B. FORMULATION EXAMPLES a) A dust is obtained by mixing 10 parts by weight of a compound of the formula (I) and/or its salts and 90 parts by weight of talc as inert substance and comminuting the mixture in a hammer mill.

b) A wettable powder which is readily dispersible in water is obtained by mixing 25 parts by weight of a compound of the formula (I) and/or its salts, 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of a compound of the formula (I) and/or its salts with 6 parts by weight of alkylphenol polyglycol ether (® Triton X 207), 3 parts by weight of isotridecanol polyglycol ether (8 EO) and 71 parts by weight of paraffinic mineral oil (boiling range for example approximately 255 up to over 277° C.) and grinding the mixture in a bowl mill to a fineness of below 5 microns.

d) An emulsifiable concentrate is obtained from 15 parts by weight of a compound of the formula (I) and/or its salts, 75 parts by weight of cyclohexanone as solvent and 10 parts by weight of ethoxylated nonylphenol as emulsifier.

e) Water-dispersible granules are obtained by mixing
75 parts by weight of a compound of the formula (I) and/or its salts,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill and granulating the powder in a fluidized bed by spraying on water as granulation liquid.

f) Water-dispersible granules are also obtained by homogenizing and precomminuting, in a colloid mill,
25 parts by weight of a compound of the formula (I) and/or its salts,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill, and atomizing and drying the resulting suspension in a spray tower by means of a single-substance nozzle.

C. BIOLOGICAL EXAMPLES

1. Herbicidal Pre-Emergence Effect Against Harmful Plants

Seeds of monocotyledonous or dicotyledonous weeds or crop plants are placed in sandy loam soil in wood-fiber pots and covered with soil. The compounds according to the invention, formulated in the form of wettable powders (WP) or emulsion concentrates (EC), are then applied to the surface of the soil cover in the form of an aqueous suspension or emulsion at a water application rate of 600 to 800 l/ha (converted), with addition of 0.2% wetter. After the treatment, the pots are placed in the greenhouse and kept under good growth conditions for the test plants. The damage to the test plants is scored visually in comparison with untreated controls after an experimental time of 3 weeks has elapsed (herbicidal activity in percent (%): 100% activity=plants have died, 0% activity=like control plants). Here, for example the compounds Nos. 3-160 and 4-160 show, at an application rate of 320 g/ha, each at least 80% strength activity against *Abutilon theophrasti* and *Amaranthus retroflexus*. The compounds Nos. 2-160 and 10a-160 show, at an application rate of 320 g/ha, each at least 80% strength activity against *Polygonum convolvulus* and *Stellaria media*.

2. Herbicidal Post-Emergence Activity Against Harmful Plants

Seeds of monocotyledonous or dicotyledonous weeds or crop plants are placed in sandy loam soil in wood-fiber pots, covered with soil and grown in the greenhouse under good growth conditions. 2 to 3 weeks after sowing, the test plants are treated in the one-leaf stage. The compounds according to the invention, formulated in the form of wettable powders (WP) or emulsion concentrates (EC), are then sprayed onto the green plant parts in the form of an aqueous suspension or emulsion at a water application rate of 600 to 800 l/ha (converted), with addition of 0.2% wetter. After the test plants have been left to stand under optimal growth conditions in the greenhouse for approximately 3 weeks, the activity of the preparations is scored visually in comparison with untreated controls (herbicidal activity in percent (%): 100% activity=plants have died, 0% activity=like control plants). Here, for example the compounds Nos. 2-160, 3-160, 4-160 and 10a-160 show, at an application rate of 80 g/ha, each at least 80% strength activity against *Abutilon theophrasti* and *Echinochloa crus galli*.

The invention claimed is:

1. A sulfinimidoyl- and sulfonimidoylbenzoyl derivative of formula (I) and/or a salt thereof

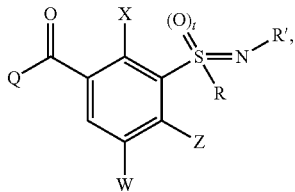

in which
Q is a radical Q1, Q2, Q3, Q4 or Q5,

Q1

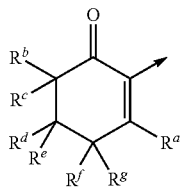

Q2

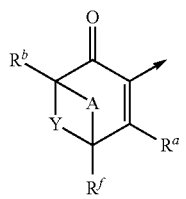

Q3

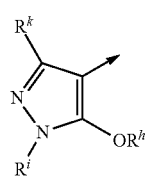

Q4

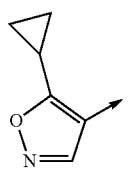

Q5

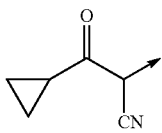

$R^a$ is hydroxyl, $R^6S$, or $R^7(R^8)N$, $R^b$, $R^c$, $R^f$ and $R^g$ independently of one another are each hydrogen or $(C_1-C_4)$-alkyl, $R^d$, $R^e$ independently of one another are each hydrogen or $(C_1-C_4)$-alkyl or together with the carbon atom to which they are attached form a carbonyl group, $R^h$ is hydrogen, $(C_1-C_6)$-alkylsulfonyl, $(C_1-C_4)$-alkoxy-$(C_1-C_6)$-alkylsulfonyl, phenylsulfonyl, phiophenyl-2-sulfonyl, benzoyl, benzoyl-$(C_1-C_6)$-alkyl, or benzyl, where the five last-mentioned radicals may optionally be mono- or polysubstituted by halogen, $(C_1-C_4)$-alkyl or $(C_1-C_4)$-alkoxy, $R^i$ is $(C_1-C_4)$-alkyl, $R^k$ is hydrogen, $(C_1-C_4)$-alkyl, or $(C_3-C_7)$-cycloalkyl, A and Y independently of one another are each oxygen, $S(O)_n$, $N(R^3)$, carbonyl or $(C_1-C_4)$-alkylene which is substituted by n radicals $R^9$ and interrupted by n elements from the group consisting of oxygen, $S(O)_n$, $N(R^3)$ and carbonyl, X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, halo-$(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkenyl-$(C_1-C_6)$-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5)_2(O)P$, $R^1(O)C—(C_1-C_6)$-alkyl, $R^1O(O)C—(C_1-C_6)$-alkyl, $(R^1)_2N(O)C—(C_1-C_6)$-alkyl, $(R^1O)(R^1)N(O)C—(C_1-C_6)$-alkyl, $(R^1)_2N(R^1)N(O)C—(C_1-C_6)$-alkyl, $R^1(O)C(R^1)N(O)C—(C_1-C_6)$-alkyl, $R^2O(O)C(R^1)N(O)C—(C_1-C_6)$-alkyl, $(R^1)_2N(O)C(R^1)N(O)C—(C_1-C_6)$-alkyl, $R^2(O)_2S(R^1)N(O)C—(C_1-C_6)$-alkyl, $R^1O(O)_2S(R^1)N(O)C—(C_1-C_6)$-alkyl, $(R^1)_2N(O)_2S(R^1)N(O)C—(C_1-C_6)$-alkyl, $NC—(C_1-C_6)$-alkyl, $R^1O—(C_1-C_6)$-alkyl, $R^1(O)CO—(C_1-C_6)$-alkyl, $R^2(O)_2SO—(C_1-C_6)$-alkyl, $R^2O(O)CO—(C_1-C_6)$-alkyl, $(R^1)_2N(O)CO—(C_1-C_6)$-alkyl, $(R^1)_2N—(C_1-C_6)$-alkyl, $R^1(O)C(R^1)N—(C_1-C_6)$-alkyl, $R^2(O)_2S(R^1)N—(C_1-C_6)$-alkyl, $R^2O(O)C(R^1)N—(C_1-C_6)$-alkyl, $(R^1)_2N(O)C(R^1)N—(C_1-C_6)$-alkyl, $R^1O(O)_2S(R^1)N—(C_1-C_6)$-alkyl, $(R^1)_2N(O)_2S(R^1)N—(C_1-C_6)$-alkyl, $R^2(O)_nS—(C_1-C_6)$-alkyl, $R^1O(O)_2S—(C_1-C_6)$-alkyl, $(R^1)_2N(O)_2S—(C_1-C_6)$-alkyl, $R^1(O)C(R^1)N(O)_2S—(C_1-C_6)$-alkyl, $R^2O(O)C(R^1)N(O)_2S—(C_1-C_6)$-alkyl, $(R^1)_2N(O)C(R^1)N(O)_2S—(C_1-C_6)$-alkyl, $(R^5O)_2(O)P—(C_1-C_6)$-alkyl, phenyl, heteroaryl, heterocyclyl, phenyl-$(C_1-C_6)$-alkyl, heteroaryl-$(C_1-C_6)$-alkyl, or heterocyclyl-$(C_1-C_6)$-alkyl, where the six last-mentioned radicals are each substituted by s radicals selected from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O—(C_1-C_6)$-alkyl, and where heterocyclyl carries n oxo groups, Z is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, halo-$(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkenyl-$(C_1-C_6)$-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)$ N, $R^2(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C$—$(C_1$-$C_6)$-alkyl, $R^1O(O)C$—$(C_1$-$C_6)$-alkyl, $(R^1)2N(O)C$—$(C_1$-$C_6)$-alkyl, $(R^1O)N(O)C$—$(C_1$-$C_6)$-alkyl, $(R^1)_2N(R^1)N(O)C$—$(C_1$-$C_6)$-alkyl, $R^1(O)C(R^1)N(O)C$—$(C_1$-$C_6)$-alkyl, $R^2O(O)C(R^1)N(O)C$—$(C_1$-$C_6)$-alkyl, $(R^1)_2N(O)C(R^1)N(O)C$—$(C_1$-$C_6)$-alkyl, $R^2(O)_2S(R^1)N(O)C$—$(C_1$-$C_6)$-alkyl, $R^1O(O)_2S(R^1)N(O)C$—$(C_1$-$C_6)$-alkyl, $(R^1)_2N(O)_2S(R^1)N(O)C$—$(C_1$-$C_6)$-alkyl, NC—$(C_1$-$C_6)$-alkyl, $R^1O$—$(C_1$-$C_6)$-alkyl, $R^1(O)CO$—$(C_1$-$C_6)$-alkyl, $R^2(O)_2$ SO—$(C_1$-$C_6)$-alkyl, $R^2O(O)CO$—$(C_1$-$C_6)$-alkyl, $(R^1)_2N(O)CO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^1O(O)_2S(R^1)N$—$(C_1$-$C_6)$-alkyl, $(R^1)_2N(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C(R^1)N(O)_2S$—$(C_1$-$C_6)$-alkyl, $R^2O(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, or heterocyclyl-$(C_1$-$C_6)$-alkyl, where the six last-mentioned radicals are each substituted by s radicals selected from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl carries n oxo groups, W is hydrogen, halogen, nitro, cyano, thiocyanato, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_7)$-cycloalkyl, halo-$(C_3$-$C_7)$-cycloalkyl, $(C_1$-$C_6)$-alkoxy, halo-$(C_1$-$C_6)$-alkoxy, $(C_1$-$C_6)$-alkyl-$(O)_nS$—, $(C_1$-$C_6)$-haloalkyl-$(O)_nS$—, $(C_1$-$C_6)$-alkoxy-$(C_1$-$C_4)$-alkyl, $(C_1$-$C_6)$-alkoxy-$(C_1$-$C_4)$-haloalkyl, $R^1(O)C$, $R^1(R^1ON=)C$, $R^1O(O)C$, $(R^1)_2N$, $R^1(O)C(R^1)N$ or $R^2(O)_2S(R^1)N$, R is $(C_1$-$C_6)$-alkyl, $(C_2$-$C_6)$-alkenyl or $(C_2$-$C_6)$-alkynyl, each of which is substituted by s radicals from the group consisting of nitro, halogen, cyano, thiocyanato, $(C_3$-$C_6)$-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2(O)CO$, $(R^1)_2N$, $R^1O(R^1)N$, $R^1(O)C(R^1)N$, $R^2(O)_2S(R^1)_2N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$ and $(R^5O)_2(O)P$, or is $(C_3$-$C_6)$-cycloalkyl, $(C_3$-$C_6)$-cycloalkenyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl, heterocyclyl-O—$(C_1$-$C_6)$-alkyl, phenyl-N($R^1$)—$(C_1$-$C_6)$-alkyl, heteroaryl-N($R^1$)—$(C_1$-$C_6)$-alkyl, heterocyclyl-N($R^1$)—$(C_1$-$C_6)$-alkyl, phenyl-S(O)$_n$—$(C_1$-$C_6)$-alkyl, heteroaryl-S(O)$_n$—$(C_1$-$C_6)$-alkyl or heterocyclyl-S(O)$_n$—$(C_1$-$C_6)$-alkyl, each of which is substituted in the cyclic moiety by s radicals selected from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$ and $R^1O$—$(C_1$-$C_6)$-alkyl, and where heterocyclyl carries n oxo groups, R' is hydrogen, nitro, halogen, cyano, $(C_1$-$C_6)$-alkyl, halo-$(C_1$-$C_6)$-alkyl, $(C_3$-$C_6)$-alkenyl, halo-$(C_3$-$C_6)$-alkenyl, $(C_2$-$C_6)$-alkynyl, halo-$(C_3$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$, $R^2O(O)C$, $(R^1)_2N(O)C$, $R^2S(O)C$, $(R^1)_2N(S)C$, $R^1(R^1O)N(O)C$, $R^2(O)_2S(R^1)N(O)C$, $(R^1)_2N(O)_2S(R^1)N(O)C$, $R^1O$, $(R^1)_2N$, $R_2(O)_nS$, $(R^2)_3Si$—$(C_1$-$C_6)$-alkyl-$(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $R^2(O)_2S(R^1)N(O)_2S$, $(R^5O)_2(O)P$, $(R^2)_3Si$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, $(R^1O)(R^1)N(O)C$—$(C_1$-$C_6)$-alkyl, $R^2(O)_2S(R^1)N(O)C$—$(C_1$-$C_6)$-alkyl, $R^1O(O)_2S(R^1)N(O)C$—$(C_1$-$C_6)$-alkyl, $(R^1)_2N(O)_2S(R^1)N(O)C$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^2O(O)CO$—$(C_1$-$C_6)$-alkyl, $(R^1)_2N(O)CO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^1O(O)_2S(R^1)N$—$(C_1$-$C_6)$-alkyl, $(R^1)_2N(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C(R^1)N(O)_2S$—$(C_1$-$C_6)$-alkyl, $R^2O(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, $(R^2)_3Si$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, or heterocyclyl-$(C_1$-$C_6)$-alkyl, where the six above-mentioned phenyl, heteroaryl and heterocyclyl radicals are substituted in the cyclic moiety by s radicals selected from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl carries n oxo groups, $R^1$ is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, $(C_3$-$C_6)$-cycloalkenyl, halo-$(C_3$-$C_6)$-cycloalkyl, $(C_3$-$C_6)$-cycloalkyl-$(C_1$-$C_6)$-alkyl, $(C_1$-$C_6)$-alkyl-O—$(C_1$-$C_6)$-alkyl, cycloalkyl-$(C_1$-$C_6)$-alkyl-O—$(C_1$-$C_6)$-alkyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl, heterocyclyl-O—$(C_1$-$C_6)$-alkyl, phenyl-N($R^3$)—$(C_1$-$C_6)$-alkyl, heteroaryl-N($R^3$)—$(C_1$-$C_6)$-alkyl, heterocyclyl-N($R^3$)—$(C_1$-$C_6)$-alkyl, phenyl-S(O)$_n$—$(C_1$-$C_6)$-alkyl, heteroaryl-S(O)$_n$—$(C_1$-$C_6)$-alkyl, or heterocyclyl-S(O)$_n$—$(C_1$-$C_6)$-alkyl, where the fifteen last-mentioned radicals are each substituted by s radicals selected from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1$-$C_6)$-alkyl, and where heterocyclyl carries n oxo groups, $R^2$ is $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$- alkynyl, $(C_3\text{-}C_6)$-cycloalkyl, $(C_3\text{-}C_6)$-cycloalkenyl, halo-$(C_3\text{-}C_6)$-cycloalkyl, $(C_3\text{-}C_6)$-cycloalkyl-$(C_1\text{-}C_6)$-alkyl, $(C_1\text{-}C_6)$-alkyl-O—$(C_1\text{-}C_6)$-alkyl, cycloalkyl-$(C_1\text{-}C_6)$-alkyl-O—$(C_1\text{-}C_6)$-alkyl, phenyl, phenyl-$(C_1\text{-}C_6)$-alkyl, heteroaryl, heteroaryl-$(C_1\text{-}C_6)$-alkyl, heterocyclyl, heterocyclyl-$(C_1\text{-}C_6)$-alkyl, phenyl-O—$(C_1\text{-}C_6)$-alkyl, heteroaryl-O—$(C_1\text{-}C_6)$-alkyl, heterocyclyl-O—$(C_1\text{-}C_6)$-alkyl, phenyl-N($R^3$)—$(C_1\text{-}C_6)$-alkyl, heteroaryl-N($R^3$)—$(C_1\text{-}C_6)$-alkyl, heterocyclyl-N($R^3$)—$(C_1\text{-}C_6)$-alkyl, phenyl-S(O)$_n$—$(C_1\text{-}C_6)$-alkyl, heteroaryl-S(O)$_n$—$(C_1\text{-}C_6)$-alkyl, or heterocyclyl-S(O)$_n$—$(C_1\text{-}C_6)$-alkyl, where the fifteen last-mentioned radicals are each substituted by s radicals selected from the group consisting of nitro, halogen, cyano, thiocyanato, $(C_1\text{-}C_6)$-alkyl, halo-$(C_1\text{-}C_6)$-alkyl, $(C_3\text{-}C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1\text{-}C_6)$-alkyl, and where heterocyclyl carries n oxo groups, $R^3$ is hydrogen, $(C_1\text{-}C_6)$-alkyl, halo-$(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkyl-$(C_1\text{-}C_6)$-alkyl or phenyl, $R^4$ is $(C_1\text{-}C_6)$-alkyl, halo-$(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkyl-$(C_1\text{-}C_6)$-alkyl or phenyl, $R^5$ is hydrogen or $(C_1\text{-}C_4)$-alkyl, $R^6$ is $(C_1\text{-}C_4)$-alkyl or is phenyl which is substituted by m radicals selected from the group consisting of halogen, nitro, cyano, $(C_1\text{-}C_4)$-alkyl, $(C_1\text{-}C_4)$-haloalkyl, $(C_1\text{-}C_4)$-alkoxy and $(C_1\text{-}C_4)$-haloalkoxy, $R^7$ is hydrogen, $(C_1\text{-}C_4)$-alkyl or $(C_1\text{-}C_4)$-alkoxy, $R^8$ is hydrogen or $(C_1\text{-}C_4)$-alkyl, or $R^7$ and $R^8$ together with the nitrogen atom to which they are attached form a 5- or 6-membered saturated, partially saturated or unsaturated ring which additionally contained n heteroatoms from the group consisting of nitrogen, oxygen and sulfur and which is substituted by m radicals selected from the group consisting of halogen, cyano, $(C_1\text{-}C_4)$-alkyl, $(C_1\text{-}C_4)$-haloalkyl, $(C_1\text{-}C_4)$-alkoxy and $(C_1\text{-}C_4)$-haloalkoxy, $R^9$ is halogen, $(C_1\text{-}C_4)$-alkyl, $(C_1\text{—}C)$-haloalkyl, $(C_1\text{-}C_4)$-alkoxy, $(C_1\text{-}C_4)$-haloalkoxy or $(C_1\text{-}C_4)$-alkoxy-$(C_1\text{-}C_4)$-alkyl, m is 0, 1, 2, 3, 4 or 5, n is 0, 1 or 2, s is 0, 1, 2 or 3, is 0 or 1.

2. The sulfinimidoyl- or sulfonimidoylbenzoyl derivative and/or salt as claimed in claim 1 in which Q is a radical Q1, Q2, Q3, Q4 or Q5,

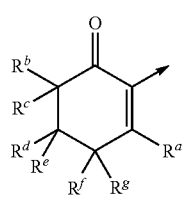
Q1

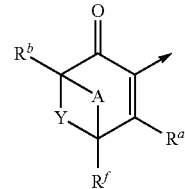
Q2

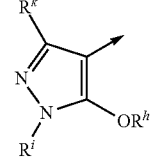
Q3

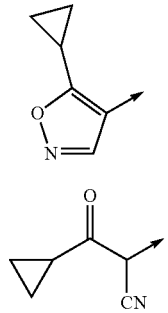
Q4

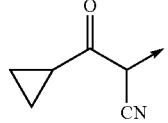
Q5

$R^a$ is hydroxyl, $R^b$, $R^c$, $R^f$ and $R^g$ independently of one another are each hydrogen or $(C_1\text{-}C_4)$-alkyl, $R^d$, $R^e$ independently of one another are each hydrogen or $(C_1\text{-}C_4)$-alkyl or together with the carbon atom to which they are attached form a carbonyl group, $R^h$ is hydrogen, $R^i$ is $(C_1\text{-}C_4)$-alkyl, $R^k$ is hydrogen, $(C_1\text{-}C_4)$-alkyl, or $(C_3\text{-}C_7)$-cycloalkyl, A and Y independently of one another are each oxygen or $(C_1\text{-}C_4)$-alkylene which is substituted by n radicals $R^9$, X is nitro, halogen, cyano, $(C_1\text{-}C_6)$-alkyl, halo-$(C_1\text{-}C_6)$-alkyl, $(C_2\text{-}C_6)$-alkenyl, $(C_2\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1\text{-}C_6)$-alkyl, $R^1O(O)C$—$(C_1\text{-}C_6)$-alkyl, $(R^1)_2N(O)C$—$(C_1\text{-}C_6)$-alkyl, NC—$(C_1\text{-}C_6)$-alkyl, $R^1O$—$(C_1\text{-}C_6)$-alkyl, $(R^1)_2N$—$(C_1\text{-}C_6)$-alkyl, $R^1(O)C(R^1)N$—$(C_1\text{-}C_6)$-alkyl, $R^2(O)_2S(R^1)N$—$(C_1\text{-}C_6)$-alkyl, $R^2O(O)C(R^1)N$—$(C_1\text{-}C_6)$-alkyl, $(R^1)_2N(O)C(R^1)N$—$(C_1\text{-}C_6)$-alkyl, $R^2(O)_nS$—$(C_1\text{-}C_6)$-alkyl, $R^1O(O)_2S$—$(C_1\text{-}C_6)$-alkyl, $(R^1)_2N(O)_2S$—$(C_1\text{-}C_6)$-alkyl, $(R^5O)_2(O)P$—$(C_1\text{-}C_6)$-alkyl, phenyl, heteroaryl, heterocyclyl, phenyl-$(C_1\text{-}C_6)$-alkyl, or heteroaryl-$(C_1\text{-}C_6)$-alkyl, heterocyclyl-$(C_1\text{-}C_6)$-alkyl, where the six last-mentioned radicals are each substituted by s radicals selected from the group consisting of nitro, halogen, cyano, thiocyanato, $(C_1\text{-}C_6)$-alkyl, halo-$(C_1\text{-}C_6)$-alkyl, $R^1O$, $(R^1)_2N$, $R^2(O)_nS$, $R^1O(O)_2S$, $(R^1)_2N(O)_2S$ and $R^1O$—$(C_1\text{-}C_6)$-alkyl and where heterocyclyl carries n oxo groups, Z is hydrogen, nitro, halogen, cyano, $(C_1\text{-}C_6)$-alkyl, halo-$(C_1\text{-}C_6)$-alkyl, $(C_2\text{-}C_6)$-alkenyl, $(C_2\text{-}C_6)$-alkynyl, $(C_3\text{-}$ $C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1(O)C$, $R^1(R^1ON\!\!=\!\!)C$, $R^1O(O)C$, $(R^1)_2N$ (O)C, $R^1O$, $(R^1)_2N$, $R^1(O)C(R^1)N$, $R^2(O)_2S(R^1)N$, $R^2O$ (O)C($R^1$)N, $(R^1)_2N(O)C(R^1)N$, $R^2(O)_nS$, $R^1O(O)_2S$, $(R^1)_2N(O)_2S$, $(R^5O)_2(O)P$, $R^1(O)C$—($C_1$-$C_6$)-alkyl, $R^1O(O)C$—($C_1$-$C_6$)-alkyl, $(R^1)_2N(O)C$—($C_1$-$C_6$)-alkyl, NC—($C_1$-$C_6$)-alkyl, $R^1O$—($C_1$-$C_6$)-alkyl, $(R^1)_2$N—($C_1$-$C_6$)-alkyl, $R^1(O)C(R^1)N$—($C_1$-$C_6$)-alkyl, $R^2(O)_2S(R^1)N$—($C_1$-$C_6$)-alkyl, $R^2O(O)C(R^1)N$—($C_1$-$C_6$)-alkyl, $(R^1)_2N(O)C(R^1)N$—($C_1$-$C_6$)-alkyl, $R^2(O)_nS$—($C_1$-$C_6$)-alkyl, $R^1O(O)_2S$—($C_1$-$C_6$)-alkyl, $(R^1)_2N(O)_2S$—($C_1$-$C_6$)-alkyl, $(R^5O)_2(O)P$—($C_1$-$C_6$)-alkyl, phenyl, heteroaryl, heterocyclyl, phenyl-($C_1$-$C_6$)-alkyl, or heteroaryl-($C_1$-$C_6$)-alkyl, heterocyclyl-($C_1$-$C_6$)-alkyl, where the six last-mentioned radicals are each substituted by s radicals selected from the group consisting of nitro, halogen, cyano, thiocyanato, ($C_1$-$C_6$)-alkyl, halo-($C_1$-$C_6$)-alkyl, $R^1O$, $(R^1)_2N$, $R^2(O)_nS$, $R^1O$ (O)$_2$S, $(R^1)_2N(O)_2S$ and $R^1O$—($C_1$-$C_6$)-alkyl and where heterocyclyl carries n oxo groups, W is hydrogen, halogen, nitro, cyano, ($C_1$-$C_6$)-alkyl, halo-($C_1$-$C_6$)-alkyl, ($C_3$-$C_7$)-cycloalkyl, ($C_1$-$C_6$)-alkoxy, ($C_1$-$C_6$)-alkyl-(O)$_n$S—, $R^1O(O)C$, $(R^1)_2N$, $R^1(O)C$ ($R^1$)N or $R^2(O)_2S(R^1)N$, R is ($C_1$-$C_6$)-alkyl which is in each case substituted by s radicals selected from the group consisting of halogen, cyano, ($C_3$-$C_6$)-cycloalkyl, $R^1(O)C$, $R^1(R^1ON\!\!=\!\!)C$, $R^1O(O)C$, $(R^1)_2N(O)C$, $R^2(O)_2S(R^1)N(O)C$, $R^1O$, $(R^1)_2$ N, $R^1(O)C(R^1)N$, $R^2(O)_2S(R^1)N$, $R^2O(O)C(R^1)$ N, $(R^1)_2N(O)C(R^1)N$, $R^2(O)_nS$, $R^1O(O)_2S$, $(R^1)_2N(O)_2$ S, $R^1(O)C(R^1)N(O)_2S$, $R^2O(O)C(R^1)N(O)_2S$ and $(R^1)_2N(O)C(R^1)N(O)_2S$ or is ($C_3$-$C_6$)-cycloalkyl which is in each case substituted by s radicals selected from the group consisting of halogen, ($C_1$-$C_6$)-alkyl, halo-($C_1$-$C_6$)-alkyl, ($C_3$-$C_6$)-cycloalkyl, $R^1O(O)C$ and $(R^1)_2N(O)C$, R' is hydrogen, nitro, cyano, ($C_1$-$C_6$)-alkyl, halo-($C_1$-$C_6$)-alkyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1(O)C$, $R^2O(O)C$, $(R^1)_2N(O)$C, $R^2(O)_2S$, $R^1(O)C$—($C_1$-$C_6$)-alkyl, $R^1O(O)C$—($C_1$-$C_6$)-alkyl, $(R^1)_2N(O)C$—($C_1$-$C_6$)-alkyl, $R^1O$—($C_1$-$C_6$)-alkyl, $(R^1)_2N$—($C_1$-$C_6$)-alkyl, or $R^2(O)_nS$—($C_1$-$C_6$)-alkyl, $R^1$ is hydrogen, ($C_1$-$C_6$)-alkyl, halo-($C_1$-$C_6$)-alkyl, ($C_3$-$C_6$)-cycloalkyl, halo-($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, cycloalkyl-($C_1$-$C_6$)-alkyl-O—($C_1$-$C_6$)-alkyl, phenyl, phenyl-($C_1$-$C_6$)-alkyl, heteroaryl, hetero aryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, or heterocyclyl-O—($C_1$-$C_6$)-alkyl, where the nine last-mentioned radicals are in each case substituted by s radicals selected from the group consisting of nitro, halogen, ($C_1$-$C_6$)-alkyl, halo-($C_1$-$C_6$)-alkyl, $R^3O(O)C$, $(R^3)_2N(O)C$, $R^3O$, $(R^3)_2N$, $R^4(O)_nS$ and $R^3O$—($C_1$-$C_6$)-alkyl, and where heterocyclyl carries n oxo groups, $R^2$ is ($C_1$-$C_6$)-alkyl, halo-($C_1$-$C_6$)-alkyl, ($C_3$-$C_6$)-cycloalkyl, halo-($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, or heterocyclyl-O—($C_1$-$C_6$)-alkyl, where the nine last-mentioned radicals are in each case substituted by s radicals selected from the group consisting of nitro, halogen, ($C_1$-$C_6$)-alkyl, halo-($C_1$-$C_6$)-alkyl, $R^3O(O)C$, $(R^3)_2N(O)C$, $R^3O$, $(R^3)_2N$, $R^4(O)_nS$ and $R^3O$—($C_1$-$C_6$)-alkyl, and where heterocyclyl carries n oxo groups, $R^3$ is hydrogen or ($C_1$-$C_6$)-alkyl, $R^4$ is ($C_1$-$C_6$)-alkyl, $R^5$ is hydrogen or ($C_1$-$C_4$)-alkyl, $R^9$ is halogen, ($C_1$-$C_4$)-alkyl, ($C_1$-$C_4$)-haloalkyl, ($C_1$-$C_4$)-alkoxy, ($C_1$-$C_4$)-haloalkoxy or ($C_1$-$C_4$)-alkoxy-($C_1$-$C_4$)-alkyl, n is 0, 1 or 2, s is 0, 1, 2 or 3, t is 0 or 1.

3. The sulfinimidoyl- or sulfonimidoylbenzoyl derivative and/or salt as claimed in claim 1 in which Q is a radical Q1, Q2, Q3, Q4 or Q5,

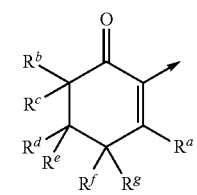

Q1

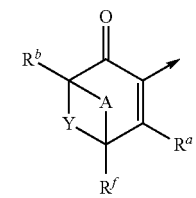

Q2

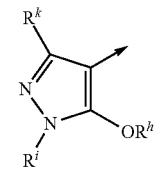

Q3

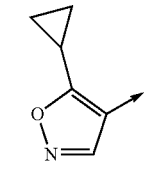

Q4

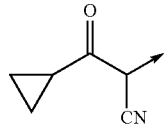

Q5

$R^a$ is hydroxyl, $R^b$, $R^e$, $R^f$ and $R^g$ independently of one another are each hydrogen or methyl, $R^d$, $R^e$ are hydrogen or together with the carbon atom to which they are attached form a carbonyl group, $R^h$ is hydrogen, $R^i$ is methyl or ethyl, $R^k$ is hydrogen, methyl or cyclopropyl, A and Y independently of one another are each $CH_2$ or $CH_2CH_2$, X is nitro, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl, methylsulfonyl, methoxymethyl, ethoxymethyl, methoxyethyl, methoxyethoxymethyl, methylthiomethyl, methylsulfinylmethyl or methylsulfonylmethyl, Z is hydrogen, nitro, cyano, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl or methylsulfonyl, W is hydrogen, chlorine or methyl, R is methyl, ethyl or n-propyl, R' is hydrogen or cyano, t is 0 or 1.

4. A herbicidal composition which comprises a herbicidally active amount of at least one compound of formula (I) and/or salt as claimed in claim 1.

5. The herbicidal composition as claimed in claim 4 in a mixture with one or more formulation auxiliaries.

6. The herbicidal composition as claimed in claim 4 which comprises at least one further pesticidally active compound selected from the group consisting of insecticides, acaricides, herbicides, fungicides, safeners and growth regulators.

7. The herbicidal composition as claimed in claim 6 which comprises a safener.

8. The herbicidal composition as claimed in claim 7 which comprises cyprosulfamide, cloquintocet-mexyl, mefenpyr-diethyl or isoxadifen-ethyl.

9. The herbicidal composition as claimed in claim 6 which comprises a further herbicide.

10. A method of controlling unwanted plants, which comprises applying an effective amount of at least one compound of the formula (I) and/or salt thereof as claimed in claim 1 to the plants and/or to a location of unwanted plant growth.

11. A compound of formula (I) and/or salt as claimed in claim 1 capable of being used for controlling one or more unwanted plants.

12. The compound and/or salt as claimed in claim 11, wherein the compound of formula (I) and/or salt is employed for controlling unwanted plants in one or more crops of useful plants.

13. The compound and/or salt as claimed in claim 12, wherein the useful plants are transgenic useful plants.

* * * * *